US011940448B2

(12) United States Patent
Hahn et al.

(10) Patent No.: US 11,940,448 B2
(45) Date of Patent: Mar. 26, 2024

(54) PROTEOMIC SCREENING FOR LYSOSOMAL STORAGE DISEASES

(71) Applicant: Seattle Children's Hospital, Seattle, WA (US)

(72) Inventors: Sihoun Hahn, Clyde Hill, WA (US); Christopher Collins, Seattle, WA (US); Remwilyn Dayuha, Lynnwood, WA (US); Fan Yi, Shoreline, WA (US)

(73) Assignee: Seattle Children's Hospital, Seattle, WA (US)

( * ) Notice: Subject to any disclaimer, the term of this patent is extended or adjusted under 35 U.S.C. 154(b) by 275 days.

(21) Appl. No.: 17/219,776

(22) Filed: Mar. 31, 2021

(65) Prior Publication Data

US 2021/0302435 A1 Sep. 30, 2021

Related U.S. Application Data

(60) Provisional application No. 63/002,992, filed on Mar. 31, 2020.

(51) Int. Cl.
G01N 33/68 (2006.01)

(52) U.S. Cl.
CPC ..... *G01N 33/6854* (2013.01); *G01N 33/6848* (2013.01); *G01N 2800/38* (2013.01)

(58) Field of Classification Search
None
See application file for complete search history.

(56) References Cited

U.S. PATENT DOCUMENTS

| | | | |
|---|---|---|---|
| 7,632,686 B2 | 12/2009 | Anderson | |
| 8,383,417 B2 | 2/2013 | Lopez et al. | |
| 9,588,126 B2 | 3/2017 | Anderson | |
| 10,590,190 B2 | 3/2020 | Rosenthal et al. | |
| 2007/0099251 A1 | 5/2007 | Zhang et al. | |
| 2007/0243191 A1 | 10/2007 | Mao et al. | |
| 2007/0265432 A1 | 11/2007 | Meikle et al. | |
| 2010/0003239 A1 | 1/2010 | Scales | |
| 2010/0009463 A1 | 1/2010 | Hornbeck et al. | |
| 2011/0217790 A1 | 9/2011 | Pass et al. | |
| 2012/0156710 A1 | 6/2012 | Nakayama et al. | |
| 2012/0184050 A1 | 7/2012 | Meikle et al. | |
| 2012/0225060 A1 | 9/2012 | Lee et al. | |
| 2013/0105684 A1 | 5/2013 | Louette et al. | |
| 2013/0137595 A1 | 5/2013 | Zangar et al. | |
| 2013/0302399 A1 | 11/2013 | Feldhaus et al. | |
| 2014/0106981 A1 | 4/2014 | Hood et al. | |
| 2014/0273275 A1 | 9/2014 | Jacobs et al. | |
| 2015/0322423 A1 | 11/2015 | Kosugi et al. | |
| 2016/0083458 A1 | 3/2016 | Katsuragi et al. | |
| 2016/0319005 A1 | 11/2016 | Lopez-Girona et al. | |
| 2018/0086846 A1 | 3/2018 | Wiltzius et al. | |
| 2018/0164301 A1 | 6/2018 | Anderson | |
| 2019/0031754 A1 | 1/2019 | Rader et al. | |
| 2019/0134164 A1 | 5/2019 | DeRosa et al. | |
| 2021/0285965 A1 | 9/2021 | Hahn et al. | |
| 2021/0341492 A1 | 11/2021 | Hahn et al. | |
| 2023/0194545 A1 | 6/2023 | Hahn | |

FOREIGN PATENT DOCUMENTS

| | | |
|---|---|---|
| WO | WO2011015602 A2 | 2/2011 |
| WO | WO2013106603 A1 | 7/2013 |
| WO | WO2013148284 A1 | 10/2013 |
| WO | WO2014037977 A1 | 3/2014 |
| WO | WO2016110584 A1 | 7/2016 |
| WO | WO2017062672 A2 | 4/2017 |
| WO | WO2017106292 A2 | 6/2017 |
| WO | WO2018097951 A | 5/2018 |
| WO | WO2019030377 A1 | 2/2019 |
| WO | WO2019126647 A1 | 6/2019 |
| WO | WO2019149816 A1 | 8/2019 |
| WO | WO2019173291 A1 | 9/2019 |

(Continued)

OTHER PUBLICATIONS

Jung S, Whiteaker JR, Zhao L, Yoo HW, Paulovich AG, Hahn SH (2017) "Quantification of ATP7B Protein in Dried Blood Spots by Peptide Immuno-SRM as a Potential Screen for Wilson's Disease", Journal of Proteome Research, 16, pp. 862-871 (Year: 2017).*
Invitation to Pay Additional Fees Dated Dec. 26, 2019 in International Application No. PCT/US2019/054856, 8 pages.
Jung, et al., "Quanitification of ATP7B Protein in Dried Blood Spots by Peptide Immuno-SRM as a Potential Screen for Wilson's Disease," J. Proteome. Res., vol. 16, No. 2, 2017, pp. 862-871.
Kerfoot, et al., "Tryptic peptide screening for primary immunodeficiency disease by LC/MS-MS," Proteomics Clin. Appl, vol. 6, No. 7-8, 2012, pp. 394-402.
Search Report and Written Opinion dated Feb. 21, 2019 for International Application No. PCT/US19/54856, 14 pages.
De Mello, et al., "Feasibility of using cryopreserved lymphoblastoid cells to diagnose some lysosomal storage diseases," Cell Proliferation, vol. 43, No. 2, 2010, pp. 164-169.

(Continued)

*Primary Examiner* — Ellen J Marcsisin
*Assistant Examiner* — Stefanie J. Kirwin
(74) *Attorney, Agent, or Firm* — Lee & Hayes P.C.; C. Rachal Winger; Janina Malone

(57) ABSTRACT

Early detection of lysosomal storage diseases (LSDs) including Mucopolysaccharidosis Type I (MPS I) and Pompe Disease can greatly improve patient outcome as each disease can be fatal once symptoms emerge. Screening for MPS I and Pompe Disease using biological samples including dried blood spots (DBS), buccal swab, peripheral blood mononuclear cells (PBMCs), or white blood cells (WBCs) is described. The disclosed methods and assays provide a robust way to screen newborns for LSDs. The disclosed methods and assays can also allow rapid prediction of whether a patient with LSD will develop an immune response to enzyme replacement therapy (ERT), thus improving treatment for patients with LSDs. The disclosed methods and assays can also further reduce the number of false positives caused by pseudo deficiency cases of LSD, such as MPS I and Pompe Disease.

21 Claims, 38 Drawing Sheets

Specification includes a Sequence Listing.

(56) References Cited

FOREIGN PATENT DOCUMENTS

| WO | WO2020072996 A1 | 4/2020 |
|---|---|---|
| WO | WO2021178545 A1 | 9/2021 |

OTHER PUBLICATIONS

Invitation to Pay Additional Fees Dated Jul. 13, 2021 in International Application No. PCT/US2021/025627, 3 Pages.
Search Report and Written Opinion dated Jul. 22, 2021 in International Application No. PCT/US2021/025270, 20 bages.
Van Doorn, et al., "Salivary a-Iduronidase Activity as a Potential New Biomarker for the Diagnosis and Monitoring the Effect of Therapy in Mucopolysaccharidosis Type I," Biology of Blood and Marrow Transplantation, vol. 24, No. 9, 2018, pp. 1808-1813.
Search Report and Written Opinion dated Sep. 21, 2021 for International Application No. PCT/US2021/025627, 14 pages.
Extended European Search Report dated Sep. 27, 2022 for European Patent Application No. 19869877.1, 25 pages.
"Buccal Swab Collection Procedure," retrieved on Apr. 22, 2021 at «https://www.chla.org/sites/default/files/atoms/files/CHLA-Clinical-Pathology-Buccal-Swab-Collection-Procedure.pdf», 1 page.
Almannai, et al., "Newborn screening: a review of history, recent advancements, and future perspectives in the era of next generation sequencing," Current Opinion in Pediatrics, vol. 28, No. 6, 2016, pp. 694-699.
America & Cordewener, "Comparative LC-MS: A landscape of peaks and valleys," Bioinformatics, vol. 8, No. 4, 2008, pp. 731-749.
Anderson & Hunter, "Quantitative Mass Spectrometric Multiple Reaction Monitoring Assays for Major Plasma Proteins," Molecular & Cellular Proteomics, vol. 5, No. 4, 2006, pp. 573-588.
Anderson, et al., "Mass spectrometric quantitation of peptides and proteins using Stable Isotope Standards and Capture by Anti-Peptide Antibodies (SISCAPA)," Journal of Proteome Research, vol. 3, No. 2, 2004, pp. 235-244.
Anderson, et al., "SISCAPA peptide enrichment on magnetic beads using an in-line bead trap device," Molecular & Cellular Proteomics, vol. 8, No. 5, 2009, pp. 995-1005.
Beeton & Chandy, "Enrichment of NK cells from human blood with the RosetteSep kit from StemCell technologies," Journal of Visualized Experiments, vol. 8, 2007, pp. 326.
Beynon, et al., "Multiplexed absolute quantification in proteomics using artificial QCAT proteins of concatenated signature peptides," Nature Methods, vol. 2, No. 8, 2005, pp. 587-589.
Bousso, et al., "Enrichment of antigen-specific T lymphocytes by panning on immobilized MHC-peptide complexes," Immunology Letters, vol. 59, No. 2, 1997, pp. 85-91.
Boyum, "Isolation of mononuclear cells and granulocytes from human blood. Isolation of monuclear cells by one centrifugation, and of granulocytes by combining centrifugation and sedimentation at 1 g," Scandinavian Journal of Clinical and Laboratory Investigation, vol. 97, 1968, pp. 77-89.
Boyum, "Separation of Lymphocytes, Lymphocyte Subgroups and Monocytes: a Review," Lymphology, vol. 10, No. 22, 1977, pp. 71-76.
Brocks, et al., "Isolation of human myeloid dendritic cells from tumor tissue and peripheral blood," In Vivo, vol. 20, No. 2, 2006, pp. 239-242.
Brun, et al., "Isotope-labeled Protein Standards: Toward Absolute Quantitative Proteomics," Molecular & Cellular Proteomics, vol. 6, No. 12, 2007, pp. 2139-2149.
Carroll, et al., "Absolute quantification of the glycolytic pathway in yeast: deployment of a complete QconCAT approach," Molecular & Cellular Proteomics, vol. 10, No. 12, 2011, 15 pages.
Chace & Kalas, "A biochemical perspective on the use of tandem mass spectrometry for newborn screening and clinical testing," Clinical Biochemistry, vol. 38, No. 4, 2005, pp. 296-309.
Chase, et al., "Mass spectrometry in newborn and metabolic screening: historical perspective and future directions," Journal of Mass Spectrometry, vol. 44, No. 2, 2009, pp. 163-170.
Chase, et al., "Rapid diagnosis of phenylketonuria by quantitative analysis for phenylalanine and tyrosine in neonatal blood spots by tandem mass spectrometry," Clinical Chemistry, vol. 39, No. 1, 1993, pp. 66-71.
Collins, et al., "Direct Measurement of ATP7B Peptides Is Highly Effective in the Diagnosis of Wilson Disease," Gastroenterology, vol. 160, 2021, pp. 2367-2382.
Collins, et al., "Multiplexed Proteomic Analysis for Diagnosis and Screening of Five Primary Immunodeficiency Disorders From Dried Blood Spots," Frontiers in Immunology, vol. 11, No. 464, 2020, 16 pages.
Collins, et al., "Rapid Multiplexed Proteomic Screening for Primary Immunodeficiency Disorders From Dried Blood Spots," Frontiers in Immunology, vol. 9, 2018, 17 pages.
Corkum, et al., "Immune cell subsets and their gene expression profiles from human PBMC isolated by Vacutainer Cell Preparation Tube (CP[TM]) and standard density gradient," BMC Immunology, vol. 16, No. 48, 2015, 18 pages.
Cutillas, "Principles of Nanoflow Liquid Chromatography and Applications to Proteomics," Current Nanoscience, vol. 1, No. 1, 2005, pp. 65-71.
Dagur & McCoy, "Collection, Storage, and Preparation of Human Blood Cells," Current Protocols in Cytometry, vol. 73, No. 1, 2015, pp. 5.1.1-5.1.16.
Ding, et al., "Quantitative analysis of cohesin complex stoichiometry and SMC3 modification-dependent protein interactions," Journal of Proteome Research, vol. 10, No. 8, 2011, pp. 3652-3659.
Dott, et al., "Metabolic disorders detectable by tandem mass spectrometry and unexpected early childhood mortality: a population-based study," American Journal of Medical Genetics Part A, vol. 140, No. 8, 2006, pp. 837-842.
Espinosa-de Aquino, et al., "Protein and RNA extraction from mucosal swabs: a minimally invasive source of ecological data for studies of natural populations," Methods in Ecology and Evolution, vol. 8, No. 3, 2017, pp. 370-378.
Faguet & Agee, "A simple technique for the rapid enrichment of class and subclass hybridoma switch variants. A 1000 jold enrichment in half the time, for half the cost," Journal of Immunological Methods, vol. 165, No. 2, 1993, pp. 217-224.
Gelb, et al., "Newborn Screening for Lysosomal Storage Disorders: Methodologies for Measurement of Enzymatic Activities in Dried Blood Spots," International Journal of Neonatal Screening, vol. 5, No. 1, 2019, 12 pages.
Gerber, et al., "Absolute quantification of proteins and phosphoproteins from cell lysates by tandem MS," PNAS USA, vol. 100, No. 12, 2003, pp. 6940-6945.
Grievink, et al., "Comparison of Three Isolation Techniques for Human Peripheral Blood Mononuclear Cells: Cell Recovery and Viability, Population Composition, and Cell Functionality," Biopreservation and Biobanking, vol. 14, No. 6, 2016, pp. 410-415.
Holman, et al., "The use of selected reaction monitoring in quantitative proteomics," Bioanalysis, vol. 4, No. 14, 2012, pp. 1763-1786.
Holzmann, et al., "Stoichiometry determination of the MP1-p14 complex using a novel and cost-efficient method to produce an equimolar mixture of standard peptides," Analytical Chemistry, vol. 81, No. 24, 2009, pp. 10254-10261.
Hoofnagle, et al., "Quantification of thyroglobulin, a low-abundance serum protein, by immunoaffinity peptide enrichment and tandem mass spectrometry," Clinical Chemistry, vol. 54, No. 11, 2011, 2008, pp. 1796-1804.
Hoofnagle, et al., "Recommendations for the Generation, Quantification, Storage, and Handling of Peptides Used for Mass Spectrometry-Based Assays" Clinical Chemistry, vol. 62, No. 1, 2016, pp. 48-69.
Jia, et al., "A Modified Ficoll-Paque Gradient Method for Isolating Mononuclear Cells from the Peripheral and Umbilical Cord Blood of Humans for Biobanks and Clinical Laboratories," Biopreservation and Biobanking, vol. 16, No. 2, 2018, pp. 82-91.

(56) References Cited

OTHER PUBLICATIONS

Johnson, et al., "Rigorous determination of the stoichiometry of protein phosphorylation using mass spectrometry," Journal of the American Society for Mass Spectrometry, vol. 20, No. 12, 2009, pp. 2211-2220.
Kennedy, et al., "Demonstrating the feasibility of large-scale development of standardized assays to quantify human proteins," Nature Methods, vol. 11, No. 2, 2014, pp. 149-155.
Kirkpatrick, et al., "The absolute quantification strategy: a general procedure for the quantification of proteins and post-translational modifications," Methods, vol. 35, No. 3, 2005, pp. 265-273.
Kito, et al., "A synthetic protein approach toward accurate mass spectrometric quantification of component stoichiometry of multiprotein complexes," Journal of Proteome Research, vol. 6, No. 2, 2007, pp. 792-800.
Kuhn, et al., "Developing Multiplexed Assays for Troponin I and Interleukin-33 in Plasma by Peptide Immunoaffinity Enrichment and Targeted Mass Spectrometry," Clinical Chemistry, vol. 55, No. 6, 2009, pp. 1108-1117.
Kuhn, et al., "Interlaboratory evaluation of automated, multiplexed peptide immunoaffinity enrichment coupled to multiple reaction monitoring mass spectrometry for quantifying proteins in plasma," Molecular & Cellular Proteomics, vol. 11, No. 6, 2012, 14 pages.
Lange, et al., "Selected reaction monitoring for quantitative proteomics: a tutorial," Molecular Systems Biology, vol. 4, No. 1, 2008, 14 pages.
Lundgren, et al., "Role of spectral counting in quantitative proteomics," Expert Review of Proteomics, vol. 7, No. 1, 2010, pp. 39-53.
Mallick, et al., "Computational prediction of proteotypic peptides for quantitative proteomics," Nature Biotechnology, vol. 25, No. 1, 2007, pp. 125-131.
Michalczyk, et al., "Fresh and cultured buccal cells as a source of mRNA and protein for molecular analysis," BioTechniques, vol. 37, No. 2, 2004, pp. 262-269.
Millington, et al., "Tandem mass spectrometry: a new method for acylcarnitine profiling with potential for neonatal screening for inborn errors of metabolism," Journal of Inherited Metabolic Disease, vol. 13, 1990, pp. 321-324.
Morgensen and Cantell "Production and preparation of human leukocyte interferon," Pharmacology & Therapeutics. Part A: Chemotherapy, Toxicology and Metabolic Inhibitors, vol. 1, No. 4, 1977, pp. 369-381.
Nelson, et al., "Mass spectrometric immunoassay," Analytical Chemistry, vol. 67, No. 7, 1995, pp. 1153-1158.
Otogenetics Corporation, "Instruction for Buccal Swab Sample Collection," retrieved on Apr. 22, 2021 at «https://www.otogenetics.com/wp-content/uploads/2018/01/buccal-swab-collection-instructions.pdf», 1 page.
Pathway Genomics, "Buccal DNA Collection Instructions," retrieved on Apr. 22, 2021 at «https://www.pathway.com/wp-content/uploads/2017/06/Buccal-Swab-Collection-Instructions.pdf», 1 page.
PCT Search Report and Written Opinion dated Jun. 4, 2021 for PCT Application No. PCT/US2021/0206797, 26 pages.
Puleo, et al., "Isolation of Peripheral Blood Mononuclear Cells Using Vacutainer "CR" Cellular Preparation Tubes (CPTTM)," Bio-Protocol, vol. 7, No. 2, 2017, 6 pages.
Sweetman, et al., "Naming and counting disorders (conditions) included in newborn screening panels," Pediatrics, vol. 117, No. 5, 2006, pp. S308-S314.
United States Centers for Disease Control and Prevention, "Interim Guidelines for Collecting and Handling of Clinical Specimens for COVID-19 Testing," retrieved on Apr. 22, 2021 at «https://www.cdc.gov/coronavirus/2019-ncov/lab/guidelines-clinical-specimens.html», United States Centers for Disease Control and Prevention, 2021, 6 pages.
Watson, et al., "Main Report," Genetics in Medicine, vol. 8, No. 5, 2006, pp. 12S-252S.
Whiteaker & Paulovich, "Peptide immunoaffinity enrichment coupled with mass spectrometry for peptide and protein quantification," Clinics in Laboratory Medicine, vol. 31, No. 3, 2011, pp. 385-396.
Whiteaker, et al., "An automated and multiplexed method for high throughput peptide immunoaffinity enrichment and multiple reaction monitoring mass spectrometry-based quantification of protein biomarkers," Molecular & Cellular Proteomics, vol. 9, No. 1, 2010, pp. 184-196.
Whiteaker, et al., "High-affinity recombinant antibody fragments (Fabs) can be applied in peptide enrichment immuno—MRM assays," Journal of Proteome Research, vol. 13, No. 4, 2014, pp. 2187-2196.
Whiteaker, et al., "Sequential multiplexed analyte quantification using peptide immunoaffinity enrichment coupled to mass spectrometry," Molecular & Cellular Proteomics, vol. 11, No. 6, 2012, 10 pages.
Zhao, et al., "Quantification of proteins using peptide immunoaffinity enrichment coupled with mass spectrometry," Journal of Visualized Experiments, vol. 53, 2011, 5 pages.
Partial European Search Report dated Jun. 24, 2022 for European Patent Application No. 19869877.1, 28 pages.

* cited by examiner

FIG. 1

| Disease | Protein Target | Peptides | Sequence | Total Mass | Parent Ion Mass | Daughter y-Ion Masses (m/z) | | |
|---|---|---|---|---|---|---|---|---|
| | | | | | | + | ++ | +++ |
| Mucopolysaccharidosis Type I (MPSI; Hurler Syndrome) | IDUA | IDUA 218-230 ("IDUA 218") | LGGPGDSFHTPPR (SEQ ID NO: 1) | 1337.438 (av.) 1336.642 (mono.) | 446.5581++ + | G [y12] - 1224.5756+ G [y11] - 1167.5541+ P [y10] - 1110.5327+ G [y9] - 1013.4799+ D [y8] - 956.4585+ S [y7] - 841.4315+ F [y6] - 754.3995+ H [y5] - 607.3311+ T [y4] - 470.2722+ P [y3] - 369.2245+ | G [y12] - 612.7914++ G [y11] - 584.2807++ P [y10] - 555.7700++ G [y9] - 507.2436++ D [y8] - 478.7329++ S [y7] - 421.2194++ F [y6] - 377.7034++ H [y5] - 304.1692++ T [y4] - 235.6397++ P [y3] - 185.1159++ | G [y12] - 408.8634+++ G [y11] - 389.8562+++ P [y10] - 370.8491+++ G [y9] - 338.4982+++ D [y8] - 319.4910+++ S [y7] - 281.1487+++ F [y6] - 252.1380+++ H [y5] - 203.1152+++ T [y4] - 157.4289+++ P [y3] - 123.7463+++ |

FIG. 1 cont'd

| Disease | Protein Target | Peptides | Sequence | Total Mass | Parent Ion Mass | Daughter b-Ion Masses (m/z) | | |
|---|---|---|---|---|---|---|---|---|
| | | | | | | + | ++ | +++ |
| Mucopolysaccharidosis Type I (MPSI; Hurler Syndrome) | IDUA | IDUA 218-230 ("IDUA 218") | LGGPGDSFHTPPR (SEQ ID NO: 1) | 1337.438 (av.) 1336.642 (mono.) | 446.5581+++ | G [b3] - 228.1343+<br>P [b4] - 325.1870+<br>G [b5] - 382.2085+<br>D [b6] - 497.2354+<br>S [b7] - 584.2675+<br>F [b8] - 731.3359+<br>H [b9] - 868.3948+<br>T [b10] - 969.4425+<br>P [b11] - 1066.4952+<br>P [b12] - 1163.5480+ | G [b3] - 114.5708++<br>P [b4] - 163.0972++<br>G [b5] - 191.6079++<br>D [b6] - 249.1214++<br>S [b7] - 292.6374++<br>F [b8] - 366.1716++<br>H [b9] - 434.7010++<br>T [b10] - 485.2249++<br>P [b11] - 533.7513++<br>P [b12] - 582.2776++ | G [b3] - 76.7163+++<br>P [b4] - 109.0672+++<br>G [b5] - 128.0743+++<br>D [b6] - 166.4167+++<br>S [b7] - 195.4273+++<br>F [b8] - 244.4501+++<br>H [b9] - 290.1364+++<br>T [b10] - 323.8190+++<br>P [b11] - 356.1699+++<br>P [b12] - 388.5209+++ |

FIG. 1 cont'd

| Disease | Protein Target | Peptides | Sequence | Total Mass | Parent Ion Mass | Daughter y-Ion Masses (m/z) | | |
|---|---|---|---|---|---|---|---|---|
| | | | | | | + | ++ | +++ |
| Mucopolysaccharidosis Type I (MPSI; Hurler Syndrome) | IDUA | IDUA 462-474 ("IDUA 462") | GVPPGPGLVYVTR (SEQ ID NO: 2) | 1311.528 (av.) 1310.724 (mono.) | 656.3746++ | V [y12] - 1254.7205+<br>P [y11] - 1155.6521+<br>P [y10] - 1058.5993+<br>G [y9] - 961.5465+<br>P [y8] - 904.5251+<br>G [y7] - 807.4723+<br>L [y6] - 750.4509+<br>V [y5] - 637.3668+<br>Y [y4] - 538.2984+<br>V [y3] - 375.2350+ | V [y12] -<br>627.8639++<br>P [y11] -<br>578.3297++<br>P [y10] -<br>529.8033++<br>G [y9] -<br>481.2769++<br>P [y8] -<br>452.7662++<br>G [y7] -<br>404.2398++<br>L [y6] -<br>375.7291++<br>V [y5] -<br>319.1870++<br>Y [y4] -<br>269.6528++<br>V [y3] -<br>188.1212++ | |

FIG. 1 cont'd

| Disease | Protein Target | Peptides | Sequence | Total Mass | Parent Ion Mass | Daughter b-Ion Masses (m/z) | | |
|---|---|---|---|---|---|---|---|---|
| | | | | | | + | ++ | +++ |
| Mucopolysac charidosis Type I (MPSI; Hurler Syndrome) | IDUA | IDUA 462-474 ("IDUA 462") | GVPPGPGLVYVTR (SEQ ID NO: 2) | 1311.528 (av.) 1310.724 (mono.) | 656.3746++ | P [b3] - 254.1499+ P [b4] - 351.2027+ G [b5] - 408.2241+ P [b6] - 505.2769+ G [b7] - 562.2984+ L [b8] - 675.3824+ V [b9] - 774.4509+ Y [b10] - 937.5142+ V [b11] - 1036.5826+ T [b12] - 1137.6303+ | P [b3] - 127.5786++ P [b4] - 176.1050++ G [b5] - 204.6157++ P [b6] - 253.1421++ G [b7] - 281.6528++ L [b8] - 338.1949++ V [b9] - 387.7291++ Y [b10] - 469.2607++ V [b11] - 518.7949++ T [b12] - 569.3188++ | |

FIG. 1 cont'd

| Disease | Protein Target | Peptides | Sequence | Total Mass | Parent Ion Mass | Daughter y-Ion Masses (m/z) | | |
|---|---|---|---|---|---|---|---|---|
| | | | | | | + | ++ | +++ |
| Pompe Disease | GAA | GAA 155-162 ("GAA 155") | TTPTFFPK (SEQ ID NO: 3) | 938.09 (av.) 937.49 (mono.) | 469.7527++ | T [y7] - 837.4505+<br>P [y6] - 736.4028+<br>T [y5] - 639.3501+<br>F [y4] - 538.3024+<br>F [y3] - 391.2340+ | T [y7] - 419.2289++<br>P [y6] - 368.7051++<br>T [y5] - 320.1787++<br>F [y4] - 269.6548++<br>F [y3] - 196.1206++ | |

| Disease | Protein Target | Peptides | Sequence | Total Mass | Parent Ion Mass | Daughter b-Ion Masses (m/z) | | |
|---|---|---|---|---|---|---|---|---|
| | | | | | | + | ++ | +++ |
| Pompe Disease | GAA | GAA 155-162 ("GAA 155") | TTPTFFPK (SEQ ID NO: 3) | 938.09 (av.) 937.49 (mono.) | 469.7527++ | P [b3] - 300.1554+<br>T [b4] - 401.2031+<br>F [b5] - 548.2715+<br>F [b6] - 695.3399+<br>P [b7] - 792.3927+ | P [b3] - 150.5813++<br>T [b4] - 201.1052++<br>F [b5] - 274.6394++<br>F [b6] - 348.1736++<br>P [b7] - 396.7000++ | |

FIG. 1 cont'd

| Disease | Protein Target | Peptides | Sequence | Total Mass | Parent Ion Mass | Daughter y-Ion Masses (m/z) | | |
|---|---|---|---|---|---|---|---|---|
| | | | | | | + | ++ | +++ |
| Pompe Disease | GAA | GAA 332-348 ("GAA 332") | STGGILDVY IFLGPEPK (SEQ ID NO: 4) | 1806.069 (av.) 1804.950 (mono.) | 903.4878++ | L [y12] - 1390.7617+<br>D [y11] - 1277.6776+<br>V [y10] - 1162.6507+<br>Y [y9] - 1063.5823+<br>I [y8] - 900.5189+<br>F [y7] - 787.4349+<br>L [y6] - 640.3665+<br>G [y5] - 527.2824+<br>P [y4] - 470.2609+<br>E [y3] - 373.2082+ | T [y16] - 859.9718++<br>G [y15] - 809.4480++<br>G [y14] - 780.9372++<br>I [y13] - 752.4265++<br>L [y12] - 695.8845++<br>D [y11] - 639.3424++<br>V [y10] - 581.8290++<br>Y [y9] - 532.2948++<br>I [y8] - 450.7631++<br>F [y7] - 394.2211++<br>L [y6] - 320.6869++<br>G [y5] - 264.1448++<br>P [y4] - 235.6341++<br>E [y3] - 187.1077++ | |

FIG. 1 cont'd

| Disease | Protein Target | Peptides | Sequence | Total Mass | Parent Ion Mass | Daughter b-Ion Masses (m/z) | | |
|---|---|---|---|---|---|---|---|---|
| | | | | | | + | ++ | +++ |
| Pompe Disease | GAA | GAA 332-348 ("GAA 332") | STGGILDVY IFLGPEPK (SEQ ID NO: 4) | 1806.069 (av.) 1804.950 (mono.) | 903.4878++ | G [b3] - 246.1084+<br>G [b4] - 303.1299+<br>I [b5] - 416.2140+<br>L [b6] - 529.2980+<br>D [b7] - 644.3250+<br>V [b8] - 743.3934+<br>Y [b9] - 906.4567+<br>I [b10] - 1019.5408+<br>F [b11] - 1166.6092+<br>L [b12] - 1279.6933+<br>G [b13] - 1336.7147+<br>P [b14] - 1433.7675+ | G [b3] - 123.5579++<br>G [b4] - 152.0686++<br>I [b5] - 208.6106++<br>L [b6] - 265.1527++<br>D [b7] - 322.6661++<br>V [b8] - 372.2003++<br>Y [b9] - 453.7320++<br>I [b10] - 510.2740++<br>F [b11] - 583.8082++<br>L [b12] - 640.3503++<br>G [b13] - 668.8610++<br>P [b14] - 717.3874++<br>E [b15] - 781.9087++<br>P [b16] - 830.4351++ | |

FIG. 1 cont'd

| Disease | Protein Target | Peptides | Sequence | Total Mass | Parent Ion Mass | Daughter y-Ion Masses (m/z) | | |
|---|---|---|---|---|---|---|---|---|
| | | | | | | + | ++ | +++ |
| Pompe Disease | GAA | GAA 376-385 ("GAA 376") | WGYSSTAITR (SEQ ID NO: 5) | 1141.25 (av.) 1140.56 (mono.) | 571.2855++ | G [y9] - 955.4843+<br>Y [y8] - 898.4629+<br>S [y7] - 735.3995+<br>S [y6] - 648.3675+<br>T [y5] - 561.3355+<br>A [y4] - 460.2878+<br>I [y3] - 389.2507+ | G [y9] - 478.2458++<br>Y [y8] - 449.7351++<br>S [y7] - 368.2034++<br>S [y6] - 324.6874++<br>T [y5] - 281.1714++<br>A [y4] - 230.6475++<br>I [y3] - 195.1290++ | |

| Disease | Protein Target | Peptides | Sequence | Total Mass | Parent Ion Mass | Daughter b-Ion Masses (m/z) | | |
|---|---|---|---|---|---|---|---|---|
| | | | | | | + | ++ | +++ |
| Pompe Disease | GAA | GAA 376-385 ("GAA 376") | WGYSSTAITR (SEQ ID NO: 5) | 1141.25 (av.) 1140.56 (mono.) | 571.2855++ | Y [b3] - 407.1714+<br>S [b4] - 494.2034+<br>S [b5] - 581.2354+<br>T [b6] - 682.2831+<br>A [b7] - 753.3202+<br>I [b8] - 866.4043+<br>T [b9] - 967.4520+ | Y [b3] - 204.0893++<br>S [b4] - 247.6053++<br>S [b5] - 291.1214++<br>T [b6] - 341.6452++<br>A [b7] - 377.1638++<br>I [b8] - 433.7058++<br>T [b9] - 484.2296++ | |

FIG. 1 cont'd

| Disease | Protein Target | Peptides | Sequence | Total Mass | Parent Ion Mass | Daughter y-Ion Masses (m/z) | | |
|---|---|---|---|---|---|---|---|---|
| | | | | | | + | ++ | +++ |
| Pompe Disease | GAA | GAA 601-608 ("GAA 376") | STFAGHGR (SEQ ID NO: 6) | 831.89 (av.) 831.40 (mono.) | 416.7067++ | T [y7] - 745.3740+<br>F [y6] - 644.3263+<br>A [y5] - 497.2579+<br>G [y4] - 426.2208+<br>H [y3] - 369.1993+ | T [y7] - 373.1906++<br>F [y6] - 322.6668++<br>A [y5] - 249.1326++<br>G [y4] - 213.6140++<br>H [y3] - 185.1033++ | |

| Disease | Protein Target | Peptides | Sequence | Total Mass | Parent Ion Mass | Daughter b-Ion Masses (m/z) | | |
|---|---|---|---|---|---|---|---|---|
| | | | | | | + | ++ | +++ |
| Pompe Disease | GAA | GAA 601-608 ("GAA 376") | STFAGHGR (SEQ ID NO: 6) | 831.89 (av.) 831.40 (mono.) | 416.7067++ | F [b3] - 336.1554+<br>A [b4] - 407.1925+<br>G [b5] - 464.2140+<br>H [b6] - 601.2729+<br>G [b7] - 658.2944+ | F [b3] - 168.5813++<br>A [b4] - 204.0999++<br>G [b5] - 232.6106++<br>H [b6] - 301.1401++<br>G [b7] - 329.6508++ | |

FIG. 1 cont'd

| Disease | Protein Target | Peptides | Sequence | Total Mass | Parent Ion Mass | Daughter y-Ion Masses (m/z) | | |
|---|---|---|---|---|---|---|---|---|
| | | | | | | + | ++ | +++ |
| Pompe Disease | GAA | GAA 855-870 ("GAA 855") | GELFWDDG ESLEVLER (SEQ ID NO: 7) | 1894.004 (av.) 1892.868 (mono.) | 947.4469++ | W [y12] - 1447.6700+<br>D [y11] - 1261.5907+<br>D [y10] - 1146.5637+<br>G [y9] - 1031.5368+<br>E [y8] - 974.5153+<br>S [y7] - 845.4727+<br>L [y6] - 758.4407+<br>E [y5] - 645.3566+<br>V [y4] - 516.3140+<br>L [y3] - 417.2456+ | E [y15] - 918.9362++<br>L [y14] - 854.4149++<br>F [y13] - 797.8728++<br>W [y12] - 724.3386++<br>D [y11] - 631.2990++<br>D [y10] - 573.7855++<br>G [y9] - 516.2720++<br>E [y8] - 487.7613++<br>S [y7] - 423.2400++<br>L [y6] - 379.7240++<br>E [y5] - 323.1819++<br>V [y4] - 258.6606++<br>L [y3] - 209.1264++ | |

FIG. 1 cont'd

| Disease | Protein Target | Peptides | Sequence | Total Mass | Parent Ion Mass | Daughter b-Ion Masses (m/z) | | |
|---|---|---|---|---|---|---|---|---|
| | | | | | | + | ++ | +++ |
| Pompe Disease | GAA | GAA 855-870 ("GAA 855") | GELFWDDG ESLEVLER (SEQ ID NO: 7) | 1894.004 (av.) 1892.868 (mono.) | 947.4469++ | L [b3] - 300.1554+<br>F [b4] - 447.2238+<br>W [b5] - 633.3031+<br>D [b6] - 748.3301+<br>D [b7] - 863.3570+<br>G [b8] - 920.3785+<br>E [b9] - 1049.4211+<br>S [b10] - 1136.4531+<br>L [b11] - 1249.5372+<br>E [b12] - 1378.5798+<br>V [b13] - 1477.6482+ | L [b3] - 150.5813++<br>F [b4] - 224.1155++<br>W [b5] - 317.1552++<br>D [b6] - 374.6687++<br>D [b7] - 432.1821++<br>G [b8] - 460.6929++<br>E [b9] - 525.2142++<br>S [b10] - 568.7302++<br>L [b11] - 625.2722++<br>E [b12] - 689.7935++<br>V [b13] - 739.3277++<br>L [b14] - 795.8698++<br>E [b15] - 860.3910++ | |

FIG. 1 cont'd

| Disease | Protein Target | Peptides | Sequence | Total Mass | Parent Ion Mass | Daughter y-Ion Masses (m/z) | | |
|---|---|---|---|---|---|---|---|---|
| | | | | | | + | ++ | +++ |
| Pompe Disease | GAA | GAA 882-891 ("GAA 882") | NNTIVNELVR (SEQ ID NO: 8) | 1171.32 (av.) 1170.64 (mono.) | 586.3251++ | N [y9] - 1057.6000+<br>T [y8] - 943.5571+<br>I [y7] - 842.5094+<br>V [y6] - 729.4254+<br>N [y5] - 630.3570+<br>E [y4] - 516.3140+<br>L [y3] - 387.2714+ | N [y9] - 529.3037++<br>T [y8] - 472.2822++<br>I [y7] - 421.7584++<br>V [y6] - 365.2163++<br>N [y5] - 315.6821++<br>E [y4] - 258.6606++<br>L [y3] - 194.1394++ | |

| Disease | Protein Target | Peptides | Sequence | Total Mass | Parent Ion Mass | Daughter b-Ion Masses (m/z) | | |
|---|---|---|---|---|---|---|---|---|
| | | | | | | + | ++ | +++ |
| Pompe Disease | GAA | GAA 882-891 ("GAA 882") | NNTIVNELVR (SEQ ID NO: 8) | 1171.32 (av.) 1170.64 (mono.) | 586.3251++ | T [b3] - 330.1408+<br>I [b4] - 443.2249+<br>V [b5] - 542.2933+<br>N [b6] - 656.3362+<br>E [b7] - 785.3788+<br>L [b8] - 898.4629+<br>V [b9] - 997.5313+ | T [b3] - 165.5740++<br>I [b4] - 222.1161++<br>V [b5] - 271.6503++<br>N [b6] - 328.6717++<br>E [b7] - 393.1930++<br>L [b8] - 449.7351++<br>V [b9] - 499.2693++ | |

FIG. 1 cont'd

| Disease | Protein Target | Peptides | Sequence | Total Mass | Parent Ion Mass | Daughter y-Ion Masses (m/z) | | |
|---|---|---|---|---|---|---|---|---|
| | | | | | | + | ++ | +++ |
| Pompe Disease | GAA | GAA 892-903 ("GAA 892") | VTSEGAGLQLQK (SEQ ID NO: 9) | 1230.38 (av.) 1229.66 (mono.) | 615.8381++ | T [y11] - 1131.6004+<br>S [y10] - 1030.5527+<br>E [y9] - 943.5207+<br>G [y8] - 814.4781+<br>A [y7] - 757.4567+<br>G [y6] - 686.4196+<br>L [y5] - 629.3981+<br>Q [y4] - 516.3140+<br>L [y3] - 388.2554+ | T [y11] - 566.3039++<br>S [y10] - 515.7800++<br>E [y9] - 472.2640++<br>G [y8] - 407.7427++<br>A [y7] - 379.2320++<br>G [y6] - 343.7134++<br>L [y5] - 315.2027++<br>Q [y4] - 258.6606++<br>L [y3] - 194.6314++ | |

FIG. 1 cont'd

| Disease | Protein Target | Peptides | Sequence | Total Mass | Parent Ion Mass | Daughter b-Ion Masses (m/z) | | |
|---|---|---|---|---|---|---|---|---|
| | | | | | | + | ++ | +++ |
| Pompe Disease | GAA | GAA 892-903 ("GAA 892") | VTSEGAGL QLQK (SEQ ID NO: 9) | 1230.38 (av.) 1229.66 (mono.) | 615.8381++ | S [b3] - 288.1554+<br>E [b4] - 417.1980+<br>G [b5] - 474.2195+<br>A [b6] - 545.2566+<br>G [b7] - 602.2780+<br>L [b8] - 715.3621+<br>Q [b9] - 843.4207+<br>L [b10] - 956.5047+<br>Q [b11] - 1084.5633+ | S [b3] - 144.5813++<br>E [b4] - 209.1026++<br>G [b5] - 237.6134++<br>A [b6] - 273.1319++<br>G [b7] - 301.6427++<br>L [b8] - 358.1847++<br>Q [b9] - 422.2140++<br>L [b10] - 478.7560++<br>Q [b11] - 542.7853++ | |

FIG. 12

>anti-IDUA 218 variable heavy domain coding sequence with leader sequence (leader sequence is underlined)
ATGGGATGGAGCTATATCATCCTCTTTTTGGTAGCAACAGTTACAGATGTCCACTCCCAGG
TCCAACTGCAGCAGCCTGGGACTGAGCTTGTGAAGCCTGGGGCTTCAGTGAAGTTGTCCT
GCAAGGCTTCTGGCTACACCTTCACCAGGTACTGGATGCACTGGGTGAAGCAGAGGCCTG
GACAAGGCCTTGAGTGGATTGGAGAGATTAATCCTAGCAATGGTGGGACTAACTACAATGA
GAAGTTCAAGAACAAGGCCACACTGAATGTTGACAAATCCTCCAGCACAGCCTACATGCAA
CTCAGCAGCCTGACATCTGAGGACTCTGCGGTCTATTACTGTACGTTAGCTATGGACTACT
GGGGTCAAGGAACCTCAGTCACCGTCTCCTCA (SEQ ID NO: 16)

>anti-IDUA 218 variable heavy domain amino acid sequence with leader sequence (leader sequence is underlined)
MGWSYIILFLVATVTDVHSQVQLQQPGTELVKPGASVKLSCKASGYTFTRYWMHWVKQRPGQ
GLEWIGEINPSNGGTNYNEKFKNKATLNVDKSSSTAYMQLSSLTSEDSAVYYCTLAMDYWGQ
GTSVTVSS (SEQ ID NO: 17)

>anti-IDUA 218 variable heavy domain amino acid sequence without leader sequence
QVQLQQPGTELVKPGASVKLSCKASGYTFTRYWMHWVKQRPGQGLEWIGEINPSNGGTNYN
EKFKNKATLNVDKSSSTAYMQLSSLTSEDSAVYYCTLAMDYWGQGTSVTVSS (SEQ ID NO: 18)

>anti-IDUA 218 variable light domain coding sequence with leader sequence (leader sequence is underlined)
ATGAGTCCTGCCCAGTTCCTGTTTCTGTTAGTGCTCTGGATTCGGGAAACCAACGGTGATG
TTGTGATGACCCAGACTCCACTCACTTTGTCGGTTACCATTGGACAACCAGCCTCCATCTC
TTGCAAGTCAAGTCAGAGCCTCTTACATAGTGATGGAAAGACATATTTGAATTGGTCGTTAC
AGAGGCCAGGCCAGTCTCCAAAGCGCCTAATCTATCTGGTGTCTAAACTGGACTCTGGAG
TCCCTGACAGGTTCACTGGCAGTGGATCAGGGACAGATTTCACACTGAAAATCAGCAGAGT
GGAGGCTGAGGATTTGGGAGTTTATTATTGCTGGCAAGGTTTACATTTTCCGTGGACGTTC
GGTGGAGGCACCAAGCTGGAAATCAAA (SEQ ID NO: 19)

>anti-IDUA 218 variable light domain amino acid sequence with leader sequence (leader sequence is underlined)
MSPAQFLFLLVLWIRETNGDVVMTQTPLTLSVTIGQPASISCKSSQSLLHSDGKTYLNWSLQRP
GQSPKRLIYLVSKLDSGVPDRFTGSGSGTDFTLKISRVEAEDLGVYYCWQGLHFPWTFGGGTK
LEIK (SEQ ID NO: 20)

>anti-IDUA 218 variable light domain amino acid sequence without leader sequence
DVVMTQTPLTLSVTIGQPASISCKSSQSLLHSDGKTYLNWSLQRPGQSPKRLIYLVSKLDSGVP
DRFTGSGSGTDFTLKISRVEAEDLGVYYCWQGLHFPWTFGGGTKLEIK (SEQ ID NO: 21)

FIG. 12 cont'd.

>anti-IDUA 462 variable heavy domain coding sequence with leader sequence (leader sequence is underlined)
<u>ATGAAATGCAGCTGGGTTATCTTCTTCCTGATGGCAGTGGTTACAGGGGTCAATTCA</u>GAGG
TTCAGCTGCAGCAGTCTGGGGCAGAGCTTGTGAAGCCAGGGGCCTCAGTCAAGTTGTCCT
GCACAGCTTCTGGCTTCAACATTAAAGACACCTATATGCACTGGGTGAACCAGAGGCCTGA
ACAGGGCCTGGAGTGGATTGGAAGGATTGATCCTGCAATGGTAATACTAAATATGGCCC
GAAGTTCCAGGGCAAGGCCACTATAACAGCAGACACATCCTCCAACACAGCCTACCTGCA
GCTCAGCAGCCTGACATCTGAGGACACTGCCGTCTATTACTGTGCCCAGACAGCTCGGGC
CCCGTTTGCTTACTGGGGCCAAGGGACTCTGGTCACTGTCTCTGCA (SEQ ID NO: 28)

>anti-IDUA 462 variable heavy domain amino acid sequence with leader sequence (leader sequence is underlined)
<u>MKCSWVIFFLMAVVTGVNS</u>EVQLQQSGAELVKPGASVKLSCTASGFNIKDTYMHWVNQRPEQ
GLEWIGRIDPANGNTKYGPKFQGKATITADTSSNTAYLQLSSLTSEDTAVYYCAQTARAPFAYW
GQGTLVTVSA (SEQ ID NO: 29)

>anti-IDUA 462 variable heavy domain amino acid sequence without leader sequence
EVQLQQSGAELVKPGASVKLSCTASGFNIKDTYMHWVNQRPEQGLEWIGRIDPANGNTKYGP
KFQGKATITADTSSNTAYLQLSSLTSEDTAVYYCAQTARAPFAYWGQGTLVTVSA (SEQ ID NO: 30)

>anti-IDUA 462 variable light domain coding sequence with leader sequence (leader sequence is underlined)
<u>ATGAGGTGCTCTCTTCAGTTCTTGGGGATGCTTATGTTCTGGATCTCTGGAGTCAGTGGGG</u>
ATATTGTGATAACCCAGGATGAAGTCTCCAATCCTGTCACTTCTGGAGAATCAGTTTCCATC
TCCTGCAGGTCTAGTAAGAGTCTCCTATATAAGGATGGGAAGACATACTTGAATTGGTTTCT
GCAGAGGCCAGGACAGTCTCCTCAGCTCCTGGTCTATTGGATGTCCACCCGTGCATCAGG
AGTCTCAGACCGGTTTAGTGGCAGTGGGTCAGGAACAGATTTCACACTGAAAATCAGTAGA
GTGAAGGCTGAGGATGTCGGTATGTATTACTGTCAACAAGTTGTAGAGTATCCATTCACGT
TCGGCACGGGGACAAAATTGGAAATAAAA (SEQ ID NO: 31)

>anti-IDUA 462 variable light domain amino acid sequence with leader sequence (leader sequence is underlined)
<u>MRCSLQFLGMLMFWISGVSG</u>DIVITQDEVSNPVTSGESVSISCRSSKSLLYKDGKTYLNWFLQR
PGQSPQLLVYWMSTRASGVSDRFSGSGSGTDFTLKISRVKAEDVGMYYCQQVVEYPFTFGTG
TKLEIK (SEQ ID NO: 32)

>anti-IDUA 462 variable light domain amino acid sequence without leader sequence
DIVITQDEVSNPVTSGESVSISCRSSKSLLYKDGKTYLNWFLQRPGQSPQLLVYWMSTRASGV
SDRFSGSGSGTDFTLKISRVKAEDVGMYYCQQVVEYPFTFGTGTKLEIK (SEQ ID NO: 33)

>anti-IDUA 218 variable heavy domain coding sequence without leader sequence
CAGGTCCAACTGCAGCAGCCTGGGACTGAGCTTGTGAAGCCTGGGGCTTCAGTGAAGTTG
TCCTGCAAGGCTTCTGGCTACACCTTCACCAGGTACTGGATGCACTGGGTGAAGCAGAGG
CCTGGACAAGGCCTTGAGTGGATTGGAGAGATTAATCCTAGCAATGGTGGGACTAACTACA
ATGAGAAGTTCAAGAACAAGGCCACACTGAATGTTGACAAATCCTCCAGCACAGCCTACAT
GCAACTCAGCAGCCTGACATCTGAGGACTCTGCGGTCTATTACTGTACGTTAGCTATGGAC
TACTGGGGTCAAGGAACCTCAGTCACCGTCTCCTCA (SEQ ID NO: 40)

FIG. 12 cont'd.

>anti-IDUA 218 variable light domain coding sequence without leader sequence
GATGTTGTGATGACCCAGACTCCACTCACTTTGTCGGTTACCATTGGACAACCAGCCTCCA
TCTCTTGCAAGTCAAGTCAGAGCCTCTTACATAGTGATGGAAAGACATATTTGAATTGGTCG
TTACAGAGGCCAGGCCAGTCTCCAAAGCGCCTAATCTATCTGGTGTCTAAACTGGACTCTG
GAGTCCCTGACAGGTTCACTGGCAGTGGATCAGGGACAGATTTCACACTGAAAATCAGCA
GAGTGGAGGCTGAGGATTTGGGAGTTTATTATTGCTGGCAAGGTTTACATTTTCCGTGGAC
GTTCGGTGGAGGCACCAAGCTGGAAATCAAA (SEQ ID NO: 41)

>anti-IDUA 462 variable heavy domain coding sequence without leader sequence
GAGGTTCAGCTGCAGCAGTCTGGGGCAGAGCTTGTGAAGCCAGGGGCCTCAGTCAAGTT
GTCCTGCACAGCTTCTGGCTTCAACATTAAAGACACCTATATGCACTGGGTGAACCAGAGG
CCTGAACAGGGCCTGGAGTGGATTGGAAGGATTGATCCTGCGAATGGTAATACTAAATATG
ACCCGAAGTTCCAGGGCAAGGCCACTATAACAGCAGACACATCCTCCAACACAGCCTACC
TGCAGCTCAGCAGCCTGACATCTGAGGACACTGCCGTCTATTACTGTGCCCAGACAGCTC
GGGCCCCGTTTGCTTACTGGGGCCAAGGGACTCTGGTCACTGTCTCTGCA (SEQ ID NO: 42)

>anti-IDUA 462 variable light domain coding sequence without leader sequence
GATATTGTGATAACCCAGGATGAAGTCTCCAATCCTGTCACTTCTGGAGAATCAGTTTCCAT
CTCCTGCAGGTCTAGTAAGAGTCTCCTATATAAGGATGGGAAGACATACTTGAATTGGTTT
CTGCAGAGGCCAGGACAGTCTCCTCAGCTCCTGGTCTATTGGATGTCCACCCGTGCATCA
GGAGTCTCAGACCGGTTTAGTGGCAGTGGGTCAGGAACAGATTTCACACTGAAAATCAGTA
GAGTGAAGGCTGAGGATGTCGGTATGTATTACTGTCAACAAGTTGTAGAGTATCCATTCAC
GTTCGGCACGGGGACAAAATTGGAAATAAAA (SEQ ID NO: 43)

>anti-GAA 155 (clone pEB0613A-3B2-H1) heavy chain coding sequence with leader sequence.
The leader sequence is underlined.
<u>ATGGAGACTGGGCTGCGCTGGCTTCTCCTGGTCGCTGTGCTCAAAGGTGTCCAGTGT</u>CAG
TCGGTGGAGGAGTCCGGGGGTCGCCTGGTCACGCCTGGGACACCCCTGACACTCACCTG
CACAGCCTCTGGATTCTCCCTCAATAGTTATGTAATGAGTTGGGTCCGCCAGGCTCCAGGG
GAGGGGCTGGAATGGATCGGGGTCATTAGTACTGGTGGTATCACATACTACGCGAACTGG
GCAAAAGGCCGATTCACCATCTCCAAAACCTCGACCACGGTGGATCTGAAAATCACCAGTC
CGAGAACCGAGGACACGGCCACCTATTTCTGTGCCAGAGGATTTAGTGGTGATAATTACGT
CTGGGGCCCAGGCACCCTGGTCACCGTCTCCTTCGGGCAACCTAAGGCTCCATCAGTCTT
CCCACTGGCCCCCTGCTGCGGGGACACACCCAGCTCCACGGTGACCCTGGGCTGCCTGG
TCAAAGGCTACCTCCCGGAGCCAGTGACCGTGACCTGGAACTCGGGCACCCTCACCAATG
GGGTACGCACCTTCCCGTCCGTCCGGCAGTCCTCAGGCCTCTACTCGCTGAGCAGCGTG
GTGAGCGTGACCTCAAGCAGCCAGCCCGTCACCTGCAACGTGGCCCACCCAGCCACCAA
CACCAAAGTGGACAAGACCGTTGCGCCCTCGACATGCAGCAAGCCCATGTGCCCACCCC
TGAACTCCTGGGGGGACCGTCTGTCTTCATCTTCCCCCAAAACCCAAGGACACCCTCAT
GATCTCACGCACCCCGAGGTCACATGCGTGGTGGTGGACGTGAGCCAGGATGACCCCG
AGGTGCAGTTCACATGGTACATAAACAACGAGCAGGTGCGCACCGCCCGGCCGCCGCTA
CGGGAGCAGCAGTTCAACAGCACGATCCGCGTGGTCAGCACCCTCCCCATCGCGCACCA
GGACTGGCTGAGGGGCAAGGAGTTCAAGTGCAAAGTCCACAACAAGGCACTCCCGGCCC
CCATCGAGAAACCATCTCCAAAGCCAGAGGGCAGCCCTGGAGCCGAAGGTCTACACCA
TGGGCCCTCCCCGGGAGGAGCTGAGCAGCAGGTCGGTCAGCCTGACCTGCATGATCAAC
GGCTTCTACCCTTCCGACATCTCGGTGGAGTGGGAGAAGAACGGGAAGGCAGAGGACAA
CTACAAGACCACGCCGGCCGTGCTGGACAGCGACGGCTCCTACTTCCTCTACAGCAAGCT
CTCAGTGCCCACGAGTGAGTGGCAGCGGGGCGACGTCTTCACCTGCTCCGTGATGCACG

FIG. 12 cont'd.

AGGCCTTGCACAACCACTACACGCAGAAGTCCATCTCCCGCTCTCCGGGTAAATGA (SEQ ID NO: 50)

>anti-GAA 155 (clone pEB0613A-3B2-H1) heavy chain coding sequence without leader sequence
CAGTCGGTGGAGGAGTCCGGGGGTCGCCTGGTCACGCCTGGGACACCCTGACACTCAC
CTGCACAGCCTCTGGATTCTCCCTCAATAGTTATGTAATGAGTTGGGTCCGCCAGGCTCCA
GGGGAGGGGCTGGAATGGATCGGGGTCATTAGTACTGGTGGTATCACATACTACGCGAAC
TGGGCAAAAGGCCGATTCACCATCTCCAAACCTCGACCACGGTGGATCTGAAAATCACCA
GTCCGAGAACCGAGGACACGGCCACCTATTTCTGTGCCAGAGGATTTAGTGGTGATAATTA
CGTCTGGGGCCCAGGCACCCTGGTCACCGTCTCCTTCGGGCAACCTAAGGCTCCATCAGT
CTTCCCACTGGCCCCTGCTGCGGGGACACACCCAGCTCCACGGTGACCCTGGGCTGCC
TGGTCAAAGGCTACCTCCCGGAGCCAGTGACCGTGACCTGGAACTCGGGCACCCTCACCA
ATGGGGTACGCACCTTCCCGTCCGTCCGGCAGTCCTCAGGCCTCTACTCGCTGAGCAGCG
TGGTGAGCGTGACCTCAAGCAGCCAGCCCGTCACCTGCAACGTGGCCCACCCAGCCACC
AACACCAAAGTGGACAAGACCGTTGCGCCCTCGACATGCAGCAAGCCCATGTGCCCACCC
CCTGAACTCCTGGGGGGACCGTCTGTCTTCATCTTCCCCCCAAAACCCAAGGACACCCTC
ATGATCTCACGCACCCCCGAGGTCACATGCGTGGTGGTGGACGTGAGCCAGGATGACCC
CGAGGTGCAGTTCACATGGTACATAAACAACGAGCAGGTGCGCACCGCCCGGCCGCCGC
TACGGGAGCAGCAGTTCAACAGCACGATCCGCGTGGTCAGCACCCTCCCCATCGCGCAC
CAGGACTGGCTGAGGGGCAAGGAGTTCAAGTGCAAAGTCCACAACAAGGCACTCCCGGC
CCCCATCGAGAAACCATCTCCAAAGCCAGAGGGCAGCCCCTGGAGCCGAAGGTCTACAC
CATGGGCCCTCCCCGGGAGGAGCTGAGCAGCAGGTCGGTCAGCCTGACCTGCATGATCA
ACGGCTTCTACCCTTCCGACATCTCGGTGGAGTGGGAGAAGAACGGGAAGGCAGAGGAC
AACTACAAGACCACGCCGGCCGTGCTGGACAGCGACGGCTCCTACTTCCTCTACAGCAAG
CTCTCAGTGCCCACGAGTGAGTGGCAGCGGGGCGACGTCTTCACCTGCTCCGTGATGCA
CGAGGCCTTGCACAACCACTACACGCAGAAGTCCATCTCCCGCTCTCCGGGTAAATGA (SEQ ID NO: 51)

>anti-GAA 155 (clone pEB0613A-3B2-H1) variable heavy domain coding sequence with leader sequence. The leader sequence is underlined.
<u>ATGGAGACTGGGCTGCGCTGGCTTCTCCTGGTCGCTGTGCTCAAAGGTGTCCAGTGT</u>CAG
TCGGTGGAGGAGTCCGGGGGTCGCCTGGTCACGCCTGGGACACCCTGACACTCACCTG
CACAGCCTCTGGATTCTCCCTCAATAGTTATGTAATGAGTTGGGTCCGCCAGGCTCCAGGG
GAGGGGCTGGAATGGATCGGGGTCATTAGTACTGGTGGTATCACATACTACGCGAACTGG
GCAAAAGGCCGATTCACCATCTCCAAACCTCGACCACGGTGGATCTGAAAATCACCAGTC
CGAGAACCGAGGACACGGCCACCTATTTCTGTGCCAGAGGATTTAGTGGTGATAATTACGT
CTGGGGCCCAGGCACCCTGGTCACCGTCTCCTTC (SEQ ID NO: 52)

>anti-GAA 155 (clone pEB0613A-3B2-H1) variable heavy domain coding sequence without leader sequence
CAGTCGGTGGAGGAGTCCGGGGGTCGCCTGGTCACGCCTGGGACACCCTGACACTCAC
CTGCACAGCCTCTGGATTCTCCCTCAATAGTTATGTAATGAGTTGGGTCCGCCAGGCTCCA
GGGGAGGGGCTGGAATGGATCGGGGTCATTAGTACTGGTGGTATCACATACTACGCGAAC
TGGGCAAAAGGCCGATTCACCATCTCCAAACCTCGACCACGGTGGATCTGAAAATCACCA
GTCCGAGAACCGAGGACACGGCCACCTATTTCTGTGCCAGAGGATTTAGTGGTGATAATTA
CGTCTGGGGCCCAGGCACCCTGGTCACCGTCTCCTTC (SEQ ID NO: 53)

FIG. 12 cont'd.

>anti-GAA 155 heavy chain amino acid sequence with leader sequence (leader sequence is underlined)
<u>METGLRWLLLVAVLKGVQC</u>QSVEESGGRLVTPGTPLTLTCTASGFSLNSYVMSWVRQAPGEG
LEWIGVISTGGITYYANWAKGRFTISKTSTTVDLKITSPRTEDTATYFCARGFSGDNYVWGPGTL
VTVSFGQPKAPSVFPLAPCCGDTPSSTVTLGCLVKGYLPEPVTVTWNSGTLTNGVRTFPSVRQ
SSGLYSLSSVVSVTSSSQPVTCNVAHPATNTKVDKTVAPSTCSKPMCPPPELLGGPSVFIFPPK
PKDTLMISRTPEVTCVVVDVSQDDPEVQFTWYINNEQVRTARPPLREQQFNSTIRVVSTLPIAH
QDWLRGKEFKCKVHNKALPAPIEKTISKARGQPLEPKVYTMGPPREELSSRSVSLTCMINGFYP
SDISVEWEKNGKAEDNYKTTPAVLDSDGSYFLYSKLSVPTSEWQRGDVFTCSVMHEALHNHY
TQKSISRSPGK (SEQ ID NO: 54)

>anti-GAA 155 heavy chain amino acid sequence without leader sequence
QSVEESGGRLVTPGTPLTLTCTASGFSLNSYVMSWVRQAPGEGLEWIGVISTGGITYYANWAK
GRFTISKTSTTVDLKITSPRTEDTATYFCARGFSGDNYVWGPGTLVTVSFGQPKAPSVFPLAPC
CGDTPSSTVTLGCLVKGYLPEPVTVTWNSGTLTNGVRTFPSVRQSSGLYSLSSVVSVTSSSQP
VTCNVAHPATNTKVDKTVAPSTCSKPMCPPPELLGGPSVFIFPPKPKDTLMISRTPEVTCVVVD
VSQDDPEVQFTWYINNEQVRTARPPLREQQFNSTIRVVSTLPIAHQDWLRGKEFKCKVHNKAL
PAPIEKTISKARGQPLEPKVYTMGPPREELSSRSVSLTCMINGFYPSDISVEWEKNGKAEDNYK
TTPAVLDSDGSYFLYSKLSVPTSEWQRGDVFTCSVMHEALHNHYTQKSISRSPGK (SEQ ID
NO: 55)

>anti-GAA 155 variable heavy domain amino acid sequence with leader sequence (leader
sequence is underlined)
<u>METGLRWLLLVAVLKGVQC</u>QSVEESGGRLVTPGTPLTLTCTASGFSLNSYVMSWVRQAPGEG
LEWIGVISTGGITYYANWAKGRFTISKTSTTVDLKITSPRTEDTATYFCARGFSGDNYVWGPGTL
VTVSF (SEQ ID NO: 56)

>anti-GAA 155 variable heavy domain amino acid sequence without leader sequence
QSVEESGGRLVTPGTPLTLTCTASGFSLNSYVMSWVRQAPGEGLEWIGVISTGGITYYANWAK
GRFTISKTSTTVDLKITSPRTEDTATYFCARGFSGDNYVWGPGTLVTVSF (SEQ ID NO: 57)

>anti-GAA 155 (clone pEB0613A-3B2-K3) light chain coding sequence with leader sequence.
The leader sequence is underlined.
<u>ATGGACACGAGGGCCCCCACTCAGCTGCTGGGGCTCCTACTGCTCTGGCTCCCAGGTGC
CAGATGT</u>GCTGACATTGTGATGACCCAGACTCCATCTTCCACGTCTGCGGCTGTGGGAGG
CACAGTCACCATCAACTGCCAGTCCAGTCAGAATGTTCATAGTAACAACTACTTATCCTGGT
TTCAGCAGAAACCAGGGCAGCCTCCCAAGCTCCTGATCTATCTGGCTTCCACTCTGGCATC
TGGGGTCCCATCGCGGTTCAAAGGCAGTGGCTCTGGGACAGAGTTCACTCTCACCATCAG
CGACCTGGAGTGTGATGATGCTGCCACTTACTACTGTCAGGCGATTATACTACTAATATTT
ATGTTTTCGGCGGAGGGACCGAGGTGGTGGTCAAAGGTGATCCAGTTGCACCTACTGTCC
TCATCTTCCCACCAGCTGCTGATCAGGTGGCAACTGGAACAGTCACCATCGTGTGTGTGG
CGAATAAATACTTTCCCGATGTCACCGTCACCTGGGAGGTGGATGGCACCACCCAAACAA
CTGGCATCGAGAACAGTAAAACACCGCAGAATTCTGCAGATTGTACCTACAACCTCAGCAG
CACTCTGACACTGACCAGCACACAGTACAACAGCCACAAAGAGTACACCTGCAAGGTGAC
CCAGGGCACGACCTCAGTCGTCCAGAGCTTCAATAGGGGTGACTGTTAG (SEQ ID NO: 58)

FIG. 12 cont'd.

>anti-GAA 155 (clone pEB0613A-3B2-K3) light chain coding sequence without leader sequence
GCTGACATTGTGATGACCCAGACTCCATCTTCCACGTCTGCGGCTGTGGGAGGCACAGTC
ACCATCAACTGCCAGTCCAGTCAGAATGTTCATAGTAACAACTACTTATCCTGGTTTCAGCA
GAAACCAGGGCAGCCTCCCAAGCTCCTGATCTATCTGGCTTCCACTCTGGCATCTGGGGT
CCCATCGCGGTTCAAAGGCAGTGGCTCTGGGACAGAGTTCACTCTCACCATCAGCGACCT
GGAGTGTGATGATGCTGCCACTTACTACTGTGCAGGCGATTATACTACTAATATTTATGTTT
TCGGCGGAGGGACCGAGGTGGTGGTCAAAGGTGATCCAGTTGCACCTACTGTCCTCATCT
TCCCACCAGCTGCTGATCAGGTGGCAACTGGAACAGTCACCATCGTGTGTGTGGCGAATA
AATACTTTCCCGATGTCACCGTCACCTGGGAGGTGGATGGCACCACCCAAACAACTGGCA
TCGAGAACAGTAAAACACCGCAGAATTCTGCAGATTGTACCTACAACCTCAGCAGCACTCT
GACACTGACCAGCACACAGTACAACAGCCACAAAGAGTACACCTGCAAGGTGACCCAGGG
CACGACCTCAGTCGTCCAGAGCTTCAATAGGGGTGACTGTTAG (SEQ ID NO: 59)

>anti-GAA 155 (clone pEB0613A-3B2-K3) variable light domain coding sequence with leader sequence. The leader sequence is underlined.
<u>ATGGACACGAGGGCCCCCACTCAGCTGCTGGGGCTCCTACTGCTCTGGCTCCCAGGTGC
CAGATGT</u>GCTGACATTGTGATGACCCAGACTCCATCTTCCACGTCTGCGGCTGTGGGAGG
CACAGTCACCATCAACTGCCAGTCCAGTCAGAATGTTCATAGTAACAACTACTTATCCTGGT
TTCAGCAGAAACCAGGGCAGCCTCCCAAGCTCCTGATCTATCTGGCTTCCACTCTGGCATC
TGGGGTCCCATCGCGGTTCAAAGGCAGTGGCTCTGGGACAGAGTTCACTCTCACCATCAG
CGACCTGGAGTGTGATGATGCTGCCACTTACTACTGTGCAGGCGATTATACTACTAATATTT
ATGTTTTCGGCGGAGGGACCGAGGTGGTGGTCAAA (SEQ ID NO: 60)

>anti-GAA 155 (clone pEB0613A-3B2-K3) variable light domain coding sequence without leader sequence
GCTGACATTGTGATGACCCAGACTCCATCTTCCACGTCTGCGGCTGTGGGAGGCACAGTC
ACCATCAACTGCCAGTCCAGTCAGAATGTTCATAGTAACAACTACTTATCCTGGTTTCAGCA
GAAACCAGGGCAGCCTCCCAAGCTCCTGATCTATCTGGCTTCCACTCTGGCATCTGGGGT
CCCATCGCGGTTCAAAGGCAGTGGCTCTGGGACAGAGTTCACTCTCACCATCAGCGACCT
GGAGTGTGATGATGCTGCCACTTACTACTGTGCAGGCGATTATACTACTAATATTTATGTTT
TCGGCGGAGGGACCGAGGTGGTGGTCAAA (SEQ ID NO: 61)

>anti-GAA 155 light chain amino acid sequence with leader sequence (leader sequence is underlined)
<u>MDTRAPTQLLGLLLLWLPGARC</u>ADIVMTQTPSSTSAAVGGTVTINCQSSQNVHSNNYLSWFQQ
KPGQPPKLLIYLASTLASGVPSRFKGSGSGTEFTLTISDLECDDAATYYCAGDYTTNIYVFGGGT
EVVVKGDPVAPTVLIFPPAADQVATGTVTIVCVANKYFPDVTVTWEVDGTTQTTGIENSKTPQN
SADCTYNLSSTLTLTSTQYNSHKEYTCKVTQGTTSVVQSFNRGDC (SEQ ID NO: 62)

>anti-GAA 155 light chain amino acid sequence without leader sequence
ADIVMTQTPSSTSAAVGGTVTINCQSSQNVHSNNYLSWFQQKPGQPPKLLIYLASTLASGVPS
RFKGSGSGTEFTLTISDLECDDAATYYCAGDYTTNIYVFGGGTEVVVKGDPVAPTVLIFPPAAD
QVATGTVTIVCVANKYFPDVTVTWEVDGTTQTTGIENSKTPQNSADCTYNLSSTLTLTSTQYNS
HKEYTCKVTQGTTSVVQSFNRGDC (SEQ ID NO: 63)

FIG. 12 cont'd.

>anti-GAA 155 variable light domain amino acid sequence with leader sequence (leader sequence is underlined)
<u>MDTRAPTQLLGLLLLWLPGARC</u>ADIVMTQTPSSTSAAVGGTVTINCQSSQNVHSNNYLSWFQQ
KPGQPPKLLIYLASTLASGVPSRFKGSGSGTEFTLTISDLECDDAATYYCAGDYTTNIYVFGGGT
EVVVK (SEQ ID NO: 64)

>anti-GAA 155 variable light domain amino acid sequence without leader sequence
ADIVMTQTPSSTSAAVGGTVTINCQSSQNVHSNNYLSWFQQKPGQPPKLLIYLASTLASGVPS
RFKGSGSGTEFTLTISDLECDDAATYYCAGDYTTNIYVFGGGTEVVVK (SEQ ID NO: 65)

>anti-GAA 376 (clone pEB0613B-4B1-H2) heavy chain coding sequence with leader sequence. The leader sequence is underlined.
<u>ATGGAGACTGGGCTGCGCTGGCTTCTCCTGGTCGCTGTGCTCAAAGGTGTCCAGTGT</u>CAG
GAGCACCTGGTGGAGTCCGGGGGAGGCCTGGTCAACCCTGGAGGATCCCTGACACTCAC
CTGCACAGCCTCTGGATTCTCCCTCAACAGCGTCGACATGAGCTGGGTCCGCCAGGCTCC
AGGGAAGGGGCTGGAGTGGATCGGATTCAGTAATGCTTATCATAGGACATACTACGCGAG
CTGGTCGAAAAGCCGATCCACCATCACCAGAAACACCAACGAGAACACGGTGACTCTGAA
AATGACCAGTCTGACAGCCGCGGACACGGCCACCTATTTCTGTGCGAGAGGTGTTCCTGG
TTATGTTACTAAAAGTAGTCTCTGGGGCCCAGGCACCCTGGTCACCGTCTCCTCAGGGCAA
CCTAAGGCTCCATCAGTCTTCCCACTGGCCCCTGCTGCGGGGACACACCCAGCTCCACG
GTGACCCTGGGCTGCCTGGTCAAAGGCTACCTCCCGGAGCCAGTGACCGTGACCTGGAA
CTCGGGCACCCTCACCAATGGGGTACGCACCTTCCCGTCCGTCCGGCAGTCCTCAGGCCT
CTACTCGCTGAGCAGCGTGGTGAGCGTGACCTCAAGCAGCCAGCCCGTCACCTGCAACGT
GGCCCACCCAGCCACCAACACCAAAGTGGACAAGACCGTTGCGCCCTCGACATGCAGCAA
GCCCATGTGCCCACCCCTGAACTCCTGGGGGACCGTCTGTCTTCATCTTCCCCCCAAA
ACCCAAGGACACCCTCATGATCTCACGCACCCCCGAGGTCACATGCGTGGTGGTGGACGT
GAGCCAGGATGACCCCGAGGTGCAGTTCACATGGTACATAAACAACGAGCAGGTGCGCAC
CGCCCGGCCGCCGCTACGGGAGCAGCAGTTCAACAGCACGATCCGCGTGGTCAGCACCC
TCCCCATCGCGCACCAGGACTGGCTGAGGGGCAAGGAGTTCAAGTGCAAAGTCCACAACA
AGGCACTCCCGGCCCCATCGAGAAAACCATCTCCAAAGCCAGAGGGCAGCCCTGGAG
CCGAAGGTCTACACCATGGGCCCTCCCCGGGAGGAGCTGAGCAGCAGGTCGGTCAGCCT
GACCTGCATGATCAACGGCTTCTACCCTTCCGACATCTCGGTGGAGTGGGAGAAGAACGG
GAAGGCAGAGGACAACTACAAGACCACGCCGGCCGTGCTGGACAGCGACGGCTCCTACT
TCCTCTACAGCAAGCTCTCAGTGCCCACGAGTGAGTGGCAGCGGGGCGACGTCTTCACCT
GCTCCGTGATGCACGAGGCCTTGCACAACCACTACACGCAGAAGTCCATCTCCCGCTCTC
CGGGTAAATGA (SEQ ID NO: 72)

FIG. 12 cont'd.

>anti-GAA 376 (clone pEB0613B-4B1-H2) heavy chain coding sequence without leader sequence
CAGGAGCACCTGGTGGAGTCCGGGGGAGGCCTGGTCAACCCTGGAGGATCCCTGACACT
CACCTGCACAGCCTCTGGATTCTCCCTCAACAGCGTCGACATGAGCTGGGTCCGCCAGGC
TCCAGGGAAGGGGCTGGAGTGGATCGGATTCAGTAATGCTTATCATAGGACATACTACGC
GAGCTGGTCGAAAAGCCGATCCACCATCACCAGAAACACCAACGAGAACACGGTGACTCT
GAAAATGACCAGTCTGACAGCCGCGGACACGGCCACCTATTTCTGTGCGAGAGGTGTTCC
TGGTTATGTTACTAAAAGTAGTCTCTGGGGCCCAGGCACCCTGGTCACCGTCTCCTCAGG
GCAACCTAAGGCTCCATCAGTCTTCCCACTGGCCCCTGCTGCGGGGACACACCCAGCTC
ACGGTGACCCTGGGCTGCCTGGTCAAAGGCTACCTCCCGGAGCCAGTGACCGTGACCT
GGAACTCGGGCACCCTCACCAATGGGGTACGCACCTTCCCGTCCGTCCGGCAGTCCTCA
GGCCTCTACTCGCTGAGCAGCGTGGTGAGCGTGACCTCAAGCAGCCAGCCCGTCACCTG
CAACGTGGCCCACCCAGCCACCAACACCAAAGTGGACAAGACCGTTGCGCCCTCGACATG
CAGCAAGCCCATGTGCCCACCCCTGAACTCCTGGGGGGACCGTCTGTCTTCATCTTCCC
CCCAAAACCCAAGGACACCCTCATGATCTCACGCACCCCCGAGGTCACATGCGTGGTGGT
GGACGTGAGCCAGGATGACCCCGAGGTGCAGTTCACATGGTACATAAACAACGAGCAGGT
GCGCACCGCCCGGCCGCCGCTACGGGAGCAGCAGTTCAACAGCACGATCCGCGTGGTCA
GCACCCTCCCCATCGCGCACCAGGACTGGCTGAGGGGCAAGGAGTTCAAGTGCAAAGTC
CACAACAAGGCACTCCCGGCCCCATCGAGAAAACCATCTCCAAAGCCAGAGGGCAGCCC
CTGGAGCCGAAGGTCTACACCATGGGCCCTCCCGGGAGGAGCTGAGCAGCAGGTCGGT
CAGCCTGACCTGCATGATCAACGGCTTCTACCCTTCCGACATCTCGGTGGAGTGGGAGAA
GAACGGGAAGGCAGAGGACAACTACAAGACCACGCCGGCCGTGCTGGACAGCGACGGCT
CCTACTTCCTCTACAGCAAGCTCTCAGTGCCCACGAGTGAGTGGCAGCGGGGCGACGTCT
TCACCTGCTCCGTGATGCACGAGGCCTTGCACAACCACTACACGCAGAAGTCCATCTCCC
GCTCTCCGGGTAAATGA (SEQ ID NO: 73)

>anti-GAA 376 (clone pEB0613B-4B1-H2) variable heavy domain coding sequence with leader sequence. The leader sequence is underlined.
<u>ATGGAGACTGGGCTGCGCTGGCTTCTCCTGGTCGCTGTGCTCAAAGGTGTCCAGTGTCAG</u>
GAGCACCTGGTGGAGTCCGGGGGAGGCCTGGTCAACCCTGGAGGATCCCTGACACTCAC
CTGCACAGCCTCTGGATTCTCCCTCAACAGCGTCGACATGAGCTGGGTCCGCCAGGCTCC
AGGGAAGGGGCTGGAGTGGATCGGATTCAGTAATGCTTATCATAGGACATACTACGCGAG
CTGGTCGAAAAGCCGATCCACCATCACCAGAAACACCAACGAGAACACGGTGACTCTGAA
AATGACCAGTCTGACAGCCGCGGACACGGCCACCTATTTCTGTGCGAGAGGTGTTCCTGG
TTATGTTACTAAAAGTAGTCTCTGGGGCCCAGGCACCCTGGTCACCGTCTCCTCA (SEQ ID NO: 74)

>anti-GAA 376 (clone pEB0613B-4B1-H2) variable heavy domain coding sequence without leader sequence
CAGGAGCACCTGGTGGAGTCCGGGGGAGGCCTGGTCAACCCTGGAGGATCCCTGACACT
CACCTGCACAGCCTCTGGATTCTCCCTCAACAGCGTCGACATGAGCTGGGTCCGCCAGGC
TCCAGGGAAGGGGCTGGAGTGGATCGGATTCAGTAATGCTTATCATAGGACATACTACGC
GAGCTGGTCGAAAAGCCGATCCACCATCACCAGAAACACCAACGAGAACACGGTGACTCT
GAAAATGACCAGTCTGACAGCCGCGGACACGGCCACCTATTTCTGTGCGAGAGGTGTTCC
TGGTTATGTTACTAAAAGTAGTCTCTGGGGCCCAGGCACCCTGGTCACCGTCTCCTCA
(SEQ ID NO: 75)

FIG. 12 cont'd.

>anti-GAA 376 heavy chain amino acid sequence with leader sequence (leader sequence is underlined)
METGLRWLLLVAVLKGVQCQEHLVESGGGLVNPGGSLTLTCTASGFSLNSVDMSWVRQAPG
KGLEWIGFSNAYHRTYYASWSKSRSTITRNTNENTVTLKMTSLTAADTATYFCARGVPGYVTK
SSLWGPGTLVTVSSGQPKAPSVFPLAPCCGDTPSSTVTLGCLVKGYLPEPVTVTWNSGTLTN
GVRTFPSVRQSSGLYSLSSVVSVTSSSQPVTCNVAHPATNTKVDKTVAPSTCSKPMCPPPELL
GGPSVFIFPPKPKDTLMISRTPEVTCVVVDVSQDDPEVQFTWYINNEQVRTARPPLREQQFNS
TIRVVSTLPIAHQDWLRGKEFKCKVHNKALPAPIEKTISKARGQPLEPKVYTMGPPREELSSRSV
SLTCMINGFYPSDISVEWEKNGKAEDNYKTTPAVLDSDGSYFLYSKLSVPTSEWQRGDVFTCS
VMHEALHNHYTQKSISRSPGK (SEQ ID NO: 76)

>anti-GAA 376 heavy chain amino acid sequence without leader sequence
QEHLVESGGGLVNPGGSLTLTCTASGFSLNSVDMSWVRQAPGKGLEWIGFSNAYHRTYYAS
WSKSRSTITRNTNENTVTLKMTSLTAADTATYFCARGVPGYVTKSSLWGPGTLVTVSSGQPKA
PSVFPLAPCCGDTPSSTVTLGCLVKGYLPEPVTVTWNSGTLTNGVRTFPSVRQSSGLYSLSSV
VSVTSSSQPVTCNVAHPATNTKVDKTVAPSTCSKPMCPPPELLGGPSVFIFPPKPKDTLMISRT
PEVTCVVVDVSQDDPEVQFTWYINNEQVRTARPPLREQQFNSTIRVVSTLPIAHQDWLRGKEF
KCKVHNKALPAPIEKTISKARGQPLEPKVYTMGPPREELSSRSVSLTCMINGFYPSDISVEWEK
NGKAEDNYKTTPAVLDSDGSYFLYSKLSVPTSEWQRGDVFTCSVMHEALHNHYTQKSISRSP
GK (SEQ ID NO: 77)

>anti-GAA 376 variable heavy domain amino acid sequence with leader sequence (leader sequence is underlined)
METGLRWLLLVAVLKGVQCQEHLVESGGGLVNPGGSLTLTCTASGFSLNSVDMSWVRQAPG
KGLEWIGFSNAYHRTYYASWSKSRSTITRNTNENTVTLKMTSLTAADTATYFCARGVPGYVTK
SSLWGPGTLVTVSS (SEQ ID NO: 78)

>anti-GAA 376 variable heavy domain amino acid sequence without leader sequence
QEHLVESGGGLVNPGGSLTLTCTASGFSLNSVDMSWVRQAPGKGLEWIGFSNAYHRTYYAS
WSKSRSTITRNTNENTVTLKMTSLTAADTATYFCARGVPGYVTKSSLWGPGTLVTVSS (SEQ
ID NO: 79)

>anti-GAA 376 (clone pEB0613B-4B1-K2) light chain coding sequence with leader sequence.
The leader sequence is underlined.
ATGGACACGAGGGCCCCCACTCAGCTGCTGGGGCTCCTGCTGCTCTGGCTCCCAGGTGC
CACATTTGCCATCGTGATGACCCAGACTCCATCTTCCAAGTCTGTCCCTGTGGGAGACACA
GTCACCATCAATTGCCAGGCCAGTCAGAGTGTTTATGGTAACAACGAATTATCCTGGTATC
AGCAGAAACCAGGACAACCTCCCAAGCTCCTGATCTACAAGGCTTCCACTCTGGCATCTG
GGGTCCCTTCGCGGTTCAAAGGCAGTGGATCTGGGACACAGTTCACTCTCACCATCAGTG
GCGTGGAGTGTGACGATGCTGCCACTTACTACTGTCAGGATATAGTAGTGGTGTGATTGA
TGTTAGTGCTTTCGGCGGGGGACCGAGGTGGTGGTCAAAGGTGATCCAGTTGCACCTAC
TGTCCTCATCTTCCCACCAGCTGCTGATCAGGTGGCAACTGGAACAGTCACCATCGTGTGT
GTGGCGAATAAATACTTTCCCGATGTCACCGTCACCTGGGAGGTGGATGGCACCACCCAA
ACAACTGGCATCGAGAACAGTAAAACACCGCAGAATTCTGCAGATTGTACCTACAACCTCA
GCAGCACTCTGACACTGACCAGCACAGTACAACAGCCACAAAGAGTACACCTGCAAGG
TGACCCAGGGCACGACCTCAGTCGTCCAGAGCTTCAATAGGGGTGACTGTTAG (SEQ ID
NO: 80)

FIG. 12 cont'd.

>anti-GAA 376 (clone pEB0613B-4B1-K2) light chain coding sequence without leader sequence
ATCGTGATGACCCAGACTCCATCTTCCAAGTCTGTCCCTGTGGGAGACACAGTCACCATCA
ATTGCCAGGCCAGTCAGAGTGTTTATGGTAACAACGAATTATCCTGGTATCAGCAGAAACC
AGGACAACCTCCCAAGCTCCTGATCTACAAGGCTTCCACTCTGGCATCTGGGGTCCCTTC
GCGGTTCAAAGGCAGTGGATCTGGGACACAGTTCACTCTCACCATCAGTGGCGTGGAGTG
TGACGATGCTGCCACTTACTACTGTGCAGGATATAGTAGTGGTGTGATTGATGTTAGTGCT
TTCGGCGGGGGGACCGAGGTGGTGGTCAAAGGTGATCCAGTTGCACCTACTGTCCTCATC
TTCCCACCAGCTGCTGATCAGGTGGCAACTGGAACAGTCACCATCGTGTGTGTGGCGAAT
AAATACTTTCCCGATGTCACCGTCACCTGGGAGGTGGATGGCACCACCCAAACAACTGGC
ATCGAGAACAGTAAAACACCGCAGAATTCTGCAGATTGTACCTACAACCTCAGCAGCACTC
TGACACTGACCAGCACACAGTACAACAGCCACAAAGAGTACACCTGCAAGGTGACCCAGG
GCACGACCTCAGTCGTCCAGAGCTTCAATAGGGGTGACTGTTAG (SEQ ID NO: 81)

>anti-GAA 376 (clone pEB0613B-4B1-K2) variable light domain coding sequence with leader sequence. The leader sequence is underlined.
<u>ATGGACACGAGGGCCCCCACTCAGCTGCTGGGGCTCCTGCTGCTCTGGCTCCCAGGTGC
CACATTTGCC</u>ATCGTGATGACCCAGACTCCATCTTCCAAGTCTGTCCCTGTGGGAGACACA
GTCACCATCAATTGCCAGGCCAGTCAGAGTGTTTATGGTAACAACGAATTATCCTGGTATC
AGCAGAAACCAGGACAACCTCCCAAGCTCCTGATCTACAAGGCTTCCACTCTGGCATCTG
GGGTCCCTTCGCGGTTCAAAGGCAGTGGATCTGGGACACAGTTCACTCTCACCATCAGTG
GCGTGGAGTGTGACGATGCTGCCACTTACTACTGTGCAGGATATAGTAGTGGTGTGATTGA
TGTTAGTGCTTTCGGCGGGGGGACCGAGGTGGTGGTCAAA (SEQ ID NO: 82)

>anti-GAA 376 (clone pEB0613B-4B1-K2) variable light domain coding sequence without leader sequence
ATCGTGATGACCCAGACTCCATCTTCCAAGTCTGTCCCTGTGGGAGACACAGTCACCATCA
ATTGCCAGGCCAGTCAGAGTGTTTATGGTAACAACGAATTATCCTGGTATCAGCAGAAACC
AGGACAACCTCCCAAGCTCCTGATCTACAAGGCTTCCACTCTGGCATCTGGGGTCCCTTC
GCGGTTCAAAGGCAGTGGATCTGGGACACAGTTCACTCTCACCATCAGTGGCGTGGAGTG
TGACGATGCTGCCACTTACTACTGTGCAGGATATAGTAGTGGTGTGATTGATGTTAGTGCT
TTCGGCGGGGGGACCGAGGTGGTGGTCAAA (SEQ ID NO: 83)

>anti-GAA 376 light chain amino acid sequence with leader sequence (leader sequence is underlined)
<u>MDTRAPTQLLGLLLLWLPGATFA</u>IVMTQTPSSKSVPVGDTVTINCQASQSVYGNNELSWYQQK
PGQPPKLLIYKASTLASGVPSRFKGSGSGTQFTLTISGVECDDAATYYCAGYSSGVIDVSAFGG
GTEVVVKGDPVAPTVLIFPPAADQVATGTVTIVCVANKYFPDVTVTWEVDGTTQTTGIENSKTP
QNSADCTYNLSSTLTLTSTQYNSHKEYTCKVTQGTTSVVQSFNRGDC (SEQ ID NO: 84)

>anti-GAA 376 light chain amino acid sequence without leader sequence
IVMTQTPSSKSVPVGDTVTINCQASQSVYGNNELSWYQQKPGQPPKLLIYKASTLASGVPSRF
KGSGSGTQFTLTISGVECDDAATYYCAGYSSGVIDVSAFGGGTEVVVKGDPVAPTVLIFPPAAD
QVATGTVTIVCVANKYFPDVTVTWEVDGTTQTTGIENSKTPQNSADCTYNLSSTLTLTSTQYNS
HKEYTCKVTQGTTSVVQSFNRGDC (SEQ ID NO: 85)

FIG. 12 cont'd.

>anti-GAA 376 variable light domain amino acid sequence with leader sequence (leader sequence is underlined)
<u>MDTRAPTQLLGLLLLWLPGATFA</u>IVMTQTPSSKSVPVGDTVTINCQASQSVYGNNELSWYQQK
PGQPPKLLIYKASTLASGVPSRFKGSGSGTQFTLTISGVECDDAATYYCAGYSSGVIDVSAFGG
GTEVVVK (SEQ ID NO: 86)

>anti-GAA 376 variable light domain amino acid sequence without leader sequence
IVMTQTPSSKSVPVGDTVTINCQASQSVYGNNELSWYQQKPGQPPKLLIYKASTLASGVPSRF
KGSGSGTQFTLTISGVECDDAATYYCAGYSSGVIDVSAFGGGTEVVVK (SEQ ID NO: 87)

```
                        SEQUENCE LISTING

<160> NUMBER OF SEQ ID NOS: 87

<210> SEQ ID NO 1
<211> LENGTH: 13
<212> TYPE: PRT
<213> ORGANISM: Homo sapiens

<400> SEQUENCE: 1

Leu Gly Gly Pro Gly Asp Ser Phe His Thr Pro Pro Arg
1               5                   10

<210> SEQ ID NO 2
<211> LENGTH: 13
<212> TYPE: PRT
<213> ORGANISM: Homo sapiens

<400> SEQUENCE: 2

Gly Val Pro Pro Gly Pro Gly Leu Val Tyr Val Thr Arg
1               5                   10

<210> SEQ ID NO 3
<211> LENGTH: 8
<212> TYPE: PRT
<213> ORGANISM: Homo sapiens

<400> SEQUENCE: 3

Thr Thr Pro Thr Phe Phe Pro Lys
1               5

<210> SEQ ID NO 4
<211> LENGTH: 17
<212> TYPE: PRT
<213> ORGANISM: Homo sapiens

<400> SEQUENCE: 4

Ser Thr Gly Gly Ile Leu Asp Val Tyr Ile Phe Leu Gly Pro Glu Pro
1               5                   10                  15

Lys

<210> SEQ ID NO 5
<211> LENGTH: 10
<212> TYPE: PRT
<213> ORGANISM: Homo sapiens

<400> SEQUENCE: 5
```

Trp Gly Tyr Ser Ser Thr Ala Ile Thr Arg
1               5                   10

<210> SEQ ID NO 6
<211> LENGTH: 8
<212> TYPE: PRT
<213> ORGANISM: Homo sapiens

<400> SEQUENCE: 6

Ser Thr Phe Ala Gly His Gly Arg
1               5

<210> SEQ ID NO 7
<211> LENGTH: 16
<212> TYPE: PRT
<213> ORGANISM: Homo sapiens

<400> SEQUENCE: 7

Gly Glu Leu Phe Trp Asp Asp Gly Glu Ser Leu Glu Val Leu Glu Arg
1               5                   10                  15

<210> SEQ ID NO 8
<211> LENGTH: 10
<212> TYPE: PRT
<213> ORGANISM: Homo sapiens

<400> SEQUENCE: 8

Asn Asn Thr Ile Val Asn Glu Leu Val Arg
1               5                   10

<210> SEQ ID NO 9
<211> LENGTH: 12
<212> TYPE: PRT
<213> ORGANISM: Homo sapiens

<400> SEQUENCE: 9

Val Thr Ser Glu Gly Ala Gly Leu Gln Leu Gln Lys
1               5                   10

<210> SEQ ID NO 10
<211> LENGTH: 5
<212> TYPE: PRT
<213> ORGANISM: Artificial Sequence
<220> FEATURE:
<223> OTHER INFORMATION: anti-IDUA 218 VH CDR1

<400> SEQUENCE: 10

Arg Tyr Trp Met His
1               5

<210> SEQ ID NO 11
<211> LENGTH: 17
<212> TYPE: PRT
<213> ORGANISM: Artificial Sequence
<220> FEATURE:
<223> OTHER INFORMATION: anti-IDUA 218 VH CDR2

<400> SEQUENCE: 11

Glu Ile Asn Pro Ser Asn Gly Gly Thr Asn Tyr Asn Glu Lys Phe Lys
1               5                   10                  15

Asn

<210> SEQ ID NO 12
<211> LENGTH: 4
<212> TYPE: PRT

<213> ORGANISM: Artificial Sequence
<220> FEATURE:
<223> OTHER INFORMATION: anti-IDUA 218 VH CDR3

<400> SEQUENCE: 12

Ala Met Asp Tyr
1

<210> SEQ ID NO 13
<211> LENGTH: 16
<212> TYPE: PRT
<213> ORGANISM: Artificial Sequence
<220> FEATURE:
<223> OTHER INFORMATION: anti-IDUA 218 VL CDR1

<400> SEQUENCE: 13

Lys Ser Ser Gln Ser Leu Leu His Ser Asp Gly Lys Thr Tyr Leu Asn
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: anti-IDUA 218 VL CDR2

<400> SEQUENCE: 14

Leu Val Ser Lys Leu Asp Ser
1               5

<210> SEQ ID NO 15
<211> LENGTH: 9
<212> TYPE: PRT
<213> ORGANISM: Artificial Sequence
<220> FEATURE:
<223> OTHER INFORMATION: anti-IDUA 218 VL CDR3

<400> SEQUENCE: 15

Trp Gln Gly Leu His Phe Pro Trp Thr
1               5

<210> SEQ ID NO 16
<211> LENGTH: 396
<212> TYPE: DNA
<213> ORGANISM: Artificial Sequence
<220> FEATURE:
<223> OTHER INFORMATION: anti-IDUA 218 variable heavy domain coding
      sequence with leader sequence

<400> SEQUENCE: 16
atgggatgga gctatatcat cctcttttg gtagcaacag ttacagatgt ccactcccag      60
gtccaactgc agcagcctgg gactgagctt gtgaagcctg gggcttcagt gaagttgtcc     120
tgcaaggctt ctggctacac cttcaccagg tactggatgc actgggtgaa gcagaggcct     180
ggacaaggcc ttgagtggat tggagagatt aatcctagca atggtgggac taactacaat     240
gagaagttca gaacaaggc cacactgaat gttgacaaat cctccagcac agcctacatg      300
caactcagca gcctgacatc tgaggactct gcggtctatt actgtacgtt agctatggac     360
tactggggtc aaggaacctc agtcaccgtc tcctca                              396

<210> SEQ ID NO 17
<211> LENGTH: 132
<212> TYPE: PRT
<213> ORGANISM: Artificial Sequence
<220> FEATURE:

<223> OTHER INFORMATION: anti-IDUA 218 variable heavy domain amino acid
      sequence with leader sequence

<400> SEQUENCE: 17

Met Gly Trp Ser Tyr Ile Ile Leu Phe Leu Val Ala Thr Val Thr Asp
1               5                   10                  15

Val His Ser Gln Val Gln Leu Gln Gln Pro Gly Thr Glu Leu Val Lys
            20                  25                  30

Pro Gly Ala Ser Val Lys Leu Ser Cys Lys Ala Ser Gly Tyr Thr Phe
        35                  40                  45

Thr Arg Tyr Trp Met His Trp Val Lys Gln Arg Pro Gly Gln Gly Leu
    50                  55                  60

Glu Trp Ile Gly Glu Ile Asn Pro Ser Asn Gly Gly Thr Asn Tyr Asn
65                  70                  75                  80

Glu Lys Phe Lys Asn Lys Ala Thr Leu Asn Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Thr Leu Ala Met Asp Tyr Trp Gly Gln Gly Thr Ser Val
        115                 120                 125

Thr Val Ser Ser
    130

<210> SEQ ID NO 18
<211> LENGTH: 113
<212> TYPE: PRT
<213> ORGANISM: Artificial Sequence
<220> FEATURE:
<223> OTHER INFORMATION: anti-IDUA 218 variable heavy domain amino acid
      sequence without leader sequence

<400> SEQUENCE: 18

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Arg Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Gly Thr Asn Tyr Asn Glu Lys Phe
    50                  55                  60

Lys Asn Lys Ala Thr Leu Asn Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Leu Ala Met Asp Tyr Trp Gly Gln Gly Thr Ser Val Thr Val Ser
            100                 105                 110

Ser

<210> SEQ ID NO 19
<211> LENGTH: 393
<212> TYPE: DNA
<213> ORGANISM: Artificial Sequence
<220> FEATURE:
<223> OTHER INFORMATION: anti-IDUA 218 variable light domain coding
      sequence with leader sequence

<400> SEQUENCE: 19
atgagtcctg cccagttcct gtttctgtta gtgctctgga ttcgggaaac caacggtgat    60

```
gttgtgatga cccagactcc actcactttg tcggttacca ttggacaacc agcctccatc      120
tcttgcaagt caagtcagag cctcttacat agtgatggaa agacatattt gaattggtcg      180
ttacagaggc caggccagtc tccaaagcgc ctaatctatc tggtgtctaa actggactct      240
ggagtccctg acaggttcac tgcagtggga tcagggacag atttcacact gaaaatcagc      300
agagtggagg ctgaggattt gggagtttat tattgctggc aaggtttaca ttttccgtgg      360
acgttcggtg gaggcaccaa gctggaaatc aaa                                   393
```

<210> SEQ ID NO 20
<211> LENGTH: 131
<212> TYPE: PRT
<213> ORGANISM: Artificial Sequence
<220> FEATURE:
<223> OTHER INFORMATION: anti-IDUA 218 variable light domain amino acid
      sequence with leader sequence

<400> SEQUENCE: 20

```
Met Ser Pro Ala Gln Phe Leu Phe Leu Leu Val Leu Trp Ile Arg Glu
1               5                   10                  15

Thr Asn Gly Asp Val Val Met Thr Gln Thr Pro Leu Thr Leu Ser Val
            20                  25                  30

Thr Ile Gly Gln Pro Ala Ser Ile Ser Cys Lys Ser Gln Ser Leu
        35                  40                  45

Leu His Ser Asp Gly Lys Thr Tyr Leu Asn Trp Ser Leu Gln Arg Pro
    50                  55                  60

Gly Gln Ser Pro Lys Arg Leu Ile Tyr Leu Val Ser Lys Leu Asp Ser
65                  70                  75                  80

Gly Val Pro Asp Arg Phe Thr Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Trp Gln Gly Leu His Phe Pro Trp Thr Phe Gly Gly Gly Thr Lys Leu
        115                 120                 125

Glu Ile Lys
    130
```

<210> SEQ ID NO 21
<211> LENGTH: 112
<212> TYPE: PRT
<213> ORGANISM: Artificial Sequence
<220> FEATURE:
<223> OTHER INFORMATION: anti-IDUA 218 variable light domain amino acid
      sequence without leader sequence

<400> SEQUENCE: 21

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Ser Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95
```

Leu His Phe Pro Trp Thr Phe Gly Gly Gly Thr Lys Leu Glu Ile Lys
            100                 105                 110

<210> SEQ ID NO 22
<211> LENGTH: 5
<212> TYPE: PRT
<213> ORGANISM: Artificial Sequence
<220> FEATURE:
<223> OTHER INFORMATION: anti-IDUA 462 VH CDR1

<400> SEQUENCE: 22

Asp Thr Tyr Met His
1               5

<210> SEQ ID NO 23
<211> LENGTH: 17
<212> TYPE: PRT
<213> ORGANISM: Artificial Sequence
<220> FEATURE:
<223> OTHER INFORMATION: anti-IDUA 462 VH CDR2

<400> SEQUENCE: 23

Arg Ile Asp Pro Ala Asn Gly Asn Thr Lys Tyr Gly Pro Lys Phe Gln
1               5                   10                  15

Gly

<210> SEQ ID NO 24
<211> LENGTH: 8
<212> TYPE: PRT
<213> ORGANISM: Artificial Sequence
<220> FEATURE:
<223> OTHER INFORMATION: anti-IDUA 462 VH CDR3

<400> SEQUENCE: 24

Thr Ala Arg Ala Pro Phe Ala Tyr
1               5

<210> SEQ ID NO 25
<211> LENGTH: 16
<212> TYPE: PRT
<213> ORGANISM: Artificial Sequence
<220> FEATURE:
<223> OTHER INFORMATION: anti-IDUA 462 VL CDR1

<400> SEQUENCE: 25

Arg Ser Ser Lys Ser Leu Leu Tyr Lys Asp Gly Lys Thr Tyr Leu Asn
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: anti-IDUA 462 VL CDR2

<400> SEQUENCE: 26

Trp Met Ser Thr Arg Ala Ser
1               5

<210> SEQ ID NO 27
<211> LENGTH: 9
<212> TYPE: PRT
<213> ORGANISM: Artificial Sequence
<220> FEATURE:
<223> OTHER INFORMATION: anti-IDUA 462 VL CDR3

<400> SEQUENCE: 27

```
<210> SEQ ID NO 28
<211> LENGTH: 408
<212> TYPE: DNA
<213> ORGANISM: Artificial Sequence
<220> FEATURE:
<223> OTHER INFORMATION: anti-IDUA 462 variable heavy domain coding
      sequence with leader sequence

<400> SEQUENCE: 28
atgaaatgca gctgggttat cttcttcctg atggcagtgg ttacaggggt caattcagag      60
gttcagctgc agcagtctgg ggcagagctt gtgaagccag gggcctcagt caagttgtcc     120
tgcacagctt ctggcttcaa cattaaagac acctatatgc actgggtgaa ccagaggcct     180
gaacagggcc tggagtggat tggaaggatt gatcctgcga atggtaatac taaatatggc     240
ccgaagttcc agggcaaggc cactataaca gcagacacat cctccaacac agcctacctg     300
cagctcagca gcctgacatc tgaggacact gccgtctatt actgtgccca gacagctcgg     360
gccccgtttg cttactgggg ccaagggact ctggtcactg tctctgca                  408

<210> SEQ ID NO 29
<211> LENGTH: 136
<212> TYPE: PRT
<213> ORGANISM: Artificial Sequence
<220> FEATURE:
<223> OTHER INFORMATION: anti-IDUA 462 variable heavy domain amino acid
      sequence with leader sequence

<400> SEQUENCE: 29

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Lys Asp Thr Tyr Met His Trp Val Asn Gln Arg Pro Glu Gln Gly Leu
    50                  55                  60

Glu Trp Ile Gly Arg Ile Asp Pro Ala Asn Gly Asn Thr Lys Tyr Gly
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Gln Thr Ala Arg Ala Pro Phe Ala Tyr Trp Gly Gln
        115                 120                 125

Gly Thr Leu Val Thr Val Ser Ala
    130                 135

<210> SEQ ID NO 30
<211> LENGTH: 117
<212> TYPE: PRT
<213> ORGANISM: Artificial Sequence
<220> FEATURE:
<223> OTHER INFORMATION: anti-IDUA 462 variable heavy domain amino acid
      sequence without leader sequence

<400> SEQUENCE: 30

Glu Val Gln Leu Gln Gln Ser Gly Ala Glu Leu Val Lys Pro Gly Ala
```

Gln Gln Val Val Glu Tyr Pro Phe Thr
1               5

```
1               5                   10                  15
Ser Val Lys Leu Ser Cys Thr Ala Ser Gly Phe Asn Ile Lys Asp Thr
            20                  25                  30

Tyr Met His Trp Val Asn Gln Arg Pro Glu Gln Gly Leu Glu Trp Ile
            35                  40                  45

Gly Arg Ile Asp Pro Ala Asn Gly Asn Thr Lys Tyr Gly Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Gln Thr Ala Arg Ala Pro Phe Ala Tyr Trp Gly Gln Gly Thr Leu
            100                 105                 110

Val Thr Val Ser Ala
            115

<210> SEQ ID NO 31
<211> LENGTH: 396
<212> TYPE: DNA
<213> ORGANISM: Artificial Sequence
<220> FEATURE:
<223> OTHER INFORMATION: anti-IDUA 462 variable light domain coding
      sequence with leader sequence

<400> SEQUENCE: 31
atgaggtgct ctcttcagtt cttggggatg cttatgttct ggatctctgg agtcagtggg    60
gatattgtga taacccagga tgaagtctcc aatcctgtca cttctggaga atcagtttcc   120
atctcctgca ggtctagtaa gagtctccta tataaggatg gaagacataa cttgaattgg   180
tttctgcaga ggccaggaca gtctcctcag ctcctggtct attggatgtc cacccgtgca   240
tcaggagtct cagaccggtt tagtggcagt gggtcaggaa cagatttcac actgaaaatc   300
agtagagtga aggctgagga tgtcggtatg tattactgtc aacaagttgt agagtatcca   360
ttcacgttcg gcacggggac aaaattggaa ataaaa                             396

<210> SEQ ID NO 32
<211> LENGTH: 132
<212> TYPE: PRT
<213> ORGANISM: Artificial Sequence
<220> FEATURE:
<223> OTHER INFORMATION: anti-IDUA 462 variable light domain amino acid
      sequence with leader sequence

<400> SEQUENCE: 32

Met Arg Cys Ser Leu Gln Phe Leu Gly Met Leu Met Phe Trp Ile Ser
1               5                   10                  15

Gly Val Ser Gly Asp Ile Val Ile Thr Gln Asp Glu Val Ser Asn Pro
            20                  25                  30

Val Thr Ser Gly Glu Ser Val Ser Ile Ser Cys Arg Ser Ser Lys Ser
            35                  40                  45

Leu Leu Tyr Lys Asp Gly Lys Thr Tyr Leu Asn Trp Phe Leu Gln Arg
    50                  55                  60

Pro Gly Gln Ser Pro Gln Leu Leu Val Tyr Trp Met Ser Thr Arg Ala
65                  70                  75                  80

Ser Gly Val Ser Asp Arg Phe Ser Gly Ser Gly Ser Gly Thr Asp Phe
                85                  90                  95

Thr Leu Lys Ile Ser Arg Val Lys Ala Glu Asp Val Gly Met Tyr Tyr
            100                 105                 110
```

```
Cys Gln Gln Val Val Glu Tyr Pro Phe Thr Phe Gly Thr Gly Thr Lys
        115                 120                 125

Leu Glu Ile Lys
    130

<210> SEQ ID NO 33
<211> LENGTH: 112
<212> TYPE: PRT
<213> ORGANISM: Artificial Sequence
<220> FEATURE:
<223> OTHER INFORMATION: anti-IDUA 462 variable light domain amino acid
      sequence without leader sequence

<400> SEQUENCE: 33

Asp Ile Val Ile Thr Gln Asp Glu Val Ser Asn Pro Val Thr Ser Gly
1               5                   10                  15

Glu Ser Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Val Tyr Trp Met Ser Thr Arg Ala Ser Gly Val Ser
    50                  55                  60

Asp Arg Phe Ser Gly Ser Gly Ser Gly Thr Asp Phe Thr Leu Lys Ile
65                  70                  75                  80

Ser Arg Val Lys Ala Glu Asp Val Gly Met Tyr Tyr Cys Gln Gln Val
                85                  90                  95

Val Glu Tyr Pro Phe Thr Phe Gly Thr Gly Thr Lys Leu Glu Ile Lys
            100                 105                 110

<210> SEQ ID NO 34
<211> LENGTH: 11
<212> TYPE: PRT
<213> ORGANISM: Artificial Sequence
<220> FEATURE:
<223> OTHER INFORMATION: Gly-Ser linker

<400> SEQUENCE: 34

Gly Gly Ser Gly Gly Gly Ser Gly Gly Ser Gly
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Gly-Ser linker

<400> SEQUENCE: 35

Gly Gly Ser Gly Gly Ser Gly Ser Gly
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Gly-Ser linker

<400> SEQUENCE: 36

Gly Gly Ser Gly Gly Gly Ser Gly
1               5
```

```
<210> SEQ ID NO 37
<211> LENGTH: 10
<212> TYPE: PRT
<213> ORGANISM: Artificial Sequence
<220> FEATURE:
<223> OTHER INFORMATION: Gly-Ser linker

<400> SEQUENCE: 37

Gly Gly Gly Gly Ser Gly Gly Gly Gly Ser
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Gly-Ser linker

<400> SEQUENCE: 38

Gly Gly Gly Ser Gly Gly Gly Ser
1               5

<210> SEQ ID NO 39
<211> LENGTH: 6
<212> TYPE: PRT
<213> ORGANISM: Artificial Sequence
<220> FEATURE:
<223> OTHER INFORMATION: Gly-Ser linker

<400> SEQUENCE: 39

Gly Gly Ser Gly Gly Ser
1               5

<210> SEQ ID NO 40
<211> LENGTH: 339
<212> TYPE: DNA
<213> ORGANISM: Artificial Sequence
<220> FEATURE:
<223> OTHER INFORMATION: anti-IDUA 218 variable heavy domain coding
      sequence without leader sequence

<400> SEQUENCE: 40
caggtccaac tgcagcagcc tgggactgag cttgtgaagc ctggggcttc agtgaagttg      60
tcctgcaagg cttctggcta caccttcacc aggtactgga tgcactgggt gaagcagagg     120
cctggacaag gccttgagtg gattggagag attaatccta gcaatggtgg actaactac      180 aatgagaagt tcaagaacaa ggccacactg aatgttgaca atcctccag cacagcctac      240 atgcaactca gcagcctgac atctgaggac tctgcggtct attactgtac gttagctatg     300
gactactggg gtcaaggaac ctcagtcacc gtctcctca                            339

<210> SEQ ID NO 41
<211> LENGTH: 336
<212> TYPE: DNA
<213> ORGANISM: Artificial Sequence
<220> FEATURE:
<223> OTHER INFORMATION: anti-IDUA 218 variable light domain coding
      sequence without leader sequence

<400> SEQUENCE: 41
gatgttgtga tgacccagac tccactcact ttgtcggtta ccattggaca accagcctcc      60
atctcttgca agtcaagtca gagcctctta catagtgatg aaagacata tttgaattgg      120 tcgttacaga ggccaggcca gtctccaaag cgcctaatct atctggtgtc taaactggac     180
tctggagtcc ctgacaggtt cactggcagt ggatcaggga cagatttcac actgaaaatc     240
```

```
agcagagtgg aggctgagga tttgggagtt tattattgct ggcaaggttt acatttttccg      300 tggacgttcg gtggaggcac caagctggaa atcaaa                                336

<210> SEQ ID NO 42
<211> LENGTH: 351
<212> TYPE: DNA
<213> ORGANISM: Artificial Sequence
<220> FEATURE:
<223> OTHER INFORMATION: anti-IDUA 462 variable heavy domain coding
      sequence without leader sequence

<400> SEQUENCE: 42
gaggttcagc tgcagcagtc tggggcagag cttgtgaagc caggggcctc agtcaagttg       60
tcctgcacag cttctggctt caacattaaa gacacctata tgcactgggt gaaccagagg      120
cctgaacagg gcctggagtg gattggaagg attgatcctg cgaatggtaa tactaaatat      180
ggcccgaagt tccagggcaa ggccactata acagcagaca catcctccaa cacagcctac      240
ctgcagctca gcagcctgac atctgaggac actgccgtct attactgtgc ccagacagct      300
cgggccccgt tgcttactg gggccaaggg actctggtca ctgtctctgc a                351

<210> SEQ ID NO 43
<211> LENGTH: 336
<212> TYPE: DNA
<213> ORGANISM: Artificial Sequence
<220> FEATURE:
<223> OTHER INFORMATION: anti-IDUA 462 variable light domain coding
      sequence without leader sequence

<400> SEQUENCE: 43
gatattgtga acccaggga tgaagtctcc aatcctgtca cttctggaga atcagtttcc        60
atctcctgca ggtctagtaa gagtctccta tataaggatg gaagacata cttgaattgg       120 tttctgcaga ggccaggaca gtctcctcag ctcctggtct attggatgtc cacccgtgca      180
tcaggagtct cagaccggtt tagtggcagt gggtcaggaa cagatttcac actgaaaatc      240
agtagagtga aggctgagga tgtcggtatg tattactgtc aacaagttgt agagtatcca      300
ttcacgttcg gcacgggac aaaattggaa ataaaa                                 336

<210> SEQ ID NO 44
<211> LENGTH: 5
<212> TYPE: PRT
<213> ORGANISM: Artificial Sequence
<220> FEATURE:
<223> OTHER INFORMATION: anti-GAA 155 VH CDR1

<400> SEQUENCE: 44

Ser Tyr Val Met Ser
1               5

<210> SEQ ID NO 45
<211> LENGTH: 16
<212> TYPE: PRT
<213> ORGANISM: Artificial Sequence
<220> FEATURE:
<223> OTHER INFORMATION: anti-GAA 155 VH CDR2

<400> SEQUENCE: 45

Val Ile Ser Thr Gly Gly Ile Thr Tyr Tyr Ala Asn Trp Ala Lys Gly
1               5                   10                  15

<210> SEQ ID NO 46
```

```
<211> LENGTH: 8
<212> TYPE: PRT
<213> ORGANISM: Artificial Sequence
<220> FEATURE:
<223> OTHER INFORMATION: anti-GAA 155 VH CDR3

<400> SEQUENCE: 46

Gly Phe Ser Gly Asp Asn Tyr Val
1               5

<210> SEQ ID NO 47
<211> LENGTH: 13
<212> TYPE: PRT
<213> ORGANISM: Artificial Sequence
<220> FEATURE:
<223> OTHER INFORMATION: anti-GAA 155 VL CDR1

<400> SEQUENCE: 47

Gln Ser Ser Gln Asn Val His Ser Asn Asn Tyr Leu Ser
1               5                   10

<210> SEQ ID NO 48
<211> LENGTH: 7
<212> TYPE: PRT
<213> ORGANISM: Artificial Sequence
<220> FEATURE:
<223> OTHER INFORMATION: anti-GAA 155 VL CDR2

<400> SEQUENCE: 48

Leu Ala Ser Thr Leu Ala Ser
1               5

<210> SEQ ID NO 49
<211> LENGTH: 10
<212> TYPE: PRT
<213> ORGANISM: Artificial Sequence
<220> FEATURE:
<223> OTHER INFORMATION: anti-GAA 155 VL CDR3

<400> SEQUENCE: 49

Ala Gly Asp Tyr Thr Thr Asn Ile Tyr Val
1               5                   10

<210> SEQ ID NO 50
<211> LENGTH: 1368
<212> TYPE: DNA
<213> ORGANISM: Artificial Sequence
<220> FEATURE:
<223> OTHER INFORMATION: anti-GAA 155 (clone pEB0613A-3B2-H1) heavy
      chain coding sequence with leader sequence

<400> SEQUENCE: 50
atggagactg ggctgcgctg gcttctcctg gtcgctgtgc tcaaaggtgt ccagtgtcag    60
tcggtggagg agtccggggg tcgcctggtc acgcctggga caccctgac actcacctgc    120 acagcctctg gattctccct caatagttat gtaatgagtt gggtccgcca ggctccaggg    180 gagggctgg aatggatcgg ggtcattagt actggtggta tcacatacta cgcgaactgg    240
gcaaaaggcc gattcaccat ctccaaaacc tcgaccacgg tggatctgaa aatcaccagt    300
ccgagaaccg aggacacggc cacctatttc tgtgccagag gatttagtgg tgataattac    360
gtctggggcc aggcaccct ggtcaccgtc tccttcgggc aacctaaggc tccatcagtc    420
ttcccactgg ccccctgctg cggggacaca cccagctcca cggtgaccct gggctgcctg    480
gtcaaaggct acctcccgga gccagtgacc gtgacctgga actcgggcac cctcaccaat    540
```

| | |
|---|---|
| ggggtacgca ccttcccgtc cgtccggcag tcctcaggcc tctactcgct gagcagcgtg | 600 |
| gtgagcgtga cctcaagcag ccagcccgtc acctgcaacg tggcccaccc agccaccaac | 660 |
| accaaagtgg acaagaccgt tgcgccctcg acatgcagca agcccatgtg cccaccccct | 720 |
| gaactcctgg ggggaccgtc tgtcttcatc ttcccccccaa aacccaagga caccctcatg | 780 |
| atctcacgca cccccgaggt cacatgcgtg gtggtggacg tgagccagga tgaccccgag | 840 |
| gtgcagttca catggtacat aaacaacgag caggtgcgca ccgccggcc gccgctacgg | 900 |
| gagcagcagt tcaacagcac gatccgcgtg gtcagcaccc tccccatcgc gcaccaggac | 960 |
| tggctgaggg gcaaggagtt caagtgcaaa gtccacaaca aggcactccc ggcccccatc | 1020 |
| gagaaaacca tctccaaagc cagagggcag cccctggagc cgaaggtcta caccatgggc | 1080 |
| cctcccccggg aggagctgag cagcaggtcg gtcagcctga cctgcatgat caacggcttc | 1140 |
| tacccttccg acatctcggt ggagtgggag aagaacggga aggcagagga caactacaag | 1200 |
| accacgccgg ccgtgctgga cagcgacggc tcctacttcc tctacagcaa gctctcagtg | 1260 |
| cccacgagtg agtggcagcg ggcgacgtc ttcacctgct ccgtgatgca cgaggccttg | 1320 |
| cacaaccact acacgcagaa gtccatctcc cgctctccgg gtaaatga | 1368 |

<210> SEQ ID NO 51
<211> LENGTH: 1311
<212> TYPE: DNA
<213> ORGANISM: Artificial Sequence
<220> FEATURE:
<223> OTHER INFORMATION: anti-GAA 155 (clone pEB0613A-3B2-H1) heavy
      chain coding sequence without leader sequence

<400> SEQUENCE: 51

| | |
|---|---|
| cagtcggtgg aggagtccgg gggtcgcctg gtcacgcctg ggacacccct gacactcacc | 60 |
| tgcacagcct ctggattctc cctcaatagt tatgtaatga gttgggtccg ccaggctcca | 120 |
| ggggaggggc tggaatggat cggggtcatt agtactggtg gtatcacata ctacgcgaac | 180 |
| tgggcaaaag gccgattcac catctccaaa acctcgacca cggtggatct gaaaatcacc | 240 |
| agtccgagaa ccgaggacac ggccacctat ttctgtgcca gaggatttag tggtgataat | 300 |
| tacgtctggg gcccaggcac cctggtcacc gtctccttcg gcaacctaa ggctccatca | 360 |
| gtcttcccac tggccccctg ctgcggggac acacccagct ccacggtgac cctgggctgc | 420 |
| ctggtcaaag gctacctccc ggagccagtg accgtgacct ggaactcggg caccctcacc | 480 |
| aatggggtac gcaccttccc gtccgtccgg cagtcctcag gcctctactc gctgagcagc | 540 |
| gtggtgagcg tgacctcaag cagccagccc gtcacctgca acgtggccca cccagccacc | 600 |
| aacaccaaag tggacaagac cgttgcgccc tcgacatgca gcaagcccat gtgcccaccc | 660 |
| cctgaactcc tggggggacc gtctgtcttc atcttcccc caaaacccaa ggacaccctc | 720 |
| atgatctcac gcacccccga ggtcacatgc gtggtggtgg acgtgagcca ggatgacccc | 780 |
| gaggtgcagt tcatggta cataaacaac gagcaggtgc gcaccgcccg ccgccgcta | 840 |
| cgggagcagc agttcaacag cacgatccgc gtggtcagca ccctccccat cgcgcaccag | 900 |
| gactggctga ggggcaagga gttcaagtgc aaagtccaca acaaggcact cccggccccc | 960 |
| atcgagaaaa ccatctccaa agccagaggg cagcccctgg agccgaaggt ctacaccatg | 1020 |
| ggccctcccc gggaggagct gagcagcagg tcggtcagcc tgacctgcat gatcaacggc | 1080 |
| ttctaccctt ccgacatctc ggtggagtgg gagaagaacg ggaaggcaga ggacaactac | 1140 |
| aagaccacgc cggccgtgct ggacagcgac ggctcctact cctctacag caagctctca | 1200 |

```
gtgcccacga gtgagtggca gcggggcgac gtcttcacct gctccgtgat gcacgaggcc   1260
ttgcacaacc actacacgca gaagtccatc tcccgctctc cgggtaaatg a            1311
```

```
<210> SEQ ID NO 52
<211> LENGTH: 396
<212> TYPE: DNA
<213> ORGANISM: Artificial Sequence
<220> FEATURE:
<223> OTHER INFORMATION: anti-GAA 155 (clone pEB0613A-3B2-H1) variable
      heavy domain coding sequence with leader sequence

<400> SEQUENCE: 52
```

```
atggagactg gctgcgctg gcttctcctg gtcgctgtgc tcaaaggtgt ccagtgtcag    60
tcggtggagg agtccggggg tcgcctggtc acgcctggga caccctgac actcacctgc   120 acagcctctg gattctccct caatagttat gtaatgagtt gggtccgcca ggctccaggg   180
gaggggctgg aatggatcgg ggtcattagt actggtggta tcacatacta cgcgaactgg   240
gcaaaaggcc gattcaccat ctccaaaacc tcgaccacgg tggatctgaa aatcaccagt   300
ccgagaaccg aggacacggc cacctatttc tgtgccagag atttagtgg tgataattac    360 gtctggggcc aggcacccct ggtcaccgtc tccttc                             396
```

```
<210> SEQ ID NO 53
<211> LENGTH: 339
<212> TYPE: DNA
<213> ORGANISM: Artificial Sequence
<220> FEATURE:
<223> OTHER INFORMATION: anti-GAA 155 (clone pEB0613A-3B2-H1) variable
      heavy domain coding sequence without leader sequence

<400> SEQUENCE: 53
```

```
cagtcggtgg aggagtccgg gggtcgcctg gtcacgcctg gacacccct gacactcacc    60 tgcacagcct ctggattctc cctcaatagt tatgtaatga gttgggtccg ccaggctcca   120
ggggaggggc tggaatggat cggggtcatt agtactggtg gtatcacata ctacgcgaac   180
tgggcaaaag gccgattcac catctccaaa acctcgacca cggtggatct gaaaatcacc   240
agtccgagaa ccgaggacac ggccacctat ttctgtgcca gaggatttag tggtgataat   300
tacgtctggg gcccaggcac cctggtcacc gtctccttc                          339
```

```
<210> SEQ ID NO 54
<211> LENGTH: 455
<212> TYPE: PRT
<213> ORGANISM: Artificial Sequence
<220> FEATURE:
<223> OTHER INFORMATION: anti-GAA 155 heavy chain amino acid sequence
      with leader sequence

<400> SEQUENCE: 54
```

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Asn
        35                  40                  45

Ser Tyr Val Met Ser Trp Val Arg Gln Ala Pro Gly Glu Gly Leu Glu
    50                  55                  60

Trp Ile Gly Val Ile Ser Thr Gly Gly Ile Thr Tyr Tyr Ala Asn Trp
65                  70                  75                  80

Ala Lys Gly Arg Phe Thr Ile Ser Lys Thr Ser Thr Thr Val Asp Leu
```

```
                85                  90                  95
Lys Ile Thr Ser Pro Arg Thr Glu Asp Thr Ala Thr Tyr Phe Cys Ala
                100                 105                 110

Arg Gly Phe Ser Gly Asp Asn Tyr Val Trp Gly Pro Gly Thr Leu Val
            115                 120                 125

Thr Val Ser Phe Gly Gln Pro Lys Ala Pro Ser Val Phe Pro Leu Ala
130                 135                 140

Pro Cys Cys Gly Asp Thr Pro Ser Ser Thr Val Thr Leu Gly Cys Leu
145                 150                 155                 160

Val Lys Gly Tyr Leu Pro Glu Pro Val Thr Val Thr Trp Asn Ser Gly
                165                 170                 175

Thr Leu Thr Asn Gly Val Arg Thr Phe Pro Ser Val Arg Gln Ser Ser
            180                 185                 190

Gly Leu Tyr Ser Leu Ser Ser Val Val Ser Val Thr Ser Ser Ser Gln
            195                 200                 205

Pro Val Thr Cys Asn Val Ala His Pro Ala Thr Asn Thr Lys Val Asp
        210                 215                 220

Lys Thr Val Ala Pro Ser Thr Cys Ser Lys Pro Met Cys Pro Pro Pro
225                 230                 235                 240

Glu Leu Leu Gly Gly Pro Ser Val Phe Ile Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Asp Asp Pro Glu Val Gln Phe Thr Trp Tyr Ile Asn
        275                 280                 285

Asn Glu Gln Val Arg Thr Ala Arg Pro Pro Leu Arg Glu Gln Gln Phe
        290                 295                 300

Asn Ser Thr Ile Arg Val Val Ser Thr Leu Pro Ile Ala His Gln Asp
305                 310                 315                 320

Trp Leu Arg Gly Lys Glu Phe Lys Cys Lys Val His Asn Lys Ala Leu
                325                 330                 335

Pro Ala Pro Ile Glu Lys Thr Ile Ser Lys Ala Arg Gly Gln Pro Leu
            340                 345                 350

Glu Pro Lys Val Tyr Thr Met Gly Pro Pro Arg Glu Glu Leu Ser Ser
            355                 360                 365

Arg Ser Val Ser Leu Thr Cys Met Ile Asn Gly Phe Tyr Pro Ser Asp
        370                 375                 380

Ile Ser Val Glu Trp Glu Lys Asn Gly Lys Ala Glu Asp Asn Tyr Lys
385                 390                 395                 400

Thr Thr Pro Ala Val Leu Asp Ser Asp Gly Ser Tyr Phe Leu Tyr Ser
                405                 410                 415

Lys Leu Ser Val Pro Thr Ser Glu Trp Gln Arg Gly Asp Val Phe Thr
            420                 425                 430

Cys Ser Val Met His Glu Ala Leu His Asn His Tyr Thr Gln Lys Ser
        435                 440                 445

Ile Ser Arg Ser Pro Gly Lys
450                 455

<210> SEQ ID NO 55
<211> LENGTH: 436
<212> TYPE: PRT
<213> ORGANISM: Artificial Sequence
<220> FEATURE:
<223> OTHER INFORMATION: anti-GAA 155 heavy chain amino acid sequence
      without leader sequence
```

<400> SEQUENCE: 55

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Asn Ser Tyr Val
            20                  25                  30

Met Ser Trp Val Arg Gln Ala Pro Gly Glu Gly Leu Glu Trp Ile Gly
        35                  40                  45

Val Ile Ser Thr Gly Gly Ile Thr Tyr Tyr Ala Asn Trp Ala Lys Gly
    50                  55                  60

Arg Phe Thr Ile Ser Lys Thr Ser Thr Thr Val Asp Leu Lys Ile Thr
65                  70                  75                  80

Ser Pro Arg Thr Glu Asp Thr Ala Thr Tyr Phe Cys Ala Arg Gly Phe
                85                  90                  95

Ser Gly Asp Asn Tyr Val Trp Gly Pro Gly Thr Leu Val Thr Val Ser
            100                 105                 110

Phe Gly Gln Pro Lys Ala Pro Ser Val Phe Pro Leu Ala Pro Cys Cys
        115                 120                 125

Gly Asp Thr Pro Ser Ser Thr Val Thr Leu Gly Cys Leu Val Lys Gly
130                 135                 140

Tyr Leu Pro Glu Pro Val Thr Val Thr Trp Asn Ser Gly Thr Leu Thr
145                 150                 155                 160

Asn Gly Val Arg Thr Phe Pro Ser Val Arg Gln Ser Ser Gly Leu Tyr
                165                 170                 175

Ser Leu Ser Ser Val Val Ser Val Thr Ser Ser Ser Gln Pro Val Thr
            180                 185                 190

Cys Asn Val Ala His Pro Ala Thr Asn Thr Lys Val Asp Lys Thr Val
        195                 200                 205

Ala Pro Ser Thr Cys Ser Lys Pro Met Cys Pro Pro Pro Glu Leu Leu
    210                 215                 220

Gly Gly Pro Ser Val Phe Ile Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

Gln Asp Asp Pro Glu Val Gln Phe Thr Trp Tyr Ile Asn Asn Glu Gln
            260                 265                 270

Val Arg Thr Ala Arg Pro Pro Leu Arg Glu Gln Gln Phe Asn Ser Thr
        275                 280                 285

Ile Arg Val Val Ser Thr Leu Pro Ile Ala His Gln Asp Trp Leu Arg
    290                 295                 300

Gly Lys Glu Phe Lys Cys Lys Val His Asn Lys Ala Leu Pro Ala Pro
305                 310                 315                 320

Ile Glu Lys Thr Ile Ser Lys Ala Arg Gly Gln Pro Leu Glu Pro Lys
                325                 330                 335

Val Tyr Thr Met Gly Pro Pro Arg Glu Glu Leu Ser Ser Arg Ser Val
            340                 345                 350

Ser Leu Thr Cys Met Ile Asn Gly Phe Tyr Pro Ser Asp Ile Ser Val
        355                 360                 365

Glu Trp Glu Lys Asn Gly Lys Ala Glu Asp Asn Tyr Lys Thr Thr Pro
    370                 375                 380

Ala Val Leu Asp Ser Asp Gly Ser Tyr Phe Leu Tyr Ser Lys Leu Ser
385                 390                 395                 400

Val Pro Thr Ser Glu Trp Gln Arg Gly Asp Val Phe Thr Cys Ser Val

```
                    405                 410                 415
Met His Glu Ala Leu His Asn His Tyr Thr Gln Lys Ser Ile Ser Arg
                420                 425                 430

Ser Pro Gly Lys
        435

<210> SEQ ID NO 56
<211> LENGTH: 132
<212> TYPE: PRT
<213> ORGANISM: Artificial Sequence
<220> FEATURE:
<223> OTHER INFORMATION: anti-GAA 155 variable heavy domain amino acid
      sequence with leader sequence

<400> SEQUENCE: 56

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Asn
        35                  40                  45

Ser Tyr Val Met Ser Trp Val Arg Gln Ala Pro Gly Glu Gly Leu Glu
    50                  55                  60

Trp Ile Gly Val Ile Ser Thr Gly Gly Ile Thr Tyr Tyr Ala Asn Trp
65                  70                  75                  80

Ala Lys Gly Arg Phe Thr Ile Ser Lys Thr Ser Thr Thr Val Asp Leu
                85                  90                  95

Lys Ile Thr Ser Pro Arg Thr Glu Asp Thr Ala Thr Tyr Phe Cys Ala
            100                 105                 110

Arg Gly Phe Ser Gly Asp Asn Tyr Val Trp Gly Pro Gly Thr Leu Val
        115                 120                 125

Thr Val Ser Phe
    130

<210> SEQ ID NO 57
<211> LENGTH: 113
<212> TYPE: PRT
<213> ORGANISM: Artificial Sequence
<220> FEATURE:
<223> OTHER INFORMATION: anti-GAA 155 variable heavy domain amino acid
      sequence without leader sequence

<400> SEQUENCE: 57

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Asn Ser Tyr Val
            20                  25                  30

Met Ser Trp Val Arg Gln Ala Pro Gly Glu Gly Leu Glu Trp Ile Gly
        35                  40                  45

Val Ile Ser Thr Gly Gly Ile Thr Tyr Tyr Ala Asn Trp Ala Lys Gly
    50                  55                  60

Arg Phe Thr Ile Ser Lys Thr Ser Thr Thr Val Asp Leu Lys Ile Thr
65                  70                  75                  80

Ser Pro Arg Thr Glu Asp Thr Ala Thr Tyr Phe Cys Ala Arg Gly Phe
                85                  90                  95

Ser Gly Asp Asn Tyr Val Trp Gly Pro Gly Thr Leu Val Thr Val Ser
            100                 105                 110

Phe
```

<210> SEQ ID NO 58
<211> LENGTH: 714
<212> TYPE: DNA
<213> ORGANISM: Artificial Sequence
<220> FEATURE:
<223> OTHER INFORMATION: anti-GAA 155 (clone pEB0613A-3B2-K3) light
      chain coding sequence with leader sequence

<400> SEQUENCE: 58

```
atggacacga gggcccccac tcagctgctg gggctcctac tgctctggct cccaggtgcc      60
agatgtgctg acattgtgat gacccagact ccatcttcca cgtctgcggc tgtgggaggc     120
acagtcacca tcaactgcca gtccagtcag aatgttcata gtaacaacta cttatcctgg     180
tttcagcaga aaccagggca gcctcccaag ctcctgatct atctggcttc cactctggca     240
tctggggtcc catcgcggtt caaaggcagt ggctctggga cagagttcac tctcaccatc     300
agcgacctgg agtgtgatga tgctgccact tactactgtg caggcgatta tactactaat     360
atttatgttt tcggcggagg gaccgagtg gtggtcaaag gtgatccagt tgcacctact     420
gtcctcatct tcccaccagc tgctgatcag gtggcaactg gaacagtcac catcgtgtgt     480
gtggcgaata aatactttcc cgatgtcacc gtcacctggg aggtggatgg caccacccaa     540
acaactggca tcgagaacag taaaacaccg cagaattctg cagattgtac ctacaacctc     600
agcagcactc tgacactgac cagcacacag tacaacagcc acaaagagta cacctgcaag     660
gtgacccagg gcacgacctc agtcgtccag agcttcaata ggggtgactg ttag          714
```

<210> SEQ ID NO 59
<211> LENGTH: 648
<212> TYPE: DNA
<213> ORGANISM: Artificial Sequence
<220> FEATURE:
<223> OTHER INFORMATION: anti-GAA 155 (clone pEB0613A-3B2-K3) light
      chain coding sequence without leader sequence

<400> SEQUENCE: 59

```
gctgacattg tgatgaccca gactccatct tccacgtctg cggctgtggg aggcacagtc      60
accatcaact gccagtccag tcagaatgtt catagtaaca actacttatc ctggtttcag     120
cagaaaccag gcagcctcc caagctcctg atctatctgg cttccactct ggcatctggg     180
gtcccatcgc ggttcaaagg cagtggctct gggacagagt tcactctcac catcagcgac     240
ctggagtgtg atgatgctgc cacttactac tgtgcaggcg attatactac taatatttat     300
gttttcggcg gagggaccga ggtggtggtc aaaggtgatc cagttgcacc tactgtcctc     360
atcttcccac cagctgctga tcaggtggca actggaacag tcaccatcgt gtgtgtggcg     420
aataaatact ttcccgatgt caccgtcacc tgggaggtgg atggcaccac ccaaacaact     480
ggcatcgaga acagtaaaac accgcagaat tctgcagatt gtacctacaa cctcagcagc     540
actctgacac tgaccagcac acagtacaac agccacaaag agtacacctg caaggtgacc     600
cagggcacga cctcagtcgt ccagagcttc aatagggg tg actgttag                 648
```

<210> SEQ ID NO 60
<211> LENGTH: 399
<212> TYPE: DNA
<213> ORGANISM: Artificial Sequence
<220> FEATURE:
<223> OTHER INFORMATION: anti-GAA 155 (clone pEB0613A-3B2-K3) variable
      light domain coding sequence with leader sequence

<400> SEQUENCE: 60

```
atggacacga gggcccccac tcagctgctg gggctcctac tgctctggct cccaggtgcc    60
agatgtgctg acattgtgat gacccagact ccatcttcca cgtctgcggc tgtgggaggc   120
acagtcacca tcaactgcca gtccagtcag aatgttcata gtaacaacta cttatcctgg   180
tttcagcaga aaccagggca gcctcccaag ctcctgatct atctggcttc cactctggca   240
tctggggtcc catcgcggtt caaaggcagt ggctctggga cagagttcac tctcaccatc   300
agcgacctgg agtgtgatga tgctgccact tactactgtg caggcgatta ctactactaat   360 atttatgttt tcggcggagg gaccgaggtg gtggtcaaa                          399
```

<210> SEQ ID NO 61
<211> LENGTH: 333
<212> TYPE: DNA
<213> ORGANISM: Artificial Sequence
<220> FEATURE:
<223> OTHER INFORMATION: anti-GAA 155 (clone pEB0613A-3B2-K3) variable
      light domain coding sequence without leader sequence

<400> SEQUENCE: 61

```
gctgacattg tgatgaccca gactccatct tccacgtctg cggctgtggg aggcacagtc    60
accatcaact gccagtccag tcagaatgtt catagtaaca actacttatc ctggtttcag   120
cagaaaccag gcagcctcc caagctcctg atctatctgg cttccactct ggcatctggg   180
gtcccatcgc ggttcaaagg cagtggctct gggacagagt tcactctcac catcagcgac   240
ctggagtgtg atgatgctgc cacttactac tgtgcaggcg attatactac taatatttat   300
gttttcggcg agggaccga ggtggtggtc aaa                                 333
```

<210> SEQ ID NO 62
<211> LENGTH: 237
<212> TYPE: PRT
<213> ORGANISM: Artificial Sequence
<220> FEATURE:
<223> OTHER INFORMATION: anti-GAA 155 light chain amino acid sequence
      with leader sequence

<400> SEQUENCE: 62

Met Asp Thr Arg Ala Pro Thr Gln Leu Leu Gly Leu Leu Leu Trp
1               5                   10                  15

Leu Pro Gly Ala Arg Cys Ala Asp Ile Val Met Thr Gln Thr Pro Ser
                20                  25                  30

Ser Thr Ser Ala Ala Val Gly Gly Thr Val Thr Ile Asn Cys Gln Ser
            35                  40                  45

Ser Gln Asn Val His Ser Asn Asn Tyr Leu Ser Trp Phe Gln Gln Lys
        50                  55                  60

Pro Gly Gln Pro Pro Lys Leu Leu Ile Tyr Leu Ala Ser Thr Leu Ala
65                  70                  75                  80

Ser Gly Val Pro Ser Arg Phe Lys Gly Ser Gly Ser Gly Thr Glu Phe
                85                  90                  95

Thr Leu Thr Ile Ser Asp Leu Glu Cys Asp Asp Ala Ala Thr Tyr Tyr
                100                 105                 110

Cys Ala Gly Asp Tyr Thr Thr Asn Ile Tyr Val Phe Gly Gly Gly Thr
            115                 120                 125

Glu Val Val Val Lys Gly Asp Pro Val Ala Pro Thr Val Leu Ile Phe
        130                 135                 140

Pro Pro Ala Ala Asp Gln Val Ala Thr Gly Thr Val Thr Ile Val Cys
145                 150                 155                 160
```

-continued

```
Val Ala Asn Lys Tyr Phe Pro Asp Val Thr Val Trp Glu Val Asp
            165                 170                 175

Gly Thr Thr Gln Thr Thr Gly Ile Glu Asn Ser Lys Thr Pro Gln Asn
        180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235
```

<210> SEQ ID NO 63
<211> LENGTH: 215
<212> TYPE: PRT
<213> ORGANISM: Artificial Sequence
<220> FEATURE:
<223> OTHER INFORMATION: anti-GAA 155 light chain amino acid sequence
      without leader sequence

<400> SEQUENCE: 63

```
Ala Asp Ile Val Met Thr Gln Thr Pro Ser Ser Thr Ser Ala Ala Val
1               5                   10                  15

Gly Gly Thr Val Thr Ile Asn Cys Gln Ser Ser Gln Asn Val His Ser
            20                  25                  30

Asn Asn Tyr Leu Ser Trp Phe Gln Gln Lys Pro Gly Gln Pro Pro Lys
        35                  40                  45

Leu Leu Ile Tyr Leu Ala Ser Thr Leu Ala Ser Gly Val Pro Ser Arg
50                  55                  60

Phe Lys Gly Ser Gly Ser Gly Thr Glu Phe Thr Leu Thr Ile Ser Asp
65                  70                  75                  80

Leu Glu Cys Asp Asp Ala Ala Thr Tyr Tyr Cys Ala Gly Asp Tyr Thr
                85                  90                  95

Thr Asn Ile Tyr Val Phe Gly Gly Thr Glu Val Val Val Lys Gly
            100                 105                 110

Asp Pro Val Ala Pro Thr Val Leu Ile Phe Pro Pro Ala Ala Asp Gln
        115                 120                 125

Val Ala Thr Gly Thr Val Thr Ile Val Cys Val Ala Asn Lys Tyr Phe
    130                 135                 140

Pro Asp Val Thr Val Thr Trp Glu Val Asp Gly Thr Thr Gln Thr Thr
145                 150                 155                 160

Gly Ile Glu Asn Ser Lys Thr Pro Gln Asn Ser Ala Asp Cys Thr Tyr
                165                 170                 175

Asn Leu Ser Ser Thr Leu Thr Leu Thr Ser Thr Gln Tyr Asn Ser His
            180                 185                 190

Lys Glu Tyr Thr Cys Lys Val Thr Gln Gly Thr Thr Ser Val Val Gln
        195                 200                 205

Ser Phe Asn Arg Gly Asp Cys
    210                 215
```

<210> SEQ ID NO 64
<211> LENGTH: 133
<212> TYPE: PRT
<213> ORGANISM: Artificial Sequence
<220> FEATURE:
<223> OTHER INFORMATION: anti-GAA 155 variable light domain amino acid
      sequence with leader sequence

<400> SEQUENCE: 64

```
Met Asp Thr Arg Ala Pro Thr Gln Leu Leu Gly Leu Leu Leu Trp
1               5                   10                  15

Leu Pro Gly Ala Arg Cys Ala Asp Ile Val Met Thr Gln Thr Pro Ser
            20                  25                  30

Ser Thr Ser Ala Ala Val Gly Gly Thr Val Thr Ile Asn Cys Gln Ser
        35                  40                  45

Ser Gln Asn Val His Ser Asn Asn Tyr Leu Ser Trp Phe Gln Gln Lys
    50                  55                  60

Pro Gly Gln Pro Pro Lys Leu Leu Ile Tyr Leu Ala Ser Thr Leu Ala
65                  70                  75                  80

Ser Gly Val Pro Ser Arg Phe Lys Gly Ser Gly Ser Gly Thr Glu Phe
                85                  90                  95

Thr Leu Thr Ile Ser Asp Leu Glu Cys Asp Asp Ala Ala Thr Tyr Tyr
            100                 105                 110

Cys Ala Gly Asp Tyr Thr Thr Asn Ile Tyr Val Phe Gly Gly Gly Thr
                115                 120                 125

Glu Val Val Val Lys
            130
```

<210> SEQ ID NO 65
<211> LENGTH: 111
<212> TYPE: PRT
<213> ORGANISM: Artificial Sequence
<220> FEATURE:
<223> OTHER INFORMATION: anti-GAA 155 variable light domain amino acid
      sequence without leader sequence

<400> SEQUENCE: 65

```
Ala Asp Ile Val Met Thr Gln Thr Pro Ser Ser Thr Ser Ala Ala Val
1               5                   10                  15

Gly Gly Thr Val Thr Ile Asn Cys Gln Ser Ser Gln Asn Val His Ser
            20                  25                  30

Asn Asn Tyr Leu Ser Trp Phe Gln Gln Lys Pro Gly Gln Pro Pro Lys
        35                  40                  45

Leu Leu Ile Tyr Leu Ala Ser Thr Leu Ala Ser Gly Val Pro Ser Arg
    50                  55                  60

Phe Lys Gly Ser Gly Ser Gly Thr Glu Phe Thr Leu Thr Ile Ser Asp
65                  70                  75                  80

Leu Glu Cys Asp Asp Ala Ala Thr Tyr Tyr Cys Ala Gly Asp Tyr Thr
                85                  90                  95

Thr Asn Ile Tyr Val Phe Gly Gly Gly Thr Glu Val Val Val Lys
            100                 105                 110
```

<210> SEQ ID NO 66
<211> LENGTH: 5
<212> TYPE: PRT
<213> ORGANISM: Artificial Sequence
<220> FEATURE:
<223> OTHER INFORMATION: anti-GAA 376 VH CDR1

<400> SEQUENCE: 66

```
Ser Val Asp Met Ser
1               5
```

<210> SEQ ID NO 67
<211> LENGTH: 16
<212> TYPE: PRT
<213> ORGANISM: Artificial Sequence
<220> FEATURE:
<223> OTHER INFORMATION: anti-GAA 376 VH CDR2

<400> SEQUENCE: 67

Phe Ser Asn Ala Tyr His Arg Thr Tyr Tyr Ala Ser Trp Ser Lys Ser
1               5                   10                  15

<210> SEQ ID NO 68
<211> LENGTH: 11
<212> TYPE: PRT
<213> ORGANISM: Artificial Sequence
<220> FEATURE:
<223> OTHER INFORMATION: anti-GAA 376 VH CDR3

<400> SEQUENCE: 68

Gly Val Pro Gly Tyr Val Thr Lys Ser Ser Leu
1               5                   10

<210> SEQ ID NO 69
<211> LENGTH: 13
<212> TYPE: PRT
<213> ORGANISM: Artificial Sequence
<220> FEATURE:
<223> OTHER INFORMATION: anti-GAA 376 VL CDR1

<400> SEQUENCE: 69

Gln Ala Ser Gln Ser Val Tyr Gly Asn Asn Glu Leu Ser
1               5                   10

<210> SEQ ID NO 70
<211> LENGTH: 7
<212> TYPE: PRT
<213> ORGANISM: Artificial Sequence
<220> FEATURE:
<223> OTHER INFORMATION: anti-GAA 376 VL CDR2

<400> SEQUENCE: 70

Lys Ala Ser Thr Leu Ala Ser
1               5

<210> SEQ ID NO 71
<211> LENGTH: 12
<212> TYPE: PRT
<213> ORGANISM: Artificial Sequence
<220> FEATURE:
<223> OTHER INFORMATION: anti-GAA 376 VL CDR3

<400> SEQUENCE: 71

Ala Gly Tyr Ser Ser Gly Val Ile Asp Val Ser Ala
1               5                   10

<210> SEQ ID NO 72
<211> LENGTH: 1386
<212> TYPE: DNA
<213> ORGANISM: Artificial Sequence
<220> FEATURE:
<223> OTHER INFORMATION: anti-GAA 376 (clone pEB0613B-4B1-H2) heavy
      chain coding sequence with leader sequence

<400> SEQUENCE: 72
atggagactg ggctgcgctg gcttctcctg gtcgctgtgc tcaaaggtgt ccagtgtcag      60
gagcacctgg tggagtccgg gggaggcctg gtcaaccctg gaggatccct gacactcacc     120
tgcacagcct ctggattctc cctcaacagc gtcgacatga gctgggtccg ccaggctcca     180
gggaaggggc tggagtggat cggattcagt aatgcttatc ataggacata ctacgcgagc     240
tggtcgaaaa gccgatccac catcaccaga aacaccaacg agaacacggt gactctgaaa     300

| | |
|---|---|
| atgaccagtc tgacagccgc ggacacggcc acctatttct gtgcgagagg tgttcctggt | 360 |
| tatgttacta aaagtagtct ctggggccca ggcaccctgg tcaccgtctc ctcagggcaa | 420 |
| cctaaggctc catcagtctt cccactggcc ccctgctgcg ggacacacc cagctccacg | 480 |
| gtgaccctgg gctgcctggt caaaggctac ctcccggagc cagtgaccgt gacctggaac | 540 |
| tcgggcaccc tcaccaatgg ggtacgcacc ttcccgtccg tccggcagtc ctcaggcctc | 600 |
| tactcgctga gcagcgtggt gagcgtgacc tcaagcagcc agcccgtcac ctgcaacgtg | 660 |
| gcccacccag ccaccaacac caaagtggac aagaccgttg cgcctcgac atgcagcaag | 720 |
| cccatgtgcc cacccctga actcctgggg ggaccgtctg tcttcatctt cccccaaaa | 780 |
| cccaaggaca ccctcatgat ctcacgcacc cccgaggtca catgcgtggt ggtggacgtg | 840 |
| agccaggatg accccgaggt gcagttcaca tggtacataa acaacgagca ggtgcgcacc | 900 |
| gcccggccgc cgctacggga gcagcagttc aacagcacga tccgcgtggt cagcacctc | 960 |
| cccatcgcgc accaggactg gctgaggggc aaggagttca gtgcaaagt ccacaacaag | 1020 |
| gcactcccgg cccccatcga gaaaaccatc tccaaagcca gagggcagcc cctggagccg | 1080 |
| aaggtctaca ccatgggccc tccccgggag gagctgagca gcaggtcggt cagcctgacc | 1140 |
| tgcatgatca cggcttcta cccttccgac atctcggtgg agtgggagaa gaacgggaag | 1200 |
| gcagaggaca actacaagac cacgccggcc gtgctggaca gcgacggctc ctacttcctc | 1260 |
| tacagcaagc tctcagtgcc cacgagtgag tggcagcggg gcgacgtctt cacctgctcc | 1320 |
| gtgatgcacg aggccttgca aaccactac acgcagaagt ccatctcccg ctctccgggt | 1380 |
| aaatga | 1386 |

<210> SEQ ID NO 73
<211> LENGTH: 1329
<212> TYPE: DNA
<213> ORGANISM: Artificial Sequence
<220> FEATURE:
<223> OTHER INFORMATION: anti-GAA 376 (clone pEB0613B-4B1-H2) heavy
      chain coding sequence without leader sequence

<400> SEQUENCE: 73

| | |
|---|---|
| caggagcacc tggtggagtc cggggaggc ctggtcaacc tggaggatc cctgacactc | 60 |
| acctgcacag cctctggatt ctccctcaac agcgtcgaca tgagctgggt ccgccaggct | 120 |
| ccagggaagg ggctggagtg gatcggattc agtaatgctt atcataggac atactacgcg | 180 |
| agctggtcga aagccgatc caccatcacc agaaacacca cgagaacac ggtgactctg | 240 |
| aaaatgacca gtctgacagc cgcggacacg gccacctatt tctgtgcgag aggtgttcct | 300 |
| ggttatgtta ctaaaagtag tctctggggc ccaggcaccc tggtcaccgt ctcctcaggg | 360 |
| caacctaagg ctccatcagt cttcccactg gccctgct gcggggacac acccagctcc | 420 |
| acggtgaccc tgggctgcct ggtcaaaggc tacctcccgg agccagtgac cgtgacctgg | 480 |
| aactcgggca ccctcaccaa tggggtacg accttcccgt ccgtccggca gtcctcaggc | 540 |
| ctctactcgc tgagcagcgt ggtgagcgtg acctcaagca gccagcccgt cacctgcaac | 600 |
| gtggcccacc cagccaccaa caccaaagtg gacaagaccg ttgcgccctc gacatgcagc | 660 |
| aagcccatgt gccaccccc tgaactcctg ggggaccg ctgtcttcat cttcccccca | 720 |
| aaacccaagg acaccctcat gatctcacgc accccgagg tcacatgcgt ggtggtggac | 780 |
| gtgagccagg atgaccccga ggtgcagttc acatggtaca taaacaacga gcaggtgcgc | 840 |
| accgcccggc cgccgctacg ggagcagcag ttcaacagca cgatccgcgt ggtcagcacc | 900 |

| | |
|---|---|
| ctccccatcg cgcaccagga ctggctgagg ggcaaggagt tcaagtgcaa agtccacaac | 960 |
| aaggcactcc cggcccccat cgagaaaacc atctccaaag ccagagggca gcccctggag | 1020 |
| ccgaaggtct acaccatggg ccctccccgg gaggagctga gcagcaggtc ggtcagcctg | 1080 |
| acctgcatga tcaacggctt ctacccttcc gacatctcgg tggagtggga agaacgggg | 1140 |
| aaggcagagg acaactacaa gaccacgccg ccgtgctgg acagcgacgg ctcctacttc | 1200 |
| ctctacagca agctctcagt gcccacgagt gagtggcagc ggggcgacgt cttcacctgc | 1260 |
| tccgtgatgc acgaggcctt gcacaaccac tacacgcaga agtccatctc ccgctctccg | 1320 |
| ggtaaatga | 1329 |

<210> SEQ ID NO 74
<211> LENGTH: 414
<212> TYPE: DNA
<213> ORGANISM: Artificial Sequence
<220> FEATURE:
<223> OTHER INFORMATION: anti-GAA 376 (clone pEB0613B-4B1-H2) variable
      heavy domain coding sequence with leader sequence

<400> SEQUENCE: 74

| | |
|---|---|
| atggagactg gctgcgctg gcttctcctg gtcgctgtgc tcaaaggtgt ccagtgtcag | 60 |
| gagcacctgg tggagtccgg gggaggcctg gtcaaccctg gaggatccct gacactcacc | 120 |
| tgcacagcct ctggattctc cctcaacagc gtcgacatga gctgggtccg ccaggctcca | 180 |
| gggaaggggc tggagtggat cggattcagt aatgcttatc ataggacata ctacgcgagc | 240 |
| tggtcgaaaa gccgatccac catcaccaga acaccaacg agaacacggt gactctgaaa | 300 |
| atgaccagtc tgacagccgc ggacacggcc acctatttct gtgcgagagg tgttcctggt | 360 |
| tatgttacta aaagtagtct ctggggccca ggcaccctgg tcaccgtctc ctca | 414 |

<210> SEQ ID NO 75
<211> LENGTH: 357
<212> TYPE: DNA
<213> ORGANISM: Artificial Sequence
<220> FEATURE:
<223> OTHER INFORMATION: anti-GAA 376 (clone pEB0613B-4B1-H2) variable
      heavy domain coding sequence without leader sequence

<400> SEQUENCE: 75

| | |
|---|---|
| caggagcacc tggtggagtc cggggaggc ctggtcaacc ctggaggatc cctgacactc | 60 |
| acctgcacag cctctggatt ctccctcaac agcgtcgaca tgagctgggt ccgccaggct | 120 |
| ccagggaagg ggctggagtg gatcggattc agtaatgctt atcataggac atactacgcg | 180 |
| agctggtcga aaagccgatc caccatcacc agaaacacca cgagaacac ggtgactctg | 240 |
| aaaatgacca gtctgacagc cgcggacacg gccacctatt tctgtgcgag aggtgttcct | 300 |
| ggttatgtta ctaaaagtag tctctggggc ccaggcaccc tggtcaccgt ctcctca | 357 |

<210> SEQ ID NO 76
<211> LENGTH: 461
<212> TYPE: PRT
<213> ORGANISM: Artificial Sequence
<220> FEATURE:
<223> OTHER INFORMATION: anti-GAA 376 heavy chain amino acid sequence
      with leader sequence

<400> SEQUENCE: 76

Met Glu Thr Gly Leu Arg Trp Leu Leu Leu Val Ala Val Leu Lys Gly
1               5                   10                  15

Val Gln Cys Gln Glu His Leu Val Glu Ser Gly Gly Gly Leu Val Asn

-continued

```
                20                  25                  30
Pro Gly Gly Ser Leu Thr Leu Thr Cys Thr Ala Ser Gly Phe Ser Leu
                35                  40                  45
Asn Ser Val Asp Met Ser Trp Val Arg Gln Ala Pro Gly Lys Gly Leu
            50                  55                  60
Glu Trp Ile Gly Phe Ser Asn Ala Tyr His Arg Thr Tyr Tyr Ala Ser
 65                  70                  75                  80
Trp Ser Lys Ser Arg Ser Thr Ile Thr Arg Asn Thr Asn Glu Asn Thr
                85                  90                  95
Val Thr Leu Lys Met Thr Ser Leu Thr Ala Ala Asp Thr Ala Thr Tyr
            100                 105                 110
Phe Cys Ala Arg Gly Val Pro Gly Tyr Val Thr Lys Ser Ser Leu Trp
            115                 120                 125
Gly Pro Gly Thr Leu Val Thr Val Ser Ser Gly Gln Pro Lys Ala Pro
        130                 135                 140
Ser Val Phe Pro Leu Ala Pro Cys Cys Gly Asp Thr Pro Ser Ser Thr
145                 150                 155                 160
Val Thr Leu Gly Cys Leu Val Lys Gly Tyr Leu Pro Glu Pro Val Thr
                165                 170                 175
Val Thr Trp Asn Ser Gly Thr Leu Thr Asn Gly Val Arg Thr Phe Pro
            180                 185                 190
Ser Val Arg Gln Ser Ser Gly Leu Tyr Ser Leu Ser Ser Val Val Ser
            195                 200                 205
Val Thr Ser Ser Ser Gln Pro Val Thr Cys Asn Val Ala His Pro Ala
        210                 215                 220
Thr Asn Thr Lys Val Asp Lys Thr Val Ala Pro Ser Thr Cys Ser Lys
225                 230                 235                 240
Pro Met Cys Pro Pro Pro Glu Leu Leu Gly Gly Pro Ser Val Phe Ile
                245                 250                 255
Phe Pro Pro Lys Pro Lys Asp Thr Leu Met Ile Ser Arg Thr Pro Glu
            260                 265                 270
Val Thr Cys Val Val Val Asp Val Ser Gln Asp Asp Pro Glu Val Gln
            275                 280                 285
Phe Thr Trp Tyr Ile Asn Asn Glu Gln Val Arg Thr Ala Arg Pro Pro
        290                 295                 300
Leu Arg Glu Gln Gln Phe Asn Ser Thr Ile Arg Val Val Ser Thr Leu
305                 310                 315                 320
Pro Ile Ala His Gln Asp Trp Leu Arg Gly Lys Glu Phe Lys Cys Lys
                325                 330                 335
Val His Asn Lys Ala Leu Pro Ala Pro Ile Glu Lys Thr Ile Ser Lys
            340                 345                 350
Ala Arg Gly Gln Pro Leu Glu Pro Lys Val Tyr Thr Met Gly Pro Pro
            355                 360                 365
Arg Glu Glu Leu Ser Ser Arg Ser Val Ser Leu Thr Cys Met Ile Asn
        370                 375                 380
Gly Phe Tyr Pro Ser Asp Ile Ser Val Glu Trp Glu Lys Asn Gly Lys
385                 390                 395                 400
Ala Glu Asp Asn Tyr Lys Thr Thr Pro Ala Val Leu Asp Ser Asp Gly
                405                 410                 415
Ser Tyr Phe Leu Tyr Ser Lys Leu Ser Val Pro Thr Ser Glu Trp Gln
            420                 425                 430
Arg Gly Asp Val Phe Thr Cys Ser Val Met His Glu Ala Leu His Asn
            435                 440                 445
```

-continued

His Tyr Thr Gln Lys Ser Ile Ser Arg Ser Pro Gly Lys
        450                 455                 460

<210> SEQ ID NO 77
<211> LENGTH: 442
<212> TYPE: PRT
<213> ORGANISM: Artificial Sequence
<220> FEATURE:
<223> OTHER INFORMATION: anti-GAA 376 heavy chain amino acid sequence
      without leader sequence

<400> SEQUENCE: 77

Gln Glu His Leu Val Glu Ser Gly Gly Gly Leu Val Asn Pro Gly Gly
1               5                   10                  15

Ser Leu Thr Leu Thr Cys Thr Ala Ser Gly Phe Ser Leu Asn Ser Val
            20                  25                  30

Asp Met Ser Trp Val Arg Gln Ala Pro Gly Lys Gly Leu Glu Trp Ile
        35                  40                  45

Gly Phe Ser Asn Ala Tyr His Arg Thr Tyr Tyr Ala Ser Trp Ser Lys
    50                  55                  60

Ser Arg Ser Thr Ile Thr Arg Asn Thr Asn Glu Asn Thr Val Thr Leu
65                  70                  75                  80

Lys Met Thr Ser Leu Thr Ala Ala Asp Thr Ala Thr Tyr Phe Cys Ala
                85                  90                  95

Arg Gly Val Pro Gly Tyr Val Thr Lys Ser Ser Leu Trp Gly Pro Gly
            100                 105                 110

Thr Leu Val Thr Val Ser Ser Gly Gln Pro Lys Ala Pro Ser Val Phe
        115                 120                 125

Pro Leu Ala Pro Cys Cys Gly Asp Thr Pro Ser Ser Thr Val Thr Leu
    130                 135                 140

Gly Cys Leu Val Lys Gly Tyr Leu Pro Glu Pro Val Thr Val Thr Trp
145                 150                 155                 160

Asn Ser Gly Thr Leu Thr Asn Gly Val Arg Thr Phe Pro Ser Val Arg
                165                 170                 175

Gln Ser Ser Gly Leu Tyr Ser Leu Ser Ser Val Val Ser Val Thr Ser
            180                 185                 190

Ser Ser Gln Pro Val Thr Cys Asn Val Ala His Pro Ala Thr Asn Thr
        195                 200                 205

Lys Val Asp Lys Thr Val Ala Pro Ser Thr Cys Ser Lys Pro Met Cys
    210                 215                 220

Pro Pro Pro Glu Leu Leu Gly Gly Pro Ser Val Phe Ile Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Asp Asp Pro Glu Val Gln Phe Thr Trp
            260                 265                 270

Tyr Ile Asn Asn Glu Gln Val Arg Thr Ala Arg Pro Pro Leu Arg Glu
        275                 280                 285

Gln Gln Phe Asn Ser Thr Ile Arg Val Val Ser Thr Leu Pro Ile Ala
    290                 295                 300

His Gln Asp Trp Leu Arg Gly Lys Glu Phe Lys Cys Lys Val His Asn
305                 310                 315                 320

Lys Ala Leu Pro Ala Pro Ile Glu Lys Thr Ile Ser Lys Ala Arg Gly
                325                 330                 335

Gln Pro Leu Glu Pro Lys Val Tyr Thr Met Gly Pro Pro Arg Glu Glu

```
                       340                 345                 350
Leu Ser Ser Arg Ser Val Ser Leu Thr Cys Met Ile Asn Gly Phe Tyr
            355                 360                 365

Pro Ser Asp Ile Ser Val Glu Trp Glu Lys Asn Gly Lys Ala Glu Asp
        370                 375                 380

Asn Tyr Lys Thr Thr Pro Ala Val Leu Asp Ser Asp Gly Ser Tyr Phe
385                 390                 395                 400

Leu Tyr Ser Lys Leu Ser Val Pro Thr Ser Glu Trp Gln Arg Gly Asp
                405                 410                 415

Val Phe Thr Cys Ser Val Met His Glu Ala Leu His Asn His Tyr Thr
            420                 425                 430

Gln Lys Ser Ile Ser Arg Ser Pro Gly Lys
            435                 440

<210> SEQ ID NO 78
<211> LENGTH: 138
<212> TYPE: PRT
<213> ORGANISM: Artificial Sequence
<220> FEATURE:
<223> OTHER INFORMATION: anti-GAA 376 variable heavy domain amino acid
      sequence with leader sequence

<400> SEQUENCE: 78

Met Glu Thr Gly Leu Arg Trp Leu Leu Leu Val Ala Val Leu Lys Gly
1               5                   10                  15

Val Gln Cys Gln Glu His Leu Val Glu Ser Gly Gly Gly Leu Val Asn
            20                  25                  30

Pro Gly Gly Ser Leu Thr Leu Thr Cys Thr Ala Ser Gly Phe Ser Leu
        35                  40                  45

Asn Ser Val Asp Met Ser Trp Val Arg Gln Ala Pro Gly Lys Gly Leu
    50                  55                  60

Glu Trp Ile Gly Phe Ser Asn Ala Tyr His Arg Thr Tyr Tyr Ala Ser
65                  70                  75                  80

Trp Ser Lys Ser Arg Ser Thr Ile Thr Arg Asn Thr Asn Glu Asn Thr
                85                  90                  95

Val Thr Leu Lys Met Thr Ser Leu Thr Ala Ala Asp Thr Ala Thr Tyr
            100                 105                 110

Phe Cys Ala Arg Gly Val Pro Gly Tyr Val Thr Lys Ser Ser Leu Trp
        115                 120                 125

Gly Pro Gly Thr Leu Val Thr Val Ser Ser
    130                 135

<210> SEQ ID NO 79
<211> LENGTH: 119
<212> TYPE: PRT
<213> ORGANISM: Artificial Sequence
<220> FEATURE:
<223> OTHER INFORMATION: anti-GAA 376 variable heavy domain amino acid
      sequence without leader sequence

<400> SEQUENCE: 79

Gln Glu His Leu Val Glu Ser Gly Gly Gly Leu Val Asn Pro Gly Gly
1               5                   10                  15

Ser Leu Thr Leu Thr Cys Thr Ala Ser Gly Phe Ser Leu Asn Ser Val
            20                  25                  30

Asp Met Ser Trp Val Arg Gln Ala Pro Gly Lys Gly Leu Glu Trp Ile
        35                  40                  45

Gly Phe Ser Asn Ala Tyr His Arg Thr Tyr Tyr Ala Ser Trp Ser Lys
```

```
                50                  55                  60
Ser Arg Ser Thr Ile Thr Arg Asn Thr Asn Glu Asn Thr Val Thr Leu
 65                  70                  75                  80

Lys Met Thr Ser Leu Thr Ala Ala Asp Thr Ala Thr Tyr Phe Cys Ala
                 85                  90                  95

Arg Gly Val Pro Gly Tyr Val Thr Lys Ser Ser Leu Trp Gly Pro Gly
            100                 105                 110

Thr Leu Val Thr Val Ser Ser
        115
```

<210> SEQ ID NO 80
<211> LENGTH: 717
<212> TYPE: DNA
<213> ORGANISM: Artificial Sequence
<220> FEATURE:
<223> OTHER INFORMATION: anti-GAA 376 (clone pEB0613B-4B1-K2) light chain coding sequence with leader sequence

<400> SEQUENCE: 80

```
atggacacga gggcccccac tcagctgctg ggctcctgc tgctctggct cccaggtgcc    60
acatttgcca tcgtgatgac ccagactcca tcttccaagt ctgtccctgt gggagacaca   120
gtcaccatca attgccaggc cagtcagagt gtttatggta caacgaatt atcctggtat   180
cagcagaaac caggacaacc tcccaagctc ctgatctaca aggcttccac tctggcatct   240
ggggtccctt cgcggttcaa aggcagtgga tctgggacac agttcactct caccatcagt   300
ggcgtggagt gtgacgatgc tgccacttac tactgtgcag atatagtag tggtgtgatt   360
gatgttagtg ctttcggcgg ggggaccgag gtggtggtca aggtgatcc agttgcacct   420
actgtcctca tcttcccacc agctgctgat caggtggcaa ctggaacagt caccatcgtg   480
tgtgtggcga ataaatactt tcccgatgtc accgtcacct gggaggtgga tggcaccacc   540
caaacaactg gcatcgagaa cagtaaaaca ccgcagaatt ctgcagattg tacctacaac   600
ctcagcagca ctctgacact gaccagcaca cagtacaaca gccacaaaga gtacacctgc   660
aaggtgaccc agggcacgac ctcagtcgtc cagagcttca taggggtga ctgttag       717
```

<210> SEQ ID NO 81
<211> LENGTH: 648
<212> TYPE: DNA
<213> ORGANISM: Artificial Sequence
<220> FEATURE:
<223> OTHER INFORMATION: anti-GAA 376 (clone pEB0613B-4B1-K2) light chain coding sequence without leader sequence

<400> SEQUENCE: 81

```
atcgtgatga cccagactcc atcttccaag tctgtccctg tgggagacac agtcaccatc    60
aattgccagg ccagtcagag tgtttatggt aacaacgaat tatcctggta tcagcagaaa   120
ccaggacaac ctcccaagct cctgatctac aaggcttcca ctctggcatc tggggtccct   180
tcgcggttca aaggcagtgg atctgggaca cagttcactc tcaccatcag tggcgtggag   240
tgtgacgatg ctgccactta ctactgtgca ggatatagta gtggtgtgat tgatgttagt   300
gctttcggcg ggggaccga ggtggtggtc aaggtgatc cagttgcacc tactgtcctc   360
atcttcccac cagctgctga tcaggtggca actggaacag tcaccatcgt gtgtgtggcg   420
aataaatact ttcccgatgt caccgtcacc tgggaggtgg atggcaccac ccaaacaact   480
ggcatcgaga acagtaaaac accgcagaat tctgcagatt gtacctacaa cctcagcagc   540
actctgacac tgaccagcac acagtacaac agccacaaag agtacacctg caaggtgacc   600
```

```
caggggcacga cctcagtcgt ccagagcttc aatagggtg actgttag              648
```

<210> SEQ ID NO 82
<211> LENGTH: 402
<212> TYPE: DNA
<213> ORGANISM: Artificial Sequence
<220> FEATURE:
<223> OTHER INFORMATION: anti-GAA 376 (clone pEB0613B-4B1-K2) variable
      light domain coding sequence with leader sequence

<400> SEQUENCE: 82

```
atggacacga gggcccccac tcagctgctg gggctcctgc tgctctggct cccaggtgcc    60
acatttgcca tcgtgatgac ccagactcca tcttccaagt ctgtccctgt gggagacaca   120
gtcaccatca attgccaggc cagtcagagt gtttatggta caacgaatt atcctggtat    180 cagcagaaac aggacaacc tcccaagctc ctgatctaca aggcttccac tctggcatct    240
ggggtccctt cgcggttcaa aggcagtgga tctgggacac agttcactct caccatcagt   300
ggcgtggagt gtgacgatgc tgccacttac tactgtgcag gatatagtag tggtgtgatt   360
gatgttagtg ctttcggcgg ggggaccgag gtggtggtca aa                      402
```

<210> SEQ ID NO 83
<211> LENGTH: 333
<212> TYPE: DNA
<213> ORGANISM: Artificial Sequence
<220> FEATURE:
<223> OTHER INFORMATION: anti-GAA 376 (clone pEB0613B-4B1-K2) variable
      light domain coding sequence without leader sequence

<400> SEQUENCE: 83

```
atcgtgatga cccagactcc atcttccaag tctgtccctg tgggagacac agtcaccatc    60
aattgccagg ccagtcagag tgtttatggt aacaacgaat tatcctggta tcagcagaaa   120
ccaggacaac ctcccaagct cctgatctac aaggcttcca ctctggcatc tggggtccct   180
tcgcggttca aaggcagtgg atctgggaca cagttcactc tcaccatcag tggcgtggag   240
tgtgacgatg ctgccactta ctactgtgca ggatatagta gtggtgtgat tgatgttagt   300
gctttcggcg gggggaccga ggtggtggtc aaa                                333
```

<210> SEQ ID NO 84
<211> LENGTH: 238
<212> TYPE: PRT
<213> ORGANISM: Artificial Sequence
<220> FEATURE:
<223> OTHER INFORMATION: anti-GAA 376 light chain amino acid sequence
      with leader sequence

<400> SEQUENCE: 84

```
Met Asp Thr Arg Ala Pro Thr Gln Leu Leu Gly Leu Leu Leu Leu Trp
1               5                   10                  15

Leu Pro Gly Ala Thr Phe Ala Ile Val Met Thr Gln Thr Pro Ser Ser
            20                  25                  30

Lys Ser Val Pro Val Gly Asp Thr Val Thr Ile Asn Cys Gln Ala Ser
        35                  40                  45

Gln Ser Val Tyr Gly Asn Asn Glu Leu Ser Trp Tyr Gln Gln Lys Pro
    50                  55                  60

Gly Gln Pro Pro Lys Leu Leu Ile Tyr Lys Ala Ser Thr Leu Ala Ser
65                  70                  75                  80

Gly Val Pro Ser Arg Phe Lys Gly Ser Gly Ser Gly Thr Gln Phe Thr
                85                  90                  95
```

-continued

```
Leu Thr Ile Ser Gly Val Glu Cys Asp Asp Ala Ala Thr Tyr Tyr Cys
                100                 105                 110

Ala Gly Tyr Ser Ser Gly Val Ile Asp Val Ser Ala Phe Gly Gly Gly
            115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
                195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235
```

```
<210> SEQ ID NO 85
<211> LENGTH: 215
<212> TYPE: PRT
<213> ORGANISM: Artificial Sequence
<220> FEATURE:
<223> OTHER INFORMATION: anti-GAA 376 light chain amino acid sequence
      without leader sequence

<400> SEQUENCE: 85

Ile Val Met Thr Gln Thr Pro Ser Ser Lys Ser Val Pro Val Gly Asp
1               5                   10                  15

Thr Val Thr Ile Asn Cys Gln Ala Ser Gln Ser Val Tyr Gly Asn Asn
            20                  25                  30

Glu Leu Ser Trp Tyr Gln Gln Lys Pro Gly Gln Pro Pro Lys Leu Leu
        35                  40                  45

Ile Tyr Lys Ala Ser Thr Leu Ala Ser Gly Val Pro Ser Arg Phe Lys
50                  55                  60

Gly Ser Gly Ser Gly Thr Gln Phe Thr Leu Thr Ile Ser Gly Val Glu
65                  70                  75                  80

Cys Asp Asp Ala Ala Thr Tyr Tyr Cys Ala Gly Tyr Ser Ser Gly Val
                85                  90                  95

Ile Asp Val Ser Ala Phe Gly Gly Gly Thr Glu Val Val Val Lys Gly
            100                 105                 110

Asp Pro Val Ala Pro Thr Val Leu Ile Phe Pro Pro Ala Ala Asp Gln
        115                 120                 125

Val Ala Thr Gly Thr Val Thr Ile Val Cys Val Ala Asn Lys Tyr Phe
    130                 135                 140

Pro Asp Val Thr Val Thr Trp Glu Val Asp Gly Thr Thr Gln Thr Thr
145                 150                 155                 160

Gly Ile Glu Asn Ser Lys Thr Pro Gln Asn Ser Ala Asp Cys Thr Tyr
                165                 170                 175

Asn Leu Ser Ser Thr Leu Thr Leu Thr Ser Thr Gln Tyr Asn Ser His
            180                 185                 190

Lys Glu Tyr Thr Cys Lys Val Thr Gln Gly Thr Thr Ser Val Val Gln
        195                 200                 205

Ser Phe Asn Arg Gly Asp Cys
```

-continued

```
              210                 215
```

<210> SEQ ID NO 86
<211> LENGTH: 134
<212> TYPE: PRT
<213> ORGANISM: Artificial Sequence
<220> FEATURE:
<223> OTHER INFORMATION: anti-GAA 376 variable light domain amino acid
      sequence with leader sequence

<400> SEQUENCE: 86

```
Met Asp Thr Arg Ala Pro Thr Gln Leu Leu Gly Leu Leu Leu Trp
1               5                   10                  15

Leu Pro Gly Ala Thr Phe Ala Ile Val Met Thr Gln Thr Pro Ser Ser
                20                  25                  30

Lys Ser Val Pro Val Gly Asp Thr Val Thr Ile Asn Cys Gln Ala Ser
            35                  40                  45

Gln Ser Val Tyr Gly Asn Asn Glu Leu Ser Trp Tyr Gln Gln Lys Pro
        50                  55                  60

Gly Gln Pro Pro Lys Leu Leu Ile Tyr Lys Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Glu Cys Asp Asp Ala Ala Thr Tyr Tyr Cys
            100                 105                 110

Ala Gly Tyr Ser Ser Gly Val Ile Asp Val Ser Ala Phe Gly Gly Gly
        115                 120                 125

Thr Glu Val Val Val Lys
            130
```

<210> SEQ ID NO 87
<211> LENGTH: 111
<212> TYPE: PRT
<213> ORGANISM: Artificial Sequence
<220> FEATURE:
<223> OTHER INFORMATION: anti-GAA 376 variable light domain amino acid
      sequence without leader sequence

<400> SEQUENCE: 87

```
Ile Val Met Thr Gln Thr Pro Ser Ser Lys Ser Val Pro Val Gly Asp
1               5                   10                  15

Thr Val Thr Ile Asn Cys Gln Ala Ser Gln Ser Val Tyr Gly Asn Asn
                20                  25                  30

Glu Leu Ser Trp Tyr Gln Gln Lys Pro Gly Gln Pro Pro Lys Leu Leu
            35                  40                  45

Ile Tyr Lys Ala Ser Thr Leu Ala Ser Gly Val Pro Ser Arg Phe Lys
        50                  55                  60

Gly Ser Gly Ser Gly Thr Gln Phe Thr Leu Thr Ile Ser Gly Val Glu
65                  70                  75                  80

Cys Asp Asp Ala Ala Thr Tyr Tyr Cys Ala Gly Tyr Ser Ser Gly Val
                85                  90                  95

Ile Asp Val Ser Ala Phe Gly Gly Gly Thr Glu Val Val Val Lys
            100                 105                 110
```

PROTEOMIC SCREENING FOR LYSOSOMAL STORAGE DISEASES

CROSS-REFERENCE TO RELATED APPLICATION

This application claims priority to U.S. Provisional Patent Application No. 63/002,992 filed on Mar. 31, 2020, which is incorporated herein by reference in its entirety as if fully set forth herein.

STATEMENT REGARDING FEDERALLY SPONSORED RESEARCH OR DEVELOPMENT

This invention was made with government support under HD098180 and AI123135 awarded by the National Institutes of Health. The government has certain rights in the invention.

STATEMENT REGARDING SEQUENCE LISTING

The Sequence Listing associated with this application is provided in text format in lieu of a paper copy and is hereby incorporated by reference into the specification. The name of the text file containing the Sequence Listing is 2GU5154_ST25.txt. The text file is 74 KB, was created on Mar. 31, 2021, and is being submitted electronically via EFS-Web.

FIELD OF THE DISCLOSURE

The current disclosure provides clinical diagnosis and newborn screening for lysosomal storage diseases (LSDs) including Mucopolysaccharidosis Type I (MPS I or Hurler Syndrome) and Pompe Disease. The disclosed methods and assays can also allow rapid prediction of whether a patient with LSD will develop an immune response to enzyme replacement therapy (ERT), thus improving treatment for patients with LSDs. The disclosed methods and assays can further reduce the number of false positives caused by pseudo deficiency cases of LSD.

BACKGROUND OF THE DISCLOSURE

There are a number of diseases with effective treatments available. However, for a number of these diseases, once symptoms emerge, the disease is already fatal or has led to irreversible damage. Examples of such disorders include metabolic disorders, such as lysosomal storage diseases (LSDs). These include Mucopolysaccharidosis Type I (MPS I) and Pompe Disease.

LSDs include a group of more than 50 rare inherited metabolic disorders that result from defects in lysosome function. Lysosomes are intracellular compartments filled with enzymes responsible for the breakdown of large molecules and the relay of the breakdown fragments to other parts of the cell for recycling. This process requires several critical enzymes, and defects in one or more of these enzymes can cause the large molecules to accumulate within the cell, eventually killing the cell. Patients having an LSD can have damage to skeletal muscle, bones, and the nervous system.

Treatment for LSDs include providing functioning exogenous enzymes (e.g., in a form of a drug) in enzyme replacement therapy (ERT). However, some patients will develop immune-mediated inhibitory reactions, including neutralizing antibodies, to ERT. Immunomodulation can be undertaken to combat this immune response in a patient but is most effective when initiated prior to ERT. Therefore, knowing whether a patient suffering from an LSD will develop an immune reaction to ERT before starting the treatment can be critical. Currently, molecular analyses to predict which patients will develop such immune reactions are slow and labor-intensive, taking months to complete. During this time, patients may have developed ERT-neutralizing antibodies. Nonetheless, currently there are no standard clinical tests with fast turn-around times that can reliably help predict immune reactions to ERT.

Newborn screening (NBS) is a standard public preventive mandatory screening test carried out routinely for the 4 million babies born every year in the U.S. NBS usually involves a blood test performed 24 to 48 hours after birth. The screening usually uses a few drops of blood from a newborn's heel deposited on filter paper. The paper containing dried blood spots (DBS) can be stored until the tests are conducted.

To conduct NBS assessments, punches of dried blood are taken from the DBS and laboratory tests are performed to detect the presence or absence of specific substances within the blood (called markers or biomarkers) that are indicative of disorders not apparent at birth but that cause serious health problems later in life. Though the disorders screened vary from state to state, most states screen for phenylketonuria, primary congenital hypothyroidism, cystic fibrosis, and sickle cell disease. NBS has proven to be highly effective at improving patient outcomes and avoiding long-term disability in affected individuals, while at the same time reducing healthcare costs.

NBS for several LSDs, including MPS I and Pompe Disease, has been approved in many states. The screening involves measurement of lysosomal enzymatic activities in DBSs, typically by tandem mass spectrometry or digital microfluidics fluorimetry. Newborns having an assay value for enzyme activity below a predetermined cut-off value are considered positive for an LSD. However, lack of analytical precision can warrant additional second-tier tests to confirm screen-positive results. The enzymatic assay relies on synthetic substrates, which are not identical to the natural substrates; thus, the enzymes will behave differently towards those artificial substrates and potentially cause misdiagnosis. Furthermore, the enzymatic assay requires that the functions and structures of the relevant enzymes remain intact, which will be difficult to control during transportation and storage of the NBS samples from various parts of the country or states.

Therefore, robust and simple methods and assays are needed to screen for LSDs with lower false positive rate and higher positive prediction rate and simultaneously allow for rapid prediction of whether a patient will develop immune reactions to ERT.

SUMMARY OF THE DISCLOSURE

The current disclosure describes development of multiplexed assays that can be used to screen subjects for LSDs including Mucopolysaccharidosis Type I (MPS I; Hurler Syndrome) and Pompe Disease. The assays can significantly improve outcomes for affected individuals by reliably diagnosing these disorders before devastating and often fatal clinical symptoms emerge. The assays can detect the presence or absence of markers associated with these disorders using DBS, among other sources of biological samples. In particular embodiments, the subjects are newborns and the DBS are already routinely collected as part of existing NBS procedures. In particular embodiments, the samples can include buccal swabs, peripheral blood mononuclear cells (PBMCs), or white blood cells (WBCs) collected in the clinic for follow up confirmation after presumptive positive result from NBS. In particular embodiments, the assays can predict whether a subject will develop an immune reaction to ERT and distinguish cases of enzyme pseudo deficiency from confirmed LSD patients.

The current disclosure describes peptides associated with each of the disorders that can be reliably detected and quantified using peptide immunoaffinity enrichment coupled to selected reaction monitoring mass spectrometry (immuno-SRM). The current disclosure also provides high affinity antibodies that can be used to enrich for the indicated peptides.

In particular embodiments, an antibody or antigen binding fragment thereof of the disclosure includes: a heavy chain variable (VH) domain including CDR1 of SEQ ID NO: 5, CDR2 of SEQ ID NO: 6, and CDR3 of SEQ ID NO: 7, and a light chain variable (VL) domain including CDR1 of SEQ ID NO: 8, CDR2 of SEQ ID NO: 9, and CDR3 of SEQ ID NO: 10. In particular embodiments, an antibody or antigen binding fragment thereof of the disclosure includes a VH domain as set forth in SEQ ID NO: 13 and a VL domain as set forth in SEQ ID NO: 16. In particular embodiments, an antibody or antigen binding fragment thereof of the disclosure includes: a VH domain including CDR1 of SEQ ID NO: 17, CDR2 of SEQ ID NO: 18, and CDR3 of SEQ ID NO: 19, and a VL domain including CDR1 of SEQ ID NO: 20, CDR2 of SEQ ID NO: 21, and CDR3 of SEQ ID NO: 22. In particular embodiments, an antibody or antigen binding fragment thereof of the disclosure includes a VH domain as set forth in SEQ ID NO: 25 and a VL domain as set forth in SEQ ID NO: 28. In particular embodiments, the disclosure provides assays and kits including an antibody or antigen binding fragment thereof described herein. In particular embodiments, the antibody or antigen binding fragment thereof is a recombinant antibody or antigen binding fragment thereof.

Particular embodiments include using the antibodies or antigen binding fragments thereof of the disclosure to screen for MPS I and/or Pompe Disease in newborns and also high-risk subjects. In particular embodiments, the antibodies or antigen-binding fragments thereof can be used to determine true positive cases, to eliminate pseudo deficiency, and to determine efficacy of one or more treatments in a subject being treated for MPS I and/or Pompe Disease. Particular embodiments include using the antibodies or antigen binding fragments thereof of the disclosure to detect one or more signature peptides of MPS I and/or Pompe Disease in one or more biological samples. The disclosure also provides a method for predicting whether a subject will develop an immune response to enzyme replacement therapy (ERT) for MPS I and/or Pompe Disease.

BRIEF DESCRIPTION OF THE DRAWINGS

Some of the drawings submitted herein may be better understood in color. Applicant considers the color versions of the drawings as part of the original submission and reserves the right to present color images of the drawings in later proceedings.

FIG. 1. Table listing protein targets and peptide sequences used for peptide immunoaffinity enrichment coupled to selected reaction monitoring mass spectrometry (immuno-SRM-MS) for Mucopolysaccharidosis Type I (MPS I; Hurler Syndrome) and Pompe Disease. Total mass, parent ion mass, daughter y-ion masses, and daughter b-ion masses are also shown.

(FIG. 3A) IDUA 218 peptide biomarker level in 100 normal controls and 11 MPS I patients (dotted line represents the cutoff for IDUA 218). (FIG. 3B) enlarged version of FIG. 3A with the focus from 0 to 10 pmol/L (dashed line represents the LOD of IDUA 218). (FIG. 3C) IDUA 462 peptide biomarker level in 100 normal controls and 11 MPS I patients (dotted line represents the cutoff for IDUA 462). (FIG. 3D) enlarged version of FIG. 3C with the focus from 0 to 5 pmol/L (dashed line represents the LOD of IDUA 462).

(FIG. 8A) GAA 332 MRM traces; (FIG. 8B) GAA 855 MRM traces.

(FIG. 10A) GAA 155 MRM traces, TTPTFFPK (SEQ ID NO: 3), parent ion mass 469.7527++; (FIG. 10B) GAA 376 MRM traces, WGYSSTAITR (SEQ ID NO: 5), parent ion mass 571.2855++ with boundary lines 102 for the peak area in the DBS samples (II) and boundary lines 104 for the peak area in the buccal swab samples (III).

Figure 2:
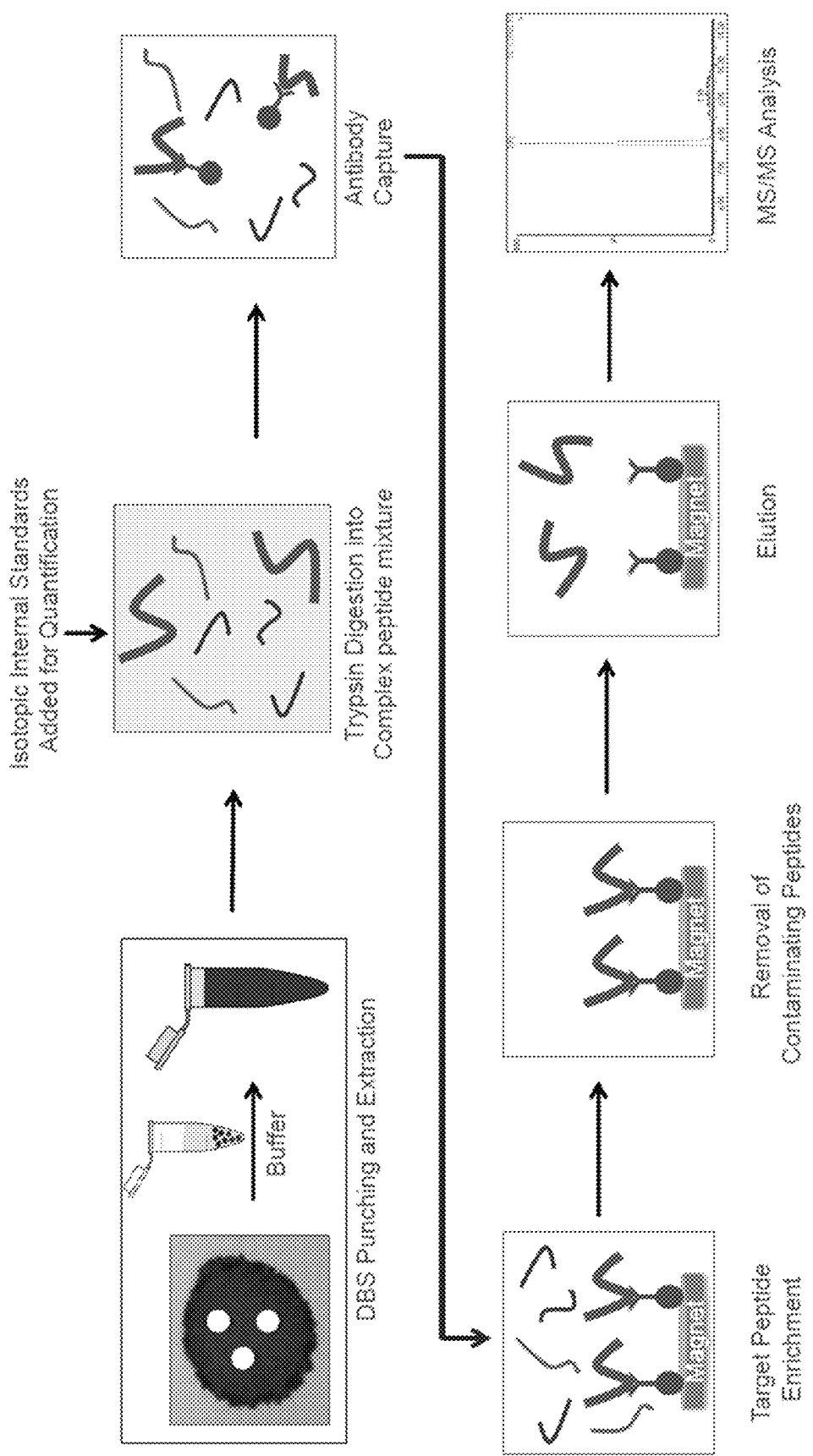
FIG. 2. Schematic illustrating the process of immuno-SRM-MS.

| SEQ ID NO: | Description |
|---|---|
| 16 | anti-IDUA 218 variable heavy domain coding sequence with leader sequence |
| 17 | anti-IDUA 218 variable heavy domain amino acid sequence with leader sequence |
| 18 | anti-IDUA 218 variable heavy domain amino acid sequence without leader sequence |
| 19 | anti-IDUA 218 variable light domain coding sequence with leader sequence |
| 20 | anti-IDUA 218 variable light domain amino acid sequence with leader sequence |
| 21 | anti-IDUA 218 variable light domain amino acid sequence without leader sequence |
| 28 | anti-IDUA 462 variable heavy domain coding sequence with leader sequence |
| 29 | anti-IDUA 462 variable heavy domain amino acid sequence with leader sequence |
| 30 | anti-IDUA 462 variable heavy domain amino acid sequence without leader sequence |
| 31 | anti-IDUA 462 variable light domain coding sequence with leader sequence |
| 32 | anti-IDUA 462 variable light domain amino acid sequence with leader sequence |
| 33 | anti-IDUA 462 variable light domain amino acid sequence without leader sequence |
| 40 | anti-IDUA 218 variable heavy domain coding sequence without leader sequence |
| 41 | anti-IDUA 218 variable light domain coding sequence without leader sequence |
| 42 | anti-IDUA 462 variable heavy domain coding sequence without leader sequence |
| 43 | anti-IDUA 462 variable light domain coding sequence without leader sequence |
| 50 | anti-GAA 155 (clone pEB0613A-3B2-H1) heavy chain coding sequence with leader sequence |
| 51 | anti-GAA 155 (clone pEB0613A-3B2-H1) heavy chain coding sequence without leader sequence |
| 52 | anti-GAA 155 (clone pEB0613A-3B2-H1) variable heavy domain coding sequence with leader sequence |
| 53 | anti-GAA 155 (clone pEB0613A-3B2-H1) variable heavy domain coding sequence without leader sequence |
| 54 | anti-GAA 155 heavy chain amino acid sequence with leader sequence |
| 55 | anti-GAA 155 heavy chain amino acid sequence without leader sequence |
| 56 | anti-GAA 155 variable heavy domain amino acid sequence with leader sequence |
| 57 | anti-GAA 155 variable heavy domain amino acid sequence without leader sequence |
| 58 | anti-GAA 155 (clone pEB0613A-3B2-K3) light chain coding sequence with leader sequence |
| 59 | anti-GAA 155 (clone pEB0613A-3B2-K3) light chain coding sequence without leader sequence |
| 60 | anti-GAA 155 (clone pEB0613A-3B2-K3) variable light domain coding sequence with leader sequence |
| 61 | anti-GAA 155 (clone pEB0613A-3B2-K3) variable light domain coding sequence without leader sequence |
| 62 | anti-GAA 155 light chain amino acid sequence with leader sequence |
| 63 | anti-GAA 155 light chain amino acid sequence without leader sequence |
| 64 | anti-GAA 155 variable light domain amino acid sequence with leader sequence |
| 65 | anti-GAA 155 variable light domain amino acid sequence without leader sequence |
| 72 | anti-GAA 376 (clone pEB0613B-4B1-H2) heavy chain coding sequence with leader sequence |
| 73 | anti-GAA 376 (clone pEB0613B-4B1-H2) heavy chain coding sequence withoutl eader sequence |
| 74 | anti-GAA 376 (clone pEB0613B-4B1-H2) variable heavy domain coding sequence with leader sequence |
| 75 | anti-GAA 376 (clone pEB0613B-4B1-H2) variable heavy domain coding sequence without leader sequence |
| 76 | anti-GAA 376 heavy chain amino acid sequence with leader sequence |
| 77 | anti-GAA 376 heavy chain amino acid sequence without leader sequence |
| 78 | anti-GAA 376 variable heavy domain amino acid sequence with leader sequence |
| 79 | anti-GAA 376 variable heavy domain amino acid sequence without leader sequence |
| 80 | anti-GAA 376 (clone pEB0613B-4B1-K2) light chain coding sequence with leader sequence |
| 81 | anti-GAA 376 (clone pEB0613B-4B1-K2) light chain coding sequence without leader sequence |
| 82 | anti-GAA 376 (clone pEB0613B-4B1-K2) variable light domain coding sequence with leader sequence |
| 83 | anti-GAA 376 (clone pEB0613B-4B1-K2) variable light domain coding sequence without leader sequence |
| 84 | anti-GAA 376 light chain amino acid sequence with leader sequence |
| 85 | anti-GAA 376 light chain amino acid sequence without leader sequence |
| 86 | anti-GAA 376 variable light domain amino acid sequence with leader sequence |
| 87 | anti-GAA 376 variable light domain amino acid sequence without leader sequence |

DETAILED DESCRIPTION

There are a number of diseases with effective treatments available. However, for a number of these diseases, once symptoms emerge, the disease is already fatal or has led to irreversible damage. Examples of disorders that would benefit from early diagnosis include metabolic disorders such as lysosomal storage diseases (LSDs) including Mucopolysaccharidosis Type I (MPS I) and Pompe Disease.

LSDs include a group of more than 50 rare inherited metabolic disorders that result from defects in lysosome function. Lysosomes are intracellular compartments filled with enzymes responsible for the breakdown of large molecules and the relay of the breakdown fragments to other parts of the cell for recycling. This process requires several critical enzymes. Defects in one or more of these enzymes can cause the large molecules to accumulate within the cell, eventually killing the cell.

Mucopolysaccharidosis Type I (MPS I; Hurler Syndrome) is a rare LSD belonging to the group of mucopolysaccharidoses. MPS I can be further divided into severe and attenuated types. The severe form of MPS I is also known as Hurler Syndrome. Severe and attenuated forms of MPS I have similar symptoms and complications; however, attenuated forms of MPS I show slower disease progression and/or later age of onset of symptoms. In particular embodiments, subjects with attenuated MPS I do not show early developmental delay and/or do not experience progressive decline in mental capabilities. In particular embodiments, onset of symptoms and complications occur between ages three and ten years for individuals with attenuated MPS I. In particular embodiments, the spectrum of disease severity is broad for individuals with attenuated MPS I, including life-threatening complications leading to death in their twenties to thirties, to a normal life span with significant joint problems and cardiorespiratory disease. In particular embodiments, linear growth decreases by age three years in individuals with severe MPS I. In particular embodiments, mental disability is progressive and profound in individuals with severe MPS I. In particular embodiments, death occurs within the first ten years of life for individuals with severe MPS I. In particular embodiments, diagnosis of individuals with severe versus attenuated MPS I is made with clinical and laboratory findings. Individuals with MPS I may have macrocephaly, a buildup of fluid in the brain, heart valve abnormalities, distinctive-looking facial features, short stature, joint deformities, an enlarged liver and spleen, and a large tongue. Upper respiratory infections and sleep apnea can occur due to a narrowed airway. People with MPS I often develop clouding of the cornea, have hearing loss, and have recurrent ear infections. Children with severe MPS I usually have a shortened lifespan, sometimes living only into late childhood. Heart disease and airway obstruction are major causes of death in people with both severe and attenuated MPS I. MPS I is caused by a variation in the IDUA gene, which encodes an alpha-L-iduronidase enzyme that is needed to break down complex carbohydrates produced in the body called glycosaminoglycans (or mucopolysaccharides). A deficiency of the IDUA enzyme leads to build up of glycosaminoglycans in the lysosomes of all cells and progressive damage of tissues. Therapies for MPS I include: providing the deficient or missing alpha-L-iduronidase enzyme in enzyme replacement therapy (ERT); hematopoietic stem cell transplantation (HSCT); bone marrow transplantation; and alleviating symptoms of the disease.

Pompe Disease (PD) is a rare inherited lysosomal storage disorder that disables the heart and skeletal muscles. PD can include infantile onset and late onset. The infantile onset PD can be further characterized as classic or non-classic. In particular embodiments, symptoms can emerge within a few months of birth for infants with the classic form of infantile onset PD. In particular embodiments, infants with the classic form of infantile onset PD can have the following symptoms: muscle weakness; poor muscle tone; an enlarged liver; heart defects; failure to gain weight and grow at the expected rate; and/or breathing problems. In particular embodiments, infants with the classic form of infantile onset PD die from heart failure in the first year of life. In particular embodiments, symptoms can emerge by one year old for infants with the non-classic form of infantile onset PD. In particular embodiments, infants with the non-classic form of infantile onset PD can have the following symptoms: delayed motor skills and progressive muscle weakness; an abnormally large heart; and/or serious breathing problems. In particular embodiments, children with non-classic infantile onset Pompe disease live only into early childhood. Late onset PD appears later in childhood, adolescence, or adulthood and is usually milder than the infantile onset forms. In particular embodiments, late onset PD is less likely to include heart problems. In particular embodiments, individuals with late onset PD experience can have progressive muscle weakness, especially in the legs, in the trunk, and in the muscles that control breathing. In particular embodiments, individuals with late onset PD can have respiratory failure. PD is caused by mutations in the GAA gene, which encodes an acid alpha-glucosidase enzyme. GAA enzyme functions in lysosomes to break down glycogen to glucose, a sugar that fuels muscles. Thus, a deficiency of GAA enzyme results in excessive amounts of lysosomal glycogen accumulation everywhere in the body, but the cells of the heart and skeletal muscles are the most seriously affected. Up to 300 different mutations in the GAA gene that cause the symptoms of PD have been identified, which can vary widely in terms of age of onset and severity. Treatment for PD include ERT. An FDA-approved drug called alglucosidase alfa (Myozyme©) can be used for the treatment of infants and children with PD. Another alglucosidase alfa drug, Lumizyme©, has been approved for late-onset (non-infantile) Pompe Disease.

Newborn screening (NBS) for several LSDs, including PD and MPS I, has been approved in many states. The screening involves measurement of lysosomal enzymatic activities in DBS by tandem mass spectrometry (MS/MS) or by digital microfluidics fluorimetry (DMF-F) (Gelb et al., *Int J Neonatal Screen.* 5(1): 1, 2019). The enzymatic assay relies on synthetic substrates, which are not identical to the natural substrates; thus, the enzymes will behave differently towards those artificial substrates and potentially cause misdiagnosis. Furthermore, the enzymatic assay requires that the functions and structures of the relevant enzymes remain intact, which will be difficult to control during transportation and storage of the NBS samples from various parts of the country or states. The current screening methods present with high false positive rates and low positive prediction rate. Moreover, the current screening methods cannot determine if the patients will develop an immune response to ERT.

ERT is effective, for example, in prolonging survival and protecting cognitive development in patients with infantile PD; and improving pulmonary functioning, stabilizing disease progression, and reducing biochemical parameters in patients with MPS I. However, some patients will develop immune-mediated inhibitory reactions (neutralizing antibodies) to ERT. Currently, molecular analysis and Cross-Reactive Immunological Material (CRIM) analysis are used to predict which patients with PD will develop immune-mediated inhibitory reactions to ERT. CRIM-negative status is a poor prognostic factor for PD. Up to 25% of patients with PD are CRIM-negative and make no GAA protein, resulting in the development of sustained high antibody titers to ERT and ineffective treatment. Immune-mediated inhibitory reactions to ERT also occur in MPS I. 90% of patients with MPS I will develop an anti-drug IgG antibody response to Laronidase ERT during the first few months of treatment. Higher anti-drug IgG antibody levels impair enzyme uptake in target tissues and lead to decreased tissue glycosaminoglycan clearance and immune-mediated hypersensitivity reactions.

Immunomodulation to reduce production of ERT-neutralizing antibodies is most effective when initiated prior to ERT. Therefore, determination of CRIM status before starting the ERT can be critical, especially for infantile PD associated with devastating, early-onset cardiomyopathy. However, CRIM status is typically determined by Western blot using cultured skin fibroblasts, a process that takes months. During this time, patients may have developed ERT-neutralizing antibodies. Currently there are no standard clinical tests with fast turn-around time that can reliably help predict the immune reactions to ERT. The disclosed assays, compositions, and methods herein determine the status of LSD patients by measuring the abundances of the relevant proteins, which not only avoids the issues with artificial substrates and enzyme function fluctuation, but also allows rapid prediction of whether a patient will develop immune reactions to ERT.

The disclosed compositions and methods can further be used to reduce the number of false positives caused by pseudo deficiency cases in NBS for MPS I and Pompe disease. A pseudo deficient allele of a gene associated with an LSD includes one or more mutations (as compared to a corresponding wild type gene) in one copy of the gene that encodes an altered protein or changes the expression of the gene but does not cause disease. Individuals with a pseudo deficient allele show greatly reduced enzyme activity, but they are healthy. In particular embodiments, clinically healthy subjects with a pseudo deficient allele of a gene associated with an LSD show reduced activity of the enzyme encoded by the gene in vitro. In particular embodiments, clinically healthy subjects with a pseudo deficient allele of a gene associated with an LSD show reduced activity of the enzyme encoded by the gene in vitro but functional activity of the same enzyme in vivo. In particular embodiments, clinically healthy subjects can have one or two copies of a pseudo deficient allele. In particular embodiments, a false positive result occurs in an enzyme assay test when test results are positive, but disease or morbidity is not present in the tested subject, or disease is present at a subclinical level in the tested subject. In particular embodiments, healthy subjects do not exhibit or exhibit very few symptoms of a disease. In particular embodiments, healthy subjects do not need treatment for a disease. In particular embodiments, healthy subjects with a pseudo deficient allele associated with an LSD do not exhibit or exhibit very few symptoms of the LSD. In particular embodiments, healthy subjects with a pseudo deficient allele associated with an LSD do not need treatment for the LSD.

The disclosed compositions and methods can further be used to identify individuals that are carriers of a pathogenic variant of a gene that causes an LSD. Most LSDs are inherited in an autosomal recessive manner. Thus, an individual manifests symptoms and complications of an LSD if they have two copies (are recessive) of a version of a gene (allele) or two different alleles associated with the LSD that causes disease (a pathogenic variant(s)), whereas carriers have only one copy of a pathogenic variant of the gene that causes the LSD but do not present with disease. In particular embodiments, carriers have one copy of a pathogenic variant of a gene that causes an LSD and one wild type copy of the corresponding gene. In particular embodiments, carriers have one copy of a pathogenic variant of a gene that causes an LSD and one pseudo deficient allele of the corresponding gene. In particular embodiments, carriers of a pathogenic variant of a gene that causes LSD do not exhibit or exhibit very few symptoms of the LSD. In particular embodiments, carriers of a pathogenic variant of a gene that causes LSD do not need treatment for the LSD.

To conduct NBS assessments, punches of dried blood are taken from the DBS and laboratory tests are performed to detect the presence or absence of specific substances within the blood (called markers or biomarkers) that are indicative of disorders not apparent at birth but that cause serious health problems later in life. Though the disorders screened vary from state to state, most states screen for phenylketonuria, primary congenital hypothyroidism, cystic fibrosis, and sickle cell disease. NBS has proven to be highly effective at improving patient outcomes and avoiding long-term disability in affected individuals, while at the same time reducing healthcare costs. Unfortunately, detection is often limited by the extremely low protein concentrations in blood cells and limited blood volume present in DBS.

Tandem mass spectrometry (MS/MS) was first applied to NBS in the 1990s, paving the way for rapid screening of multiple metabolites and thus several diseases from DBS samples collected at birth (Chace, J Mass Spectrom. Wiley-Blackwell; 2009; 44: 163-170; Millington et al., J. Inherit. Metab. Dis. 1990; 13: 321-324; Sweetman et al. Pediatrics. 2006; 117: S308-S314; Almannai et al., Curr. Opin. Pediatr. 2016; 28: 694-699; Watson et al., Genet. Med. Nature Publishing Group; 2006. pp. 1S-252S; Chace et al., Clin. Chem. 1993; 39: 66-71). Selected reaction monitoring mass spectrometry (SRM-MS) performed on triple quadrupole mass spectrometers further enabled the precise, high-throughput, and analytically-robust quantification of specific biomarkers; as such, it is now the standard of care at clinical NBS laboratories across the world (Chace, J Mass Spectrom. Wiley-Blackwell; 2009; 44: 163-170; Chace & Kalas, Clinical Biochemistry. 2005; 38: 296-309; Dott et al., American Journal of Medical Genetics Part A. Wiley Subscription Services, Inc., A Wiley Company; 2006; 140: 837-842).

It was previously shown that an MS-based approach for the quantification of signature peptides for BTK, WASP, and a T-Cell marker CD3ε from tryptic digests of PBMCs can be used to screen X-linked agammaglobulinemia (XLA), Wiskott-Aldrich Syndrome (WAS), and SCID, respectively (Kerfoot et al., Proteomics Clin Appl, 2012. 6(7-8): p. 394-402). CD3ε was chosen as a general representation of T-Cell number as all SCID patients share T-Cell lymphopenia despite genetic heterogeneity. Each patient in the blinded study was deficient in the signature peptide specific for their respective disease (i.e., XLA patient lacking Bruton's Tyrosine Kinase (BTK) and WAS patient missing WAS protein (WASP), etc.).

SRM-MS utilizes proteolytically-generated signature peptides as stoichiometric surrogates of a protein of interest. This may, in turn, be used to estimate the number of a particular cell-type expressing that protein in a sample (i.e. quantification of CD3ε for an indication of the amount of CD3+ T-cells in blood). The high specificity of MS for each signature peptide is conferred by three physiochemical properties—its mass, retention times upon high-performance liquid chromatography (HPLC) separation, and resultant target-specific fragmentation patterns (Kennedy et al. Nat. Methods. 2014; 11: 149-155). Despite these advances, with a typical limit of quantification ranging from 100 to 1000 ng protein/mL, the use of complex matrices such as blood or plasma often precludes accurate quantification of low-abundance targets by SRM-MS based assays.

Peptide immunoaffinity enrichment coupled to SRM-MS (immuno-SRM) is a method that enables precise quantification of low abundance markers. Immuno-SRM generally involves the following steps: (i) selection of target proteins that are indicative of the presence or absence of a disorder; (ii) treatment of a biological sample that would include the target protein, if present, with enzymes to digest all proteins in the biological sample into smaller fragments called peptides; (iii) enrichment for selected peptide markers derived from the target protein; and (iv) analysis and quantification of the enriched peptides of interest in a mass spectrometer.

Immuno-SRM, also referred to as Stable Isotope Standards and Capture by Anti-Peptide Antibodies (SISCAPA), increases the sensitivity of SRM-MS assays by utilizing anti-peptide antibodies to purify and enrich peptides of interest from a complex biologic sample prior to SRM-MS analysis (Zhao et al. J Vis Exp. 2011; 53: 2812; Whiteaker et al. Mol. Cell Proteomics. American Society for Biochemistry and Molecular Biology; 2010; 9: 184-196; Whiteaker et al. Mol. Cell Proteomics. American Society for Biochemistry and Molecular Biology; 2012; 11: M111.015347; Kuhn et al. Clin. Chem. 2009; 55: 1108-1117; Anderson et al. J Proteome Res. 2004; 3(2): 235-244; Collins et al., Frontiers in Immunology, 2018. 9(2756); Collins et al., Frontiers in Immunology, 2020; 11:464; Jung et al., J Proteome Res, 2017. 16(2): p. 862-871; Collins et al., Gastroenterology, 2021: Feb. 25; 50016-5085(21)00457-1). A representative immuno-SRM process is illustrated in FIG. 2.

Immuno-affinity enrichment of signature peptide biomarkers using anti-peptide antibodies isolates peptides of interest from complex biological matrices. This simplifies the sample matrix, reduces background, and concentrates analytes to enhance the sensitivity of the liquid chromatography-tandem mass spectrometry (LC-MS/MS) assay (Anderson et al., J Proteome Res, 2004. 3(2): p. 235-44; Anderson and Hunter, Mol Cell Proteomics, 2006. 5(4): p.

573-88). Immuno-SRM allows for quantification of proteins present at low picomolar concentrations in blood with high reproducibility (Whiteaker et al., Mol Cell Proteomics, 2010. 9(1): p. 184-96; Whiteaker et al., J Proteome Res, 2014. 13(4): p. 2187-96; Hoofnagle et al., Clin Chem, 2008. 54(11): p. 1796-804; Hoofnagle et al., Clin Chem, 2016. 62(1): p. 48-69; Kuhn et al., Mol Cell Proteomics, 2012. 11(6): p. M111.013854). Using this methodology, in a blinded screen of 82 samples (42 patient samples with 40 normal controls), all were significantly reduced in their respective peptides and diagnostic cutoffs allowed for the positive identification of every molecularly confirmed case of XLA (n=26), WAS (n=11) and 2 of 3 cases of SCID (PCT/US2019/054856; Collins et al., Frontiers in Immunology, 2018. 9(2756)).

Signature peptide markers and antibodies that bind to them have also been developed to diagnose primary immunodeficiencies such as X-linked chronic granulomatous disease (X-CGD), X-linked lymphoproliferative syndrome (XLP1; SH2D1A deficiency), familial hemophagocytic lymphohistiocytosis 2 (FHL2), ataxia telangiectasia (AT), common variable immunodeficiency (CVID; B-cell dysfunctions), adenosine deaminase (ADA) deficiency, and dedicator of cytokinesis 8 (DOCK8) deficiency (PCT/US2021/020679), and to detect cell specific markers for platelets (CD42) and natural killer cells (CD56) (PCT/US2021/020679), using immuno-SRM.

In samples from 28 primary immunodeficiency disease (PIDD) patients including two carriers, representing X-Linked Agammaglobulinemia (XLA), Wiskott-Aldrich Syndrome (WAS), X-CGD, DOCK8 Deficiency, and ADA deficiency, peptides representing each disease were significantly reduced relative to normal controls and patient identification had excellent agreement with clinical and molecular diagnosis. Also included in the multiplex panel were cell specific markers for platelets (CD42) and natural killer cells (CD56). In patients with WAS, CD42 levels were found to be significantly reduced consistent with characteristic thrombocytopenia. A patient with WAS analyzed before and after bone marrow transplant showed normalized WAS protein and platelet CD42 after treatment, highlighting the ability of immuno-SRM to monitor the effects of PIDD treatment. (Collins et al., Frontiers in Immunology, 2020. 11(464)).

Many aspects of an immuno-SRM assay depend on the disorder being diagnosed, the biomarkers available for each disorder, the ability to develop molecular entities that can enrich for peptides of interest, and the behavior of each peptide of interest in the mass spectrometer. All of these aspects and more require careful consideration and experimentation to achieve a reliable assay that can reliably detect disorders in an NBS panel using DBS before clinical symptoms emerge.

The present disclosure provides a multiplexed immuno-SRM method to reliably diagnose LSDs including MPS I and PD. The multiplexed immuno-SRM assay disclosed herein can utilize anti-peptide antibodies generated against peptides of proteins reduced or absent in MPS I and PD. The disclosed methods and assays can allow rapid prediction of whether a patient with an LSD will develop an immune response to enzyme replacement therapy (ERT). The disclosed methods and assays can further reduce the number of false positives caused by pseudo deficiency cases of LSD.

The following aspects of the disclosure are now described in more detail: (I) Collection and Processing of Biological Samples; (II) Peptide Markers for MPS I and Pompe Disease; (Ill) Enzymatic Digestion of Proteins in a Biological Sample; (IV) Antibodies to Enrich for the Peptide Markers; (V) Variants; (VI) Enrichment Strategies for Peptides; (VII) Liquid Chromatography (LC); (VIII) Mass Spectrometry (MS); (IX) Methods of Use; (X) Kits; (XI) Exemplary Embodiments; (XII) Experimental Examples; and (XIII) Closing Paragraphs.

(I) Collection and Processing of Biological Samples

In particular embodiments, biological samples that can be used in the methods of the present disclosure include samples derived from blood or cells. In particular embodiments, samples used in the methods of the present disclosure are DBS. In particular embodiments, whole blood from a subject can be prepared by placing blood onto a filter paper card and allowing the blood to dry.

In particular embodiments, whole blood from a subject can be collected in any anticoagulant. In particular embodiments, whole blood from a subject can be collected in heparin. DBS can be prepared by pipetting 50-100 µL (e.g., 70 µL) blood/spot onto filter paper card (e.g., Protein Saver™ 903® Card, Whatman Inc, Piscataway, N.J.), and allowed to dry at room temperature. In particular embodiments, blood is allowed to dry on filter paper card overnight. DBS can be stored, for example, in sealed plastic bags at −80° C. until use. In particular embodiments, the whole DBS can be used in the immuno-SRM assays of the disclosure. In particular embodiments, one or more 3-mm punches from the DBS can be used in the immuno-SRM assays of the disclosure. In particular embodiments, DBS can be solubilized with 0.1% Triton X-100 in 50 mM ammonium bicarbonate.

In particular embodiments, samples used in the methods of the present disclosure include cells obtained from buccal swabs or mucosal samples. In particular embodiments, mucosal samples include oral, nasal, genital, and rectal samples (Espinosa-de Aquino et al. (2017) Methods in Ecology and Evolution 8:370-378). In particular embodiments, buccal swab samples include cells from the cheek or mouth. In particular embodiments, buccal swab samples can be obtained from a subject following a protocol described in the following: CHLA. (2016, April 4). Buccal Swab Collection Procedure. CHLA-Clinical Pathology; (2016, July 27). Buccal DNA Collection Instructions. Pathway Genomics; (2017, Dec. 14). Instruction for Buccal Swab Sample Collection. Otogenetics; PDXL PDXL. (2017, Nov. 28). *Buccal Swab collection procedure—PersonalizedDx Labs* [Video]. YouTube. On World Wide Web at youtu.be/3ftvHkfM71o?t=146; and Centers of Disease Control and Prevention (CDC). (2020, July 8). Interim Guidelines for collecting, handling, and testing clinical specimens for Covid-19. On World Wide Web at cdc.gov/coronavirus/2019-ncov/lab/guidelines-clinical-specimens.html.

In particular embodiments, buccal swab samples can be obtained from a subject with the following protocol. Prior to sample collection, the patient does not smoke, eat, drink, chew gum or brush their teeth for at least 30 minutes. A swab is carefully removed from the package, making sure the tip does not touch any objects or surfaces. The swab is inserted into the buccal cavity, which is located to one side of the mouth between the cheek, teeth and upper gum. The tip of the swab is pressed inside of one cheek and rubbed back and forth, up and down, in a circular motion. The handle is rotated during the rub to cover the entire tip with cells from the cheek. The tip is not allowed to touch the teeth, gums and lips during the collection process. The swab is not allowed to be over saturated with saliva. After collection, the swab is removed from the mouth without touching the teeth, gums or lips. The swab is allowed to air dry at room temperature for at least 30 minutes. The swab, with the handle removed, may be stored in a cryogenic vial. The steps may be repeated with a second swab on the opposite cheek. Buccal swab samples may be stored at 2-8° C. for up to 72 hours after collection or in the freezer at −80° C. or below if longer than 72 hours. In particular embodiments, the collection of cells with the buccal swab may be for at least 30 seconds. In particular embodiments, the collection of cells with the buccal swab may be collected from maximum mucosal surfaces. In particular embodiments, one to five buccal swab samples may be collected per subject. In particular embodiments, the buccal swab sample may be air dried on a sterile surface for at least five min, at least 10 min, at least 15 min, at least 20 min, at least 25 min, at least 30 min, or longer. In particular embodiments, the subject may rinse their mouth with clean water prior to sample collection. In particular embodiments, the area of sample collection may be moistened with saline using a separate swab. In particular embodiments, buccal swab samples may be stored at 25° C., 20° C., 15° C., 10° C., 5° C., 0° C., −5° C., −10° C., −15° C., −20° C., or below. In particular embodiments, buccal swab samples may be stored at −20° C. for one to two weeks. In particular embodiments, buccal samples may be collected from a water and/or mouthwash rinse instead of a swab (Michalczyk et al. (2004) BioTechniques 37(2):262-269).

In particular embodiments, cells from a buccal swab sample can be solubilized with 0.1% Triton X-100 in 50 mM ammonium bicarbonate. In particular embodiments, proteins may be isolated from buccal swab samples following the protocol described in Espinosa-de Aquino et al. (2017). In particular embodiments, cells from buccal swab samples may be extracted with an appropriate buffer such as TRIzol (Thermo Fisher Scientific, Waltham, Mass.) and the supernatant after nucleic acid precipitation may be used for protein extraction. In particular embodiments, proteins may be precipitated with acetone, the protein pellet may be resuspended in an appropriate buffer (e.g., guanidine hydrochloride in 95% ethanol supplemented with 2.5% glycerol), the pellet may be dispersed by sonication, the pellet may be centrifuged and washed, the pellet may be dried, and the pellet may be solubilized in an appropriate buffer (e.g., PBS and sodium dodecyl sulfate). In particular embodiments, the solubilized pellet may be heated at 100° C. and then centrifuged to obtain a supernatant for use.

In particular embodiments, samples used in the methods of the present disclosure include peripheral blood mononuclear cells (PBMCs). PBMCs come from peripheral blood and originate from hematopoietic stem cells (HSCs) that reside in the bone marrow. A PBMC is a blood cell with a round nucleus and can include many types of cells including monocytes, lymphocytes (including T cells, B cells, and NK cells), dendritic cells, and stem cells. PBMC can be isolated by any technique known in the art, including density centrifugation (e.g., with Ficoll-Paque). Density gradient centrifugation separates cells by cell density. In particular embodiments, whole blood or buffy coat layer may be layered over or under a density medium without mixing of the two layers followed by centrifugation. In particular embodiments, the PBMC appears as a thin white layer at the interface between the plasma and the density gradient medium. In particular embodiments, Vacutainer® blood draw tubes containing Ficoll-Hypaque and a gel plug that separates the Ficoll solution from the blood to be drawn can be used (cell preparation tubes CPT™, BD Biosciences, San Jose, Calif.; Puleo et al. (2017) Bio-protocol 7(2): e2103). In particular embodiments, SepMate™ tubes (STEMCELL™ Technologies, Vancouver, Calif.) designed with an insert to keep the density gradient medium and the sample from mixing prior to centrifugation can be used. (Kerfoot et al., Proteomics Clin Appl, 2012. 6(7-8):394-402; Grievink et al., Biopresery Biobank. 2016 October; 14(5):410-415; Corkum et al. (2015) BMC Immunol. 16:48; Jia et al. (2018) Biopresery Biobank 16(2):82-91). In particular embodiments, PBMC can be isolated by leukapheresis. A leukapheresis machine is an automated device that takes whole blood from a donor and separates out the target PBMC fraction using high-speed centrifugation while returning the remaining portion of the blood, including plasma, red blood cells, and granulocytes, back to the donor. In particular embodiments, isolated PBMCs can be solubilized with 0.1% Triton X-100 in 50 mM ammonium bicarbonate.

In particular embodiments, samples used in the methods of the present disclosure include white blood cells (WBC; leukocytes). WBCs are part of the immune system and protect the body from infections and foreign invaders. In particular embodiments, WBCs include granulocytes (polymorphonuclear cells), lymphocytes (mononuclear cells), and monocytes (mononuclear cells). In particular embodiments, WBCs include lymphocytes and monocytes but not granulocytes. WBC can be isolated and optionally enriched by any technique known in the art, including: density gradient centrifugation (Boyum (1968) Isolation of mononuclear cells and granulocytes from human blood. Isolation of mononuclear cells by one centrifugation and of granulocytes by combining centrifugation and sedimentation at 1 g. Scand. J. Clin. Lab Invest. Suppl. 97:77; Boyum (1977) Lymphology, 10(2): 71-76); erythrocyte lysis by osmotic shock (Morgensen and Cantrell (1977) Pharm Therap. 1: 369-383); RosetteSep™ (STEMCELL™ Technologies, Vancouver, Calif.) including antibody mediated binding of unwanted cells to red blood cells and removal by density gradient separation (Beeton and Chandy (2007) J Vis Exp. (8): 326); magnetic bead for cell enrichment or depletion (Brocks et al (2006) In vivo 20(2): 239); complement-mediated lysis to enrich for B and/or NK cells (Faguet and Agee (1993) J Imm Meth 165(2): 217); and panning to remove unwanted cells including cell enrichment or depletion by adherence to an antibody coated plate (Brousso et al (1997) Immunol Let 59(2):85). See Dagur and McCoy (2015) Curr Protoc Cytom. 73:5.1.1-5.1.16 for a review on isolation and enrichment protocols for WBC.

(II) Peptide Markers for MPS I and Pompe Disease

There are many theoretical proteolytic peptides from target proteins. Those can be potential candidates for monoclonal antibody production. Nonetheless, the best potential candidate peptides were chosen after screening their characteristics by MS/MS. Those signature peptides with the highest sensitivity and specificity were selected to develop corresponding monoclonal antibodies and validated using clinical samples. In particular embodiments, multiple peptides and antibodies can be included in a multiplex analysis to increase the throughput of an immuno-SRM assay and reduce the cost and time required by the assay.

Typically, one or two signature proteotypic peptides that are unique to the protein of interest and that are consistently observed in MS experiments are selected to stoichiometrically represent the protein of interest (Mallick et al. Nat Biotechnol 2007; 25: 125-131). Signature peptides can be selected by detection in previous MS experiments, use of computational tools to predict the peptides most likely observable by MS, or a combination of both. In particular embodiments, tryptic peptides 5-22 amino acids in length with moderate hydrophobicity can be selected. Very hydrophilic and very hydrophobic peptides can be less stable due to retention time variation in HPLC and loss to surfaces. In particular embodiments, methionine residues (oxidation), N-terminal glutamine (cyclization), asparagine followed by glycine or proline (prone to deamidation), and dibasic termini (e.g. neighboring lysine or arginine residues such as KK, KR, RR, RK have the potential for variable digestion efficiency) can be undesirable (Whiteaker and Paulovich, Clin Lab Med. 2011; 31(3): 385-396). Shorter peptides and those containing proline residues can be better targets for SRM (Lange et al., Molecular Systems Biology 2008; 4: 222).

In particular embodiments, the peptides include portions of IDUA and/or GAA. In particular embodiments, the peptides include SEQ ID NOs: 1-9. In particular embodiments, peptides of the present disclosure include those described in Table 1A-1C and FIG. 1.

In particular embodiments, exemplary CDR sequences of antibodies of the present disclosure are shown in Table 1A. In particular embodiments, exemplary variable heavy (VH) and variable light (VL) domain sequences of antibodies of the present disclosure are shown in Table 1B. In particular embodiments, SEQ ID NOs of exemplary peptides and antibodies of the present disclosure are shown in Table 10.

TABLE 1A

Exemplary CDR sequences of antibodies of the present disclosure

| Antibody/Disease | VH CDRs | VL CDRs |
| --- | --- | --- |
| Anti-IDUA 218/<br>Mucopolysaccharidosis<br>Type 1 (MPS I) | CDR1: RYWMH<br>(SEQ ID NO: 10)<br>CDR2: EINPSNGGTNYNEKFKN<br>(SEQ ID NO: 11)<br>CDR3: AMDY<br>(SEQ ID NO: 12) | CDR1: KSSQSLLHSDGKTYLN<br>(SEQ ID NO: 13)<br>CDR2: LVSKLDS<br>(SEQ ID NO: 14)<br>CDR3: WQGLHFPWT<br>(SEQ ID NO: 15) |
| Anti-IDUA 462/<br>MPS I | CDR1: DTYMH<br>(SEQ ID NO: 22)<br>CDR2: RIDPANGNTKYGPKFQG<br>(SEQ ID NO: 23)<br>CDR3: TARAPFAY<br>(SEQ ID NO: 24) | CDR1: RSSKSLLYKDGKTYLN<br>(SEQ ID NO: 25)<br>CDR2: WMSTRAS<br>(SEQ ID NO: 26)<br>CDR3: QQVVEYPFT<br>(SEQ ID NO: 27) |
| Anti-GAA 155/<br>Pompe Disease | CDR1: SYVMS<br>(SEQ ID NO: 44)<br>CDR2: VISTGGITYYANWAKG<br>(SEQ ID NO: 45)<br>CDR3: GFSGDNYV<br>(SEQ ID NO: 46) | CDR1: QSSQNVHSNNYLS<br>(SEQ ID NO: 47)<br>CDR2: LASTLAS<br>(SEQ ID NO: 48)<br>CDR3: AGDYTTNIYV<br>(SEQ ID NO: 49) |
| Anti-GAA 376/<br>Pompe Disease | CDR1: SVDMS<br>(SEQ ID NO: 66)<br>CDR2: FSNAYHRTYYASWSKS<br>(SEQ ID NO: 67)<br>CDR3: GVPGYVTKSSL<br>(SEQ ID NO: 68) | CDR1: QASQSVYGNNELS<br>(SEQ ID NO: 69)<br>CDR2: KASTLAS<br>(SEQ ID NO: 70)<br>CDR3: AGYSSGVIDVSA<br>(SEQ ID NO: 71) |

TABLE 1B

Exemplary variable heavy (VH) and variable light (VL) domain sequences of antibodies of the present disclosure

| Variable domain | SEQ ID NO: | Amino acid sequence |
| --- | --- | --- |
| Anti-IDUA 218 VH | 18 | QVQLQQPGTELVKPGASVKLSCKASGYTFTRYWMHWVKQRPGQ<br>GLEWIGEINPSNGGTNYNEKFKNKATLNVDKSSSTAYMQLSSLTSE<br>DSAVYYCTLAMDYWGQGTSVTVSS |
| Anti-IDUA 218 VL | 21 | DVVMTQTPLTLSVTIGQPASISCKSSQSLLHSDGKTYLNWSLQRPG<br>QSPKRLIYLVSKLDSGVPDRFTGSGSGTDFTLKISRVEAEDLGVYYC<br>WQGLHFPWTFGGGTKLEIK |
| Anti-IDUA 462 VH | 30 | EVQLQQSGAELVKPGASVKLSCTASGFNIKDTYMHWVNQRPEQGL<br>EWIGRIDPANGNTKYGPKFQGKATITADTSSNTAYLQLSSLTSEDTA<br>VYYCAQTARAPFAYWGQGTLVTVSA |
| Anti-IDUA 462 VL | 33 | DIVITQDEVSNPVTSGESVSISCRSSKSLLYKDGKTYLNWFLQRPG<br>QSPQLLVYWMSTRASGVSDRFSGSGSGTDFTLKISRVKAEDVGMY<br>YCQQVVEYPFTFGTGTKLEIK |
| Anti-GAA 155 VH | 57 | QSVEESGGRLVTPGTPLTLTCTASGFSLNSYVMSWVRQAPGEGLE<br>WIGVISTGGITYYANWAKGRFTISKTSTTVDLKITSPRTEDTATYFCA<br>RGFSGDNYVWGPGTLVTVSF |

TABLE 1B-continued

Exemplary variable heavy (VH) and variable light (VL) domain sequences of antibodies of the present disclosure

| Variable domain | SEQ ID NO: | Amino acid sequence |
|---|---|---|
| Anti-GAA 155 VL | 65 | ADIVMTQTPSSTSAAVGGTVTINCQSSQNVHSNNYLSWFQQKPGQ PPKLLIYLASTLASGVPSRFKGSGSGTEFTLTISDLECDDAATYYCA GDYTTNIYVFGGGTEVVVK |
| Anti-GAA 376 VH | 79 | QEHLVESGGGLVNPGGSLTLTCTASGFSLNSVDMSWVRQAPGKG LEWIGFSNAYHRTYYASWSKSRSTITRNTNENTVTLKMTSLTAADT ATYFCARGVPGYVTKSSLWGPGTLVTVSS |
| Anti-GAA 376 VL | 87 | IVMTQTPSSKSVPVGDTVTINCQASQSVYGNNELSWYQQKPGQPP KLLIYKASTLASGVPSRFKGSGSGTQFTLTISGVECDDAATYYCAGY SSGVIDVSAFGGGTEVVVK |

TABLE 1C

SEQ ID NOs for exemplary peptides and antibodies of the present disclosure

| Disease or Target Cell | Target Protein | Peptides SEQ ID NO | SEQ ID NOS VH CDRs | VL CDRs | VH domain | VL domain |
|---|---|---|---|---|---|---|
| Mucopolysaccharidosis Type 1 (MPS I) | IDUA | IDUA 218-230 SEQ ID NO: 1 | 10-12 | 13-15 | 16-18, 40 | 19-21, 41 |
| MPS I | IDUA | IDUA 462-474 SEQ ID NO: 2 | 22-24 | 25-27 | 28-30, 42 | 31-33, 43 |
| Pompe Disease | GAA | GAA 155-162 SEQ ID NO: 3 | 44-46 | 47-49 | 52, 53, 56, 57 [50, 51, 54, 55]^ | 60, 61, 64, 65 [58, 59, 62, 63]^ |
| Pompe Disease | GAA | GAA 332-348 SEQ ID NO: 4 | | | | |
| Pompe Disease | GAA | GAA 376-385 SEQ ID NO: 5 | 66-68 | 69-71 | 74, 75, 78, 79 [72, 73, 76, 77]^ | 82, 83, 86, 87 [80, 81, 84, 85]^ |
| Pompe Disease | GAA | GAA 601-608 SEQ ID NO: 6 | | | | |
| Pompe Disease | GAA | GAA 855-870 SEQ ID NO: 7 | | | | |
| Pompe Disease | GAA | GAA 882-891 SEQ ID NO: 8 | | | | |
| Pompe Disease | GAA | GAA 892-903 SEQ ID NO: 9 | | | | |

*Underlined SEQ ID NOs denote nucleotide sequences. Non-underlined SEQ ID NOs denote amino acid sequences.
^Heavy and light chain SEQ ID NOs are in brackets.

(III) Enzymatic Digestion of Proteins in a Biological Sample

Proteins in a biological sample can be subjected to proteolysis to produce peptides that can be further selected by immunoaffinity purification before analysis by LC-SRM-MS. In particular embodiments, a biological sample includes DBS, cells from a buccal swab sample, PBMCs, or WBCs. Proteolysis can be accomplished using site specific endoproteases, such as pepsin, arg-C proteinase, asp-N endopeptidase, BNPS-skatole, caspase 1, caspase 2, caspase 3, caspase 4, caspase 5, caspase 6, caspase 7, caspase 8, caspase 9, caspase 10, chymotrypsin, clostripain (clostridiopeptidase B), enterokinase, factor Xa, glutamyl endopeptidase, granzyme B, lysC, proline-endopeptidase, proteinase K, staphylococcal peptidase I, thermolysin, thrombin, and trypsin. Chemicals which cleave site specifically can also be used. Combinations of enzymes and/or chemicals can be used to obtain desirable analytes.

In particular embodiments, proteins in a biological sample can be digested into peptides with trypsin. Trypsin cleaves exclusively C-terminal to arginine and lysine residues and can be a preferred choice to generate peptides because the masses of generated peptides are compatible with the detection ability of most mass spectrometers (up to 3000 m/z) and because there are efficient algorithms available for the generation of databases of theoretical trypsin-generated peptides. High cleavage specificity, availability, and low cost are other advantages of trypsin. Peptides formed by the treatment of a protein with trypsin are known as tryptic peptides.

(IV) Antibodies to Enrich for the Peptide Markers

An antibody includes a polypeptide ligand substantially encoded by an immunoglobulin gene or immunoglobulin genes, or functional fragments thereof, whether natural, or partially or wholly synthetically produced. An antibody specifically (or selectively) binds and recognizes an epitope (e.g., an antigen). An antibody can include any protein having a binding domain that is homologous or largely homologous to an immunoglobulin binding domain. An antibody preparation may be monoclonal or polyclonal. The antibody may be a member of any immunoglobulin class, including any of the human classes: IgG, IgM, IgA, IgD, and IgE, etc. The recognized immunoglobulin genes include the kappa and lambda light chain constant region genes, the alpha, gamma, delta, epsilon and mu heavy chain constant region genes, and the myriad immunoglobulin variable region genes. "Fc" portion of an antibody refers to that portion of an immunoglobulin heavy chain that includes one or more heavy chain constant region domains, CH1, CH2 and CH3, but does not include the heavy chain variable region.

An intact antibody can include at least two heavy (H) chains and two light (L) chains inter-connected by disulfide bonds. Each heavy chain is composed of a heavy chain variable region (abbreviated herein as VH or VH) and a heavy chain constant region. The heavy chain constant region includes three domains, CH1, CH2 and CH3. Each light chain is composed of a light chain variable region (abbreviated herein as VL or VL) and a light chain constant region. The light chain constant region includes one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The precise amino acid sequence boundaries of a given CDR or FR can be readily determined using any of a number of well-known schemes, including those described by: Kabat et al. (1991) "Sequences of Proteins of Immunological Interest," 5th Ed. Public Health Service, National Institutes of Health, Bethesda, Md. (Kabat numbering scheme); Al-Lazikani et al. (1997) J Mol Biol 273: 927-948 (Chothia numbering scheme); Maccallum et al. (1996) J Mol Biol 262: 732-745 (Contact numbering scheme); Martin et al. (1989) Proc. Natl. Acad. Sci., 86: 9268-9272 (AbM numbering scheme); Lefranc M P et al. (2003) Dev Comp Immunol 27(1): 55-77 (IMGT numbering scheme); and Honegger and Pluckthun (2001) J Mol Biol 309(3): 657-670 ("Aho" numbering scheme). The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. In particular embodiments, the antibody CDR sequences disclosed herein are according to Kabat numbering.

An antibody fragment includes any derivative or portion of an antibody that is less than full-length. In particular embodiments, the antibody fragment retains at least a significant portion of the full-length antibody's specific binding ability as a binding partner. Examples of antibody fragments include Fab, Fab', Fab'-SH, F(ab')$_2$, single chain variable fragment (scFv), Fv, dsFv diabody, and Fd fragments, and/or any biologically effective fragments of an immunoglobulin that bind specifically to an epitope described herein. Antibodies or antibody fragments include all or a portion of polyclonal antibodies, monoclonal antibodies, human antibodies, humanized antibodies, synthetic antibodies, chimeric antibodies, bispecific antibodies, mini bodies, and linear antibodies.

A single chain variable fragment (scFv) is a fusion protein of the variable regions of the heavy and light chains of immunoglobulins connected with a short linker peptide. Fv fragments include the VL and VH domains of a single arm of an antibody. Although the two domains of the Fv fragment, VL and VH, are coded by separate genes, they can be joined, using, for example, recombinant methods, by a synthetic linker that enables them to be made as a single protein chain in which the VL and VH regions pair to form monovalent molecules (single chain Fv (scFv)). For additional information regarding Fv and scFv, see e.g., Bird, et al., Science 242 (1988) 423-426; Huston, et al., Proc. Natl. Acad. Sci. USA 85 (1988) 5879-5883; Plueckthun, in The Pharmacology of Monoclonal Antibodies, vol. 113, Rosenburg and Moore (eds.), Springer-Verlag, New York), (1994) 269-315; WO1993/16185; U.S. Pat. Nos. 5,571,894; and 5,587,458.

A Fab fragment is a monovalent antibody fragment including VL, VH, CL and CH1 domains. A F(ab')$_2$ fragment is a bivalent fragment including two Fab fragments linked by a disulfide bridge at the hinge region. For discussion of Fab and F(ab')$_2$ fragments having increased in vivo half-life, see U.S. Pat. No. 5,869,046. Diabodies include two epitope-binding sites that may be bivalent. See, for example, EP 0404097; WO1993/01161; and Holliger, et al., Proc. Natl. Acad. Sci. USA 90 (1993) 6444-6448. Dual affinity retargeting antibodies (DART™; based on the diabody format but featuring a C-terminal disulfide bridge for additional stabilization (Moore et al., Blood 117, 4542-51 (2011)) can also be used. Antibody fragments can also include isolated CDRs. For a review of antibody fragments, see Hudson, et al., Nat. Med. 9 (2003) 129-134.

The antibody fragment may be produced by any means. For example, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may include a single chain antibody fragment. In another embodiment, the fragment may include multiple chains that are linked together, for example, by disulfide linkages. The fragment may also include a multimolecular complex. A functional antibody fragment may typically include at least 50 amino acids and more typically will include at least 200 amino acids.

In particular embodiments, recombinant immunoglobulins can be produced. See, Cabilly, U.S. Pat. No. 4,816,567, and Queen et al., Proc Natl Acad Sci USA, 86:10029-10033 (1989).

As indicated, in particular embodiments, binding domains of an engineered antibody or antigen binding fragment may be joined through a linker. A linker is an amino acid sequence which can provide flexibility and room for conformational movement between the binding domains of an engineered antibody or antigen binding fragment. Any appropriate linker may be used. Examples of linkers can be found in Chen et al., Adv Drug Deliv Rev. 2013 Oct. 15; 65(10): 1357-1369. Linkers can be flexible, rigid, or semi-rigid, depending on the desired functional domain presentation to a target. Commonly used flexible linkers include Gly-Ser linkers such as GGSGGGSGGSG (SEQ ID NO: 34), GGSGGGSGSG (SEQ ID NO: 35) and GGSGGGSG (SEQ ID NO: 36). Additional examples include: GGGGSGGGGS (SEQ ID NO: 37); GGGSGGGS (SEQ ID NO: 38); and GGSGGS (SEQ ID NO: 39). Linkers that include one or more antibody hinge regions and/or immunoglobulin heavy chain constant regions, such as CH3 alone or a CH2CH3 sequence can also be used.

In some situations, flexible linkers may be incapable of maintaining a distance or positioning of binding domains needed for a particular use. In these instances, rigid or semi-rigid linkers may be useful. Examples of rigid or semi-rigid linkers include proline-rich linkers. In particular embodiments, a proline-rich linker is a peptide sequence having more proline residues than would be expected based on chance alone. In particular embodiments, a proline-rich linker is one having at least 30%, at least 35%, at least 36%, at least 39%, at least 40%, at least 48%, at least 50%, or at least 51% proline residues. Particular examples of proline-rich linkers include fragments of proline-rich salivary proteins (PRPs) (Carlson, Biochimie 70(11):1689-1695, 1988).

It will also be understood by one of ordinary skill in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation.

A monoclonal antibody includes an antibody obtained from a population of substantially homogeneous antibodies, i.e., the individual antibodies including the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. This type of antibody is produced by the daughter cells of a single antibody-producing hybridoma. A monoclonal antibody typically displays a single binding affinity for any epitope with which it binds.

The modifier "monoclonal" indicates the character of the antibody as being obtained from a homogeneous population of antibodies and is not to be construed as requiring production of the antibody by any particular method. Monoclonal antibodies recognize only one type of antigen. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies. Techniques for the production of antibodies are well known in the art and described in, e.g., Harlow and Lane "Antibodies, A Laboratory Manual", Cold Spring Harbor Laboratory Press, 1988; Harlow and Lane "Using Antibodies: A Laboratory Manual" Cold Spring Harbor Laboratory Press, 1999; Tickle et al. JALA: Journal of the Association for Laboratory Automation. 2009; 14(5): 303-307; Babcook et al., Proc. Natl. Acad. Sci. U.S.A. 1996; 93: 7843-7848; and U.S. Pat. No. 5,627,052.

In particular embodiments "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and peptide). The affinity of a molecule X for its partner Y can generally be represented by the dissociation constant ($K_D$) or the association constant ($K_A$). Affinity can be measured by common methods known in the art.

In particular embodiments, "bind" means that the binding domain of an antibody associates with its target peptide with a dissociation constant ($K_D$) of $10^{-8}$ M or less, in particular embodiments of from $10^{-5}$ M to $10^{-13}$ M, in particular embodiments of from $10^{-5}$ M to $10^{-10}$ M, in particular embodiments of from $10^{-5}$ M to $10^{-7}$ M, in particular embodiments of from $10^{-8}$ M to $10^{-13}$ M, or in particular embodiments of from $10^{-9}$ M to $10^{-13}$ M. The term can be further used to indicate that the binding domain does not bind to other biomolecules present, (e.g., it binds to other biomolecules with a dissociation constant ($K_D$) of $10^{-4}$ M or more, in particular embodiments of from $10^{-4}$ M to 1 M).

In particular embodiments, "bind" means that the binding domain of an antibody associates with its target peptide with an affinity constant (i.e., association constant, $K_A$) of $10^7$ $M^{-1}$ or more, in particular embodiments of from $10^5$ $M^{-1}$ to $10^{13}$ $M^{-1}$, in particular embodiments of from $10^5$ $M^{-1}$ to $10^{10}$ $M^1$, in particular embodiments of from $10^5$ $M^{-1}$ to $10^8$ $M^{-1}$, in particular embodiments of from $10^7$ $M^{-1}$ to $10^{13}$ $M^{-1}$, or in particular embodiments of from $10^7$ $M^{-1}$ to $10^8$ $M^{-1}$. The term can be further used to indicate that the binding domain does not bind to other biomolecules present, (e.g., it binds to other biomolecules with an association constant ($K_A$) of $10^4$ $M^{-1}$ or less, in particular embodiments of from $10^4$ $M^{-1}$ to 1 $M^{-1}$).

Antibodies of the present disclosure can be used for immunoaffinity enrichment of peptides described herein detected in SRM assays for diagnosis of MPS I and Pompe Disease. Particular embodiments of the high affinity antibodies include anti-IDUA 218, anti-IDUA 462, anti-GAA 155, anti-GAA 332, anti-GAA 376, anti-GAA 601, anti-GAA 855, anti-GAA 882, and anti-GAA 892.

In particular embodiments, the exemplary antibodies include the SEQ ID NOs of VH CDRs, VH domains, heavy chains, LH CDRs, VL domains, and light chains presented in Table 1A-1C and FIG. 12.

In particular embodiments, an exemplary antibody includes a heavy chain or light chain coding sequence with a leader sequence. In particular embodiments, an exemplary antibody includes a variable heavy domain or variable light domain coding sequence with a leader sequence. In particular embodiments, an exemplary antibody includes a heavy chain or light chain amino acid sequence with a leader peptide. In particular embodiments, an exemplary antibody includes a heavy chain or light chain amino acid sequence without a leader peptide. In particular embodiments, an exemplary antibody includes a variable heavy domain or variable light domain amino acid sequence with a leader peptide. In particular embodiments, an exemplary antibody includes a variable heavy domain or variable light domain amino acid sequence without a leader peptide.

(V) Variants

Variants of the sequences disclosed and referenced herein are also included. Functional variants include one or more residue additions or substitutions that do not substantially impact the physiological effects of the protein. Functional fragments include one or more deletions or truncations that do not substantially impact the physiological effects of the protein. A lack of substantial impact can be confirmed by observing experimentally comparable results in a binding study. Functional variants and functional fragments of binding domains bind their cognate antigen or ligand at a level comparable to a wild-type reference.

Guidance in determining which amino acid residues can be substituted, inserted, or deleted without abolishing biological activity can be found using computer programs well known in the art, such as DNASTAR™ (Madison, Wis.) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

In particular embodiments, a binding domain VH region can be derived from or based on a VH of a known antibody or an antibody disclosed herein and can optionally contain one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the VH of the known antibody or antibody disclosed herein. An insertion, deletion or substitution may be anywhere in the VH region, including at the amino- or carboxy-terminus or both ends of this region, provided that each CDR includes zero changes or at most one, two, or three changes and provided a binding domain containing the modified VH region can still specifically bind its target with an affinity similar to the wild type binding domain.

In particular embodiments, a VL region in a binding domain is derived from or based on a VL of a known antibody or an antibody disclosed herein and optionally contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared with the VL of the known antibody or antibody disclosed herein. An insertion, deletion or substitution may be anywhere in the VL region, including at the amino- or carboxy-terminus or both ends of this region, provided that each CDR includes zero changes or at most one, two, or three changes and provided a binding domain containing the modified VL region can still specifically bind its target with an affinity similar to the wild type binding domain.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including (but not limited to) those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

(VI) Enrichment Strategies for Peptides

Enrichment of a desired peptide target prior to SRM can be accomplished by any means known in the art. A host of enrichment procedures are available, including immunoadsorption-based depletion of abundant protein species from samples, precipitation, chromatography, electrophoresis, solvent partitioning, immunoprecipitation, immunoelectrophoresis, and immunochromatography. In particular embodiments, a SISCAPA method for specific antibody-based capture of individual tryptic peptides from a digest of a sample can be used (Anderson et al., J. Proteome Research 2004; 3: 235-244; U.S. Pat. No. 7,632,686).

In particular embodiments, the antibodies that bind the peptide markers, such as the antibodies disclosed herein, can be attached to a solid support. Particular embodiments use an affinity column, where antibodies are covalently coupled to chromatography media. In particular embodiments, POROS (Applied Biosystems, Foster City, Calif.) nanocolumns can be used in SISCAPA enrichment and features high binding capacity, a relatively high concentration of antibodies allowing for rapid enrichment of target peptides, and the ability to prepare columns with a variety of functionalized groups. Alternatively, antibodies can be attached to beads, magnetic beads, or other solid particles. One means of attachment is conjugation of the antibody to a protein coated on the beads. For example, Protein G coated particles offer the binding of antibodies in a preferred orientation. Other means of attachment can be used, such as direct coating of a bead with the antibody. Magnetic particles are available in a wide array of chemistries allowing for coupling to antibodies. Enrichment with antibodies attached to particles can allow parallel processing of samples. Magnetic particle processing has been automated in 96 well plates for the SISCAPA enrichment step with elution in the plates for analysis by mass spectrometry. Other particular embodiments use a novel bead trap device developed to perform the bead handling steps in line with a nanoflow chromatography system (Anderson et al. Mol Cell Proteomics 2009; 8(5): 995-1005). This minimizes losses of peptides to containers between elution and analysis steps. Peptide enrichment can also be implemented by immobilizing anti-peptide antibodies in pipet tips (Nelson et al., Anal Chem. 1995; 67(7): 1153-1158). After separation of the antibody bound peptide from free peptides, the bound peptide can be eluted. Any elution means can be used. One elution means which has been found to be efficient is 5% acetic acid/3% acetonitrile. Other elution means, including other acids, and other concentrations of acetic acid can be used, as is efficient for a particular peptide.

(VII) Liquid Chromatography (LC)

In particular embodiments, one or more LC purification steps are performed prior to SRM-MS. A mixture of enriched peptides (the mobile phase) can be passed through a column packed with material (stationary phase) to separate the peptides based on their weight and affinity for the mobile and stationary phases of the column. Traditional LC analysis relies on the chemical interactions between sample components and column packing materials, where laminar flow of the sample through the column is the basis for separation of the analyte of interest from the test sample. The skilled artisan will understand that separation in such columns is a diffusional process. A variety of column packing materials are available for chromatographic separation of samples, and selection of an appropriate separation protocol is an empirical process that depends on the sample characteristics, the analyte of interest, the interfering substances present and their characteristics, etc. Various packing chemistries can be used depending on the needs (e.g., structure, polarity, and solubility of compounds being purified). In particular embodiments the columns are polar, ion exchange (both cation and anion), hydrophobic interaction, phenyl, C-2, C-8, C-18 columns, polar coating on porous polymer, or others that are commercially available. During chromatography, the separation of materials is affected by variables such as choice of eluant (also known as a "mobile phase"), choice of gradient elution and the gradient conditions, temperature, etc. In particular embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. As discussed above, such procedures may enrich the amount of one or more analytes of interest relative to one or more other components of the sample. In particular embodiments, the LC is microflow LC (microLC). In microflow LC, chromatographic separations are performed using flow rates in the range of low microliter per minute. In particular embodiments, the LC is nanoflow LC (nanoLC). In nanoflow LC (nanoLC) chromatographic separations are performed using a flow rate of 300 nanoliter per minute. The slowed flow rates result in high analytical sensitivity due to the large concentration efficiency afforded by this type of chromatography (Cutillas, Current Nanoscience, 2005; 1: 65-71).

(VIII) Mass Spectrometry (MS)

A mass spectrometer includes a gas phase ion spectrometer that measures a parameter that can be translated into mass-to-charge (m/z) ratios of gas phase ions. Mass spectrometry refers to the use of a mass spectrometer to detect gas phase ions. Mass spectrometers generally include an ion source and a mass analyzer. Examples of mass spectrometers are time-of-flight (TOF), magnetic sector, quadrupole filter, ion trap, ion cyclotron resonance, electrostatic sector analyzer and hybrids of these. A laser desorption mass spectrometer includes a mass spectrometer that uses laser energy as a means to desorb, volatilize, and ionize an analyte. A tandem mass spectrometer includes any mass spectrometer that is capable of performing two successive stages of m/z-based discrimination or measurement of ions, including ions in an ion mixture. The phrase includes mass spectrometers having two mass analyzers that are capable of performing two successive stages of m/z-based discrimination or measurement of ions tandem-in-space. The phrase further includes mass spectrometers having a single mass analyzer that is capable of performing two successive stages of m/z-based discrimination or measurement of ions tandem-in-time. The phrase thus explicitly includes Qq-TOF mass spectrometers, ion trap mass spectrometers, ion trap-TOF mass spectrometers, TOF-TOF mass spectrometers, Fourier transform ion cyclotron resonance mass spectrometers, electrostatic sector-magnetic sector mass spectrometers, triple quadrupole mass spectrometers, and combinations thereof.

Ionization in mass spectrometry includes the process by which analytes in a sample are ionized. Such analytes may become charged molecules used for further analysis. For example, sample ionization may be performed by electrospray ionization (ESI), laserspray ionization (LSI) atmospheric pressure chemical ionization (APCI), photoionization, electron ionization, fast atom bombardment (FAB)/liquid secondary ionization (LSIMS), matrix assisted laser desorption ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

A mass analyzer includes the component of the mass spectrometer that takes ionized masses and separates them based on m/z ratios and outputs them to the detector where they are detected and later converted to a digital output. Suitable mass analyzers for determining m/z ratios include quadrupole mass analyzer, time-of-flight (TOF) mass analyzer, magnetic or electrostatic sector mass analyzer and ion trap (e.g. ion cyclotron resonance) mass analyzer.

A selected reaction monitoring (SRM)-MS assay targets a predetermined set of peptides for a given protein of interest. SRM is a tandem mass spectrometry mode in which an ion of a particular mass, the parent or precursor ion, is selected in the first stage of tandem mass spectrometry, and an ion product of a fragmentation reaction of the precursor ion is selected in the second mass spectrometry stage for detection. The specific pair of m/z values associated with a selected precursor ion and fragment ion is referred to as a transition. For each signature peptide, those fragment ions that provide optimal signal intensity and discriminate the targeted peptide from other species present in the sample are identified. Optimized transitions contribute to an effective SRM assay. Several such transitions (precursor/fragment ion pairs) are monitored over time, yielding a set of chromatographic traces with the retention time and signal intensity for a specific transition as coordinates. SRM-MS analysis of signature peptides is generally performed on a triple quadrupole mass spectrometer (QQQ-MS), an instrument with the capability to selectively isolate precursor ions corresponding to the m/z of the signature peptides and to selectively monitor peptide-specific fragment ions. In SRM analysis, the specificity depends on multiple mass analyzers (mass filters). The first quadrupole is to select the desired parent or precursor ion. The third quadrupole is to monitor the (one or more) fragment ion(s). The fragment ion(s) is generated through collisional induced dissociation in the second quadrupole. The two levels of mass selection allow high selectivity, as co-eluting background ions are filtered out very effectively. Unlike conventional tandem mass spectrometry (MS/MS) experiments that survey all analytes in a sample, SRM analysis selectively targets (filters) particular analytes, which translates into an increased sensitivity by one or two orders of magnitude compared with conventional 'full scan' techniques. In addition, SRM provides a linear response over a wide dynamic range up to five orders of magnitude. This enables the detection of low-abundance proteins in highly complex mixtures. Therefore, SRM is a highly specific detection/monitoring method with low background interference. When multiple parent ions are monitored in a single MS run, this type of analysis is known as multiple reaction monitoring (MRM). Using MRM analysis, multiple proteins and multiple regions (signature peptides) of a protein can be monitored in a single mass spectrometry run. Selected reaction monitoring/multiple reaction monitoring mass spectrometry (SRM/MRM-MS) is described in, e.g., U.S. Pat. No. 8,383,417, WO 2013/106603, and US 2013/105684.

In particular embodiments, the following parameters can be used to specify an LC-SRM-MS assay of a protein under a particular LC-SRM-MS system: (1) an enriched tryptic peptide of a given protein; (2) the retention time (RT) of the peptide on an LC column; (3) the m/z value of the peptide precursor ion; (4) the declustering potential used to ionize the precursor ion; (5) the m/z value of a fragment ion generated from the peptide precursor ion; and (6) the collision energy (CE) used to fragment the peptide precursor ion that is optimized for the particular peptide. RT includes the elapsed time between injection and elution of an analyte. Declustering potential (DP) includes a voltage potential to dissolvate and dissociate ion clusters. It is also known as "fragmentor voltage" or "ion transfer capillary offset voltage" depending on the manufacturer. Collision energy (CE) includes the amount of energy precursor ions receive as they are accelerated into the collision cell.

To facilitate accurate quantification of the peptides by the methods disclosed herein, a set of isotopically labeled synthetic versions of the peptides of interest may be added in known amounts to the sample for use as internal standards. Since the isotopically labeled peptides have physical and chemical properties identical to the corresponding surrogate peptide, they co-elute from the chromatographic column and are easily identifiable on the resultant mass spectrum (Gerber et al. Proc. Natl. Asso. Sci. 2003; 100: 6940-6945; Kirkpatrick et al. Methods 2005; 35: 265-273). The isotopes with which amino acids in a given peptide can be labeled include $^{13}C$, $^{2}H$, $^{15}N$, $^{17}O$, $^{18}O$, and $^{34}S$. In particular embodiments, a peptide is labeled with $^{13}C$ and/or $^{15}N$ heavy isotopes. The addition of the labeled standards may occur before or after proteolytic digestion. In particular embodiments, the labeled internal standard peptides are added after proteolytic digestion. Methods of synthesizing isotopically labeled peptides will be known to those of skill in the art. Thus, in particular embodiments, the experimental samples contain internal standard peptides. In particular embodiments, internal standard peptides include reference signature peptides. In particular embodiments, a signature peptide concentration can be determined by combining: (i) a ratio calculated from comparing the peak area of the signature peptide to the peak area of its corresponding reference signature peptide obtained from an LC-MRM-MS assay, and (ii) the known concentration of the reference signature peptide. Peptides selected as reference standards and suitable for quantification are sometimes referred to as quantotypic peptides (Q-peptides). Q-peptides include all of the characteristics of proteotypic peptides but also place restrictions on the residues that can constitute the reference peptide to eradicate artefactual modification and/or incomplete cleavage (Holman et al. Bioanalysis 2012; 4(14): 1763-1786).

Absolute quantitative levels of a given protein, or proteins, can be determined by the SRM/MRM methodology whereby the SRM/MRM signature peak area of an individual peptide from a given protein in one biological sample is compared to the SRM/MRM signature peak area of a known amount of a "spiked" internal standard. In particular embodiments, the internal standard is a synthetic version of the same exact peptide that contains one or more amino acid residues labeled with one or more heavy isotopes. Such isotope labeled internal standards are synthesized so that mass spectrometry analysis generates a predictable and consistent SRM/MRM signature peak that is different and distinct from the native peptide signature peak, and which can be used as a comparator peak. Thus, when the internal standard is spiked in known amounts into a protein preparation from a biological sample and analyzed by mass spectrometry, the signature peak area of the native peptide is compared to the signature peak area of the internal standard peptide, and this numerical comparison indicates either the absolute molarity and/or absolute weight of the native peptide present in the original protein preparation from the biological sample. Absolute quantitative data for fragment peptides are displayed according to the amount of protein analyzed per sample. Absolute quantitation can be performed across many peptides, and thus proteins, simultaneously in a single sample and/or across many samples to gain insight into absolute protein amounts in individual biological samples and in entire cohorts of individual samples.

Another strategy for absolute quantitation of peptides is equimolarity through equalizer peptide. This methodology involves chemically synthesizing the isotopically labeled Q-peptides of interest as dipeptides. A common amino acid sequence is positioned N-terminal to the Q-peptide and is referred to as the equalizer peptide. After solubilization and proteolytic digestion, the amount of Q-peptide can be accurately determined through reference to a single light-labeled peptide. Appropriate amounts of each standard peptide can then be added to a sample of interest (either predigested or prior to proteolysis) to facilitate absolute quantification (Holzmann et al. Anal. Chem. 2009; 81: 10254-10261). Absolute quantification can also employ quantification concatemer (QconCAT) proteins (Beynon et al. Nat. Methods 2005; 2: 587-589; Johnson et al. J. Am. Soc. Mass Spectrom. 2009; 20: 2211-2220; Ding et al. J. Proteome Res. 2011; 10: 3652-3659; Carroll et al. Molecular & Cellular Proteomics 2011; Sep. 19: mcp-M111). In this strategy, a recombinant artificial protein that is an affinity tagged, concatenation of standard peptides from several proteins of interest is heterologously produced in *Escherichia coli* grown in stable iso-topically enriched media. The QconCAT protein is then affinity purified and co-digested with the sample, generating a stoichiometric mixture of all the 'heavy' Q-peptides of which it is composed, and the proteolytic peptides from the native proteins and internal standard are subsequently analyzed. A variant of the QconCAT approach, termed peptide-concatenated standards (PCS), uses flanking regions between the Q-peptides in the artificial protein sequence that mirror their endogenous environment (Kito et al. J. Proteome Res. 2007; 6: 792-800). Other particular embodiments use protein standards for absolute quantification (PSAQ) (Brun et al. Mol. Cell. Proteomics 2007; 6: 2139-2149). PSAQ uses recombinant proteins but rather than being a concatenation of peptides from several proteins, the entire protein to be quantified is expressed in stable isotope-labeled form. One or several PSAQs can then be added to the sample pre-digestion to facilitate quantification.

Particular embodiments use label-free strategies for protein quantification such as intensity-based measurements (America and Cordewener, Proteomics 2008; 8: 731-749) or spectral counting (Lundgren et al. Expert Rev. Proteomics 2010; 7: 39-53).

To obtain relative quantitative levels of a given peptide, the mass spectrometry-derived signature peak area (or the peak height if the peaks are sufficiently resolved) of an individual peptide, or multiple peptides, from a given protein, in one biological sample can be compared to the signature peak area determined for the same peptide, or peptides, from the same protein, in one or more additional and different biological samples, using the same SRM/MRM methodology. In this way, the amount of a particular peptide, or peptides, from a given protein, is determined relative to the same peptide, or peptides, from the same protein across two or more biological samples under the same experimental conditions. In addition, relative quantitation can be determined for a given peptide, or peptides, from a single protein within a single sample by comparing the signature peak area for that peptide for that given protein by SRM/MRM methodology to the signature peak area for another different peptide, or peptides, from a different protein within the same protein preparation from the biological sample. In this way, the amount of a particular peptide from a given protein, and therefore the amount of the given protein, is determined relative to another protein within the same sample. These approaches generate quantitation of an individual peptide, or peptides, from a given protein to the amount of another peptide, or peptides, from the same protein or from a different protein between samples and within samples wherein the amounts as determined by signature peak area are relative one to another, regardless of the absolute weight to volume or weight to weight amounts of peptides in the protein preparation from the biological sample. Relative quantitative data about individual signature peak areas between different samples can be normalized to the amount of protein analyzed per sample. Relative quantitation can be performed across many peptides simultaneously in a single sample and/or across many samples to gain insight into relative protein amounts.

Signature peptide levels can be expressed in concentration units (e.g., pmol/L). In particular embodiments, the mean concentration of a signature peptide in a test sample derived from a subject being screened for MPS I and/or Pompe Disease can be compared to the mean concentration of the corresponding peptide in a normal control sample. In particular embodiments, a normal control sample can be derived from one or more normal control subjects or from a population of normal control subjects. In particular embodiments, a normal control subject includes a subject who does not have or is not known to have MPS I and/or Pompe Disease.

In particular embodiments, a normal control subject includes a subject who does not have genetic mutations associated with MPS I or Pompe Disease.

In particular embodiments, the mean concentration of an IDUA 218 signature peptide in DBS from a population of normal control subjects includes a concentration in a range of 10 pmol/L to 350 pmol/L, in a range of 15 pmol/L to 300 pmol/L, and in a range of 20 pmol/L to 250 pmol/L. In particular embodiments, the mean concentration of an IDUA 218 signature peptide in DBS from a population of normal control subjects includes a concentration of 10 pmol/L, 15 pmol/L, 20 pmol/L, 25 pmol/L, 30 pmol/L, 35 pmol/L, 40 pmol/L, 45 pmol/L, 50 pmol/L, 55 pmol/L, 60 pmol/L, 65 pmol/L, 70 pmol/L, 75 pmol/L, 80 pmol/L, 85 pmol/L, 90 pmol/L, 95 pmol/L, 100 pmol/L, 110 pmol/L, 120 pmol/L, 130 pmol/L, 140 pmol/L, 150 pmol/L, 160 pmol/L, 170 pmol/L, 180 pmol/L, 190 pmol/L, 200 pmol/L, 210 pmol/L, 220 pmol/L, 230 pmol/L, 240 pmol/L, 250 pmol/L, 260 pmol/L, 270 pmol/L, 280 pmol/L, 290 pmol/L, 300 pmol/L, 310 pmol/L, 320 pmol/L, 330 pmol/L, 340 pmol/L, 350 pmol/L, or more.

In particular embodiments, the mean concentration of an IDUA 218 signature peptide in PBMCs from a population of normal control subjects includes a concentration in a range of 300 pmol/L to 1000 pmol/L, in a range of 350 pmol/L to 800 pmol/L, and in a range of 400 pmol/L to 700 pmol/L. In particular embodiments, the mean concentration of an IDUA 218 signature peptide in PBMCs from a population of normal control subjects includes a concentration of 300 pmol/L, 310 pmol/L, 320 pmol/L, 330 pmol/L, 340 pmol/L, 350 pmol/L, 360 pmol/L, 370 pmol/L, 380 pmol/L, 390 pmol/L, 400 pmol/L, 410 pmol/L, 420 pmol/L, 430 pmol/L, 440 pmol/L, 450 pmol/L, 460 pmol/L, 470 pmol/L, 480 pmol/L, 490 pmol/L, 500 pmol/L, 510 pmol/L, 520 pmol/L, 530 pmol/L, 540 pmol/L, 550 pmol/L, 560 pmol/L, 570 pmol/L, 580 pmol/L, 590 pmol/L, 600 pmol/L, 610 pmol/L, 620 pmol/L, 630 pmol/L, 640 pmol/L, 650 pmol/L, 660 pmol/L, 670 pmol/L, 680 pmol/L, 690 pmol/L, 700 pmol/L, 710 pmol/L, 720 pmol/L, 730 pmol/L, 740 pmol/L, 750 pmol/L, 760 pmol/L, 770 pmol/L, 780 pmol/L, 790 pmol/L, 800 pmol/L, 810 pmol/L, 820 pmol/L, 830 pmol/L, 840 pmol/L, 850 pmol/L, 860 pmol/L, 870 pmol/L, 880 pmol/L, 890 pmol/L, 900 pmol/L, 910 pmol/L, 920 pmol/L, 930 pmol/L, 940 pmol/L, 950 pmol/L, 960 pmol/L, 970 pmol/L, 980 pmol/L, 990 pmol/L, 1000 pmol/L, or more.

In particular embodiments, the mean concentration of an IDUA 218 signature peptide in buccal swab samples from a population of normal control subjects includes a concentration in a range of 100 pmol/L to 1000 pmol/L, in a range of 100 pmol/L to 900 pmol/L, and in a range of 100 pmol/L to 800 pmol/L. In particular embodiments, the mean concentration of an IDUA 218 signature peptide in buccal swab samples from a population of normal control subjects includes a concentration of 100 pmol/L, 125 pmol/L, 150 pmol/L, 175 pmol/L, 200 pmol/L, 225 pmol/L, 250 pmol/L, 275 pmol/L, 300 pmol/L, 325 pmol/L, 350 pmol/L, 375 pmol/L, 400 pmol/L, 425 pmol/L, 450 pmol/L, 475 pmol/L, 500 pmol/L, 525 pmol/L, 550 pmol/L, 575 pmol/L, 600 pmol/L, 625 pmol/L, 650 pmol/L, 675 pmol/L, 700 pmol/L, 725 pmol/L, 750 pmol/L, 775 pmol/L, 800 pmol/L, 825 pmol/L, 850 pmol/L, 875 pmol/L, 900 pmol/L, 925 pmol/L, 950 pmol/L, 975 pmol/L, 1000 pmol/L, or more. In particular embodiments, the mean concentration of an IDUA 218 signature peptide in buccal swab samples from a population of normal control subjects includes a concentration in a range of 30 pmol/g of protein to 85 pmol/g of protein, in a range of 30 pmol/g of protein to 80 pmol/g of protein, and in a range of 30 pmol/g of protein to 70 pmol/g of protein. In particular embodiments, the mean concentration of an IDUA 218 signature peptide in buccal swab samples from a population of normal control subjects includes a concentration of 30 pmol/g of protein, 35 pmol/g of protein, 40 pmol/g of protein, 45 pmol/g of protein, 50 pmol/g of protein, 55 pmol/g of protein, 60 pmol/g of protein, 65 pmol/g of protein, 70 pmol/g of protein, 75 pmol/g of protein, 80 pmol/g of protein, 85 pmol/g of protein, or more.

In particular embodiments, the mean concentration of an IDUA 462 signature peptide in DBS from a population of normal control subjects includes a concentration in a range of 10 pmol/L to 250 pmol/L, in a range of 10 pmol/L to 200 pmol/L, and in a range of 20 pmol/L to 150 pmol/L. In particular embodiments, the mean concentration of an IDUA 462 signature peptide in DBS from a population of normal control subjects includes a concentration of 10 pmol/L, 15 pmol/L, 20 pmol/L, 25 pmol/L, 30 pmol/L, 35 pmol/L, 40 pmol/L, 45 pmol/L, 50 pmol/L, 55 pmol/L, 60 pmol/L, 65 pmol/L, 70 pmol/L, 75 pmol/L, 80 pmol/L, 85 pmol/L, 90 pmol/L, 95 pmol/L, 100 pmol/L, 110 pmol/L, 120 pmol/L, 130 pmol/L, 140 pmol/L, 150 pmol/L, 160 pmol/L, 170 pmol/L, 180 pmol/L, 190 pmol/L, 200 pmol/L, 210 pmol/L, 220 pmol/L, 230 pmol/L, 240 pmol/L, 250 pmol/L, or more.

In particular embodiments, the mean concentration of an IDUA 462 signature peptide in PBMCs from a population of normal control subjects includes a concentration in a range of 350 pmol/L to 1000 pmol/L, in a range of 400 pmol/L to 900 pmol/L, and in a range of 450 pmol/L to 850 pmol/L. In particular embodiments, the mean concentration of an IDUA 462 signature peptide in PBMCs from a population of normal control subjects includes a concentration of 350 pmol/L, 360 pmol/L, 370 pmol/L, 380 pmol/L, 390 pmol/L, 400 pmol/L, 410 pmol/L, 420 pmol/L, 430 pmol/L, 440 pmol/L, 450 pmol/L, 460 pmol/L, 470 pmol/L, 480 pmol/L, 490 pmol/L, 500 pmol/L, 510 pmol/L, 520 pmol/L, 530 pmol/L, 540 pmol/L, 550 pmol/L, 560 pmol/L, 570 pmol/L, 580 pmol/L, 590 pmol/L, 600 pmol/L, 610 pmol/L, 620 pmol/L, 630 pmol/L, 640 pmol/L, 650 pmol/L, 660 pmol/L, 670 pmol/L, 680 pmol/L, 690 pmol/L, 700 pmol/L, 710 pmol/L, 720 pmol/L, 730 pmol/L, 740 pmol/L, 750 pmol/L, 760 pmol/L, 770 pmol/L, 780 pmol/L, 790 pmol/L, 800 pmol/L, 810 pmol/L, 820 pmol/L, 830 pmol/L, 840 pmol/L, 850 pmol/L, 860 pmol/L, 870 pmol/L, 880 pmol/L, 890 pmol/L, 900 pmol/L, 910 pmol/L, 920 pmol/L, 930 pmol/L, 940 pmol/L, 950 pmol/L, 960 pmol/L, 970 pmol/L, 980 pmol/L, 990 pmol/L, 1000 pmol/L, or more.

In particular embodiments, the mean concentration of an IDUA 462 signature peptide in buccal swab samples from a population of normal control subjects includes a concentration in a range of 100 pmol/L to 1000 pmol/L, in a range of 100 pmol/L to 900 pmol/L, and in a range of 150 pmol/L to 850 pmol/L. In particular embodiments, the mean concentration of an IDUA 462 signature peptide in buccal swab samples from a population of normal control subjects includes a concentration of 100 pmol/L, 125 pmol/L, 150 pmol/L, 175 pmol/L, 200 pmol/L, 225 pmol/L, 250 pmol/L, 275 pmol/L, 300 pmol/L, 325 pmol/L, 350 pmol/L, 375 pmol/L, 400 pmol/L, 425 pmol/L, 450 pmol/L, 475 pmol/L, 500 pmol/L, 525 pmol/L, 550 pmol/L, 575 pmol/L, 600 pmol/L, 625 pmol/L, 650 pmol/L, 675 pmol/L, 700 pmol/L, 725 pmol/L, 750 pmol/L, 775 pmol/L, 800 pmol/L, 825 pmol/L, 850 pmol/L, 875 pmol/L, 900 pmol/L, 925 pmol/L, 950 pmol/L, 975 pmol/L, 1000 pmol/L, or more. In particular embodiments, the mean concentration of an IDUA 462 signature peptide in buccal swab samples from a population of normal control subjects includes a concentration in a range of 30 pmol/g of protein to 80 pmol/g of protein, in a range of 30 pmol/g of protein to 75 pmol/g of protein, and in a range of 30 pmol/g of protein to 70 pmol/g of protein. In particular embodiments, the mean concentration of an IDUA 462 signature peptide in buccal swab samples from a population of normal control subjects includes a concentration of 30 pmol/g of protein, 35 pmol/g of protein, 40 pmol/g of protein, 45 pmol/g of protein, 50 pmol/g of protein, 55 pmol/g of protein, 60 pmol/g of protein, 65 pmol/g of protein, 70 pmol/g of protein, 75 pmol/g of protein, 80 pmol/g of protein, or more.

In particular embodiments, the mean concentration of a GAA 376 signature peptide in DBS from a population of normal control subjects includes a concentration in a range of 25 pmol/L to 200 pmol/L, in a range of 30 pmol/L to 180 pmol/L, and in a range of 35 pmol/L to 160 pmol/L. In particular embodiments, the mean concentration of a GAA 376 signature peptide in DBS from a population of normal control subjects includes a concentration of 25 pmol/L, 30 pmol/L, 35 pmol/L, 40 pmol/L, 45 pmol/L, 50 pmol/L, 55 pmol/L, 60 pmol/L, 65 pmol/L, 70 pmol/L, 75 pmol/L, 80 pmol/L, 85 pmol/L, 90 pmol/L, 95 pmol/L, 100 pmol/L, 110 pmol/L, 120 pmol/L, 130 pmol/L, 140 pmol/L, 150 pmol/L, 160 pmol/L, 170 pmol/L, 180 pmol/L, 190 pmol/L, 200 pmol/L, or more.

One or more standard peptides may be synthesized with any method known in the pertinent art. Such synthetic peptides may further include amino acids with one or more natural modifications. Such natural modifications may include deamination of glutamine and asparagine, amination, oxidation, and hydroxylation.

(IX) Methods of Use

The methods of the present disclosure include identifying individuals with MPS I and/or Pompe Disease. In particular embodiments, diagnosing individuals with MPS I and/or Pompe Disease, is performed early, for example, as part of NBS, or before symptoms of a disorder are evident in the individual. In particular embodiments, the methods of the present disclosure include identifying individuals with a severe form of MPS I. In particular embodiments, the methods of the present disclosure include identifying individuals with an attenuated form of MPS I. In particular embodiments, the methods of the present disclosure include differentiating individuals with a severe form of MPS I from individuals with an attenuated form of MPS I. In particular embodiments, the methods of the present disclosure include identifying individuals with infantile onset Pompe Disease. In particular embodiments, the methods of the present disclosure include identifying individuals with late onset Pompe Disease. In particular embodiments, the methods of the present disclosure include differentiating individuals with a infantile onset Pompe Disease from individuals with late onset Pompe Disease.

The methods of the present disclosure include obtaining DBS, buccal swab, PBMC, or WBC samples. In particular embodiments, DBS, buccal swab, PBMC, or WBC samples are obtained according to a method described herein. In particular embodiments, DBS, buccal swab, PBMC, or WBC samples are obtained from a DBS, a buccal swab, a PBMC, or a WBC repository or lab that stores DBS, buccal swab, PBMC, or WBC samples for future testing.

The methods of the present disclosure include digesting proteins in a biological sample with digestion enzymes. In particular embodiments, a biological sample includes DBS, cells from buccal swabs, PBMCs, or WBCs. In particular embodiments, one or more punches of the DBS, whole DBS, cells from buccal swabs, PBMCs, or WBCs can be solubilized in an appropriate buffer, and an appropriate digestion enzyme described herein can be added to digest proteins present in DBS, cells from buccal swabs, PBMCs, or WBCs into peptide fragments. In particular embodiments, DBS, cells from buccal swabs, PBMCs, or WBCs can be solubilized with 0.1% Triton X-100 in 50 mM ammonium bicarbonate and digested with trypsin.

The methods of the present disclosure include enriching for signature peptides that are used in screening for MPS I and/or Pompe Disease. Signature peptides include: IDUA 218 for MPS I; IDUA 462 for MPS I; GAA 155 for Pompe Disease; GAA 332 for Pompe Disease; GAA 376 for Pompe Disease; GAA 601 for Pompe Disease; GAA 855 for Pompe Disease; GAA 882 for Pompe Disease; and GAA 892 for Pompe Disease. In particular embodiments, enriching for signature peptides include contacting mixtures of peptide fragments from a digested biological sample with one or more binding entities that recognize the signature peptides. In particular embodiments, a biological sample includes DBS, cells from buccal swabs, PBMCs, or WBCs. In particular embodiments, the binding entities are antibodies or antigen binding fragments thereof. In particular embodiments, the antibodies include those disclosed in Table 1A-1C and FIG. 12. In particular embodiments, amino acid sequences of antibodies of the disclosure include SEQ ID NOs: 10-15, 17, 18, 20, 21, 22-27, 29, 30, 32, 33, 44-49, 54-57, 62-71, 76-79, and 84-87. In particular embodiments, coding sequences of antibodies of the disclosure include SEQ ID NOs: 16, 19, 28, 31, 40-43, 50-53, 58-61, 72-75, and 80-83. In particular embodiments, the antibodies include antibodies that bind: IDUA 218, IDUA 462, GAA 155, GAA 332, GAA 376, GAA 601, GAA 855, GAA 882, and GAA 892. In particular embodiments, antibodies including SEQ ID NOs: 10-15, 17, 18, 20, and 21 are used to enrich for an IDUA peptide including SEQ ID NO: 1. In particular embodiments, antibodies including SEQ ID NOs: 22-27, 29, 30, 32, and 33 are used to enrich for an IDUA peptide including SEQ ID NO: 2. In particular embodiments, antibodies including SEQ ID NOs: 44-49, 54-57, and 62-65 are used to enrich for a GAA peptide including SEQ ID NO: 3. In particular embodiments, antibodies including SEQ ID NOs: 66-71, 76-79, and 84-87 are used to enrich for a GAA peptide including SEQ ID NO: 5.

In particular embodiments, antibodies are used to enrich for a GAA peptide including SEQ ID NO: 4. In particular embodiments, antibodies are used to enrich for a GAA peptide including SEQ ID NO: 6. In particular embodiments, antibodies are used to enrich for a GAA peptide including SEQ ID NO: 7. In particular embodiments, antibodies are used to enrich for a GAA peptide including SEQ ID NO: 8. In particular embodiments, antibodies are used to enrich for a GAA peptide including SEQ ID NO: 9.

In particular embodiments, any combination of one or more antibodies disclosed in Table 1A-1C and FIG. 12 that bind their cognate signature peptides can be used to screen for MPS I. In particular embodiments, any combination of one or more antibodies disclosed in Table 1A-1C and FIG. 12 that bind their cognate signature peptides can be used to screen a population for MPS I. In particular embodiments, any combination of one or more antibodies disclosed in Table 1A-1C and FIG. 12 that bind their cognate signature peptides can be used to screen for Pompe Disease. In particular embodiments, any combination of one or more antibodies disclosed in Table 1A-1C and FIG. 12 that bind their cognate signature peptides can be used to screen a population for Pompe Disease.

The methods of the present disclosure include optionally performing liquid chromatography on the immunoaffinity enriched peptides to separate the peptides prior to MS analysis. Liquid chromatography can separate peptides based on their weight and affinity for the mobile and stationary phases of the column.

The methods of the present disclosure include performing SRM-MS or MRM-MS on the immunoaffinity enriched peptides to quantify the amount of a given signature peptide. In particular embodiments, the SRM-MS or MRM-MS is carried out as described herein. In particular embodiments, the quantification of a signature peptide includes using a reference peptide that is introduced into an assay in known amounts. In particular embodiments, a reference peptide can be identical to the signature peptide in every respect except that the reference peptide has been differentially labeled, for example, with one or more heavy isotopes, to distinguish the reference peptide from the signature peptide.

In particular embodiments, SRM-MS or MRM-MS detects a reduction or absence in an IDUA peptide. In particular embodiments, the IDUA peptide includes SEQ ID NO: 1. In particular embodiments, the IDUA peptide includes SEQ ID NO: 2.

In particular embodiments, SRM-MS or MRM-MS detects a reduction or absence in a GAA peptide. In particular embodiments, the GAA peptide includes SEQ ID NO: 3. In particular embodiments, the GAA peptide includes SEQ ID NO: 4. In particular embodiments, the GAA peptide includes SEQ ID NO: 5. In particular embodiments, the GAA peptide includes SEQ ID NO: 6. In particular embodiments, the GAA peptide includes SEQ ID NO: 7. In particular embodiments, the GAA peptide includes SEQ ID NO: 8. In particular embodiments, the GAA peptide includes SEQ ID NO: 9.

Particular embodiments include monitoring subjects for signature peptide levels using immuno-SRM as described herein over a period of time. In particular embodiments, a subject is selected for monitoring according to the systems and methods disclosed herein because they exhibit signs or symptoms of MPS I and/or Pompe Disease as described herein or are undergoing treatment for MPS I and/or Pompe Disease.

Particular embodiments disclosed herein include determining efficacy of a treatment in a subject being treated for MPS I and/or Pompe Disease including obtaining biological samples derived from the subject prior to one or more treatments and during and/or after one or more treatments; detecting signature peptide levels in the subject prior to the treatment using immuno-SRM described herein; detecting signature peptide levels in the subject during or after the one or more treatments using immuno-SRM described herein; and determining that the treatment is effective if the signature peptide levels during or after the treatment is higher than the signature peptide levels prior to the treatment, or determining that the treatment is not effective if the signature peptide levels during or after the treatment is equal to or lower than the signature peptide levels prior to the treatment. In particular embodiments, the biological sample includes DBS, cells from buccal swabs, PBMC, or WBC.

In particular embodiments, determining efficacy of a treatment in a subject being treated for MPS I and/or Pompe Disease can guide whether the one or more treatments should be continued or discontinued, or whether a new treatment should be implemented. In particular embodiments, one or more treatments can be continued if the signature peptide levels in the subject during or after the one or more treatments is higher than the signature peptide levels in the subject prior to the one or more treatments. In particular embodiments, the one or more treatments can be discontinued if the signature peptide levels during or after the one or more treatments in the subject is greater than 1%, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, greater than 100%, or more of signature peptide levels measured in a normal control subject or control subject unaffected by MPS I and/or Pompe Disease. In particular embodiments, a new treatment can be implemented if the signature peptide levels in the subject during or after the treatment is equal to or lower than the signature peptide levels in the subject prior to the treatment or if the signature peptides are absent.

In particular embodiments, "stable" measures of signature peptide levels are measures evaluated in relation to a previous comparison in the same subject and denote a signature peptide level that has not changed significantly (as determined by a statistical measure known in the art such as a t-test or p-value, e.g., p value>0.05) since the last measurement. In particular embodiments, "stable" measures are measures evaluated in relation to a previous comparison in the same patient and denote a signature peptide level that has not changed significantly (as determined by a statistical measure known in the art such as a t-test or p-value, e.g., p value>0.05) since an aggregated or averaged group of previous measurements (e.g., the last 3, 4, or 5 measurements).

"Unchanged" measures of signature peptide levels are measures evaluated in relation to a previous comparison in the same patient and denote a failure to achieve a statistically significant change in a score towards or away from a reference signature peptide level in the particular subject. In particular embodiments, "unchanged" measures are measures evaluated in relation to a previous comparison in the same patient or since an aggregated or averaged group of previous measurements (e.g., the last 3, 4, or 5 measurements).

In particular embodiments of lysosomal storage diseases (LSDs), the ability to predict which patients may develop an immune response to enzyme replacement therapy (ERT) is increasingly important as more infants receive early diagnosis through NBS. In particular embodiments, an infused enzyme drug can be recognized as foreign by a subject, triggering an immune response. In particular embodiments, developing an immune response includes developing neutralizing antidrug antibodies to the provided exogenous enzyme drug. In particular embodiments, an immune response to ERT for MPS I and/or Pompe Disease can be predicted by quantification of the ERT-naïve enzyme concentrations in a biological sample. In particular embodiments, the biological sample includes DBS, cells from buccal swabs, PBMC, or WBC. In particular embodiments, an immune response to ERT for MPS I occurs when IDUA 218 and/or IDUA 462 are absent. In particular embodiments, an immune response to ERT for Pompe Disease occurs when GAA 155, GAA 332, GAA 376, GAA 601, GAA 855, GAA 882, GAA 892, or a combination thereof, are absent.

When an immune response to ERT for MPS I and/or Pompe Disease is predicted or identified in a subject, the subject or the subject's family can be informed and a plan can be put in place to prevent or treat the immune response. In particular embodiments, strategies to treat an immune response to ERT can include the prevention of antidrug antibody formation in ERT-naïve patients and acute reduction of existing antidrug antibodies. In particular embodiments, prevention of antidrug antibody formation in ERT-naïve patients can include B cell depletion, immunosuppression, mTOR (mechanistic target of rapamycin) inhibition, and/or immunomodulation. In particular embodiments, prevention of antidrug antibody formation in ERT-naïve patients can include administration of methotrexate (MTX), rituximab, and/or intravenous immunoglobulin (IVIG) before ERT initiation or during ERT. In particular embodiments, acute reduction of existing antidrug antibodies can include inhibition of the folic acid metabolism (blocking de novo DNA synthesis), alkylation of DNA (blocking DNA replication), antibody-mediated specific B cell depletion, B cell/plasma cell depletion, and/or immunosuppression proteasome inhibition. In particular embodiments, acute reduction of existing antidrug antibodies can include administration of mycophenolate mofetil, MTX, IVIG, rituximab, bortezomib, cyclophosphamide, and/or plasma exchange.

In particular embodiments, the disclosed assays and methods allow a reduction in the number of false positive results in assays arising from pseudo deficiency cases in LSD. In particular embodiments, the disclosed assays and methods allow an increase in the positive predictive rate (i.e., positive predictive value) of screening for LSDs. In particular embodiments, the methods allow use of the disclosed immuno-SRM assays as a primary or second-tier assay to reduce the number of false positives obtained in screening of LSDs. In particular embodiments, the disclosed assays and methods distinguish cases of enzyme pseudo deficiency from confirmed LSD cases because the disclosed assays and methods can measure signature peptide concentration differences between cases of enzyme pseudo deficiency and confirmed LSD cases. In particular embodiments, a false positive result occurs when an assay result for a subject being screened for a disease is positive (i.e., indicating that a subject has a disease), but the subject is healthy. In particular embodiments, healthy subjects do not exhibit or exhibit very few symptoms of a disease. In particular embodiments, healthy subjects do not need treatment for a disease. In particular embodiments, the positive predictive rate (i.e., positive predictive value) refers to the probability that subjects with a positive screening test truly have the disease. In particular embodiments, patients with a pseudo deficient allele show greatly reduced enzyme activity, but they are healthy. In particular embodiments, patients with an enzyme pseudo deficiency for an LSD show reduced enzyme activity as compared with normal controls and show similar enzyme activity to patients confirmed to have an LSD (a 'true positive' patient). In particular embodiments, a subject is confirmed to have an LSD by molecular genetic testing of the subject for the presence of two copies of the same or different pathogenic variant(s) of the gene associated with the LSD. In particular embodiments, a subject is confirmed to be have a pseudo deficiency in an LSD by molecular genetic testing. Molecular genetic testing can include an assay that can detect mutations, deletions, and/or insertions in a gene, including sequencing, fluorescence in situ hybridization, single nucleotide polymorphism microarray, and polymerase chain reaction (PCR).

Figure 7A:
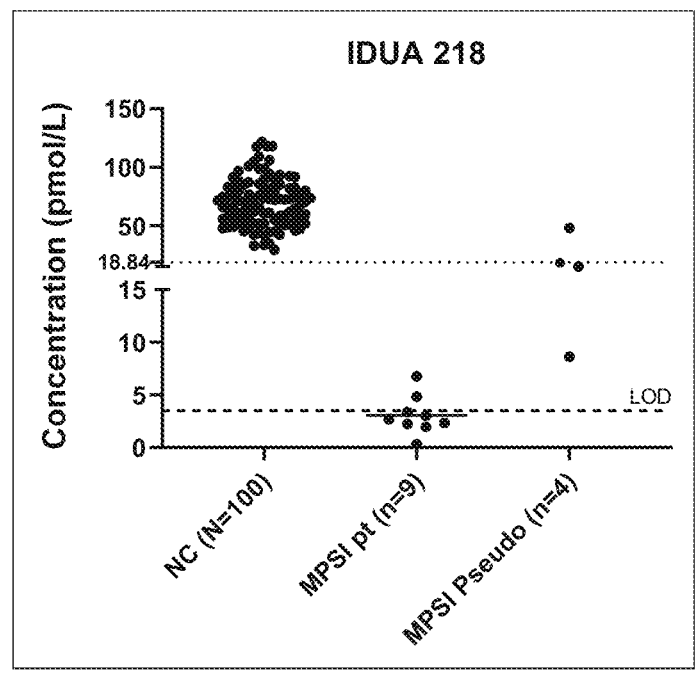
FIGS. 7A, 7B. Comparison of IDUA concentrations among 100 normal controls (NC), 9 MPS I patients (MPS I pt), and 4 MPS I pseudo deficient cases (MPS I Pseudo) for IDUA 218 peptide biomarker (FIG. 7A) and IDUA 462 peptide biomarker (FIG. 7B).
Figure 7B:
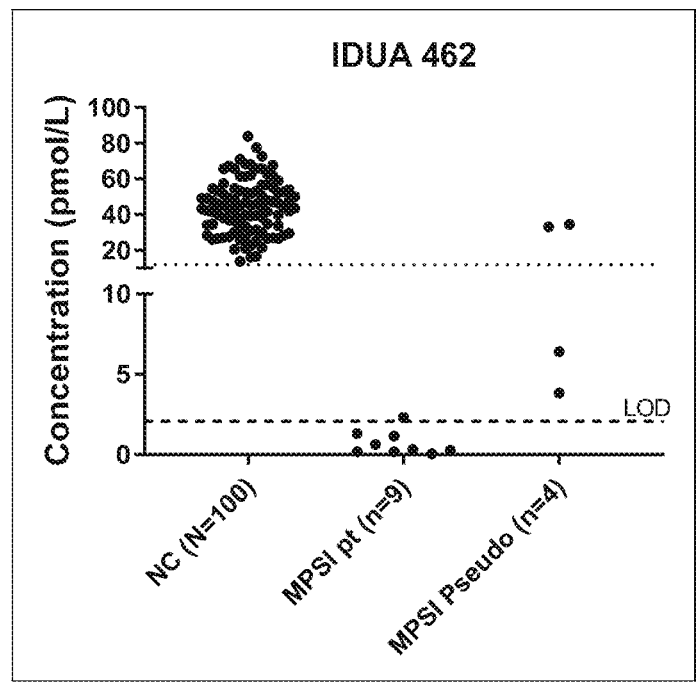

As demonstrated in FIGS. 7A and 7B, an immuno-SRM assay allows differentiation of subjects who have a pseudo deficient allele in an LSD versus a subject who has the LSD. In particular embodiments, a subject has an LSD when they have two copies of the same or different pathogenic variant(s) of a gene associated with the LSD. In particular embodiments, a subject who has an LSD is considered to be a 'true positive'. In particular embodiments, a subject is identified by an immuno-SRM assay to be a true positive for an LSD when a measured signature peptide concentration is lower than a predetermined threshold concentration for that measured signature peptide. A predetermined threshold concentration can be calculated from a standard deviation of the mean concentration of each signature peptide in corresponding biological samples from a population of normal control subjects as described herein. In particular embodiments, a subject is identified by an immuno-SRM assay to be a true positive for an LSD when a measured signature peptide concentration is below a lower limit of detection (LOD) concentration for that signature peptide. In particular embodiments, a subject having a pseudo deficiency in an LSD has a measured signature peptide concentration that is higher than the corresponding mean signature peptide concentration of a subject who is a true positive for, or confirmed to have, the LSD. In particular embodiments, a subject having a pseudo deficiency in an LSD has a measured signature peptide concentration that is within a range of the corresponding signature peptide concentration from a population of normal control subjects. An LOD of a signature peptide of the present disclosure includes the lowest concentration of the signature peptide that can reliably be detected using an immuno-SRM assay. In particular embodiments, an LOD of a signature peptide includes the lowest concentration of the signature peptide that can be statistically distinguished from a negative control sample that does not include the signature peptide. Calculating an LOD is known to one of skill in the art. As an example, a negative control sample that does not include the signature peptide can be assayed 20 times in an immuno-SRM assay, and the mean and standard deviation of the results are calculated. In particular embodiments, an LOD is considered to be 2 standard deviations or 3 standard deviations above the mean of the negative control.

In particular embodiments, an LOD for an IDUA 218 signature peptide includes 10 pmol/L or less, 9 pmol/L or less, 8 pmol/L or less, 7 pmol/L or less, 6 pmol/L or less, 5 pmol/L or less, 4 pmol/L or less, 3 pmol/L or less, 2 pmol/L or less, 1 pmol/L or less, or less. In particular embodiments, an LOD for an IDUA 218 signature peptide includes 3.5 pmol/L or less.

In particular embodiments, an LOD for an IDUA 462 signature peptide includes 10 pmol/L or less, 9 pmol/L or less, 8 pmol/L or less, 7 pmol/L or less, 6 pmol/L or less, 5 pmol/L or less, 4 pmol/L or less, 3 pmol/L or less, 2 pmol/L or less, 1 pmol/L or less, or less. In particular embodiments, an LOD for an IDUA 462 peptide includes 2.1 pmol/L or less.

In particular embodiments, an LOD for a GAA 155 signature peptide includes 10 pmol/L or less, 9 pmol/L or less, 8 pmol/L or less, 7 pmol/L or less, 6 pmol/L or less, 5 pmol/L or less, 4 pmol/L or less, 3 pmol/L or less, 2 pmol/L or less, 1 pmol/L or less, or less.

In particular embodiments, an LOD for a GAA 376 signature peptide includes 10 pmol/L or less, 9 pmol/L or less, 8 pmol/L or less, 7 pmol/L or less, 6 pmol/L or less, 5 pmol/L or less, 4 pmol/L or less, 3 pmol/L or less, 2 pmol/L or less, 1 pmol/L or less, or less.

In particular embodiments, a subject is identified by an immuno-SRM assay as having MPS I (i.e. subject is a true positive for MPS I) when a measured signature peptide concentration of IDUA 218, IDUA 462, or a combination thereof, is lower than a predetermined threshold concentration for the corresponding signature peptide. A predetermined threshold concentration can be calculated from a standard deviation of the mean concentration of each signature peptide in corresponding biological samples from a population of normal control subjects as described herein. In particular embodiments, a subject is identified by an immuno-SRM assay as having MPS I (i.e. subject is a true positive for MPS I) when a measured signature peptide concentration of IDUA 218, IDUA 462, or a combination thereof, is below LOD concentration for the corresponding signature peptide. In particular embodiments, a subject having a pseudo deficiency in MPS I has measured signature peptide concentrations of IDUA 218, IDUA 462, or a combination thereof, that are higher than the corresponding mean IDUA peptide concentrations from samples from a subject or a population of subjects confirmed to have, or are true positives for, MPS I. In particular embodiments, a subject having a pseudo deficiency in MPS I has measured signature peptide concentrations of IDUA 218, IDUA 462, or a combination thereof, within ranges of the corresponding IDUA peptide concentrations from a population of normal control subjects. In particular embodiments, a subject is confirmed to have MPS I by molecular genetic testing of the subject for the presence of two copies of the same or different pathogenic variant(s) of the IDUA gene. In particular embodiments, a subject is confirmed to have a pseudo deficient allele of MPS I by molecular genetic testing. In particular embodiments, normal control subjects do not exhibit or exhibit very few symptoms of MPS I. In particular embodiments, normal control subjects do not have MPS I.

In particular embodiments, a subject is identified by an immuno-SRM assay as having Pompe disease (i.e. subject is a true positive for Pompe disease) when measured signature peptide concentrations of GAA 155, GAA 332, GAA 376, GAA 601, GAA 855, GAA 882, GAA 892, or a combination thereof, are lower than a predetermined threshold concentration for the corresponding signature peptide. A predetermined threshold concentration can be calculated from a standard deviation of the mean concentration of each signature peptide in corresponding biological samples from a population of normal control subjects as described herein. In particular embodiments, a subject is identified by an immuno-SRM assay as having Pompe disease (i.e. subject is a true positive for Pompe disease) when measured signature peptide concentrations of GAA 155, GAA 332, GAA 376, GAA 601, GAA 855, GAA 882, GAA 892, or a combination thereof, are below LOD concentrations for the corresponding signature peptides. In particular embodiments, a subject having pseudo deficiency in Pompe disease has measured signature peptide concentrations of GAA 155, GAA 332, GAA 376, GAA 601, GAA 855, GAA 882, GAA 892, or a combination thereof, that are higher than corresponding mean GAA peptide concentrations from samples from a subject or a population of subjects confirmed to have, or are true positives for, Pompe disease. In particular embodiments, a subject having pseudo deficiency in Pompe disease has measured signature peptide concentrations of GAA 155, GAA 332, GAA 376, GAA 601, GAA 855, GAA 882, GAA 892, or a combination thereof, within ranges of the corresponding GAA peptide concentrations from a population of normal control subjects. In particular embodiments, a subject is confirmed to have Pompe Disease by molecular genetic testing of the subject for the presence of two copies of the same or different pathogenic variant(s) of the GAA gene. In particular embodiments, a subject is confirmed to have a pseudo deficient allele of Pompe Disease by molecular genetic testing. In particular embodiments, normal control subjects do not exhibit or exhibit very few symptoms of Pompe Disease. In particular embodiments, normal control subjects do not have Pompe Disease.

In particular embodiments, the disclosed assays and methods differentiate individuals with a severe form of MPS I from individuals with an attenuated form of MPS I. In particular embodiments, a subject is identified by an immuno-SRM assay as having an attenuated form of MPS I when the peptide concentrations of IDUA 218 and/or IDUA 462 are lower than the corresponding mean IDUA peptide concentrations from control samples derived from a population of healthy subjects and are higher than the corresponding mean IDUA peptide concentrations from samples from a subject or a population of subjects confirmed to have a severe form of MPS I. In particular embodiments, a subject is identified by an immuno-SRM assay as having a severe form of MPS I when the peptide concentrations of IDUA 218 and/or IDUA 462 are lower than the corresponding mean IDUA peptide concentrations from control samples from a population of healthy subjects and lower than the corresponding mean IDUA peptide concentrations from samples from a subject or a population of subjects confirmed to have an attenuated form of MPS I, or are absent. In particular embodiments, a subject is confirmed to have an attenuated or severe form of MPS I by clinical and laboratory findings, including: observations and/or measurements of symptoms of MPS I; patient and family history; measurements of IDUA enzyme activity level; measurements of glycosaminoglycan levels; and/or molecular genetic testing to identify IDUA gene variants. In particular embodiments, IDUA 218 and/or IDUA 462 peptides are present in a biological sample from a subject who has attenuated MPS I and are absent in a corresponding biological sample from a subject who has severe MPS I as measured in an immuno-SRM assay. In particular embodiments, healthy subjects do not exhibit or exhibit very few symptoms of MPS I. In particular embodiments, healthy subjects do not have MPS I. In particular embodiments, a biological sample includes cells from buccal swabs, PBMCs, or WBCs.

In particular embodiments, the disclosed assays and methods differentiate individuals with infantile onset Pompe Disease (PD) from individuals with late onset PD. In particular embodiments, a subject is identified by an immuno-SRM assay as having late onset PD when the peptide concentrations of GAA 155, GAA 332, GAA 376, GAA 601, GAA 855, GAA 882, GAA 892 peptides, or a combination thereof, are lower than the corresponding mean GAA peptide concentrations from control samples derived from a population of healthy subjects and are higher than the corresponding mean GAA peptide concentrations from samples from a subject or a population of subjects confirmed to have infantile onset PD. In particular embodiments, a subject is identified by an immuno-SRM assay as having infantile onset PD when the peptide concentrations of GAA 155, GAA 332, GAA 376, GAA 601, GAA 855, GAA 882, GAA 892 peptides, or a combination thereof, are lower than the corresponding mean GAA peptide concentrations from control samples derived from a population of healthy subjects and lower than the corresponding mean GAA peptide concentrations from samples from a population of subjects confirmed to have late onset PD, or are absent. In particular embodiments, a subject is confirmed to have infantile onset PD or late onset PD by clinical and laboratory findings, including: tests that measure symptoms of PD such as sleep studies, lung function tests, muscle function tests (e.g., magnetic image resonance), heart function tests (e.g., chest x-ray, electrocardiography, echocardiography); patient and family history; measurements of GAA enzyme activity level; and/or molecular genetic testing to identify GAA gene variants. In particular embodiments, GAA 155, GAA 332, GAA 376, GAA 601, GAA 855, GAA 882, and/or GAA 892 peptides are present in a biological sample from a subject who has late onset PD and are absent in a corresponding biological sample from a subject who has infantile onset PD as measured in an immuno-SRM assay. In particular embodiments, healthy subjects do not exhibit or exhibit very few symptoms of PD. In particular embodiments, healthy subjects do not have PD. In particular embodiments, a biological sample includes cells from buccal swabs, PBMCs, or WBCs.

In particular embodiments, antibodies of the present disclosure can also be used in complimentary clinical tests for the diagnosis of MPS I and/or Pompe Disease for those patients with ambiguous biochemical results, and for patients who carry variants of unknown significance (VUS) from genetic tests. In particular embodiments, subjects having VUS in genes encoding IDUA of MPS I and/or GAA of Pompe Disease disclosed herein can be tested with the immuno-SRM assays of the disclosure to determine if the VUS affects the respective signature peptide levels in these subjects.

In particular embodiments, a predetermined cut-off value is used as a threshold for a given signature peptide. A concentration of a given signature peptide above the threshold indicates that the assayed biological sample (e.g., DBS, cells from buccal swabs, PBMC, or WBC) is from an individual not afflicted by MPS I or Pompe Disease. A concentration of a given signature peptide below the threshold or absent indicates that the assayed biological sample (e.g., DBS, cells from buccal swabs, PBMC, or WBC) is from an individual afflicted by MPS I or Pompe Disease. In particular embodiments, the threshold can be determined by analysis of a population of normal controls and calculation of standard deviation (SD) of a concentration of a given signature peptide in this population. The threshold can be set at a certain SD from the mean concentration of the given signature peptide. In particular embodiments, the threshold is −1 SD, −1.1 SD, −1.2 SD, −1.3 SD, −1.4 SD, −1.5 SD, −1.6 SD, −1.7 SD, −1.8 SD, −1.9 SD, −2.0 SD, −2.1 SD, −2.2 SD, −2.3 SD, −2.4 SD, −2.5 SD, −2.6 SD, −2.7 SD, −2.8 SD, −2.9 SD, −3.0 SD, or more SD from the mean concentration of the given signature peptide. In particular embodiments, for diagnosis or screening of MPS I or Pompe Disease, the threshold can be determined by analysis of a population of normal controls and calculation of standard deviation (SD) of a ratio of a concentration of a given signature peptide to an endogenous concentration of ATP7B in this population. Peptide concentration cutoffs for each LSD can be set at a certain SD derived from mean concentration of each signature peptide or ratio of a concentration of a given signature peptide to an endogenous concentration of ATP7B.

In particular embodiments, the threshold concentration for a signature peptide of the disclosure includes −1.0 SD, −1.25 SD, −1.3 SD, −1.35 SD, −1.4 SD, −1.45 SD, −1.5 SD, −1.55 SD, −1.6 SD, −1.65 SD, −1.7 SD, −1.75 SD, −1.8 SD, −1.85 SD, −1.9 SD, −1.95 SD, −2.0 SD, −2.25 SD, −2.3 SD, −2.35 SD, −2.4 SD, −2.45 SD, −2.5 SD, −2.55 SD, −2.6 SD, −2.65 SD, −2.7 SD, −2.75 SD, −2.8 SD, −2.85 SD, −2.9 SD, −2.95 SD, −3.0 SD, or more from the mean concentration of the corresponding signature peptide in a population of normal controls.

In particular embodiments, the threshold concentration for the IDUA 218 peptide in DBS includes 35 pmol/L or less, 34 pmol/L or less, 33 pmol/L or less, 32 pmol/L or less, 31 pmol/L or less, 30 pmol/L or less, 29 pmol/L or less, 28 pmol/L or less, 27 pmol/L or less, 26 pmol/L or less, 25 pmol/L or less, 24 pmol/L or less, 23 pmol/L or less, 22 pmol/L or less, 21 pmol/L or less, 20 pmol/L or less, 19.5 pmol/L or less, 19 pmol/L or less, 18.5 pmol/L or less, 18 pmol/L or less, 17.5 pmol/L or less, 17 pmol/L or less, 16.5 pmol/L or less, 16 pmol/L or less, 15.5 pmol/L or less, 15 pmol/L or less, 14.5 pmol/L or less, 14 pmol/L or less, 13.5 pmol/L or less, 13 pmol/L or less, 12.5 pmol/L or less, 12 pmol/L or less, 11.5 pmol/L or less, 11 pmol/L or less, 10.5 pmol/L or less, 10 pmol/L or less.

In particular embodiments, the threshold concentration for the IDUA 462 peptide in DBS includes 25 pmol/L or less, 24 pmol/L or less, 23 pmol/L or less, 22 pmol/L or less, 21 pmol/L or less, 20 pmol/L or less, 19.5 pmol/L or less, 19 pmol/L or less, 18.5 pmol/L or less, 18 pmol/L or less, 17.5 pmol/L or less, 17 pmol/L or less, 16.5 pmol/L or less, 16 pmol/L or less, 15.5 pmol/L or less, 15 pmol/L or less, 14.5 pmol/L or less, 14 pmol/L or less, 13.5 pmol/L or less, 13 pmol/L or less, 12.5 pmol/L or less, 12 pmol/L or less, 11.5 pmol/L or less, 11 pmol/L or less, 10.5 pmol/L or less, 10 pmol/L or less, 9.5 pmol/L or less, 9 pmol/L or less, 8.5 pmol/L or less, 8 pmol/L or less, 7.5 pmol/L or less, 7 pmol/L or less, 6.5 pmol/L or less, 6 pmol/L or less, 5.5 pmol/L or less, 5 pmol/L or less.

In particular embodiments, the threshold concentration for the GAA 376 peptide in DBS includes 30 pmol/L or less, 29 pmol/L or less, 28 pmol/L or less, 27 pmol/L or less, 26 pmol/L or less, 25 pmol/L or less, 24 pmol/L or less, 23 pmol/L or less, 22 pmol/L or less, 21 pmol/L or less, 20 pmol/L or less, 19.5 pmol/L or less, 19 pmol/L or less, 18.5 pmol/L or less, 18 pmol/L or less, 17.5 pmol/L or less, 17 pmol/L or less, 16.5 pmol/L or less, 16 pmol/L or less, 15.5 pmol/L or less, 15 pmol/L or less, 14.5 pmol/L or less, 14 pmol/L or less, 13.5 pmol/L or less, 13 pmol/L or less, 12.5 pmol/L or less, 12 pmol/L or less, 11.5 pmol/L or less, 11 pmol/L or less, 10.5 pmol/L or less, 10 pmol/L or less, 9.5 pmol/L or less, 9 pmol/L or less, 8.5 pmol/L or less, 8 pmol/L or less, 7.5 pmol/L or less, 7 pmol/L or less, 6.5 pmol/L or less, 6 pmol/L or less, 5.5 pmol/L or less, 5 pmol/L or less.

In particular embodiments, a signature peptide can be considered a primary biomarker for diagnosis or screening of a given disease. A primary signature peptide can include peptides that are used first to diagnose or screen for a given disease. In particular embodiments, a primary marker can be reproducibly obtained from a digestion of the corresponding protein, has high affinity antibodies for immunoaffinity enrichment, and/or is reproducible across independent liquid chromatography columns and/or mass spectrometry instruments. In particular embodiments, a signature peptide can be considered a secondary marker for diagnosis or screening of a given disease. A secondary signature peptide can include peptides that are used second to confirm a diagnosis or screening of a given disease with a primary marker. In particular embodiments, an IDUA peptide can be used as a primary biomarker to screen for subjects who have MPS I. In particular embodiments, an IDUA peptide can be used as a secondary biomarker to confirm that subjects have MPS I. In particular embodiments, a GAA peptide can be used as a primary biomarker to screen for subjects who have Pompe Disease. In particular embodiments, a GAA peptide can be used as a secondary biomarker to confirm that subjects have Pompe Disease.

Methods disclosed herein include treating subjects (e.g., humans) based upon the outcome of screening for MPS I and/or Pompe Disease with compositions and methods disclosed herein. Treating subjects includes delivering therapeutically effective amounts. Therapeutically effective amounts include those that provide effective amounts, prophylactic treatments and/or therapeutic treatments.

An "effective amount" is the amount of a composition necessary to result in a desired physiological change in the subject. For example, an effective amount can provide an alleviation of symptoms, an elimination of symptoms, or a cure for MPS I and/or Pompe Disease. Effective amounts are often administered for research purposes. Effective amounts disclosed herein can cause a statistically significant effect in an animal model or in vitro assay relevant to the assessment of a disease's development, progression, and/or resolution.

Particular embodiments may include administering compositions as a "prophylactic treatment." Prophylactic treatments include those administered to a subject who does not display signs or symptoms of MPS I and/or Pompe Disease or displays only early signs or symptoms of MPS I and/or Pompe Disease, such that treatment is administered for the purpose of diminishing or decreasing the risk of developing the disorder. Thus, a prophylactic treatment functions as a preventative treatment against MPS I and/or Pompe Disease.

In particular embodiments, a prophylactic treatment can prevent, delay, or reduce the onset of MPS I and/or Pompe Disease. In particular embodiments, a prophylactic treatment can prevent or reduce the severity of symptoms or complications associated with MPS I and/or Pompe Disease.

Symptoms and complications for MPS I include weight loss, congestion, repeated vomiting, reflux, and/or skin rashes. Symptoms and complications for Pompe Disease include weak muscles, enlarged liver; failure to thrive, trouble breathing, feeding problems, respiratory infections, and/or hearing problems.

A "therapeutic treatment" includes a treatment administered to a subject who displays symptoms or signs of MPS I and/or Pompe Disease and is administered to the subject for the purpose of diminishing or eliminating those signs or symptoms of MPS I and/or Pompe Disease. In particular embodiments, the therapeutic treatment can reduce lysosomal glycosaminoglycans in cells in subjects afflicted with MPS I. In particular embodiments, the therapeutic treatment can reduce lysosomal glycogen in cells in subjects afflicted with Pompe Disease. In particular embodiments, the therapeutic treatment can reduce, control, or eliminate symptoms and complications of MPS I and/or Pompe Disease such as those described above.

Prophylactic treatments and therapeutic treatments need not be mutually exclusive, and in particular embodiments, administered dosages may accomplish more than one treatment type. In particular embodiments, methods of treatment include enzyme therapy for MPS I and Pompe Disease.

In particular embodiments, therapeutically effective amounts prevent accumulation of glycosaminoglycans in lysosomes of cells in subjects diagnosed with MPS I. In particular embodiments, methods of treatment include providing a laronidase enzyme for MPS I. In particular embodiments, providing laronidase alleviates or eliminates symptoms of MPS I as described above.

In particular embodiments, therapeutically effective amounts prevent accumulation of glycogen in lysosomes of cells in subjects diagnosed with Pompe Disease. In particular embodiments, methods of treatment include providing an alglucosidase alfa enzyme for Pompe Disease. In particular embodiments, providing alglucosidase alfa alleviates or eliminates symptoms of Pompe Disease as described above.

In particular embodiments, administration of a therapeutic composition can be accompanied with administration of a separate adjuvant. Exemplary adjuvants include alum, bentonite, latex, and acrylic particles; incomplete Freund's adjuvant, complete Freund's adjuvant; aluminum-based salts such as aluminum hydroxide; calcium-based salts; silica or any TLR biological ligand(s); Sigma Adjuvant System (SAS); and Ribi adjuvants.

For administration, therapeutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian, or researcher, considering parameters such as physical and physiological factors including target, body weight, severity of condition, previous or concurrent therapeutic interventions, idiopathy of the subject, and route of administration.

Therapeutically effective amounts of cells can range from $10^4$ cells/kg to $10^9$ cells/kg. In particular embodiments, a therapeutically effective amount of cells can include $10^4$ cells/kg, $10^5$ cells/kg, $10^6$ cells/kg, $10^7$ cells/kg, $10^8$ cells/kg, $10^9$ cells/kg, or more.

Useful doses can range from 0.1 to 5 µg/kg or from 0.5 to 1 µg/kg. In particular embodiments, a dose can include 1 µg/kg, 15 µg/kg, 30 µg/kg, 50 µg/kg, 55 µg/kg, 70 µg/kg, 90 µg/kg, 150 µg/kg, 350 µg/kg, 500 µg/kg, 750 µg/kg, 1000 µg/kg, 0.1 to 5 mg/kg or from 0.5 to 1 mg/kg. In particular embodiments, a dose can include 1 mg/kg, 10 mg/kg, 30 mg/kg, 50 mg/kg, 70 mg/kg, 100 mg/kg, or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly).

(X) Kits

Kits to test for congenital disorders are also provided. Kits can include lancets to prick for blood, filter cards to collect blood drops, buccal swabs to collect cheek epithelial cells, tubes to collect blood, solutions to solubilize DBS or cells, and appropriate buffers and enzymes to digest marker proteins in the DBS or cells. Kits can further include one or more containers including anti-peptide binding agents (e.g., antibodies) and/or reagents or supplies to assess absence or reduction in IDUA and/or GAA. In particular embodiments, the kits include one or more containers including the following anti-peptide antibodies: anti-IDUA 218, anti-IDUA 462, anti-GAA 155, anti-GAA 332, anti-GAA 376, anti-GAA 601, anti-GAA 855, anti-GAA 882, and anti-GAA 892. In particular embodiments, anti-IDUA 218 antibodies include SEQ ID NOs: 10-21, 40, and 41. In particular embodiments, anti-IDUA 462 antibodies include SEQ ID NOs: 22-33, 42, and 43. In particular embodiments, anti-GAA 155 antibodies include SEQ ID NOs: 44-65. In particular embodiments, anti-GAA 376 antibodies include SEQ ID NOs: 66-87. The antibodies may be immobilized on a solid support, such as a column or beads. Kits can further include elution buffers to release peptides from antibodies. In particular embodiments, kits can include one or more labeled reference peptides to perform absolute quantification of the signature peptides. In particular embodiments, kits can also include some or all of the necessary laboratory and/or medical supplies needed to use the kit effectively, such as gauze, sterile adhesive strips, gloves, tubes, and the like. Variations in contents of any of the kits described herein can be made.

Components of the kit can be prepared for storage and later use. Associated with such container(s) can be a notice in the form prescribed by a governmental agency regulating the manufacture, use, or sale of the kit, which notice reflects approval by the agency of manufacture, use, or sale, when required.

Optionally, the kits further include instructions for using the kit in the methods. In various embodiments, the instructions can include appropriate instructions to interpret results associated with using the kit; proper disposal of the related waste; and the like. The instructions can be in the form of printed instructions provided within the kit or the instructions can be printed on a portion of the kit itself. Instructions may be in the form of a sheet, pamphlet, brochure, CD-ROM, or computer-readable device, or can provide directions to instructions at a remote location, such as a website.

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

(XI) Exemplary Embodiments

1. A method of detecting one or more signature peptides of Mucopolysaccharidosis Type I (MPS I) and/or Pompe Disease in a biological sample, the method including:
    obtaining the biological sample from a subject;
    digesting proteins from the biological sample with an enzyme to yield a mixture of peptides;
    enriching, from within the mixture of peptides, for:
        a first IDUA signature peptide of MPS I of SEQ ID NO: 1 with an antibody or antigen-binding fragment thereof that binds the first IDUA signature peptide and includes: a heavy chain variable (VH) domain including CDRH1 of SEQ ID NO: 10, CDRH2 of SEQ ID NO: 11, and CDRH3 of SEQ ID NO: 12, and a light chain variable (VL) domain including CDRL1 of SEQ ID NO: 13, CDRL2 of SEQ ID NO: 14, and CDRL3 of SEQ ID NO: 15;
        a second IDUA signature peptide of SEQ ID NO: 2 with an antibody or antigen-binding fragment thereof that binds the second IDUA signature peptide and includes: a VH domain including CDRH1 of SEQ ID NO: 22, CDRH2 of SEQ ID NO: 23, and CDRH3 of SEQ ID NO: 24, and a VL domain including CDRL1 of SEQ ID NO: 25, CDRL2 of SEQ ID NO: 26, and CDRL3 of SEQ ID NO: 27;
        a first GAA signature peptide of Pompe Disease of SEQ ID NO: 3 with an antibody or antigen binding fragment thereof that binds the first GAA signature peptide and includes: a VH domain including CDRH1 of SEQ ID NO: 44, CDRH2 of SEQ ID NO: 45, and CDRH3 of SEQ ID NO: 46, and a VL domain including CDRL1 of SEQ ID NO: 47, CDRL2 of SEQ ID NO: 48, and CDRL3 of SEQ ID NO: 49;
        a second GAA signature peptide of Pompe Disease of SEQ ID NO: 4 with an antibody or antigen binding fragment thereof that binds the second GAA signature peptide;
        a third GAA signature peptide of Pompe Disease of SEQ ID NO: 5 with an antibody or antigen binding fragment thereof that binds the third GAA signature peptide and includes: a VH domain including CDRH1 of SEQ ID NO: 66, CDRH2 of SEQ ID NO: 67, and CDRH3 of SEQ ID NO: 68, and a VL domain including CDRL1 of SEQ ID NO: 69, CDRL2 of SEQ ID NO: 70, and CDRL3 of SEQ ID NO: 71;
        a fourth GAA signature peptide of Pompe Disease of SEQ ID NO: 6 with an antibody or antigen binding fragment thereof that binds the fourth GAA signature peptide;
        a fifth GAA signature peptide of Pompe Disease of SEQ ID NO: 7 with an antibody or antigen binding fragment thereof that binds the fifth GAA signature peptide;
        a sixth GAA signature peptide of Pompe Disease of SEQ ID NO: 8 with an antibody or antigen binding fragment thereof that binds the sixth GAA signature peptide; and/or a seventh GAA signature peptide of Pompe Disease of SEQ ID NO: 9 with an antibody or antigen binding fragment thereof that binds the seventh GAA signature peptide;
    and
    performing liquid chromatography-multiple reaction monitoring mass spectrometry (LC-MRM-MS) on the enriched peptides to determine a concentration of each signature peptide, thereby detecting one or more signature peptides of MPS I and/or Pompe Disease in the biological sample.
2. The method of embodiment 1, wherein the method is performed as part of a newborn screening (NBS) that additionally screens the subject for one or more of phenylketonuria, primary congenital hypothyroidism, cystic fibrosis, and sickle cell disease.
3. The method of embodiment 1 or 2, wherein the method is performed in the absence of clinical symptoms of Pompe Disease and/or MPS I in the subject.
4. The method of any one of embodiments 1-3, wherein the biological sample is dried blood spot (DBS), a buccal swab, peripheral blood mononuclear cells (PBMCs), or white blood cells (WBCs).
5. The method of any one of embodiments 1-4, wherein the enzyme is trypsin.
6. The method of any one of embodiments 1-5, further including
comparing the concentration of each signature peptide to that of a corresponding predetermined threshold concentration; and
diagnosing the subject with:
MPS I when the concentrations of the first and/or second IDUA signature peptides are lower than corresponding predetermined threshold concentrations or when the first and/or second IDUA signature peptides are absent; and/or
Pompe Disease when the concentrations of the first, second, third, fourth, fifth, sixth, and/or seventh GAA signature peptides are lower than corresponding predetermined threshold concentrations or when the first, second, third, fourth, fifth, sixth, and/or seventh GAA signature peptides are absent.
7. The method of embodiment 6, wherein the predetermined threshold concentration for each signature peptide is calculated from a standard deviation of the mean concentration of each signature peptide in corresponding biological samples from a population of normal control subjects.
8. The method of embodiment 7, wherein the biological sample is DBS and the mean concentration of the first IDUA signature peptide of MPS I of SEQ ID NO: 1 in DBS from a population of normal control subjects includes a concentration in a range of 10 pmol/L to 350 pmol/L.
9. The method of any one of embodiments 6-8, wherein the biological sample is DBS and the predetermined threshold concentration of the first IDUA signature peptide of MPS I of SEQ ID NO: 1 includes 35 pmol/L or less.
10. The method of embodiment 7, wherein the biological sample is PBMC and the mean concentration of the first IDUA signature peptide of MPS I of SEQ ID NO: 1 in PBMC from a population of normal control subjects includes a concentration in a range of 300 pmol/L to 1000 pmol/L.
11. The method of embodiment 7, wherein the biological sample is a buccal swab and the mean concentration of the first IDUA signature peptide of MPS I of SEQ ID NO: 1 in buccal swabs from a population of normal control subjects includes a concentration in a range of 100 pmol/L to 1000 pmol/L.
12. The method of embodiment 7, wherein the biological sample is a buccal swab and the mean concentration of the first IDUA signature peptide of MPS I of SEQ ID NO: 1 in buccal swabs from a population of normal control subjects includes a concentration in a range of 30 pmol/g to 85 pmol/g.
13. The method of any one of embodiments 7-9, wherein the biological sample is DBS and the mean concentration of the second IDUA signature peptide of MPS I of SEQ ID NO: 2 in DBS from a population of normal control subjects includes a concentration in a range of 10 pmol/L to 250 pmol/L.
14. The method of any one of embodiments 6-9 and 13, wherein the biological sample is DBS and the predetermined threshold concentration of the second IDUA signature peptide of MPS I of SEQ ID NO: 2 includes 25 pmol/L or less.
15. The method of embodiment 7 or 10, wherein the biological sample is PBMC and the mean concentration of the second IDUA signature peptide of MPS I of SEQ ID NO: 2 in PBMC from a population of normal control subjects includes a concentration in a range of 350 pmol/L to 1000 pmol/L.
16. The method of any one of embodiments 7, 11, and 12, wherein the biological sample is a buccal swab and the mean concentration of the second IDUA signature peptide of MPS I of SEQ ID NO: 2 in buccal swabs from a population of normal control subjects includes a concentration in a range of 100 pmol/L to 1000 pmol/L.
17. The method of any one of embodiments 7, 11, 12, and 13, wherein the biological sample is a buccal swab and the mean concentration of the second IDUA signature peptide of MPS I of SEQ ID NO: 2 in buccal swabs from a population of normal control subjects includes a concentration in a range of 30 pmol/g to 80 pmol/g.
18. The method of any one of embodiments 6-9, 13, and 14, wherein the biological sample is DBS and the mean concentration of the third GAA signature peptide of Pompe Disease of SEQ ID NO: 5 in DBS from a population of normal control subjects includes a concentration in a range of 25 pmol/L to 250 pmol/L.
19. The method of any one of embodiments 6-9, 13, 14, and 18, wherein the biological sample is DBS and the predetermined threshold concentration of the third GAA signature peptide of Pompe Disease of SEQ ID NO: 5 includes 30 pmol/L or less.
20. The method of any one of embodiments 1-19, wherein the antibody or antigen-binding fragment thereof used for enrichment of the first IDUA signature peptide of SEQ ID NO: 1 includes a VH domain of SEQ ID NO: 18 and/or a VL domain of SEQ ID NO: 21.
21. The method of any one of embodiments 1-20, wherein the antibody or antigen-binding fragment thereof used for enrichment of the second IDUA signature peptide of SEQ ID NO: 2 includes a VH domain of SEQ ID NO: 30 and/or a VL domain of SEQ ID NO: 33.
22. The method of any one of embodiments 1-21, wherein the antibody or antigen-binding fragment thereof used for enrichment of the first GAA signature peptide of SEQ ID NO: 3 includes one or more of: a VH domain of SEQ ID NO: 57; a VL domain of SEQ ID NO: 65; a heavy chain of SEQ ID NO: 55; or a light chain of SEQ ID NO: 63.
23. The method of any one of embodiments 1-22, wherein the antibody or antigen-binding fragment thereof used for enrichment of the third GAA signature peptide of SEQ ID NO: 5 includes one or more of: a VH domain of SEQ ID NO: 79; a VL domain of SEQ ID NO: 87; a heavy chain of SEQ ID NO: 77; or a light chain of SEQ ID NO: 85.
24. The method of any one of embodiments 1-23, wherein the subject is undergoing one or more treatments for MPS I and/or Pompe Disease and the biological sample is obtained prior to the one or more treatments, and the method further includes
repeating the obtaining, digesting, enriching, and performing on a second biological sample derived from the subject during or after the one or more treatments; and
determining that the one or more treatments is effective for:
MPS I when the concentration of the first and/or second IDUA signature peptides during or after the one or more treatments is higher than the corresponding peptide concentrations of the first and/or second IDUA signature peptides prior to the one or more treatments; and/or Pompe Disease when the concentration of the first, second, third, fourth, fifth, sixth, and/or seventh GAA signature peptides during or after the one or more treatments is higher than the corresponding concentrations of the first, second, third, fourth, fifth, sixth, and/or seventh GAA signature peptides prior to the one or more treatments, or determining that the one or more treatments is not effective for:

MPS I when the concentration of the first and/or second IDUA signature peptides during or after the one or more treatments are equal to or lower than the corresponding concentrations of the first and/or second IDUA signature peptides prior to the one or more treatments or when the first and/or second IDUA signature peptides are absent; and/or Pompe Disease when the concentration of the first, second, third, fourth, fifth, sixth, and/or seventh GAA signature peptides during or after the one or more treatments are equal to or lower than the corresponding concentrations of the first, second, third, fourth, fifth, sixth, and/or seventh GAA signature peptides prior to the one or more treatments or when the first, second, third, fourth, fifth, sixth, and/or seventh GAA signature peptides are absent.

25. The method of any one of embodiments 1-24, further including predicting that the subject will develop an immune response to enzyme replacement therapy (ERT) for:

MPS I when the concentrations of the first and/or second IDUA signature peptides are absent; and/or Pompe Disease when the concentrations of the first, second, third, fourth, fifth, sixth, and/or seventh GAA signature peptides are absent.

26. The method of embodiment 25, further including administering mycophenolate mofetil, methotrexate (MTX), intravenous immunoglobulin (IVIG), rituximab, bortezomib, cyclophosphamide, and/or plasma exchange to the subject to reduce or prevent the immune response.

27. The method of embodiment 25 or 26, wherein the immune response includes developing neutralizing antidrug antibodies to an enzyme in ERT.

28. An assay for the screening of Mucopolysaccharidosis Type I (MPS I) and/or Pompe Disease in a subject, the assay including:

(i) an antibody or antigen-binding fragment thereof including:

a heavy chain variable (VH) domain including CDRH1 of SEQ ID NO: 10, CDRH2 of SEQ ID NO: 11, and CDRH3 of SEQ ID NO: 12, and a light chain variable (VL) domain including CDRL1 of SEQ ID NO: 13, CDRL2 of SEQ ID NO: 14, and CDRL3 of SEQ ID NO: 15 that binds an IDUA signature peptide of MPS I of SEQ ID NO: 1;

a VH domain including CDRH1 of SEQ ID NO: 22, CDRH2 of SEQ ID NO: 23, and CDRH3 of SEQ ID NO: 24, and a VL domain including CDRL1 of SEQ ID NO: 25, CDRL2 of SEQ ID NO: 26, and CDRL3 of SEQ ID NO: 27 that binds an IDUA signature peptide of MPS I of SEQ ID NO: 2;

a VH domain including CDRH1 of SEQ ID NO: 44, CDRH2 of SEQ ID NO: 45, and CDRH3 of SEQ ID NO: 46, and a VL domain including CDRL1 of SEQ ID NO: 47, CDRL2 of SEQ ID NO: 48, and CDRL3 of SEQ ID NO: 49 that binds a GAA signature peptide of Pompe Disease of SEQ ID NO: 3; and/or a VH domain including CDRH1 of SEQ ID NO: 66, CDRH2 of SEQ ID NO: 67, and CDRH3 of SEQ ID NO: 68, and a VL domain including: CDRL1 of SEQ ID NO: 69, CDRL2 of SEQ ID NO: 70, and CDRL3 of SEQ ID NO: 71 that binds a GAA signature peptide of Pompe Disease of SEQ ID NO: 5;

and/or (ii) an antibody or antigen-binding fragment thereof that binds a GAA signature peptide of Pompe Disease of SEQ ID NO: 4;

an antibody or antigen-binding fragment thereof that binds a GAA signature peptide of Pompe Disease of SEQ ID NO: 6;

an antibody or antigen-binding fragment thereof that binds a GAA signature peptide of Pompe Disease of SEQ ID NO: 7;

an antibody or antigen-binding fragment thereof that binds a GAA signature peptide of Pompe Disease of SEQ ID NO: 8; and/or an antibody or antigen-binding fragment thereof that binds a GAA signature peptide of Pompe Disease of SEQ ID NO: 9;

and/or (iii) reference signature peptides including:

an IDUA signature peptide of MPS I of SEQ ID NO: 1;

an IDUA signature peptide of MPS I of SEQ ID NO: 2;

a GAA signature peptide of Pompe Disease of SEQ ID NO: 3;

a GAA signature peptide of Pompe Disease of SEQ ID NO: 4;

a GAA signature peptide of Pompe Disease of SEQ ID NO: 5;

a GAA signature peptide of Pompe Disease of SEQ ID NO: 6;

a GAA signature peptide of Pompe Disease of SEQ ID NO: 7;

a GAA signature peptide of Pompe Disease of SEQ ID NO: 8; and/or a GAA signature peptide of Pompe Disease of SEQ ID NO: 9.

29. The assay of embodiment 28, wherein the reference signature peptides are isotopically labeled.

30. The assay of embodiment 28 or 29, wherein the antibodies or antigen-binding fragments thereof are attached to magnetic beads.

31. An antibody or antigen binding fragment thereof including: a heavy chain variable (VH) domain including CDRH1 of SEQ ID NO: 10, CDRH2 of SEQ ID NO: 11, and CDRH3 of SEQ ID NO: 12, and a light chain variable (VL) domain including CDRL1 of SEQ ID NO: 13, CDRL2 of SEQ ID NO: 14, and CDRL3 of SEQ ID NO: 15.

32. The antibody or antigen binding fragment thereof of embodiment 31, wherein the VH domain is set forth in SEQ ID NO: 18 and the VL domain is set forth in SEQ ID NO: 21.

33. An antibody or antigen binding fragment thereof including: a heavy chain variable (VH) domain including CDRH1 of SEQ ID NO: 22, CDRH2 of SEQ ID NO: 23, and CDRH3 of SEQ ID NO: 24, and a light chain variable (VL) domain including CDRL1 of SEQ ID NO: 25, CDRL2 of SEQ ID NO: 26, and CDRL3 of SEQ ID NO: 27.

34. The antibody or antigen binding fragment thereof of embodiment 33, wherein the VH domain is set forth in SEQ ID NO: 30 and the VL domain is set forth in SEQ ID NO: 33.

35. An antibody or antigen binding fragment thereof including: a heavy chain variable (VH) domain including CDRH1 of SEQ ID NO: 44, CDRH2 of SEQ ID NO: 45, and CDRH3 of SEQ ID NO: 46, and a light chain variable (VL) domain including CDRL1 of SEQ ID NO: 47, CDRL2 of SEQ ID NO: 48, and CDRL3 of SEQ ID NO: 49.

36. The antibody or antigen binding fragment thereof of embodiment 35, wherein the VH domain is set forth in SEQ ID NO: 57 and/or the heavy chain is set forth in SEQ ID NO: 55; and the VL domain is set forth in SEQ ID NO: 65 and/or the light chain is set forth in SEQ ID NO: 63.

37. An antibody or antigen binding fragment thereof including: a heavy chain variable (VH) domain including CDRH1 of SEQ ID NO: 66, CDRH2 of SEQ ID NO: 67, and CDRH3 of SEQ ID NO: 68, and a light chain variable (VL) domain including CDRL1 of SEQ ID NO: 69, CDRL2 of SEQ ID NO: 70, and CDRL3 of SEQ ID NO: 71.

38. The antibody or antigen binding fragment thereof of embodiment 37, wherein
the VH domain is set forth in SEQ ID NO: 79 and/or the heavy chain is set forth in SEQ ID NO: 77; and
the VL domain is set forth in SEQ ID NO: 87 and/or the light chain is set forth in SEQ ID NO: 85.

39. A kit including:
   (i) an antibody or antigen-binding fragment thereof including:
      a heavy chain variable (VH) domain including CDRH1 of SEQ ID NO: 10, CDRH2 of SEQ ID NO: 11, and CDRH3 of SEQ ID NO: 12, and a light chain variable (VL) domain including CDRL1 of SEQ ID NO: 13, CDRL2 of SEQ ID NO: 14, and CDRL3 of SEQ ID NO: 15 that binds an IDUA signature peptide of MPS I of SEQ ID NO: 1;
      a VH domain including CDRH1 of SEQ ID NO: 22, CDRH2 of SEQ ID NO: 23, and CDRH3 of SEQ ID NO: 24, and a VL domain including CDRL1 of SEQ ID NO: 25, CDRL2 of SEQ ID NO: 26, and CDRL3 of SEQ ID NO: 27 that binds an IDUA signature peptide of MPS I of SEQ ID NO: 2;
      a VH domain including CDRH1 of SEQ ID NO: 44, CDRH2 of SEQ ID NO: 45, and CDRH3 of SEQ ID NO: 46, and a VL domain including CDRL1 of SEQ ID NO: 47, CDRL2 of SEQ ID NO: 48, and CDRL3 of SEQ ID NO: 49 that binds a GAA signature peptide of Pompe Disease of SEQ ID NO: 3; and/or
      a VH domain including CDRH1 of SEQ ID NO: 66, CDRH2 of SEQ ID NO: 67, and CDRH3 of SEQ ID NO: 68, and a VL domain including CDRL1 of SEQ ID NO: 69, CDRL2 of SEQ ID NO: 70, and CDRL3 of SEQ ID NO: 71 that binds a GAA signature peptide of Pompe Disease of SEQ ID NO: 5;
   and/or
   (ii) an antibody or antigen-binding fragment thereof that binds a GAA signature peptide of Pompe Disease of SEQ ID NO: 4;
      an antibody or antigen-binding fragment thereof that binds a GAA signature peptide of Pompe Disease of SEQ ID NO: 6;
      an antibody or antigen-binding fragment thereof that binds a GAA signature peptide of Pompe Disease of SEQ ID NO: 7;
      an antibody or antigen-binding fragment thereof that binds a GAA signature peptide of Pompe Disease of SEQ ID NO: 8; and/or
      an antibody or antigen-binding fragment thereof that binds a GAA signature peptide of Pompe Disease of SEQ ID NO: 9;
   and/or
   (iii) reference signature peptides including:
      an IDUA signature peptide of MPS I of SEQ ID NO: 1;
      an IDUA signature peptide of MPS I of SEQ ID NO: 2;
      a GAA signature peptide of Pompe Disease of SEQ ID NO: 3;
      a GAA signature peptide of Pompe Disease of SEQ ID NO: 4;
      a GAA signature peptide of Pompe Disease of SEQ ID NO: 5;
      a GAA signature peptide of Pompe Disease of SEQ ID NO: 6;
      a GAA signature peptide of Pompe Disease of SEQ ID NO: 7;
      a GAA signature peptide of Pompe Disease of SEQ ID NO: 8; and/or
      a GAA signature peptide of Pompe Disease of SEQ ID NO: 9.

40. The kit of embodiment 39, further including one or more of filter paper card, punch tool, buccal swab, blood collection tube, digestion enzymes, digestion buffers, solid support for the antibodies or antigen-binding fragments thereof; and elution buffers.

41. The kit of embodiment 39 or 40, wherein the reference signature peptides are isotopically labeled.

42. The kit of any one of embodiments 39-41, wherein the antibodies or antigen-binding fragments thereof are attached to magnetic beads.

(XII) Experimental Examples

Example 1. This study demonstrated the effectiveness of two IDUA signature peptide biomarkers and their associated antibodies for screening MPS I patients with an immuno-SRM method using DBS as biological samples. This study also demonstrated that the two IDUA signature peptide biomarkers were detected in commercially available PBMC using the associated antibodies.

Materials and Methods. A standard immuno-SRM protocol was used for this study. Briefly, one ¼-inch DBS punch were obtained for each sample and placed into a designated well on the 96-well plate (96 Well MASTERBLOCK®, polypropylene, 0.5 ml, Greiner). To each well, 200 µL of 0.1% triton in 50 mM ammonium bicarbonate buffer and 6 µL of 0.2 M dithiothreitol (DTT) were added and DBS was extracted for half an hour in a 37° C. oven (Hybridization oven, Illumina). After the extraction, 37.5 µL of trypsin (1 µg/µL in 50 mM acetic acid) (TPCK-treated trypsin, Worthington, LS003742) was added to each well to perform digestion for 2 hours in the 37° C. oven. Afterwards, an appropriate amount of internal standard (IS) and 10 µL of Tris buffer (pH 8.0) was added to each sample after digestion and mixed well at 1000 rpm for 2 minutes.

200 µL of digested solution was then transferred to new wells, leaving the protein saver paper (from DBS) behind. An appropriate amount of monoclonal antibody (mAb)-coated magnetic beads (Dynabeads-Protein G magnetic beads, Invitrogen, No. 10004D) for each targeted peptide was added to the solution and the mixture was left at 4° C. at 1000 rpm overnight. The next day mAb-bead-peptide complexes were washed twice with 250 µL of 0.1×PBS+ 0.01% CHAPS using a magnetic plate rack. After the second wash, 30 µL of 5% acetic acid+3% ACN in water was added to the mAb-bead-peptide complexes for peptide elution and left at 1000 rpm for 5 minutes. Then, eluent and beads were separated on a magnetic plate rack. Eluent was transferred to a different 96 well plate and centrifuged at 3000 rpm for 2 minutes. 15 µL of clear eluent from each well was transferred to new wells for data analysis with LC-MS/MS. The remaining eluent was stored at −20° C. as backup.

LC-MS/MS of isolated peptide mixtures was performed on a Waters Xevo TQ-XS with Ionkey source and dual M-Class gradient and loading chromatography pumps (Milford, Mass.). Chromatographic solvents were A: $H_2O+0.1\%$ FA and B: ACN+0.1% FA. As an initial step, peptides were loaded onto an M-Class Trap Symmetry C18 column (300 µM×25 mm, 100 A, 5 uM) for three minutes with a constant flow of 98:2 A:B at 20 µL/min. After loading, the flow was reversed. Peptides were eluted from the trapping column and separated using a 150 µM×100 mm BEH C18 ionkey (130 A, 1.7 µM). SRM transitions were acquired in unit resolution in both Q1 and Q3 quadrupoles. Precursor and fragment masses for each peptide were chosen to generate the highest intensity transitions. Precursor mass, fragment mass, and collision energy were tuned to optimize the generated signal.

Signature peptide biomarkers IDUA 218 and IDUA 462 were developed for monitoring iduronidase (IDUA) level in DBS to screen for Mucopolysaccharidosis type I (MPS I) patients. With the standard immuno-SRM protocol, 1 µg and 4 µg of antibodies for IDUA 218 and IDUA 462, respectively, were used in the assay to capture both endogenous peptides and 1.25 fmol of IS. The study included 11 MPS I patients (2 patients having the attenuated form with one patient providing both pre-ERT and post-ERT samples; 4 patients having the severe form with one patient providing pre-ERT, post-ERT, and post-bone marrow transplant (BMT) samples; 3 patients having an unknown form of MPS I; and 2 post-BMT patients). All pre-treatment patients exhibited extremely low levels of IDUA regardless of disease severity, while the normal controls and post-treatment patients showed a level of IDUA in the normal range (FIGS. 3A-3D). The IDUA peptide biomarkers can be used to diagnose and/or predict MPS I.

Figure 4A:
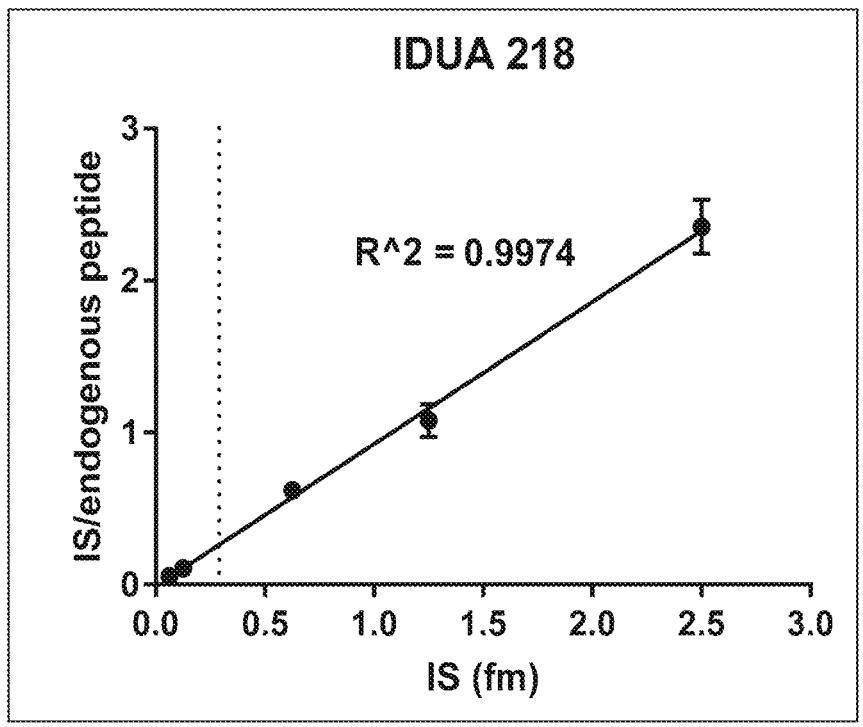
FIGS. 4A, 4B. Linear response of IDUA peptides when an internal standard was spiked into the dried blood spot (DBS) matrix (the dotted line represents the lowest level of peptide found in normal cohort).
Figure 4B:
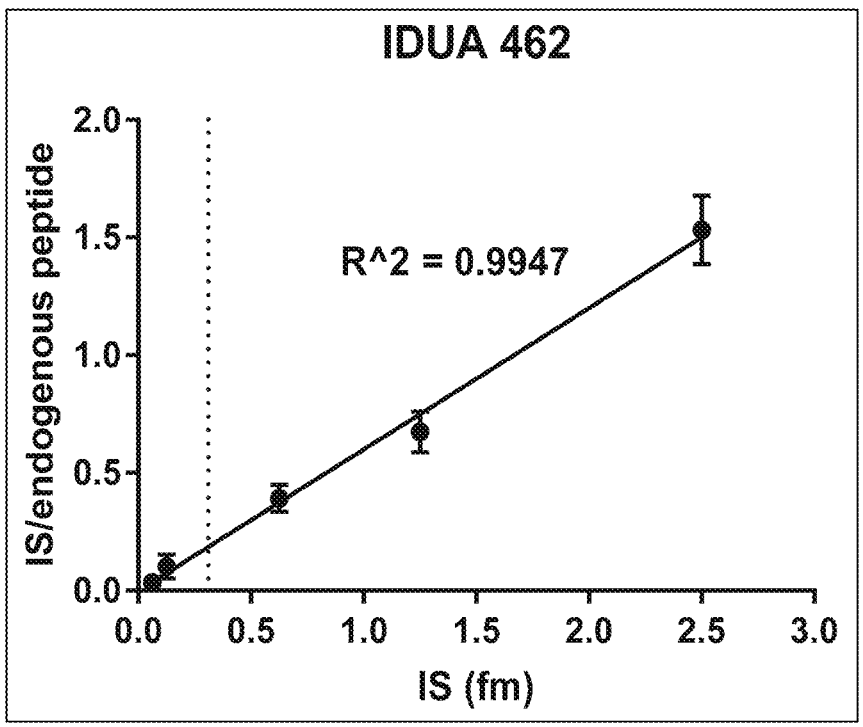

As shown in FIGS. 4A and 4B, linearity curves were constructed for both IDUA peptide biomarkers by spiking different amounts of IS into the DBS matrix. The dotted line in the figures shows the lowest amount of peptide that was quantified in a normal cohort, which is 0.64 fmol (29.43 pmol/L) and 0.30 fmol (13.77 pmol/L) for IDUA 218 and IDUA 462, respectively. Table 2 summarizes the normal range, tentative cutoff, lower limit of detection (LOD), lower limit of quantification (LOQ), intra- and inter-day coefficient of variants (CV), and the relative stability of IDUA peptides for the IDUA immuno-SRM method. Intra- and inter-day assay CVs were obtained by performing 5 replicates of the assay on 5 different days. Intra-day CV evaluates the consistency of the results from the 5 assays from identical samples within the same day, while inter-day CV evaluates the consistency of the results from the assays from 5 different days. As summarized in Table 2, all CVs for IDUA analysis were less than 15%. The relative stabilities of the IDUA peptides in the DBS samples were evaluated by storing DBS under different temperatures, including −20° C., room temperature (RT) and 37° C., over a course of two weeks. The relative stabilities were calculated by comparing the IDUA concentrations from DBS stored at RT and 37° C. to the DBS stored at −20° C. Together, these data show that the immuno-SRM method for IDUA analysis could be performed in a highly quantitative fashion.

TABLE 2

Analytical figures of merit for IDUA peptide immuno-SRM method.

| Peptide | Normal range (Mean ± SD) (pmol/L) | Tentative cutoff (pmol/L) | LOD (pmol/L) | LOQ (pmol/L) | Intra-day assay CV | Inter-day assay CV | Relative stability (RT) | Relative stability (37° C.) |
|---|---|---|---|---|---|---|---|---|
| IDUA 218 | 69.89 ± 20.42 | 18.84 | 3.51 | 4.10 | 11.5% | 13.6% | −5.8% | −0.7% |
| IDUA 462 | 44.46 ± 14.82 | 11.84 | 2.08 | 4.53 | 9.9% | 10.5% | −11.9% | −17.0% |

Figure 3A:
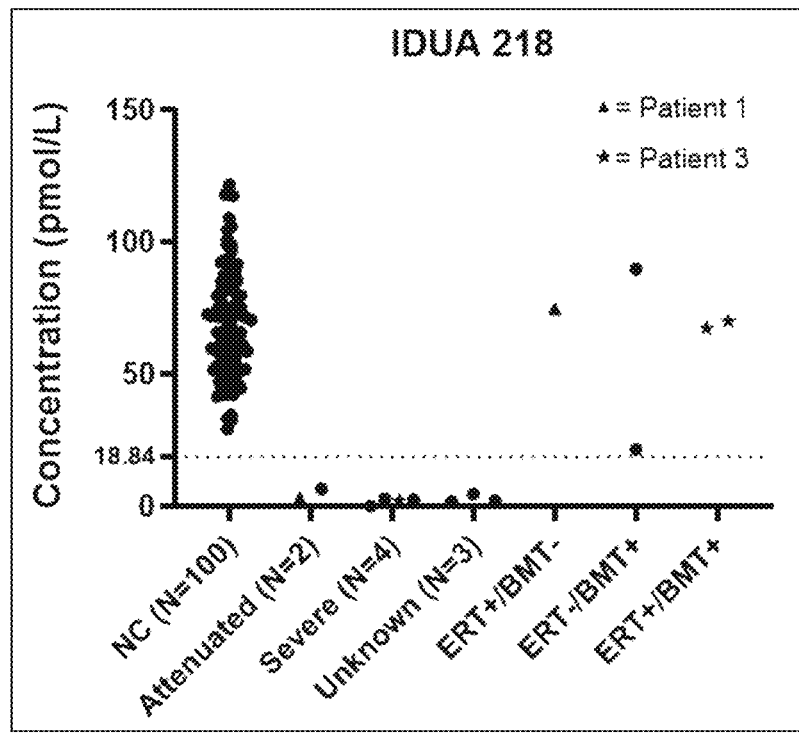
FIGS. 3A-3D. A study of 11 MPS I disease patients (9 pre-treatment patients including 2 with post-treatment samples: 2 attenuated form; 4 severe form; and 3 unknown form. Two post-treatment patients) (ERT: enzyme replacement therapy; BMT: bone marrow transplant; LOD: lower limit of detection).
Figure 3B:
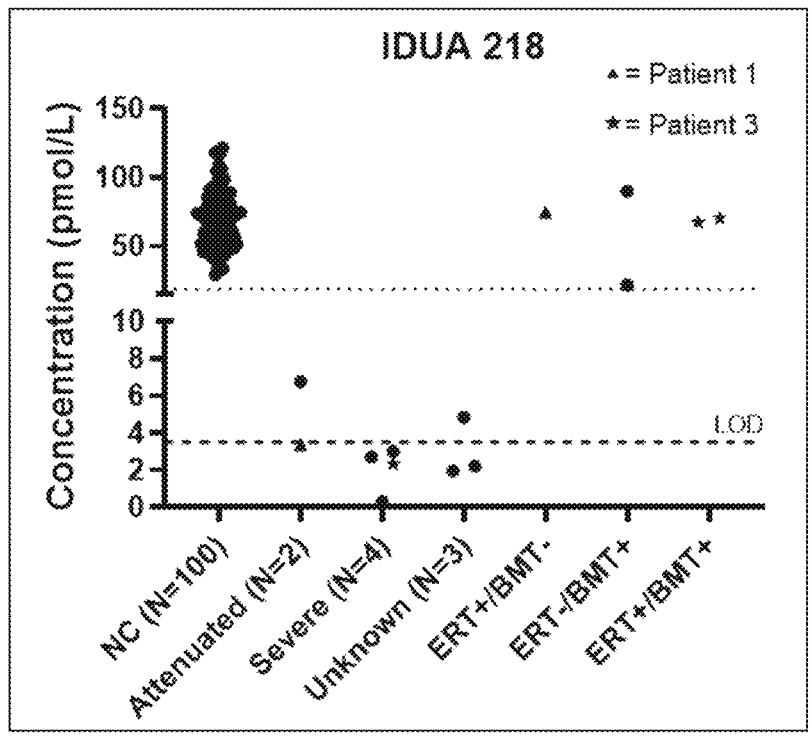
Figure 3C:
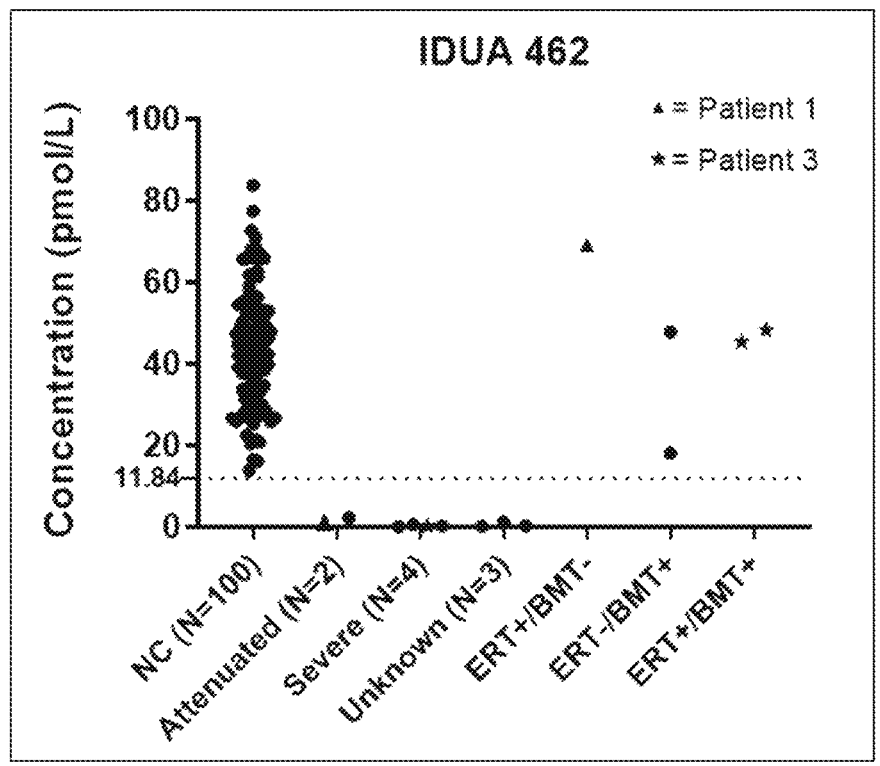
Figure 3D:
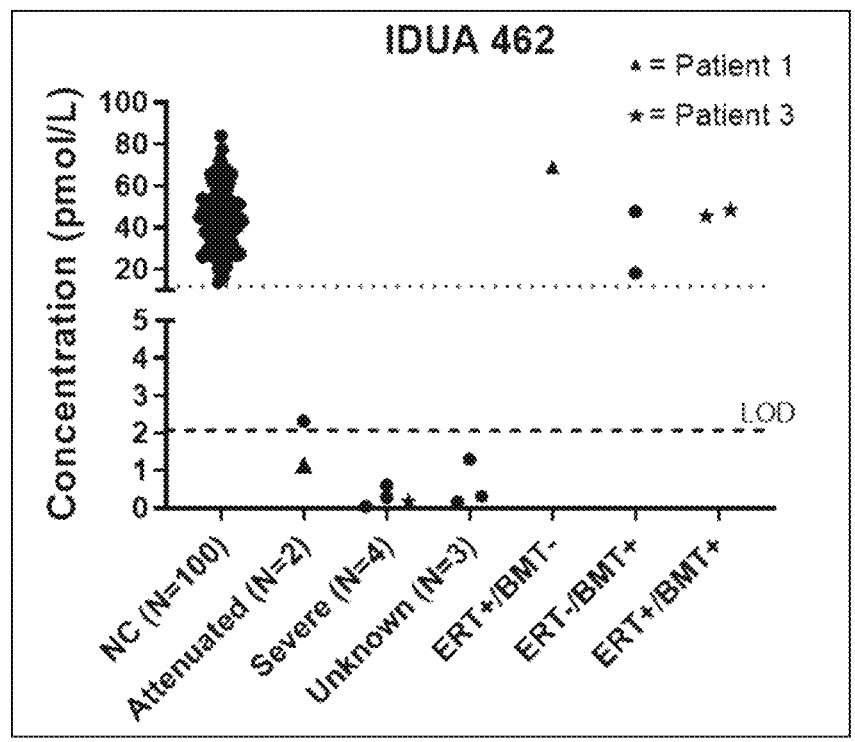

LOD—lower limit of detection; LOQ—lower limit of quantification; CV—coefficient of variant; RT—room temperature As shown in FIGS. 3B and 3D, despite most MPS I patients showing absent levels of IDUA, i.e. the IDUA concentrations were below the LOD of both IDUA peptides, one patient with attenuated MPS I showed slightly elevated IDUA concentration (above the LOD of both IDUA peptides). With a biological sample that has more concentrated proteins, such as leukocyte, PBMC, or buccal swab, it is expected that the immuno-SRM method should allow a more nuanced investigation of the protein concentration differences between these two patient populations.

Figure 5A:
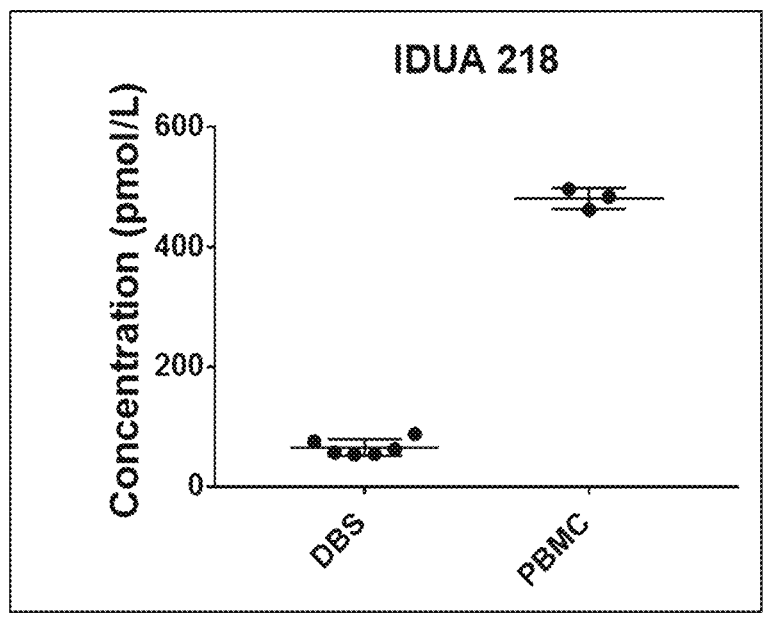
FIGS. 5A, 5B. IDUA peptide concentrations in DBS and peripheral blood mononuclear cell (PBMC) samples. (DBS: five 3 mm punches; PBMC: 250 µg of protein).
Figure 5B:
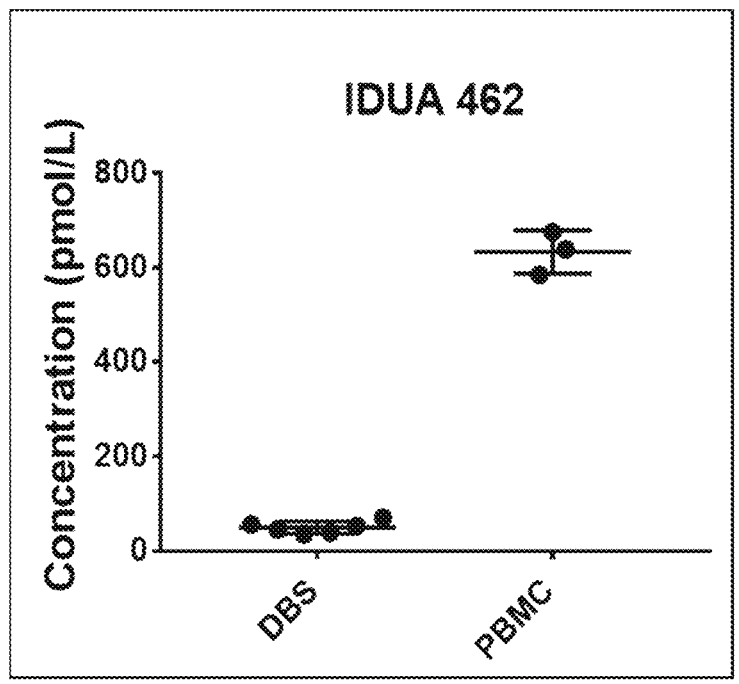

As shown in FIGS. 5A and 5B, with 500 µL of commercial PBMC samples (500 µg of protein/mL), there was an 8-12 fold increase in the detected peptide concentration for both IDUA peptide biomarkers when compared to the control DBS samples.

Example 2. This study demonstrated that two IDUA signature peptide biomarkers were detected by an immuno-SRM method using their associated antibodies as described in Example 1 in cells from buccal swabs.

Buccal Swab Samples. The controlling institutional review board approved the protocol for buccal swab samples and all subjects gave written informed consent. Normal control buccal swab samples were obtained from commercial vendors. All buccal swab samples were stored in the lab at −20° C. or −80° C. Blind samples were labeled with an ID provided by the sender and identified and consented patient samples were given a lab ID upon receipt. Nylon Flocked Dry Swabs in Peel Pouches, Copan Diagnostics 502CS01 were obtained from Fisher Scientific (Chicago, Ill.; Cat no. 23-600-951). 2-mL Cryogenic Storage Vials Internal Thread are obtained from Fisher Scientific (Chicago, Ill.; Cat no. 12-567-501). Buccal swab sample collection followed protocols described in: CHLA. (2016, April 4). Buccal Swab Collection Procedure. CHLA-Clinical Pathology; (2016, July 27). Buccal DNA Collection Instructions. Pathway Genomics; (2017, Dec. 14). Instruction for Buccal Swab Sample Collection. Otogenetics; PDXL PDXL. (2017, Nov. 28). *Buccal Swab collection procedure—PersonalizedDx Labs* [Video]. YouTube. On World Wide Web at youtube/ 3ftvHkfM71o?t=146; and Centers of Disease Control and Prevention (CDC). (2020, July 8). Interim Guidelines for collecting, handling, and testing clinical specimens for Covid-19. On World Wide Web at cdc.gov/coronavirus/ 2019-ncov/lab/guidelines-clinical-specimens.html. The tip of a buccal swab containing cells was clipped into a tube for solubilization and digestion as described above for DBS.

Figure 6A:
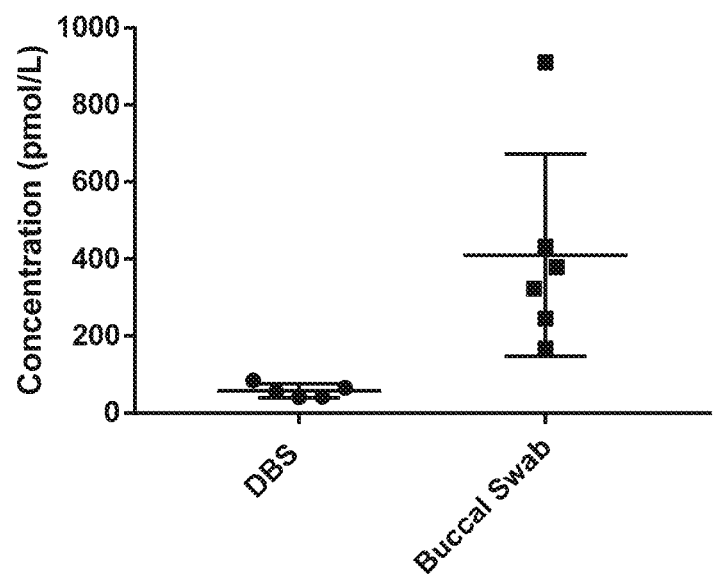
FIGS. 6A, 6B. IDUA peptide concentrations in DBS and buccal swab samples. (DBS: five 3 mm punches).
Figure 6B:
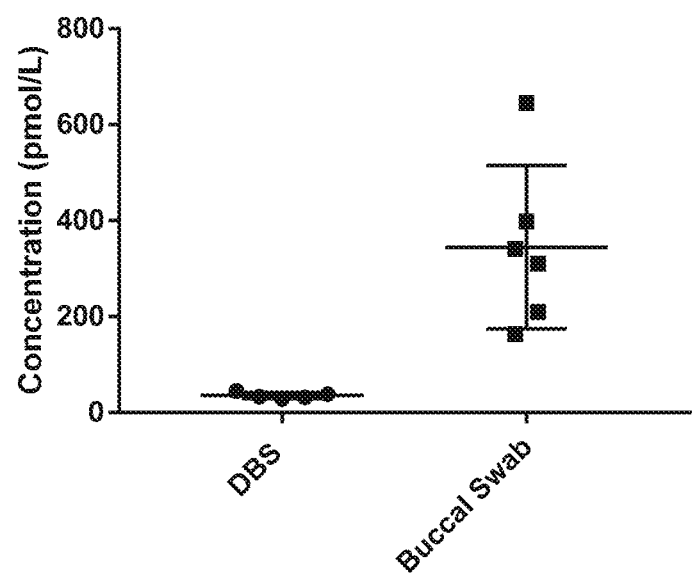

As shown in FIGS. 6A and 6B, epithelial cells collected using a buccal swab generated an 2.9-18.2-fold increase in the peptide concentration for both IDUA peptide biomarkers compared to DBS samples, assuming a similar volume of saliva.

Example 3. This study demonstrated that the immuno-SRM method is a viable option to distinguish pseudo deficient cases for MPS I from confirmed MPS I patients.

The experiment was carried out according to standard immuno-SRM protocol as discussed in Example 1. FIGS. 7A and 7B show the peptide concentrations for both IDUA 218 and IDUA 462 for 4 MPS I pseudo deficient cases. There was a wide range for the pseudo deficient IDUA concentrations. However, even the lowest IDUA concentrations for the pseudo deficient cases (8.63 pmol/L and 3.82 pmol/L, respectively, for IDUA 218 and IDUA 462) were still higher than the highest IDUA concentrations for the confirmed MPS I patients (6.76 pmol/L and 2.32 pmol/L, respectively, for IDUA 218 and IDUA 462). This study shows that immuno-SRM can be used as a primary or second-tier test for NBS of MPS I to reduce the false positive rate from pseudo deficient cases. A future large cohort pilot study using immuno-SRM as a primary screening method will be conducted to test for a superior false positive rate compared to current methods for screening MPS I and Pompe Disease.

Example 4. This study demonstrated that it is feasible to develop monoclonal antibodies against the GAA peptides.

Antibody production was performed as follows: i) peptides were synthesized with an N-terminal cysteine and conjugated to adjuvant proteins before rabbit immunization; ii) serum samples from the immunized rabbit were collected and the antibodies within the sera were used in a peptide capture test by immuno-SRM for rabbit selection; iii) after 2 to 3 times of immunization boosts (multiple immunizations to the rabbits), the best rabbit was selected and its plasma cells were isolated by cell sorting and cultured to provide antibodies; iv) immuno-SRM was performed as described in Example 1 to validate that the plasma cells were producing a viable antibody for the intended target. The cDNA was cloned and expressed to produce the final monoclonal antibodies.

Figure 8A:
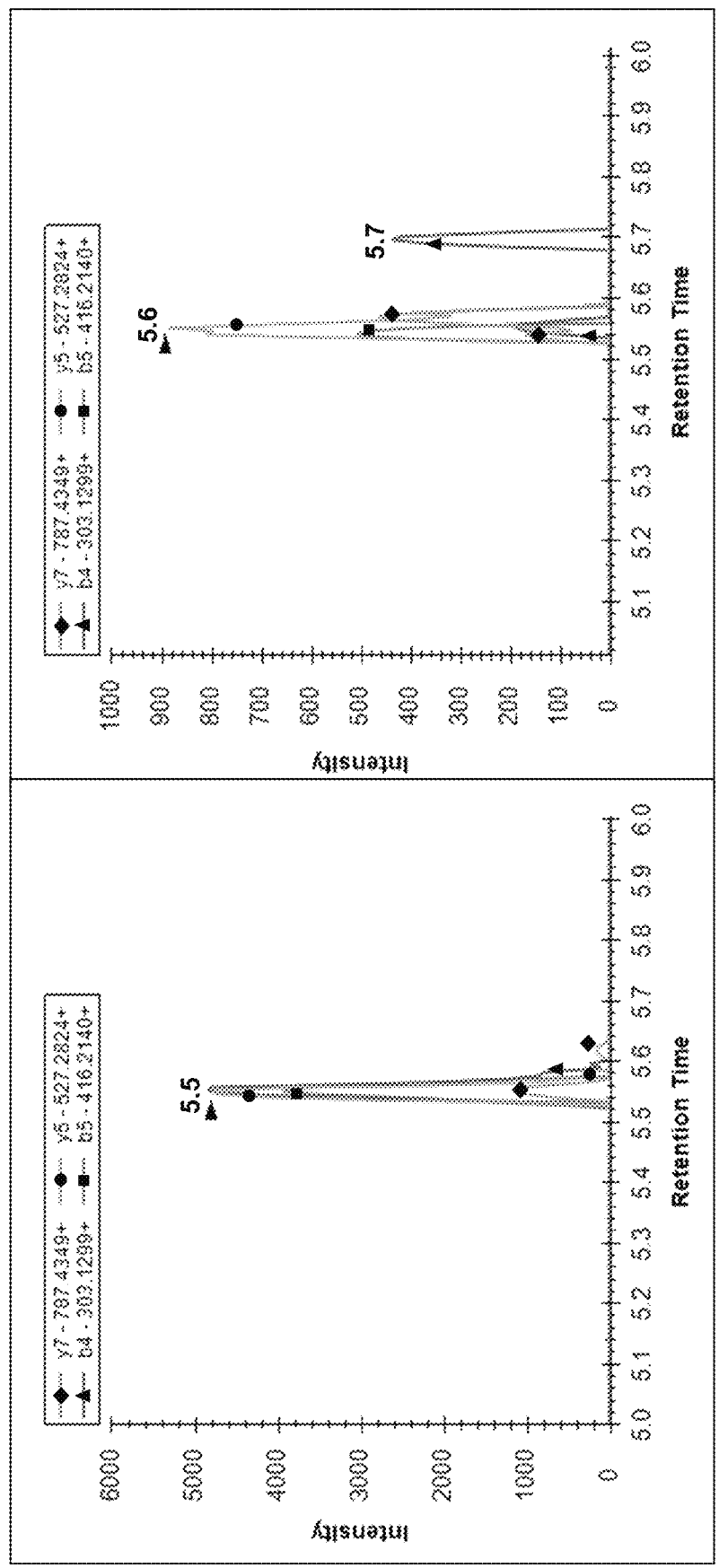
FIGS. 8A, 8B. Multiple reaction monitoring (MRM) traces for GAA peptides from purified peptides (left) and DBS samples (right) after peptide capture by sera antibodies from immunized rabbits.
Figure 8B:
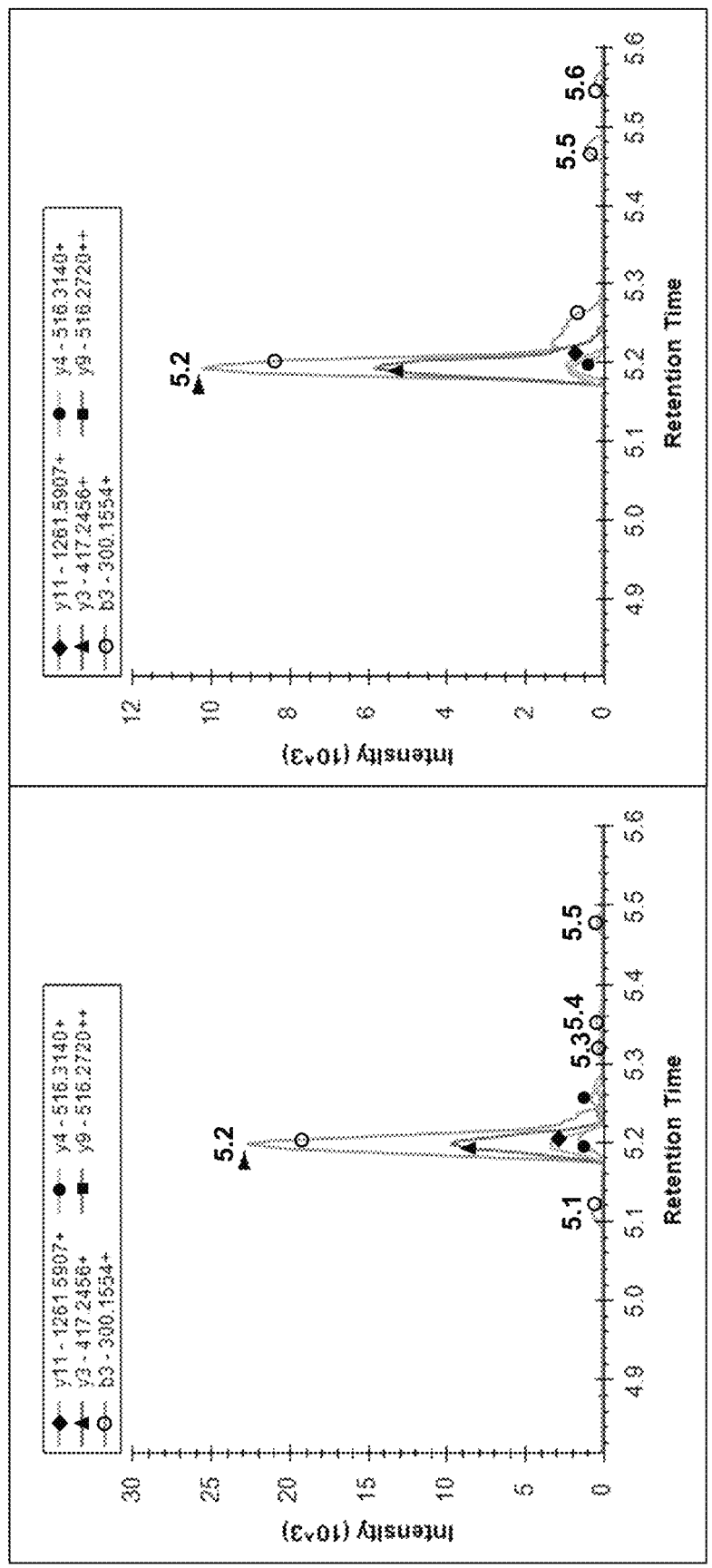
Figure 9:
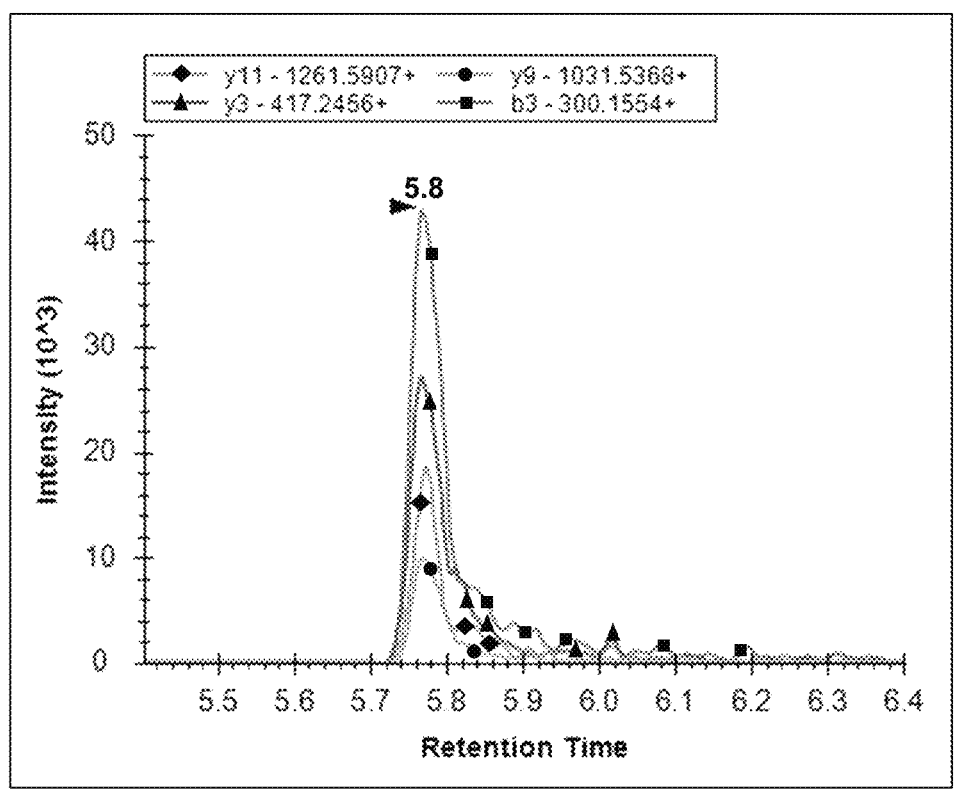
FIG. 9. Endogenous multiple reaction monitoring (MRM) traces for GAA 855 from PBMC sample after peptide capture by supernatant antibodies from isolated plasma cells.

To develop monoclonal antibodies against GAA 332 and GAA 855, antibodies in the serum samples of the immunized rabbits were used to capture purified GAA 332 and GAA 855 peptides as well as the endogenous GAA 332 and GAA 855 peptide from DBS samples as shown in FIGS. 8A and 8B. This data shows that the immunized rabbits can produce corresponding antibodies against GAA 332 and GAA 855 peptides. Supernatants containing the antibodies were used in the immuno-SRM assay with PBMC. As shown in FIG. 9, the antibodies in the supernatants for GAA 855 were able to yield a strong signal after peptide capture from the PBMC sample (500 µL of commercial PBMC sample (500 µg of protein/mL)). This study shows that rabbits can generate anti GAA peptide antibodies.

Figure 10A:
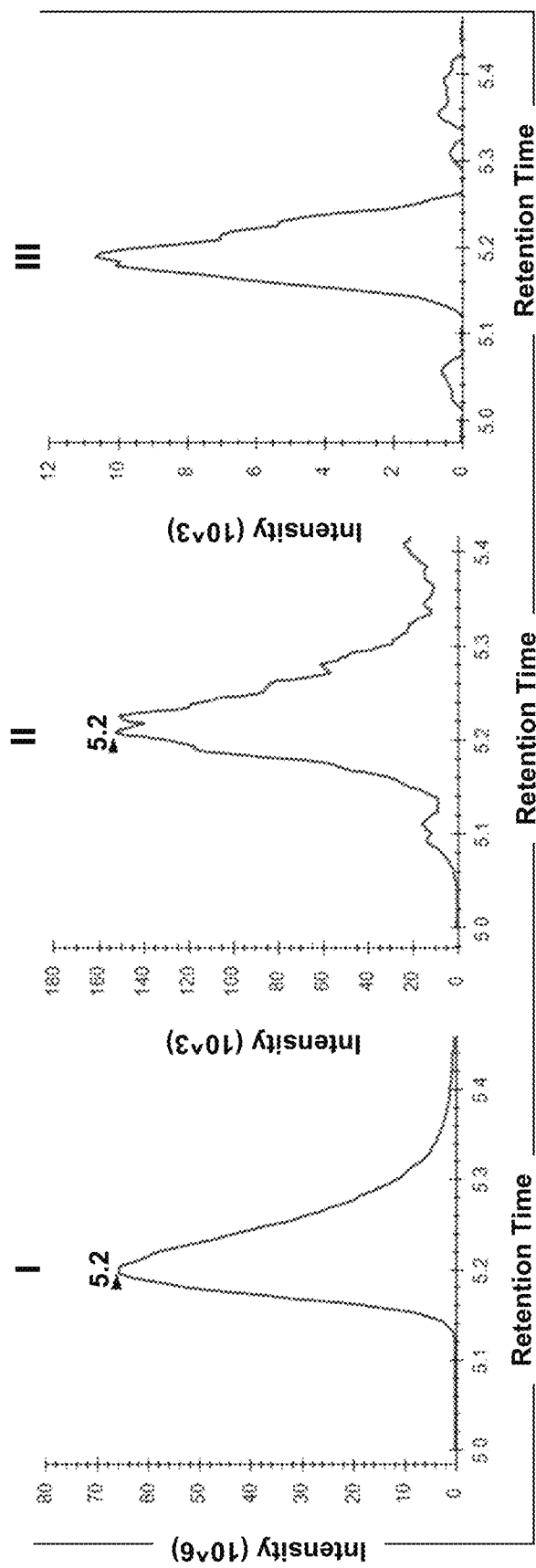
FIGS. 10A, 10B. Multiple reaction monitoring (MRM) traces for GAA peptides from purified peptides (I), DBS samples (II), and buccal swab samples (III) after peptide capture by sera antibodies from immunized rabbits.
Figure 10B:
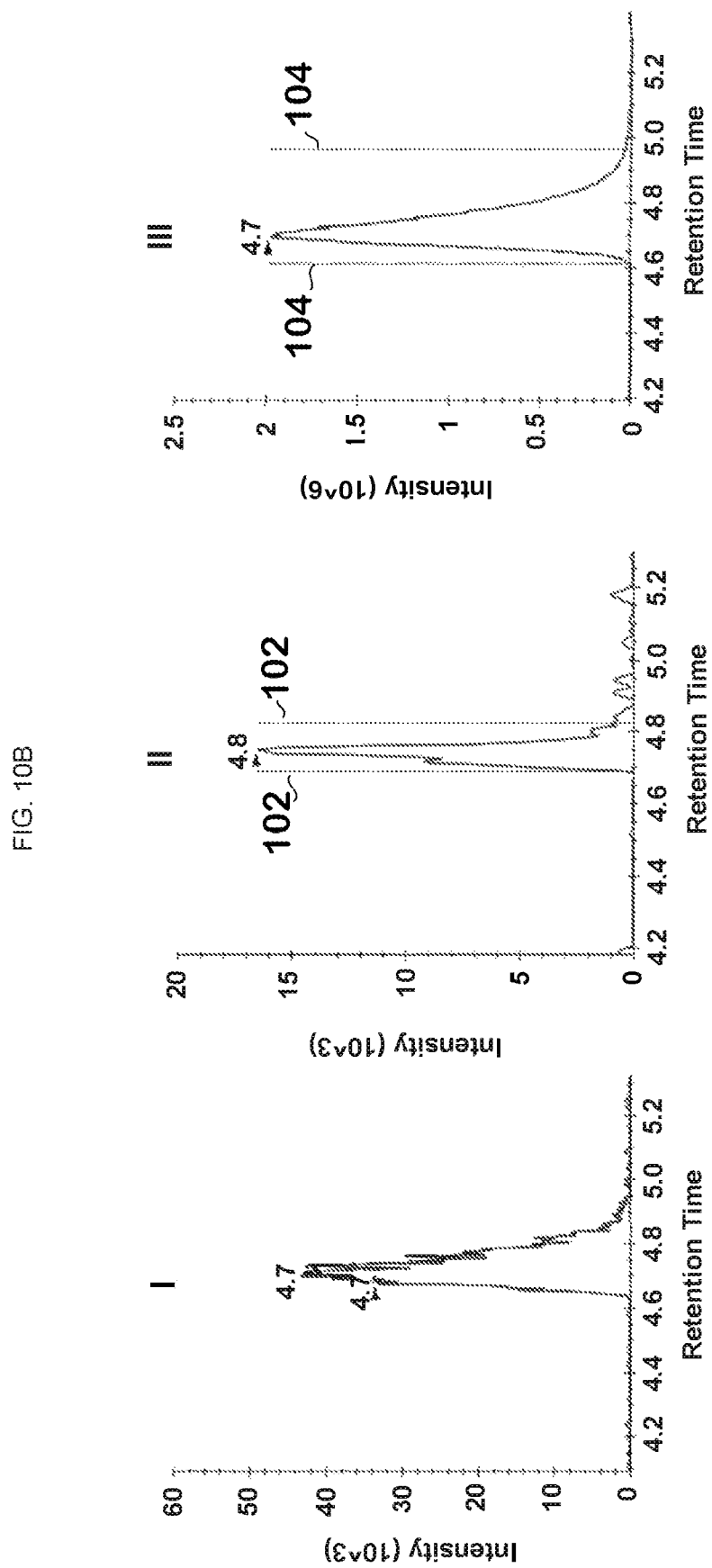

To develop monoclonal antibodies against GAA 155 and GAA 376, antibodies in the serum samples of the immunized rabbits were used to capture purified GAA 155 and GAA 376 peptides, endogenous GAA 155 and GAA 376 peptide from DBS samples, and endogenous GAA 155 and GAA 376 peptide from buccal swab samples as shown in FIGS. 10A and 10B. The DBS and buccal swab samples were obtained and peptides from the samples prepared for immuno-SRM as described in Examples 1 and 2. This data shows that the immunized rabbits can produce corresponding antibodies against GAA 155 and GAA 376 peptides. Supernatants containing the antibodies were used in the immuno-SRM assay with buccal swabs. As shown in FIGS. 10A and 10B, the antibodies in the supernatants for GAA 155 and GAA 376 were able to yield a 2-100-fold greater analytical response in buccal swabs than DBS. This study shows that rabbits can generate anti GAA peptide antibodies for enrichment from DBS and buccal swab.

Figure 11:
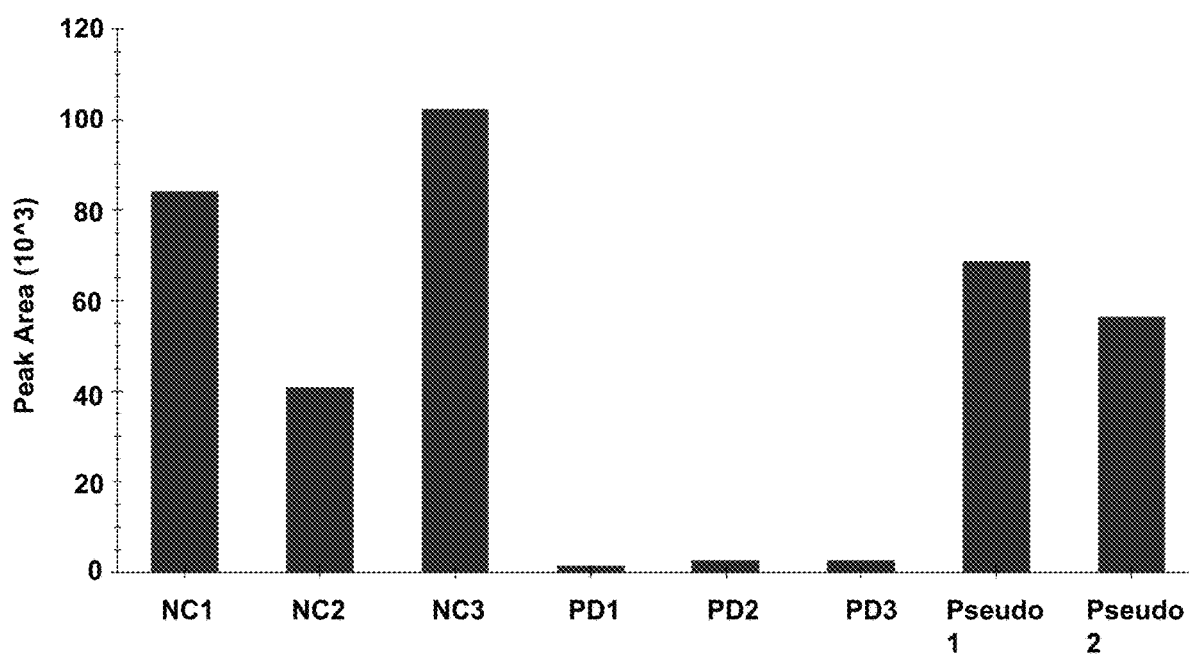
FIG. 11. Comparison of GAA concentrations in DBS among three normal controls (NC1, NC2, NC3), three true positive Pompe patients (PD1, PD2, PD3), and two pseudo-deficient cases (Pseudo 1 and Pseudo 2) for GAA 376 peptide biomarker (WGYSSTAITR (SEQ ID NO: 5), parent ion mass 571.2855++).

Example 5. The experiment was carried out according to standard immuno-SRM protocol with DBS samples as discussed in Example 1. As shown in FIG. 11, this study demonstrated that the immuno-SRM method is a viable option to distinguish Pompe patients from pseudo deficiency of the acid alpha-glucosidase enzyme. The GAA peptides were significantly reduced or absent in true positive Pompe patients. There were subtle differences in GAA concentration between patients with infantile and late onset forms of Pompe disease from DBS. With a biological sample that has more concentrated proteins, such as leukocyte, PBMC or buccal swab, it is expected that the immuno-SRM method will allow a more nuanced investigation of the protein concentration differences between these two patient populations. Those patients with absent GAA could be compatible with CRIM negative status and could ultimately need immune modulation to reduce blocking antibody before the ERT.

As shown in FIG. 11, this study demonstrated that the immuno-SRM method was a viable option to distinguish pseudo deficient cases from confirmed Pompe patients. Thus, immuno-SRM can be used as a primary or second-tier test for NBS of Pompe disease to reduce the false positive rate from pseudo deficient cases.

Prophetic Example 1. Immuno-SRM assay of GAA signature peptide(s) for diagnosis of Pompe Disease (PD).

Peripheral Blood Mononuclear Cells (PBMCs) and White Blood Cells (WBCs). PBMCs and WBCs can be collected by protocols known in the art, such as ones described in Kerfoot et al., Proteomics Clin Appl, 2012. 6(7-8):394-402; Grievink et al. (2016) Biopresery Biobank 14(5):410-415; Corkum et al. (2015) BMC Immunol. 16:48; Jia et al. (2018) Biopresery Biobank 16(2):82-91; Boyum (1968) Scand. J. Clin. Lab Invest. Suppl. 97:77; Boyum (1977) Lymphology 10(2): 71-76; Morgensen and Cantrell (1977) Pharm Therap.

1: 369-383; Beeton and Chandy (2007) J Vis Exp. (8): 326; Brocks et al (2006) In vivo 20(2): 239; Faguet and Agee (1993) J Imm Meth 165(2): 217; Brousso et al (1997) Immunol Let 59(2):85; and Dagur and McCoy (2015) Curr Protoc Cytom. 73:5.1.1-5.1.16. The isolated PBMCs or WBCs can be solubilized and proteins from the cells digested as described above for DBS.

DBS, buccal swab samples, PBMCs, or WBCs (as described herein) from patients with PD or from patients suspected of having PD, along with the corresponding samples from normal controls, will be analyzed by immuno-SRM using GAA 155, GAA 332, GAA 376, GAA 601, GAA 855, GAA 882, GAA 892 signature peptides, or a combination thereof, as described herein. The immuno-SRM diagnoses will be compared to clinical diagnoses. If available, genetic information for the GAA gene and treatment information will be obtained for each patient. The immuno-SRM assay can be multiplexed with signature peptides to test for MPS I (IDUA 218 and/or IDUA 462). These studies will show that immuno-SRM assays utilizing the antibodies described herein can be used to detect the disclosed GAA and/or IDUA signature peptides in a biological sample including DBS, buccal swab samples, PBMCs, or WBCs and to diagnose whether subjects have Pompe Disease and/or MPS I based on the detected levels of the signature peptides. Moreover, the study will show that pseudo deficient cases of Pompe Disease and/or MPS I can be distinguished from true cases of Pompe Disease and/or MPS I, reducing the false positive rate of diagnosing these LSDs.

(XIII) Closing Paragraphs

Each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in the ability to reliably diagnose MPS I and/or Pompe Disease utilizing DBS, cells from a buccal swab, PBMC, or WBC, the antibodies disclosed herein, and immuno-SRM.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

The invention claimed is:

1. A method of detecting one or more signature peptides of Mucopolysaccharidosis Type I (MPSI) and/or Pompe Disease in a biological sample, the method comprising:
   obtaining a biological sample from a subject;
   digesting proteins from the biological sample with an enzyme to yield a digested biological sample comprising peptides;
   enriching the digested biological sample for the one or more signature peptides by contacting the sample with an antibody or antigen binding fragment thereof for each of the one or more signature peptides, the enriching step comprising enriching for:
   (A) an alpha-L-iduronidase enzyme (IDUA) signature peptide of MPSI of SEQ ID NO: 2 with an antibody or antigen-binding fragment thereof that binds the IDUA signature peptide and comprises: a heavy chain variable (VH) domain comprising a complementarity determining region (CDR)H1 as set forth in SEQ ID NO: 22, a CDRH2 as set forth in SEQ ID NO: 23, and a CDRH3 as set forth in SEQ ID NO: 24, and a light chain variable (VL) domain comprising a CDRL1 as set forth in SEQ ID NO: 25, a CDRL2 as set forth in SEQ ID NO: 26, and a CDRL3 as set forth in SEQ ID NO: 27; and
   an acid alpha-glucosidase enzyme (GAA) signature peptide of Pompe Disease of SEQ ID NO: 5 with an antibody or antigen binding fragment thereof that binds the GAA signature peptide and comprises: a VH domain comprising a CDRH1 as set forth in SEQ ID NO: 66, a CDRH2 as set forth in SEQ ID NO: 67, and a CDRH3 as set forth in SEQ ID NO: 68, and VL domain comprising a CDRL1 as set forth in SEQ ID NO: 69, a CDRL2 as set forth in SEQ ID NO: 70, and a CDRL3 as set forth in SEQ ID NO: 71; or
   (B) a first IDUA signature peptide of MPSI of SEQ ID NO: 1 with an antibody or antigen-binding fragment thereof that binds the first IDUA signature peptide and comprises: a VH domain comprising a CDRH1 as set forth in SEQ ID NO: 10, a CDRH2 as set forth in SEQ ID NO: 11, and a CDRH3 as set forth in SEQ ID NO: 12, and a VL domain comprising a CDRL1 as set forth in SEQ ID NO: 13, a CDRL2 as set forth in SEQ ID NO: 14, and a CDRL3 as set forth in SEQ ID NO: 15; and
   a second IDUA signature peptide of MPSI of SEQ ID NO: 2 with an antibody or antigen-binding fragment thereof that binds the second IDUA signature peptide and comprises: a VH domain comprising a CDRH1 as set forth in SEQ ID NO: 22, a CDRH2 as set forth in SEQ ID NO: 23, and a CDRH3 as set forth in SEQ ID NO: 24, and a VL domain comprising a CDRL1 as set forth in SEQ ID NO: 25, a CDRL2 as set forth in SEQ ID NO: 26, and a CDRL3 as set forth in SEQ ID NO: 27; or
   (C) a first IDUA signature peptide of MPSI of SEQ ID NO: 1 with an antibody or antigen-binding fragment thereof that binds the first IDUA signature peptide and comprises: a VH domain comprising a CDRH1 as set forth in SEQ ID NO: 10, a CDRH2 as set forth in SEQ ID NO: 11, and a CDRH3 as set forth in SEQ ID NO: 12, and a VL domain comprising a CDRL1 as set forth in SEQ ID NO: 13, a CDRL2 as set forth in SEQ ID NO: 14, and a CDRL3 as set forth in SEQ ID NO: 15;
   a second IDUA signature peptide of MPSI of SEQ ID NO: 2 with an antibody or antigen-binding fragment thereof that binds the second IDUA signature peptide and comprises: a VH domain comprising a CDRH1 as set forth in SEQ ID NO: 22, a CDRH2 as set forth in SEQ ID NO: 23, and a CDRH3 as set forth in SEQ ID NO: 24, and a VL domain comprising a CDRL1 as set forth in SEQ ID NO: 25, a CDRL2 as set forth in SEQ ID NO: 26, and a CDRL3 as set forth in SEQ ID NO: 27; and
   a GAA signature peptide of Pompe Disease of SEQ ID NO: 5 with an antibody or antigen binding fragment thereof that binds the GAA signature peptide and comprises: a VH domain comprising a CDRH1 as set forth in SEQ ID NO: 66, a CDRH2 as set forth in SEQ ID NO: 67, and a CDRH3 as set forth in SEQ ID NO: 68, and a VL domain comprising a CDRL1 as set forth in SEQ ID NO: 69, a CDRL2 as set forth in SEQ ID NO: 70, and a CDRL3 as set forth in SEQ ID NO: 71; or
   (D) a first IDUA signature peptide of MPSI of SEQ ID NO: 1 with an antibody or antigen-binding fragment thereof that binds the first IDUA signature peptide and comprises: a VH domain comprising a CDRH1 as set forth in SEQ ID NO: 10, a CDRH2 as set forth in SEQ ID NO: 11, and a CDRH3 as set forth in SEQ ID NO: 12, and a VL domain comprising a CDRL1 as set forth in SEQ ID NO: 13, a CDRL2 as set forth in SEQ ID NO: 14, and a CDRL3 as set forth in SEQ ID NO: 15;
   a second IDUA signature peptide of MPSI of SEQ ID NO: 2 with an antibody or antigen-binding fragment thereof that binds the second IDUA signature peptide and comprises: a VH domain comprising a CDRH1 as set forth in SEQ ID NO: 22, a CDRH2 as set forth in SEQ ID NO: 23, and a CDRH3 as set forth in SEQ ID NO: 24, and a VL domain comprising a CDRL1 as set forth in SEQ ID NO: 25, a CDRL2 as set forth in SEQ ID NO: 26, and a CDRL3 as set forth in SEQ ID NO: 27; and
   a GAA signature peptide of Pompe Disease of SEQ ID NO: 3 with an antibody or antigen binding fragment thereof that binds the GAA signature peptide and comprises: a VH domain comprising a CDRH1 as set forth in SEQ ID NO: 44, a CDRH2 as set forth in SEQ ID NO: 45, and a CDRH3 as set forth in SEQ ID NO: 46, and a VL domain comprising a CDRL1 as set forth in SEQ ID NO: 47, a CDRL2 as set forth in SEQ ID NO: 48, and a CDRL3 as set forth in SEQ ID NO: 49; or
   (E) a first GAA signature peptide of Pompe Disease of SEQ ID NO: 3 with an antibody or antigen binding fragment thereof that binds the first GAA signature peptide and comprises: a VH domain comprising a CDRH1 as set forth in SEQ ID NO: 44, a CDRH2 as set forth in SEQ ID NO: 45, and a CDRH3 as set forth in SEQ ID NO: 46, and a VL domain comprising a CDRL1 as set forth in SEQ ID NO: 47, a CDRL2 as set forth in SEQ ID NO: 48, and a CDRL3 as set forth in SEQ ID NO: 49; and
   a second GAA signature peptide of Pompe Disease of SEQ ID NO: 5 with an antibody or antigen binding fragment thereof that binds the GAA signature peptide and comprises: a VH domain comprising a CDRH1 as set forth in SEQ ID NO: 66, a CDRH2 as set forth in SEQ ID NO: 67, and a CDRH3 as set forth in SEQ ID NO: 68, and a VL domain comprising a CDRL1 as set forth in SEQ ID NO: 69, a CDRL2 as set forth in SEQ ID NO: 70, and a CDRL3 as set forth in SEQ ID NO: 71; or (F) a first IDUA signature peptide of MPSI of SEQ ID NO: 1 with an antibody or antigen-binding fragment thereof that binds the first IDUA signature peptide and comprises: a VH domain comprising a CDRH1 as set forth in SEQ ID NO: 10, a CDRH2 as set forth in SEQ ID NO: 11, and a CDRH3 as set forth in SEQ ID NO: 12, and VL domain comprising a CDRL1 as set forth in SEQ ID NO: 13, a CDRL2 as set forth in SEQ ID NO: 14, and a CDRL3 as set forth in SEQ ID NO: 15;
a second IDUA signature peptide of MPSI of SEQ ID NO: 2 with an antibody or antigen-binding fragment thereof that binds the second IDUA signature peptide and comprises: a VH domain comprising a CDRH1 as set forth in SEQ ID NO: 22, a CDRH2 as set forth in SEQ ID NO: 23, and a CDRH3 as set forth in SEQ ID NO: 24, and a VL domain comprising a CDRL1 as set forth in SEQ ID NO: 25, a CDRL2 as set forth in SEQ ID NO: 26, and a CDRL3 as set forth in SEQ ID NO: 27;
a first GAA signature peptide of Pompe Disease of SEQ ID NO: 3 with an antibody or antigen binding fragment thereof that binds the first GAA signature peptide and comprises: a VH domain comprising a CDRH1 as set forth in SEQ ID NO: 44, a CDRH2 as set forth in SEQ ID NO: 45, and a CDRH3 as set forth in SEQ ID NO: 46, and a VL domain comprising a CDRL1 as set forth in SEQ ID NO: 47, a CDRL2 as set forth in SEQ ID NO: 48, and a CDRL3 as set forth in SEQ ID NO: 49;
and a second GAA signature peptide of Pompe Disease of SEQ ID NO: 5 with an antibody or antigen binding fragment thereof that binds the GAA signature peptide and comprises: a VH domain comprising a CDRH1 as set forth in SEQ ID NO: 66, a CDRH2 as set forth in SEQ ID NO: 67, and a CDRH3 as set forth in SEQ ID NO: 68, and a VL domain comprising a CDRL1 as set forth in SEQ ID NO: 69, a CDRL2 as set forth in SEQ ID NO: 70, and a CDRL3 as set forth in SEQ ID NO: 71; or
(G) a first IDUA signature peptide of MPSI of SEQ ID NO: 1 with an antibody or antigen-binding fragment thereof that binds the first IDUA signature peptide and comprises: a VH domain comprising a CDRH1 as set forth in SEQ ID NO: 10, a CDRH2 as set forth in SEQ ID NO: 11, and a CDRH3 as set forth in SEQ ID NO: 12, and a VL domain comprising a CDRL1 as set forth in SEQ ID NO: 13, a CDRL2 as set forth in SEQ ID NO: 14, and a CDRL3 as set forth in SEQ ID NO: 15;
a second IDUA signature peptide of MPSI of SEQ ID NO: 2 with an antibody or antigen-binding fragment thereof that binds the second IDUA signature peptide and comprises: a VH domain comprising a CDRH1 as set forth in SEQ ID NO: 22, a CDRH2 as set forth in SEQ ID NO: 23, and a CDRH3 as set forth in SEQ ID NO: 24, and a VL domain comprising a CDRL1 as set forth in SEQ ID NO: 25, a CDRL2 as set forth in SEQ ID NO: 26, and a CDRL3 as set forth in SEQ ID NO: 27;
a first GAA signature peptide of Pompe Disease of SEQ ID NO: 3 with an antibody or antigen binding fragment thereof that binds the first GAA signature peptide and comprises: a VH domain comprising a CDRH1 as set forth in SEQ ID NO: 44, a CDRH2 as set forth in SEQ ID NO: 45, and a CDRH3 as set forth in SEQ ID NO: 46, and a VL domain comprising a CDRL1 as set forth in SEQ ID NO: 47, a CDRL2 as set forth in SEQ ID NO: 48, and a CDRL3 as set forth in SEQ ID NO: 49; and
a second GAA signature peptide of Pompe Disease of SEQ ID NO: 5 with an antibody or antigen binding fragment thereof that binds the GAA signature peptide and comprises: a VH domain comprising a CDRH1 as set forth in SEQ ID NO: 66, a CDRH2 as set forth in SEQ ID NO: 67, and a CDRH3 as set forth in SEQ ID NO: 68, and a VL domain comprising a CDRL1 as set forth in SEQ ID NO: 69, a CDRL2 as set forth in SEQ ID NO: 70, and a CDRL3 as set forth in SEQ ID NO: 71;
and performing liquid chromatography-multiple reaction monitoring mass spectrometry (LC-MRM-MS) on the enriched peptides to determine a concentration of each enriched signature peptide, thereby detecting one or more signature peptide of MPSI and/or Pompe Disease in the biological sample.

2. The method of claim 1, wherein the biological sample is dried blood spot (DBS), a buccal swab, peripheral blood mononuclear cells (PBMCs), or white blood cells (WBCs).

3. The method of claim 1, further comprising comparing the concentration of each signature peptide to that of a corresponding predetermined threshold concentration.

4. The method of claim 3, further comprising diagnosing the subject with: MPSI when the concentrations of the first and/or second IDUA signature peptides are lower than corresponding predetermined threshold concentrations or when the first and/or second IDUA signature peptides are absent; and Pompe Disease when the concentrations of the first and/or second GAA signature peptides are lower than corresponding predetermined threshold concentrations or when the first and/or second GAA signature peptides are absent.

5. The method of claim 1, wherein the method is performed as part of a newborn screening (NBS) that additionally screens the subject for one or more of phenylketonuria, primary congenital hypothyroidism, cystic fibrosis, and sickle cell disease.

6. The method of claim 1, wherein the method is performed in the absence of clinical symptoms of Pompe Disease and/or MPSI in the subject.

7. The method of claim 3, wherein the predetermined threshold concentration for each signature peptide is calculated from a standard deviation of the mean concentration of each signature peptide from a population of normal control subjects.

8. The method of claim 7, wherein the biological sample is DBS and the mean concentration of the first IDUA signature peptide of MPSI of SEQ ID NO: 1 in DBS from a population of normal control subjects comprises a concentration in a range of 10 pmol/L to 350 pmol/L.

9. The method of claim 7, wherein the biological sample is PBMC and the mean concentration of the first IDUA signature peptide of MPSI of SEQ ID NO: 1 in PBMC from a population of normal control subjects comprises a concentration in a range of 300 pmol/L to 1000 pmol/L.

10. The method of claim 7, wherein the biological sample is a buccal swab and the mean concentration of the first IDUA signature peptide of MPSI of SEQ ID NO: 1 in buccal swabs from a population of normal control subjects comprises a concentration in a range of 100 pmol/L to 1000 pmol/L.

11. The method of claim 7, wherein the biological sample is a buccal swab and the mean concentration of the first IDUA signature peptide of MPSI of SEQ ID NO: 1 in buccal swabs from a population of normal control subjects comprises a concentration in a range of 30 pmol/g to 85 pmol/g.

12. The method of claim 7, wherein the biological sample is DBS and the mean concentration of the second IDUA signature peptide of MPSI of SEQ ID NO: 2 in DBS from a population of normal control subjects comprises a concentration in a range of 10 pmol/L to 250 pmol/L.

13. The method of claim 7, wherein the biological sample is PBMC and the mean concentration of the second IDUA signature peptide of MPSI of SEQ ID NO: 2 in PBMC from a population of normal control subjects comprises a concentration in a range of 350 pmol/L to 1000 pmol/L.

14. The method of claim 7, wherein the biological sample is a buccal swab and the mean concentration of the second IDUA signature peptide of MPSI of SEQ ID NO: 2 in buccal swabs from a population of normal control subjects comprises a concentration in a range of 100 pmol/L to 1000 pmol/L.

15. The method of claim 7, wherein the biological sample is a buccal swab and the mean concentration of the second IDUA signature peptide of MPSI of SEQ ID NO: 2 in buccal swabs from a population of normal control subjects comprises a concentration in a range of 30 pmol/g of protein to 80 pmol/g of protein.

16. The method of claim 7, wherein the biological sample is DBS and the mean concentration of the third GAA signature peptide of Pompe Disease of SEQ ID NO: 5 in DBS from a population of normal control subjects comprises a concentration in a range of 25 pmol/L to 250 pmol/L.

17. The method of claim 7, wherein the biological sample is a buccal swab and the mean concentration of the third GAA signature peptide of Pompe Disease of SEQ ID NO: 5 in buccal swabs from a population of normal control subjects comprises a concentration in a range of 30 pmol/g of protein to 150 pmol/g of protein.

18. The method of claim 1, further comprising predicting that the subject will develop an immune response to enzyme replacement therapy (ERT) for: MPSI when the concentrations of the first and/or second IDUA signature peptides are absent; and/or Pompe Disease when the concentrations of the first and/or second GAA signature peptides are absent.

19. An assay kit for the screening of Mucopolysaccharidosis Type I (MPSI) and/or Pompe Disease in a subject, the assay kit comprising:

(A) an antibody or antigen-binding fragment thereof comprising: a VH domain comprising a complementarity determining region (CDR)H1 as set forth in SEQ ID NO: 22, a CDRH2 as set forth in SEQ ID NO: 23, and a CDRH3 as set forth in SEQ ID NO: 24, and a VL domain comprising a CDRL1 as set forth in SEQ ID NO: 25, a CDRL2 as set forth in SEQ ID NO: 26, and a CDRL3 as set forth in SEQ ID NO: 27; and
an antibody or antigen binding fragment thereof comprising: a VH domain comprising a CDRH1 as set forth in SEQ ID NO: 66, a CDRH2 as set forth in SEQ ID NO: 67, and a CDRH3 as set forth in SEQ ID NO: 68, and a VL domain comprising a CDRL1 as set forth in SEQ ID NO: 69, a CDRL2 as set forth in SEQ ID NO: 70, and a CDRL3 as set forth in SEQ ID NO: 71; or (B) an antibody or antigen-binding fragment thereof comprising: a VH domain comprising a CDRH1 as set forth in SEQ ID NO: 10, a CDRH2 as set forth in SEQ ID NO: 11, and a CDRH3 as set forth in SEQ ID NO: 12, and a VL domain comprising a CDRL1 as set forth in SEQ ID NO: 13, a CDRL2 as set forth in SEQ ID NO: 14, and a CDRL3 as set forth in SEQ ID NO: 15; and
an antibody or antigen-binding fragment thereof comprising: a VH domain comprising a CDRH1 as set forth in SEQ ID NO: 22, a CDRH2 as set forth in SEQ ID NO: 23, and a CDRH3 as set forth in SEQ ID NO: 24, and a VL domain comprising a CDRL1 as set forth in SEQ ID NO: 25, a CDRL2 as set forth in SEQ ID NO: 26, and a CDRL3 as set forth in SEQ ID NO: 27; or (C) an antibody or antigen-binding fragment thereof comprising: a VH domain comprising a CDRH1 as set forth in SEQ ID NO: 10, a CDRH2 as set forth in SEQ ID NO: 11, and a CDRH3 as set forth in SEQ ID NO: 12, and a VL domain comprising a CDRL1 as set forth in SEQ ID NO: 13, a CDRL2 as set forth in SEQ ID NO: 14, and a CDRL3 as set forth in SEQ ID NO: 15;
an antibody or antigen-binding fragment thereof comprising: a VH domain comprising a CDRH1 as set forth in SEQ ID NO: 22, a CDRH2 as set forth in SEQ ID NO: 23, and a CDRH3 as set forth in SEQ ID NO: 24, and a VL domain comprising a CDRL1 as set forth in SEQ ID NO: 25, a CDRL2 as set forth in SEQ ID NO: 26, and a CDRL3 as set forth in SEQ ID NO: 27; and
an antibody or antigen binding fragment thereof comprising: a VH domain comprising a CDRH1 as set forth in SEQ ID NO: 66, a CDRH2 as set forth in SEQ ID NO: 67, and a CDRH3 as set forth in SEQ ID NO: 68, and a VL domain comprising a CDRL1 as set forth in SEQ ID NO: 69, a CDRL2 as set forth in SEQ ID NO: 70, and a CDRL3 as set forth in SEQ ID NO: 71; or (D) an antibody or antigen-binding fragment thereof comprising: a VH domain comprising a CDRH1 as set forth in SEQ ID NO: 10, a CDRH2 as set forth in SEQ ID NO: 11, and a CDRH3 as set forth in SEQ ID NO: 12, and a VL domain comprising a CDRL1 as set forth in SEQ ID NO: 13, a CDRL2 as set forth in SEQ ID NO: 14, and a CDRL3 as set forth in SEQ ID NO: 15;
an antibody or antigen-binding fragment thereof comprising: a VH domain comprising a CDRH1 as set forth in SEQ ID NO: 22, a CDRH2 as set forth in SEQ ID NO: 23, and a CDRH3 as set forth in SEQ ID NO: 24, and a VL domain comprising a CDRL1 as set forth in SEQ ID NO: 25, a CDRL2 as set forth in SEQ ID NO: 26, and a CDRL3 as set forth in SEQ ID NO: 27;
and an antibody or antigen binding fragment thereof comprising: a VH domain comprising a CDRH1 as set forth in SEQ ID NO: 44, a CDRH2 as set forth in SEQ ID NO: 45, and a CDRH3 as set forth in SEQ ID NO: 46, and a VL domain comprising a CDRL1 as set forth in SEQ ID NO: 47, a CDRL2 as set forth in SEQ ID NO: 48, and a CDRL3 as set forth in SEQ ID NO: 49; or (E) an antibody or antigen binding fragment thereof comprising: a VH domain comprising a CDRH1 as set forth in SEQ ID NO: 44, a CDRH2 as set forth in SEQ ID NO: 45, and a CDRH3 as set forth in SEQ ID NO: 46, and a VL domain comprising a CDRL1 as set forth in SEQ ID NO: 47, a CDRL2 as set forth in SEQ ID NO: 48, and a CDRL3 as set forth in SEQ ID NO: 49; and
an antibody or antigen binding fragment thereof comprising: a VH domain comprising a CDRH1 as set forth in SEQ ID NO: 66, a CDRH2 as set forth in SEQ ID NO: 67, and a CDRH3 as set forth in SEQ ID NO: 68, and a VL domain comprising a CDRL1 as set forth in SEQ ID NO: 69, a CDRL2 as set forth in SEQ ID NO: 70, and a CDRL3 as set forth in SEQ ID NO: 71; or (F) an antibody or antigen-binding fragment thereof comprising: a VH domain comprising a CDRH1 as set forth in SEQ ID NO: 10, a CDRH2 as set forth in SEQ ID NO: 11, and a CDRH3 as set forth in SEQ ID NO: 12, and a VL domain comprising a CDRL1 as set forth in SEQ ID NO: 13, a CDRL2 as set forth in SEQ ID NO: 14, and a CDRL3 as set forth in SEQ ID NO: 15;

an antibody or antigen-binding fragment thereof comprising: VH domain comprising a CDRH1 as set forth in SEQ ID NO: 22, a CDRH2 as set forth in SEQ ID NO: 23, and a CDRH3 as set forth in SEQ ID NO: 24, and VL domain comprising a CDRL1 as set forth in SEQ ID NO: 25, a CDRL2 as set forth in SEQ ID NO: 26, and a CDRL3 as set forth in SEQ ID NO: 27;

an antibody or antigen binding fragment thereof comprising: VH domain comprising a CDRH1 as set forth in SEQ ID NO: 44, a CDRH2 as set forth in SEQ ID NO: 45, and a CDRH3 as set forth in SEQ ID NO: 46, and VL domain comprising a CDRL1 as set forth in SEQ ID NO: 47, a CDRL2 as set forth in SEQ ID NO: 48, and a CDRL3 as set forth in SEQ ID NO: 49; and an antibody or antigen binding fragment thereof comprising: a VH domain comprising a CDRH1 as set forth in SEQ ID NO: 66, a CDRH2 as set forth in SEQ ID NO: 67, and a CDRH3 as set forth in SEQ ID NO: 68, and a VL domain comprising a CDRL1 as set forth in SEQ ID NO: 69, a CDRL2 as set forth in SEQ ID NO: 70, and a CDRL3 as set forth in SEQ ID NO: 71; or (G) an antibody or antigen-binding fragment thereof comprising: a VH domain comprising a CDRH1 as set forth in SEQ ID NO: 10, a CDRH2 as set forth in SEQ ID NO: 11, and a CDRH3 as set forth in SEQ ID NO: 12, and a VL domain comprising a CDRL1 as set forth in SEQ ID NO: 13, a CDRL2 as set forth in SEQ ID NO: 14, and a CDRL3 as set forth in SEQ ID NO: 15;

an antibody or antigen-binding fragment thereof comprising: a VH domain comprising a CDRH1 as set forth in SEQ ID NO: 22, a CDRH2 as set forth in SEQ ID NO: 23, and a CDRH3 as set forth in SEQ ID NO: 24, and a VL domain comprising a CDRL1 as set forth in SEQ ID NO: 25, a CDRL2 as set forth in SEQ ID NO: 26, and a CDRL3 as set forth in SEQ ID NO: 27;

an antibody or antigen binding fragment thereof comprising: a VH domain comprising a CDRH1 as set forth in SEQ ID NO: 44, a CDRH2 as set forth in SEQ ID NO: 45, and a CDRH3 as set forth in SEQ ID NO: 46, and a VL domain comprising a CDRL1 as set forth in SEQ ID NO: 47, a CDRL2 as set forth in SEQ ID NO: 48, and a CDRL3 as set forth in SEQ ID NO: 49; and an antibody or antigen binding fragment thereof comprising: a VH domain comprising a CDRH1 as set forth in SEQ ID NO: 66, a CDRH2 as set forth in SEQ ID NO: 67, and a CDRH3 as set forth in SEQ ID NO: 68, and a VL domain comprising a CDRL1 as set forth in SEQ ID NO: 69, a CDRL2 as set forth in SEQ ID NO: 70, and a CDRL3 as set forth in SEQ ID NO: 71.

20. A recombinant antibody or antigen binding fragment thereof comprising: (A) heavy chain variable (VH) domain comprising: a complementarity determining region (CDR) H1 as set forth in SEQ ID NO: 10, a CDRH2 as set forth in SEQ ID NO: 11, and a CDRH3 as set forth in SEQ ID NO: 12, and a light chain variable (VL) domain comprising a CDRL1 as set forth in SEQ ID NO: 13, a CDRL2 as set forth in SEQ ID NO: 14, and a CDRL3 as set forth in SEQ ID NO: 15;

(B) a VH domain comprising a CDRH1 as set forth in SEQ ID NO: 22, a CDRH2 as set forth in SEQ ID NO: 23, and a CDRH3 as set forth in SEQ ID NO: 24, and a VL domain comprising a CDRL1 as set forth in SEQ ID NO: 25, a CDRL2 as set forth in SEQ ID NO: 26, and a CDRL3 as set forth in SEQ ID NO: 27;

(C) VH domain comprising a CDRH1 as set forth in SEQ ID NO: 44, a CDRH2 as set forth in SEQ ID NO: 45, and a CDRH3 as set forth in SEQ ID NO: 46, and VL domain comprising a CDRL1 as set forth in SEQ ID NO: 47, a CDRL2 as set forth in SEQ ID NO: 48, and a CDRL3 as set forth in SEQ ID NO: 49; or (D) VH domain comprising a CDRH1 as set forth in SEQ ID NO: 66, a CDRH2 as set forth in SEQ ID NO: 67, and a CDRH3 as set forth in SEQ ID NO: 68, and VL domain comprising a CDRL1 as set forth in SEQ ID NO: 69, a CDRL2 as set forth in SEQ ID NO: 70, and a CDRL3 as set forth in SEQ ID NO: 71.

21. The recombinant antibody or antigen binding fragment thereof of claim 19, wherein (A) the VH domain is as set forth in SEQ ID NO: 18 and the VL domain is as set forth in SEQ ID NO: 21;

(B) the VH domain is as set forth in SEQ ID NO: 30 and the VL domain is as set forth in SEQ ID NO: 33;

(C) the VH domain is as set forth in SEQ ID NO: 57 and/or the heavy chain is as set forth in SEQ ID NO: 55; and the VL domain is as set forth in SEQ ID NO: 65 and/or the light chain is as set forth in SEQ ID NO: 63;

(D) the VH domain is as set forth in SEQ ID NO: 79 and/or the heavy chain is as set forth in SEQ ID NO: 77; and the VL domain is as set forth in SEQ ID NO: 87 and/or the light chain is as set forth in SEQ ID NO: 85.

* * * * *